(12) United States Patent
Brameld et al.

(10) Patent No.: US 8,273,773 B2
(45) Date of Patent: Sep. 25, 2012

(54) HETEROCYCLIC ANTIVIRAL COMPOUNDS

(75) Inventors: Kenneth Albert Brameld, Palo Alto, CA (US); David Scott Carter, Sunnyvale, CA (US); Elbert Chin, San Jose, CA (US); Javier de Vicente Fidalgo, Mountain View, CA (US); Jim Li, San Francisco, CA (US); Ryan Craig Schoenfeld, San Jose, CA (US); Eric Brian Sjogren, Mountain View, CA (US); Francisco Xavier Talamas, Mountain View, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 465 days.

(21) Appl. No.: 12/460,658

(22) Filed: Jul. 22, 2009

(65) Prior Publication Data

US 2010/0021423 A1    Jan. 28, 2010

Related U.S. Application Data

(60) Provisional application No. 61/082,847, filed on Jul. 23, 2008, provisional application No. 61/207,925, filed on Feb. 17, 2009, provisional application No. 61/179,837, filed on May 20, 2009.

(51) Int. Cl.
*A61K 31/4412* (2006.01)
*C07D 213/64* (2006.01)

(52) U.S. Cl. ........ 514/345; 514/344; 514/348; 514/351; 546/288; 546/290; 546/296; 546/300; 546/301; 546/302; 546/303

(58) Field of Classification Search ................. 546/288, 546/290, 296, 300, 301, 302, 303; 514/344, 514/345, 348, 351
See application file for complete search history.

(56) References Cited

U.S. PATENT DOCUMENTS

| 2004/0097492 | A1 | 5/2004 | Pratt et al. |
| 2009/0186912 | A1 | 7/2009 | Flengte et al. |

FOREIGN PATENT DOCUMENTS

| WO | WO00/09543 | A2 | 2/2000 |
| WO | WO01/85172 | A1 | 11/2001 |
| WO | 2009032116 | A1 | 3/2009 |
| WO | 2009032123 | A2 | 3/2009 |
| WO | 2009032125 | A1 | 3/2009 |
| WO | 2009039127 | A1 | 3/2009 |
| WO | WO2009/039135 | A1 | 3/2009 |
| WO | 2009064848 | A1 | 5/2009 |
| WO | 2009064852 | A1 | 5/2009 |
| WO | WO2010/111436 | A2 | 9/2010 |
| WO | WO2010/111437 | A1 | 9/2010 |

*Primary Examiner* — Patricia Morris
(74) *Attorney, Agent, or Firm* — Brian L. Buckwalter

(57) ABSTRACT

Compounds having the formula I wherein $R^1$, $R^2$, $R^3$, $R^{4a}$, $R^{4b}$, $R^{4c}$, $R^5$, $R^6$, $R^9$ and n are as defined herein are Hepatitis C virus NS5b polymerase inhibitors. Also disclosed are compositions and methods for treating an HCV infection and inhibiting HCV replication.

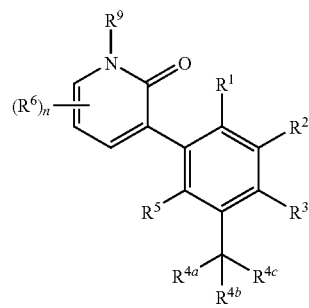

(1)

33 Claims, No Drawings

HETEROCYCLIC ANTIVIRAL COMPOUNDS

CROSS REFERENCE TO PRIOR APPLICATIONS

This application claims the benefit of priority to U.S. Ser. No. 61/082,847 filed Jul. 23, 2008, to U.S. Ser. No. 61/207,925 filed Feb. 17, 2009 and to U.S. Ser. No. 61/179,837 filed May 20, 2009 all of which are hereby incorporated by reference in their entirety.

FIELD OF THE INVENTION

The present invention provides non-nucleoside compounds and certain derivatives thereof which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of-approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forns and J. Bukh, *Clinics in Liver Disease* 1999 3:693-716; J. Bukh et al., *Semin. Liv. Dis.* 1995 15:41-63). Unfortunately Type 1 infectious is more resistant to therapy than either type 2 or 3 genotypes (N. N. Zein, *Clin. Microbiol. Rev.*, 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of non-structural protein 5) remain unknown. It is believed that most of the non-structural proteins encoded by the HCV RNA genome are involved in RNA replication Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.*, 1999 19:5; Di Besceglie, A. M. and Bacon, B. R., *Scientific American*, October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patent on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. Investing. Drugs* 2003 12(8): 1269-1280; S.-L. Tan et al., Hepatitis C Therapeutics: Current Status and Emerging Strategies, *Nature Rev. Drug Discov.* 2002 1:867-881; J. Z. Wu and Z. Hong, Targeting NS5B RNA-Dependent RNA Polymerase for Anti-HCV Chemotherapy, *Curr. Drug Targ.—Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118: S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted to ribavirin by adenosine deaminase in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release* 2001 72:217-224).

Combination therapy of HCV with ribavirin and interferon-α currently is the optimal therapy for HCV. Combining ribavirin and PEG-IFN (infra) results in a sustained viral response (SVR) in 54-56% of patients with type 1 HCV. The SVR approaches 80% for type 2 and 3 HCV. (Walker, supra) Unfortunately, combination therapy also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the NS3 protease, the NS3 helicase and the NS5B polymerase.

The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor that interferes with nucleotide binding to the polymerase. To function as a chain terminator the nucleoside analog must be taken up by the cell in vivo and be converted in vivo to its triphosphate form to compete as a substrate at the polymerase nucleotide binding site. This conversion to the triphosphate is commonly mediated by cellular kinases which impart additional structural limitations on any nucleoside. In addition this requirement for phosphorylation limits the direct evaluation of nucleosides as inhibitors of HCV replication to cell-based assays (J. A. Martin et al., U.S. Pat. No. 6,846,810; C. Pierra et al., *J. Med. Chem.* 2006 49(22):6614-6620; J. W. Tomassini et al., *Antimicrob. Agents and Chemother.* 2005 49(5):2050; J. L. Clark et al., *J. Med. Chem.* 2005 48(17):2005).

Compounds of the present invention and their isomeric forms and pharmaceutically acceptable salts thereof are also useful in treating viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as combination therapy with at least one of the compounds of the present invention.

Other interferons currently in development include albinterferon-α-2b (Albuferon), IFN-omega with DUROS, LOCTERON™ and interferon-α-2b XL. As these and other interferons reach the marketplace their use in combination therapy with compounds of the present invention is anticipated.

HCV polymerase inhibitors are another target for drug discovery and compounds in development include R-1626, R-7128, IDX184/IDX102, PF-868554 (Pfizer), VCH-759 (ViroChem), GS-9190 (Gilead), A-837093 and A-848837 (Abbot), MK-3281 (Merck), GSK949614 and GSK625433 (Glaxo), ANA598 (Anadys), VBY 708 (ViroBay).

Inhibitors of the HCV NS3 protease also have been identified as potentially useful for treatment of HCV. Protease inhibitors in clinical trials include VX-950 (Telaprevir, Vertex), SCH503034 (Broceprevir, Schering), TMC435350 (Tibotec/Medivir) and ITMN-191 (Intermune). Other protease inhibitors in earlier stages of development include MK7009 (Merck), BMS-790052 (Bristol Myers Squibb), VBY-376 (Virobay), IDXSCA/IDXSCB (Idenix), BI12202 (Boehringer), VX-500 (Vertex), PHX1766 Phenomix).

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

SUMMARY OF THE INVENTION

There is currently no preventive treatment of Hepatitis C virus (HCV) and currently approved therapies, which exist only against HCV, are limited. Design and development of new pharmaceutical compounds is essential.

The present invention provides a compound according to formula I, or a pharmaceutically acceptable salt thereof and the use of compounds according to formula I for the treatment of a patient infected with HCV wherein:

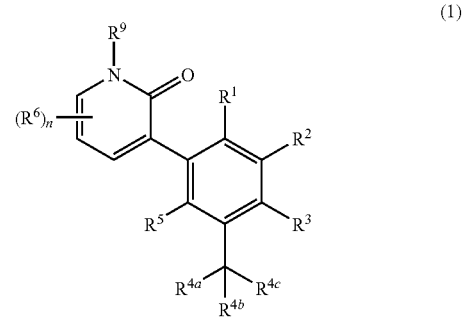

(1)

$R^1$ is hydrogen, $C_{1-6}$ alkyl, $C_{1-6}$ haloalkyl, halogen, hydroxy, $C_{1-6}$ alkoxy, $C_{1-6}$ haloalkoxy, cyano, $NR^aR^b$, carboxy, $C_{1-3}$ alkoxycarbonyl, carboxamido, amino $C_{1-3}$alkyl, $C_{1-3}$ acylamino $C_{1-3}$alkyl, $C_{1-6}$ hydroxyalkoxy.

$R^2$ is selected from the group consisting of: (a) —[C$(R^8)_2]_p$—$Ar^1$ (b) —[C$(R^8)_2]_p$—$OAr^1$, (c) —$(CH_2)_m$C(=O)X, (d) —$NR^7$C(=O)$Ar^4$, (e) $C_{1-6}$ alkyl, (f) $C_{1-6}$ haloalkyl, (g) $C_{1-6}$ alkoxy, (h) $C_{1-6}$ haloalkoxy, (i) $C_{1-6}$ hydroxyalkyl, (j) hydroxy, (k) halogen, (l) hydrogen, (m) phenylsulfonyl, (n) —O(CH$_2$)$_m$Ar$^1$, (o) —[C$(R^8)_2]_p$—$NR^eR^f$, (p) (E)- or (Z) —$R^{10}$C=$CR^{10}Ar^1$, (q) —C≡$CAr^1$ wherein $R^8$ is independently in each occurrence hydrogen, carboxyl, $C_{1-3}$ alkoxycarbonyl, carboxamido, $C_{1-3}$ hydroxyalkyl, $C_{1-3}$ alkyl, —$(CH_2)_rNR^gR^h$ or cyano, $R^{10}$ is independently in each occurrence hydrogen, $C_{1-6}$ alkyl, $C_{1-6}$ hydroxyalkyl, cyano, $C_{1-3}$ alkoxycarbonyl, carboxamido, carboxyl or $C_{1-3}$alkoxy-$C_{1-6}$alkyl, p is zero to four, and r is 1 to 3.

$Ar^1$ is phenyl, naphthyl, pyridinyl, pyrimidinyl, pyrazinyl, pyridazinyl or quinolinyl optionally independently substituted with one to three substituents selected from the group consisting of (a) hydroxy, (b) $C_{1-6}$ alkoxy, (c) $C_{1-6}$ alkyl, (d) $C_{1-10}$ hydroxyalkyl wherein one or two carbon atoms optionally can be replaced by oxygen provided the replacement does not form a oxygen-oxygen bond, (e) $C_{1-3}$ alkoxy-$C_{1-6}$ alkyl, (f) halogen, (g) cyano, (h) $C_{1-6}$ alkoxycarbonyl, (i) $C_{1-6}$ alkylsulfonyl, (j) $X^1$(CH$_2$)$_{1-6}$CO$_2$H, (k) $C_{1-3}$ acylamino-$C_{1-6}$ alkyl, (l) (CH$_2$)$_n$NR$^a$R$^b$, (m) (CH$_2$)$_n$CONR$^a$R$^b$, (n) —O(CH$_2$)$_n$CONR$^a$R$^b$, (o) $X^2$(CH$_2$)$_{2-6}$NR$^g$R$^h$, (p) $X^1$—$C_{1-6}$ hydroxyalkyl, (q) $C_{1-6}$ haloalkyl or (r) carboxyl;

$R^a$ and $R^b$ are (i) independently in each occurrence (a) hydrogen, (b) $C_{1-6}$ alkyl, (c) $C_{1-3}$ haloalkyl, (d) $C_{1-6}$ acyl, (e) $C_{1-6}$ alkylsulfonyl, (f) $C_{1-6}$ haloalkylsulfonyl, (g) $C_{3-7}$ cycloalkylsulfonyl, (h) $C_{3-7}$ cycloalkyl-$C_{1-3}$ alkyl-sulfonyl, (i) $C_{1-6}$ alkoxy-$C_{1-6}$ alkylsulfonyl, (j) (CH$_2$)$_{1-3}$NR$^g$R$^h$, (k) SO$_2$(CH$_2$)$_{1-6}$NR$^g$R$^h$ wherein R$^g$ and R$^h$ are as defined above, (l) sulfamoyl, (m) $C_{1-3}$ alkylsulfamoyl, (n) $C_{1-3}$ dialkylsulfamoyl, (o) carbamoyl, (p) $C_{1-3}$ alkylcarbamoyl, (q) $C_{1-3}$ dialkylcarbamoyl, (r) benzoyl said benzoyl optionally independently substituted with one or two groups selected from the group consisting of amino, halogen, $C_{1-6}$ alkyl or $C_{1-3}$ alkylsulfonylamido, (s) $C_{1-6}$ carboxyalkylsulfonyl, (t) $C_{2-6}$ hydroxyalkylsulfonyl or (ii) $R^a$ and $R^b$ taken together with the nitrogen to which they are attached are (a) an optionally substituted cyclic amine (b) $(CH_2)_{2-3}OC(O)$ or (c) 2-oxo-oxazolidine;

$R^e$ and $R^f$ when (i) taken independently are selected from (a) hydrogen, (b) $C_{1-3}$ alkyl, (c) $C_{4-7}$ cycloalkyl, (d) $C_{3-7}$ cycloalkylcarbonyl (e) phenyl said cycloalkyl and said phenyl moieties optionally independently substituted with one to three groups selected from $C_{1-3}$ alkylsulfonylamido, $C_{1-3}$ alkyl, $C_{1-3}$ alkoxy or halogen or (ii) when taken together along with the nitrogen to which they are attached are a cyclic amine independently substituted with one to three groups selected from $C_{1-3}$ alkylsulfonylamido, $C_{1-3}$ alkyl, $C_{1-3}$ alkoxy or halogen.

X is OH, $C_{1-6}$ alkoxy, $NR^cR^d$ or $Ar^3$.

$Ar^3$ is phenyl each optionally substituted with one to three substitutents selected from the group consisting of: (a) halogen, (b) hydroxy, (c) $C_{1-3}$ hydroxyalkyl, (d) amino, (e) amino-$C_{1-3}$ alkyl, (f) $C_{1-3}$ alkylamino (g) $C_{1-3}$ alkylamino-$C_{1-3}$ alkyl, (h) $C_{1-3}$ dialkylamino, (i) $C_{1-3}$ dialkylamino-$C_{1-3}$ alkyl, (j) carboxamido, (k) $C_{1-6}$ alkylsulfonylamido, (l) $C_{1-6}$ alkylsulfonylamido-$C_{1-3}$ alkyl, (m) $NR^7$—$C_{1-3}$ alkyl-$C_{1-6}$ alkylsulfonamido, (n) $C_{1-6}$ alkyl, (o) $C_{1-6}$ alkoxycarbonyl and (p) carboxyl.

$R^c$ and $R^d$ are (i) independently in each occurrence: (a) hydrogen, (b) $Ar^2$, (c) $Ar^2$—$C_{1-6}$ alkyl, (d) $C_{3-6}$ cycloalkyl optionally with substituted $C_{1-3}$ dialkylamino, $C_{1-6}$ alkylsulfonamido or $C_{1-3}$ hydroxyalkyl, (e) $C_{1-6}$ alkyl-$C_{3-7}$ cycloalkyl, (f) $C_{1-3}$ alkoxy-$C_{1-3}$ alkyl, (g) pyridinyl or pyridinyl $C_{1-6}$ alkyl said pyridinyl optionally substituted with amino, $C_{1-3}$ alkylamino, $C_{1-3}$ dialkylamino, $C_{1-6}$ alkylsulfonylamido, sulfamoyl, $C_{1-3}$ alkylsulfamoyl, $C_{1-3}$ dialkylsulfamoyl, (h) thienyl optionally substituted with $C_{1-3}$ alkyl, (i) heterocyclyl or heterocyclyl $C_{1-6}$ alkyl wherein the heterocyclyl group is pyrrolidine or piperidine said heterocyclyl group is optionally substituted with $C_{1-3}$ alkyl or oxo, (j) $C_{1-3}$ alkyl-imidazol-4-yl or (k) $(CH_2)_{2-4}NR^gR^h$; or (ii) $R^c$ and $R^d$ together with the nitrogen to which they are attached are pyrrolidinyl or piperidinyl both of which are optionally substituted with $C_{1-3}$ alkyl, hydroxy or hydroxy-$C_{1-3}$ alkyl.

$Ar^2$ is phenyl optionally substituted with one to three substituents independently selected from the group consisting of (a) $C_{1-3}$ alkyl (b) amino, (c) amino $C_{1-3}$ alkyl, (d) $C_{1-3}$ alkylamino, (e) $C_{1-3}$ alkylamino-$C_{1-3}$ alkyl, (f) $C_{1-3}$ dialkylamino, (g) $OCH_2CO$ $NR^gR^h$, (h) $C_{1-3}$ alkylsulfonylamido, (i) $C_{1-3}$ alkylsulfonamido-$C_{1-3}$ alkyl, (j) N—$C_{1-3}$ alkyl-$C_{1-6}$ alkylsulfonamido and (k) $C_{1-3}$ hydroxyalkyl, and (l) hydroxy.

$Ar^4$ is phenyl, pyridinyl, pyrazinyl, pyridazinyl or pyrimidinyl each optionally substituted with one to three substituents independently selected in each occurrence from the group consisting of (a) amino, (b) $C_{1-3}$ alkylamino, (c) di-$C_{1-3}$ alkylamino, (d) $C_{1-3}$ haloalkylamino, (e) $C_{1-6}$ alkylsulfonylamido, (f) sulfamoyl, (g) $C_{1-3}$ alkylsulfamoyl, (h) $C_{1-3}$ dialkylsulfamoyl, (i) $C_{1-6}$ alkylsulfonylamido-$C_{1-3}$ alkyl, (j) $NR^7$—$C_{1-3}$ alkyl-$C_{1-6}$ alkylsulfonamido, (k) halogen, (l) $C_{1-3}$ alkyl, (m) $C_{1-3}$ alkoxy, (n) $C_{1-6}$ acylamino, (o) hydroxy, (p) $(CH_2)$ $CONR^aR^b$, (q) —$O(CH_2)_nCONR^aR^b$, (r) —$O(CH_2)_nNR^i$ $R^j$, (s) —$NR^i(CH_2)_nOR^j$, (t) $C_{1-3}$-haloalkyl, (u) $C_{1-3}$ alkoxy-$C_{1-6}$ alkoxy, (v) $C_{3-6}$ cycloalkylamine wherein $R^i$ and $R^j$ are independently hydrogen or $C_{1-3}$ alkyl.

$R^7$ is independently in each occurrence hydrogen or $C_{1-3}$ alkyl.

$R^3$ is hydrogen, $C_{1-6}$ alkyl, $C_{1-6}$ haloalkyl, $C_{1-6}$ alkoxy, $C_{1-6}$ haloalkoxy, $C_{1-3}$ alkoxy-$C_{1-6}$ alkoxy, halogen, $O(CH_2)_{2-6}X^3$ wherein $X^3$ is OH or $N(R^7)_2$ or $R^3$ and $R^{4a}$ together are $CH_2$—O and together with atoms to which they are attached form a 2,3-dihydrobenzofuran or an indane;

$R^{4a}$, $R^{4b}$ and $R^{4c}$ (a) when taken independently are each selected independently from (i) $C_{1-3}$ alkyl, (ii) $C_{1-2}$ alkoxy, (iii) $C_{1-2}$ fluoroalkyl, (iv) $C_{1-3}$ hydroxyalkyl, (v) hydroxy (vi) $CO_2H$, (vii) $C_{1-6}$ alkoxycarbonyl, (viii) cyano or (ix) $N(R^7)_2$ or (b) when taken together, (i) $R^{4a}$ and $R^{4b}$ together are $C_{2-4}$ methylene and $R^{4c}$ is hydrogen, $C_{1-3}$ alkyl, $C_{1-2}$ alkoxy, halogen, cyano or $C_{1-2}$ fluoroalkyl or (ii) $R^{4a}$ and $R^{4b}$ together with the carbon to which they are attached are 3-oxetanyl $R^{4c}$ is hydrogen, $C_{1-3}$ alkyl, or (c) either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl or (d) $R^{4a}$, $R^{4b}$, $R^{4c}$ together with the carbon to which they are attached are cyclopropyl, trifluoromethyl or 2,2,2-trifluoroethyl;

$R^5$ is hydrogen, halogen, $C_{1-6}$ alkyl, hydroxy or $R^5$ and $R^{4a}$ together are $CH_2$—O and together with atoms to which they are attached form a 2,3-dihydrobenzofuran or an indane;

$R^6$ is (a) halogen, (b) $C_{1-6}$ alkyl wherein one or two non-adjacent carbon atoms optionally can be replaced by oxygen, (c) $C_{1-3}$ haloalkyl, (d) $C_{1-3}$ alkoxy, (e) $X^1$—$C_{2-6}$ hydroxyalkyl wherein one or two non-adjacent carbon atoms optionally can be replaced by oxygen, (f) cyano-$C_{1-3}$ alkyl, (g) $X^1(CH_2)_{1-6}$ $CO_2H$ or (h) $X^1$—$(CH_2)_{2-6}NR^gR^h$.

$R^9$ is hydrogen, $CH_2OH$, $CH_2OR^{9a}$, $CH(Me)OH$, $CH(Me)OR^{9a}$ wherein $R^{9a}$ is (a) $CO(CH_2)_sCO_2H$ wherein s is one to four, (b) $C(O)CHR^{9b}NHR^{9c}$ wherein $R^{9b}$ is hydrogen, methyl, iso-propyl, iso-butyl, sec-butyl, phenyl or 4-hydroxyphenyl and $R^{9c}$ is hydrogen or $C_{1-6}$ alkoxycarbonyl or $R^{9b}$ and $R^{9c}$ together are $(CH_2)_3$, (c) —$P(O)(OH)_2$ or (d) $COR^{11}$ wherein $R^{11}$ is $C_{1-6}$ alkyl, piperidin-4-yl methyl or optionally substituted aryl;

$X^1$ is O, N $R^7$, or a bond;

$X^2$ is O or N $R^7$;

$R^g$ and $R^h$ are independently hydrogen or $C_{1-6}$ alkyl or $R^g$ and $R^h$ together with the nitrogen to which they are attached are an optionally substituted cyclic amine;

$R^7$ is independently in each occurrence hydrogen of $C_{1-3}$ alkyl;

m is zero to three.

n is independently in each occurrence zero to two.

The present invention further comprises the neutral molecule or pharmaceutically acceptable salts thereof when acidic or basic atoms are present which can be converted to a salt.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, "a compound" refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " ------ " drawn through a bond each refer to the point of attachment of a functional group or other chemical moiety to the rest of the molecule of which it is a part. Thus, for example:

MeC(═O)OR$^4$ wherein

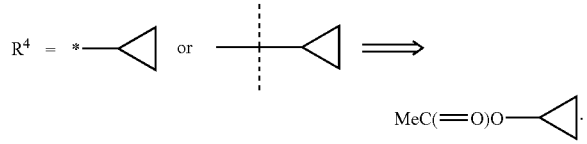

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, unless specifically indicated otherwise, the word "or" is used in the "inclusive" sense of "and/or" and not the "exclusive" sense of "either/or".

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(═O)—CH— ⇌ —C(—OH)═CH—), amide/imidic acid (—C(═O)—NH— ⇌ —C(—OH)═N—) and amidine (—C(═NR)—NH— ⇌ —C(—NHR)═N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. It will be further appreciated by the skilled artisan that substitution of the tropane ring can be in either endo- or exo-configuration, and the present invention covers both configurations. The present invention includes all the individual stereoisomers (e.g. enantiomers), racemic mixtures or partially resolved mixtures of the compounds of formula I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, α-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

The compounds of formula I may contain an acidic or basic functional groups. Suitable acid addition salts are formed by protonation of a basic center with an acid. Deprotonation of an acidic center by a base likewise forms a salt. Salt formation may confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. For a review on suitable salts see Berge et al, *J. Pharm. Sci.,* 1977 66:1-19 and G. S. Paulelahn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics,* 10$^{th}$ Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations,* 2$^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

In one embodiment of the present invention there is provided a compound according to formula I, or a pharmaceutically acceptable salt thereof, wherein $R^1$, $R^2$, $R^3$, $R^{4a}$, $R^{4b}$, $R^{4c}$, $R^5$, $R^6$, $R^7$, $R^8$, $R^9$, m, n and p are as described herein above. In all other embodiments provided below, substituents which can be present in each embodiment and which are not explicitly defined retain the broadest definition provided in the Summary of the Invention.

In another embodiment of the present invention there is provided a compound according to formula I wherein: $R^1$ is hydrogen, $C_{1-6}$ alkyl, $C_{1-6}$ haloalkyl, halogen, hydroxy, $C_{1-6}$ alkoxy, $C_{1-6}$ haloalkoxy, cyano, $NR^aR^b$, carboxy, $C_{1-3}$ alkoxycarbonyl, carboxamido, amino $C_{1-3}$alkyl, $C_{1-3}$ acylamino $C_{1-3}$alkyl, $C_{1-6}$ hydroxyalkoxy; $R^2$ is selected from the group consisting of: (a) —$[C(R^8)_2]_p$—$Ar^1$ (b) —$[C(R^8)_2]_p$—$OAr^1$, (c) —$(CH_2)_mC(=O)X$, (d) —$NR^7C(=O)Ar^4$, (e) —$C_{1-6}$ alkyl, (f) —$C_{1-6}$ haloalkyl, (g) $C_{1-6}$ alkoxy, (h) $C_{1-6}$ haloalkoxy, (i) $C_{1-6}$ alkyl, (j) $C_{1-6}$ hydroxyalkyl, (k) hydroxy, (l) halogen, (m) hydrogen, (o) phenylsulfonyl, (p) —O(CH$_2$)$_m$Ar$^1$, (q) —$[C(R^8)_2]_p$—$NR^eR^f$, (r) $C_{2-4}$ (alkenylene)Ar$^1$ and wherein $R^8$ is hydrogen, carboxyl, $C_{1-3}$ alkoxycarbonyl, carboxamido, $C_{1-3}$ hydroxyalkyl, $C_{1-3}$ alkyl or cyano and p is zero to four; Ar$^1$ is phenyl, pyridinyl, pyrimidinyl, pyrazinyl or pyridazinyl optionally independently substituted with one to three substituents selected from the group consisting of hydroxy, $C_{1-6}$ alkoxy, $C_{1-6}$ alkyl, $C_{1-6}$ hydroxyalkyl, halogen, $(CH_2)_nNR^aR^b$, $(CH_2)_nCONR^aR^b$ and —$O(CH_2)_nCONR^aR^b$; $R^a$ and $R^b$ are independently in hydrogen, $C_{1-6}$ alkyl, $C_{1-6}$ acyl, $C_{1-6}$ sulfonyl, sulfamoyl $C_{1-3}$ alkylsulfamoyl, $C_{1-3}$ dialkylsulfamoyl, carbamoyl, $C_{1-3}$ alkylcarbamoyl, $C_{1-3}$ dialkylcarbamoyl or benzoyl said benzoyl optionally independently substituted with one or two groups selected from the group consisting of amino, halogen, $C_{1-6}$ alkyl or $C_{1-3}$ alkylsulfonylamido; $R^e$ and $R^f$ when (i) taken independently are selected from hydrogen, $C_{1-3}$ alkyl, $C_{4-7}$ cycloalkyl or phenyl said cycloalkyl and said phenyl optionally independently substituted with one to three groups selected from $C_{1-3}$ alkylsulfonylamido, $C_{1-3}$ alkyl, $C_{1-3}$ alkoxy or halogen or (ii) when taken together along with the nitrogen to which they are attached are a pyrrolidine, a piperidine or an azepinyl ring optionally independently substituted with one to three groups selected from $C_{1-3}$ alkylsulfonylamido, $C_{1-3}$ alkyl, $C_{1-3}$ alkoxy or halogen; X is OH, $C_{1-6}$ alkoxy, $NR^cR^d$ or Ar$^3$; Ar$^3$ is phenyl, pyridinyl or thienyl each optionally substituted with one to three substituents selected from the group consisting of: (i) halogen, (ii) hydroxy, (iii) $C_{1-3}$ hydroxyalkyl, (iv) amino, (v) amino-$C_{1-3}$ alkyl, (vi) $C_{1-3}$ alkylamino, (vii) $C_{1-3}$ alkylamino-$C_{1-3}$ alkyl, (viii) $C_{1-3}$ dialkylamino, (xi) $C_{1-3}$ dialkylamino-$C_{1-3}$ alkyl, (x) carboxamido, (xi) $C_{1-6}$ alkylsulfonylamido, (xii) $C_{1-6}$ alkylsulfonylamido-$C_{1-3}$ alkyl and (xiii) N—$C_{1-3}$ alkyl-$C_{1-6}$ alkylsulfonamido; $R^c$ and $R^d$ are (i) independently in each occurrence $R^c$ and $R^d$ are (i) independently in each occurrence: (a) hydrogen, (b) Ar$^2$, (c) Ar$^2$—$C_{1-6}$ alkyl, (d) $C_{3-6}$ cycloalkyl optionally substituted $C_{1-3}$ dialkylamino or $C_{1-3}$ hydroxyalkyl, (e) $C_{1-6}$ alkyl-$C_{3-7}$ cycloalkyl, (f) $C_{1-3}$ alkoxy-$C_{1-3}$ alkyl, (g) pyridinyl or pyridinyl $C_{1-6}$ alkyl said pyridinyl optionally substituted with amino, $C_{1-3}$ alkylamino, $C_{1-3}$ dialkylamino, $C_{1-6}$ alkylsulfonylamido, sulfamoyl, $C_{1-3}$ alkylsulfamoyl, $C_{1-3}$ dialkylsulfamoyl, (h) thienyl optionally substituted with $C_{1-3}$ alkyl, (i) heterocyclyl or heterocyclyl $C_{1-6}$ alkyl wherein the heterocyclyl group is pyrrolidine or piperidine said heterocyclyl group is optionally substituted with $C_{1-3}$ alkyl or oxo, (j) $C_{1-3}$ alkylimidazol-4-yl, (k) $(CH_2)_{2-4}NR^gR^h$, or (ii) $R^c$ and $R^d$ together with the nitrogen to which they are attached are pyrrolidinyl or piperidinyl both of which are optionally substituted with $C_{1-3}$ alkyl, hydroxy or hydroxy-$C_{1-3}$ alkyl; Ar$^2$ is phenyl optionally substituted with one to three substituents independently selected from the group consisting of (a) $C_{1-3}$ alkyl (b) amino, (c) amino $C_{1-3}$ alkyl, (d) $C_{1-3}$ alkylamino, (e) $C_{1-3}$ alkylamino-$C_{1-3}$ alkyl, (f) $C_{1-3}$ dialkylamino, (g) $C_{1-3}$ alkylamino-$C_{1-3}$ alkyl, (h) $C_{1-3}$ alkylsulfonylamido, (i) $C_{1-3}$ alkylsulfonamido-$C_{1-3}$ alkyl, (j) N—$C_{1-3}$ alkyl-$C_{1-6}$ alkylsulfonamido and (k) $C_{1-3}$ hydroxyalkyl, (l) hydroxy and (m) OCH$_2$CONR$^g$R$^h$; Ar$^4$ is phenyl or pyridinyl both optionally substituted with one to three substituents independently selected in each occurrence from the group consisting of (a) amino, (b) $C_{1-6}$ alkylsulfonylamido, (c) sulfamoyl, (d) $C_{1-3}$ alkylsulfamoyl, (e) $C_{1-3}$ dialkylsulfamoyl, (f) $C_{1-6}$ alkylsulfonylamido-$C_{1-3}$ alkyl, (g) N—$C_{1-3}$ alkyl-$C_{1-6}$ alkylsulfonamido, (h) halogen, (i) $C_{1-3}$ alkyl, (j) $C_{1-3}$ alkoxy, (k) $C_{1-6}$ acylamino, (l) hydroxy, (m) halogen; (n) $(CH_2)_nCONR^aR^b$ and (o) —$O(CH_2)_nCONR^aR^b$; $R^7$ is hydrogen or $C_{1-3}$ alkyl; $R^3$ is hydrogen, $C_{1-6}$ alkyl, $C_{1-6}$ haloalkyl, $C_{1-6}$ alkoxy, $C_{1-6}$ haloalkoxy or halogen; $R^{4a}$, $R^{4b}$ and $R^{4c}$ (i) when taken independently are selected independently from $C_{1-3}$ alkyl, $C_{1-2}$ alkoxy or $C_{1-2}$ fluoroalkyl or (ii) when taken together, $R^{4a}$ and $R^{4b}$ together are C24 methylene and $R^{4c}$ is $C_{1-3}$ alkyl, $C_{1-2}$ alkoxy or $C_{1-2}$ fluoroalkyl; $R^5$ is hydrogen or fluorine; $R^6$ is halogen, $C_{1-6}$ alkyl, $C_{1-3}$ haloalkyl or $C_{1-3}$ alkoxy; m is zero to three; n is independently in each occurrence zero to two; or, pharmaceutically acceptable salts thereof.

In another embodiment of the present invention there is provided a compound according to formula I wherein: $R^1$ is hydrogen, $C_{1-6}$ alkyl, $C_{1-6}$ haloalkyl, halogen, hydroxy, $C_{1-6}$ alkoxy, $C_{1-6}$ haloalkoxy, cyano, $NR^aR^b$, carboxy, $C_{1-3}$ alkoxycarbonyl, carboxamido, amino $C_{1-3}$alkyl, $C_{1-3}$ acylamino $C_{1-3}$alkyl, $C_{1-6}$ hydroxyalkoxy, $R^2$ is selected from the group consisting of: (a) —$[C(R^8)_2]_p$—$Ar^1$ (b) —$[C(R^8)_2]_p$—$OAr^1$, (c) —$(CH_2)_mC(=O)X$, (d) —$NR^7C(=O)Ar^4$, (e) —$C_{1-6}$ alkyl, (f) —$C_{1-6}$ haloalkyl, (g) $C_{1-6}$ alkoxy, (h) $C_{1-6}$ haloalkoxy, (i) $C_{1-6}$alkyl, (j) $C_{1-6}$ hydroxyalkyl, (k) hydroxy, (l) halogen, (m) hydrogen, (o) phenylsulfonyl, (p) —$O(CH_2)_mAr^1$, (q) —$[C(R^8)_2]_p$—$NR^eR^f$, (r) (E)- or (Z) —$R^8C=CR^8Ar^1$— wherein $R^8$ is hydrogen, carboxyl, $C_{1-3}$ alkoxycarbonyl, carboxamido, $C_{1-3}$ hydroxyalkyl, $C_{1-3}$ alkyl or cyano and p is zero to four and (s) hydrogen; $Ar^1$ is phenyl, pyridinyl, pyrimidinyl, pyrazinyl or pyridazinyl optionally independently substituted with one to three substitutents selected from the group consisting of hydroxy, $C_{1-6}$ alkoxy, $C_{1-6}$ alkyl, $C_{1-6}$ hydroxyalkyl, halogen, cyano, $C_{1-6}$ alkoxycarbonyl], carboxyl, $C_{1-3}$ acylamino-$C_{1-6}$ alkyl, $(CH_2)_n NR^aR^b$, $(CH_2)_nCONR^aR^b$, —$O(CH_2)_nCONR^aR^b$ $X^2$ $(CH_2)_{2-6}NR^gR^h$, $C_{1-6}$ haloalkyl or carboxy; $R^a$ and $R^b$ are independently in hydrogen, $C_{1-6}$ alkyl, $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl, $C_{1-6}$ alkoxy-$C_{1-6}$ alkylsulfonyl, sulfamoyl $C_{1-3}$ alkylsulfamoyl, $C_{1-3}$ dialkylsulfamoyl $NHSO_2NMe_2$, carbamoyl, $C_{1-3}$ alkylcarbamoyl, $C_{1-3}$ dialkylcarbamoyl or benzoyl said benzoyl optionally independently substituted with one or two groups selected from the group consisting of amino, halogen, $C_{1-6}$ alkyl or $C_{1-3}$ alkylsulfonylamido; $R^e$ and $R^f$ when (i) taken independently are selected from hydrogen, $C_{1-3}$ alkyl, $C_{4-7}$ cycloalkyl or phenyl said cycloalkyl and said phenyl optionally independently substituted with one to three groups selected from $C_{1-3}$ alkylsulfonylamido, $C_{1-3}$ alkyl, $C_{1-3}$ alkoxy or halogen or (ii) when taken together along with the nitrogen to which they are attached are a pyrrolidine, a piperidine or an azepinyl ring optionally independently substituted with one to three groups selected from $C_{1-3}$ alkylsulfonylamido, $C_{1-3}$ alkyl, $C_{1-3}$ alkoxy or halogen; X is OH, $C_{1-6}$ alkoxy, $NR^cR^d$ or $Ar^3$; $Ar^3$ is phenyl, pyridinyl or thienyl each optionally substituted with one to three substitutents selected from the group consisting of: (i) halogen, (ii) hydroxy, (iii) $C_{1-3}$ hydroxyalkyl, (iv) amino, (v) amino-$C_{1-3}$ alkyl, (vi) $C_{1-3}$ alkylamino (vii) $C_{1-3}$ alkylamino-$C_{1-3}$ alkyl, (viii) $C_{1-3}$ dialkylamino, (ix) $C_{1-3}$ dialkylamino-$C_{1-3}$ alkyl, (x) carboxamido, (x) $C_{1-6}$ alkylsulfonylamido, (xi) $C_{1-6}$ alkylsulfonylamido-$C_{1-3}$ alkyl and (xii) N—$C_{1-3}$ alkyl-$C_{1-6}$ alkylsulfonamido; $R^c$ and $R^d$ are (i) independently in each occurrence $R^c$ and $R^d$ are (i) independently in each occurrence: (a) hydrogen, (b) $Ar^2$ (c) $Ar^2$—$C_{1-6}$ alkyl, (d) $C_{3-6}$ cycloalkyl optionally substituted $C_{1-3}$ dialkylamino or $C_{1-3}$ hydroxyalkyl, (e) $C_{1-6}$ alkyl-$C_{3-7}$ cycloalkyl, (f) $C_{1-3}$ alkoxy-$C_{1-3}$ alkyl, (g) pyridinyl or pyridinyl $C_{1-6}$ alkyl said pyridinyl optionally substituted with amino, $C_{1-3}$ alkylamino, $C_{1-3}$ dialkylamino, $C_{1-6}$ alkylsulfonylamido, sulfamoyl, $C_{1-3}$ alkylsulfamoyl, $C_{1-3}$ dialkylsulfamoyl, (h) thienyl optionally substituted with $C_{1-3}$ alkyl, (i) heterocyclyl or heterocyclyl $C_{1-6}$ alkyl wherein the heterocyclyl group is pyrrolidine or piperidine said heterocyclyl group is optionally substituted with $C_{1-3}$ alkyl or oxo, (j) $C_{1-3}$ alkyl-imidazol-4-yl, (k) $(CH_2)_{2-4}NR^gR^h$ or (ii) $R^c$ and $R^d$ together with the nitrogen to which they are attached are pyrrolidinyl or piperidinyl both of which are optionally substituted with $C_{1-3}$ alkyl, hydroxy or hydroxy-$C_{1-3}$ alkyl; $Ar^2$ is phenyl optionally substituted with one to three substituents independently selected from the group consisting of (a) $C_{1-3}$ alkyl (b) amino, (c) amino $C_{1-3}$ alkyl, (d) $C_{1-3}$ alkylamino, (e) $C_{1-3}$ alkylamino-$C_{1-3}$ alkyl, (f) $C_{1-3}$ dialkylamino, (g) $C_{1-3}$ alkylamino-$C_{1-3}$ alkyl, (h) $C_{1-3}$ alkylsulfonylamido, (i) $C_{1-3}$ alkylsulfonamido-$C_{1-3}$ alkyl, (j) N—$C_{1-3}$ alkyl-$C_{1-6}$ alkylsulfonamido and (k) $C_{1-3}$ hydroxyalkyl; $Ar^4$ is phenyl, pyridinyl, pyrazinyl, pyridazinyl or pyrimidinyl each optionally substituted with one to three substituents independently selected in each occurrence from the group consisting of (a) amino, (b) $C_{1-6}$ alkylsulfonylamido, (c) sulfamoyl, (d) $C_{1-3}$ alkylsulfamoyl, (e) $C_{1-3}$ dialkylsulfamoyl, (f) $C_{1-6}$ alkylsulfonylamido-$C_{1-3}$ alkyl, (g) N—$C_{1-3}$ alkyl-$C_{1-6}$ alkylsulfonamido, (h) halogen, (i) $C_{1-3}$ alkyl, (j) $C_{1-3}$ alkoxy, (k) $C_{1-6}$ acylamino, (l) hydroxy, (m) halogen; (n) $(CH_2)_nCONR^aR^b$ and (o) —$O(CH_2)_nCONR^aR^b$; $R^7$ is hydrogen or $C_{1-3}$ alkyl; $R^3$ is hydrogen, $C_{1-6}$ alkyl, $C_{1-6}$ haloalkyl, $C_{1-6}$ alkoxy, $C_{1-6}$ haloalkoxy, halogen or $R^3$ and $R^{4a}$ together are $CH_2$—O and together with atoms to which they are attached form a 2,3-dihydrobenzofuran; $R^{4a}$, $R^{4b}$ and $R^{4c}$ (i) when taken independently are selected independently from $C_{1-3}$ alkyl, $C_{1-2}$ alkoxy, $C_{1-2}$ fluoroalkyl or hydroxy or (ii) when taken together, $R^{4a}$ and $R^{4b}$ together are $C_{2-4}$ methylene and $R^{4c}$ is $C_{1-3}$ alkyl, $C_{1-2}$ alkoxy, halogen or $C_{1-2}$ fluoroalkyl or (iii) either $R^5$ or $R^3$ and $R^{4a}$ together are $CH_2$—O and together with atoms to which they are attached for a 2,3-dihydro-benzofuran and $R^{4b}$ and $R^{4c}$ are $C_{1-3}$ alkyl; $R^5$ is hydrogen, fluorine or $R^5$ and $R^{4a}$ together are $CH_2$—O and together with atoms to which they are attached form a 2,3-dihydrobenzofuran; $R^6$ is halogen, $C_{1-6}$ alkyl wherein one or two non-adjacent carbon atoms optionally can be replaced by oxygen, $C_{1-3}$ haloalkyl, $C_{1-3}$ alkoxy, $C_{1-6}$ hydroxyalkyl; m is zero to three; n is independently in each occurrence zero to two; or, pharmaceutically acceptable salts thereof.

In still another embodiment of the present invention there is provided a compound according to formula I wherein $R^1$ is hydrogen, $C_{1-6}$ alkyl, $C_{1-6}$ haloalkyl, halogen, hydroxy, $C_{1-6}$ alkoxy, $C_{1-6}$ haloalkoxy, cyano, $NR^aR^b$, carboxy, $C_{1-3}$ alkoxycarbonyl, carboxamido, amino $C_{1-3}$alkyl, $C_{1-3}$ acylamino $C_{1-3}$alkyl, $C_{1-6}$ hydroxyalkoxy; $R^2$ is selected from the group consisting of: (a) —$[C(R^8)_2]_p$—$Ar^1$ (b) —$[C(R^8)_2]_p$—$OAr^1$, (c) —$(CH_2)_mC(=O)X$, (d) —$NR^7C(=O)Ar^4$, (e) —$C_{1-6}$ alkyl, (f) —$C_{1-6}$ haloalkyl, (g) $C_{1-6}$ alkoxy, (h) $C_{1-6}$ haloalkoxy, (i) $C_{1-6}$ alkyl, (j) $C_{1-6}$ hydroxyalkyl, (k) hydroxy, (l) halogen, (m) hydrogen, (o) phenylsulfonyl, (p) —$O(CH_2)_mAr^1$, (q) —$[C(R^8)_2]_p$—$NR^eR^f$, (r) (E)- or (Z) —$R^{10}C=CR^{10}Ar^1$—, (s) hydrogen, (t) —$C\equiv CAr^1$ wherein $R^8$ is hydrogen, carboxyl, $C_{1-3}$ alkoxycarbonyl, carboxamido, $C_{1-3}$ hydroxyalkyl, $C_{1-3}$ alkyl, —$(CH_2)_rNR^gR^h$ or cyano, $R^{10}$ is independently in each occurrence hydrogen, $C_{1-6}$ alkyl, $C_{1-6}$ hydroxyalkyl, cyano, $C_{1-3}$ alkoxycarbonyl, carboxamido, or $C_{1-3}$alkoxy-$C_{1-6}$alkyl, p is zero to four, r is 1 to 3, and $R^g$ and $R^h$ are independently hydrogen or $C_{1-6}$ alkyl or $R^g$ and $R^h$ together with the nitrogen to which they are attached are an optionally substituted cyclic amine; $Ar^1$ is phenyl, naphthyl, pyridinyl, pyrimidinyl, pyrazinyl, pyridazinyl quinolinyl optionally independently substituted with one to three substituents selected from the group consisting of (a) hydroxy, (b) $C_{1-6}$ alkoxy, (c) $C_{1-6}$ alkyl, (d) $C_{1-10}$ hydroxyalkyl wherein one or two carbon atoms optionally can be replaced by oxygen provided the replacement does not form a oxygen-oxygen bond, (e) $C_{1-3}$ alkoxy-$C_{1-6}$ alkyl, (f) halogen, (g) cyano, (h) $C_{1-6}$ alkoxycarbonyl, (i) $C_{1-6}$ alkylsulfonyl, (j) carboxyl, (k) $C_{1-3}$ acylamino-$C_{1-6}$ alkyl, (l) $(CH_2)_nNR^aR^b$, (m) $(CH_2)_nCONR^aR^b$ and (n) —$O(CH_2)_nCONR^aR^b$; $R^a$ and $R^b$ are (i) independently in each occurrence (a) hydrogen, (b) $C_{1-6}$ alkyl, (c) $C_{1-3}$ haloalkyl, (d) $C_{1-6}$ acyl, (e) $C_{1-6}$ alkylsulfonyl, (f) $C_{1-6}$ haloalkylsulfonyl, (g) $C_{3-7}$ cycloalkylsulfonyl, (h) $C_{3-7}$ cycloalkyl-$C_{1-3}$ alkyl-sulfonyl, (i) $C_{1-6}$ alkoxy-$C_{1-6}$ alkylsulfonyl, (j) $(CH_2)_{1-3}NR^gR^h$, (k) $SO_2(CH_2)_{1-6}NR^gR^h$ wherein $R^g$ and $R^h$ are as defined above, (l) sulfamoyl $C_{1-3}$ alkylsulfamoyl, (m) $C_{1-3}$ dialkylsulfamoyl, (n) carbamoyl, (o) $C_{1-3}$ alkylcarbamoyl, (p) $C_{1-3}$ dialkylcarbamoyl, or (q) benzoyl said benzoyl optionally independently substituted with one or two groups selected from the group consisting of amino, halogen, $C_{1-6}$ alkyl or $C_{1-3}$ alkylsulfonylamido; or (ii) $R^a$ and $R^b$ taken together with the nitrogen to which they are attached are (a) an optionally substituted cyclic amine (b) $(CH_2)_{2-3}OC(O)$ or (c) 2-oxo-oxazolidine; $R^e$ and $R^f$ when (i) taken independently are selected from (a) hydrogen, (b) $C_{1-3}$ alkyl, (c) $C_{4-7}$ cycloalkyl or (d) phenyl said cycloalkyl and said phenyl optionally independently substituted with one to three groups selected from $C_{1-3}$ alkylsulfonylamido, $C_{1-3}$ alkyl, $C_{1-3}$ alkoxy or halogen or (ii) when taken together along with the nitrogen to which they are attached are a cyclic amine independently substituted with one to three groups selected from $C_{1-3}$ alkylsulfonylamido, $C_{1-3}$ alkyl, $C_{1-3}$ alkoxy or halogen; X is OH, $C_{1-6}$ alkoxy, $NR^cR^d$ or $Ar^3$; $Ar^3$ is phenyl optionally substituted with one to three substituents selected from the group consisting of: (a) halogen, (b) hydroxy, (c) $C_{1-3}$ hydroxyalkyl, (d) amino, (e) amino-$C_{1-3}$ alkyl, (f) $C_{1-3}$ alkylamino (g) $C_{1-3}$ alkylamino-$C_{1-3}$ alkyl, (h) $C_{1-3}$ dialkylamino, (i) $C_{1-3}$ dialkylamino-$C_{1-3}$ alkyl, (j) carboxamido, (k) $C_{1-6}$ alkylsulfonylamido, (l) $C_{1-6}$ alkylsulfonylamido-$C_{1-3}$ alkyl, (m) $NR^7$—$C_{1-3}$ alkyl-$C_{1-6}$ alkylsulfonamido, (n) $C_{1-6}$ alkyl, (o) $C_{1-6}$ alkoxycarbonyl and (p) carboxyl; $R^c$ and $R^d$ are (i) independently in each occurrence $R^c$ and $R^d$ are (i) independently in each occurrence: (a) hydrogen, (b) $Ar^2$, (c) $Ar^2$—$C_{1-6}$ alkyl, (d) $C_{3-6}$ cycloalkyl optionally substituted $C_{1-3}$ dialkylamino, $C_{1-6}$ alkylsulfonamido or $C_{1-3}$ hydroxyalkyl, (e) $C_{1-6}$ alkyl-$C_{3-7}$ cycloalkyl, (f) $C_{1-3}$ alkoxy-$C_{1-3}$ alkyl, (g) pyridinyl or pyridinyl $C_{1-6}$ alkyl said pyridinyl optionally substituted with amino, $C_{1-3}$ alkylamino, $C_{1-3}$ dialkylamino, $C_{1-6}$ alkylsulfonylamido, sulfamoyl, $C_{1-3}$ alkylsulfamoyl, $C_{1-3}$ dialkylsulfamoyl, (h) thienyl optionally substituted with $C_{1-3}$ alkyl, (i) heterocyclyl or heterocyclyl $C_{1-6}$ alkyl wherein the heterocyclyl group is pyrrolidine or piperidine said heterocyclyl group is optionally substituted with $C_{1-3}$ alkyl or oxo; or (ii) $R^c$ and $R^d$ together with the nitrogen to which they are attached are pyrrolidinyl or piperidinyl both of which are optionally substituted with $C_{1-3}$ alkyl, hydroxy or hydroxy-$C_{1-3}$ alkyl; $Ar^2$ is phenyl optionally substituted with one to three substituents independently selected from the group consisting of (a) $C_{1-3}$ alkyl (b) amino, (c) amino $C_{1-3}$ alkyl, (d) $C_{1-3}$ alkylamino, (e) $C_{1-3}$ alkylamino-$C_{1-3}$ alkyl, (f) $C_{1-3}$ dialkylamino, (g) $C_{1-3}$ alkylamino-$C_{1-3}$ alkyl, (h) $C_{1-3}$ alkylsulfonylamido, (i) $C_{1-3}$ alkylsulfonamido-$C_{1-3}$ alkyl, (j) N—$C_{1-3}$ alkyl-$C_{1-6}$ alkylsulfonamido, (k) $C_{1-3}$ hydroxyalkyl, and (l) hydroxy; $Ar^4$ is phenyl, pyridinyl, pyrazinyl, pyridazinyl or pyrimidinyl each optionally substituted with one to three substituents independently selected in each occurrence from the group consisting of (a) amino, (b) $C_{1-3}$ alkylamino, (c) di-$C_{1-3}$ alkylamino, (d) $C_{1-3}$ haloalkylamino, (e) $C_{1-6}$ alkylsulfonylamido, (f) sulfamoyl, (g) $C_{1-3}$ alkylsulfamoyl, (h) $C_{1-3}$ dialkylsulfamoyl, (i) $C_{1-6}$ alkylsulfonylamido-$C_{1-3}$ alkyl, (j) $NR^7$—$C_{1-3}$ alkyl-$C_{1-6}$ alkylsulfonamido, (k) halogen, (l) $C_{1-3}$ alkyl, (m) $C_{1-3}$ alkoxy, (n) $C_{1-6}$ acylamino, (o) hydroxy, (p) halogen; (q) $(CH_2)$ $CONR^aR^b$, (r) —O $(CH_2)_nCONR^aR^b$, (s) —$O(CH_2)_nNR^iR^j$ wherein $R^i$ and $R^j$ are independently hydrogen or $C_{1-3}$ alkyl, (t) —$NR^i(CH_2)_nOR^j$, (u) $C_{1-3}$-haloalkyl, (v) $C_{1-3}$ alkoxy-$C_{1-6}$ alkoxy, (w) $C_{3-6}$ cycloalkylamine; $R^7$ is independently in each occurrence hydrogen or $C_{1-3}$ alkyl; $R^3$ is hydrogen, $C_{1-6}$ alkyl, $C_{1-6}$ haloalkyl, $C_{1-6}$ alkoxy, $C_{1-6}$ haloalkoxy, $C_{1-3}$ alkoxy-$C_{1-6}$ alkoxy, halogen or $R^3$ and $R^{4a}$ together are $CH_2$—O and together with atoms to which they are attached form a 2,3-dihydrobenzofuran or an indane; $R^{4a}$, $R^{4b}$ and $R^{4c}$ (a) when taken independently are each selected independently from (i) $C_{1-3}$ alkyl, (ii) $C_{1-2}$ alkoxy, (iii) $C_{1-2}$ fluoroalkyl, (iv) $C_{1-3}$ hydroxyalkyl or (v) hydroxy or (b) when taken together, (i) $R^{4a}$ and $R^{4b}$ together are $C_{2-4}$ methylene and $R^{4c}$ is $C_{1-3}$ alkyl, $C_{1-2}$ alkoxy, halogen, cyano or $C_{1-2}$ fluoroalkyl or (ii) $R^{4a}$ and $R^{4b}$ together with the carbon to which they are attached are 3-oxetanyl $R^{4c}$ is hydrogen, $C_{1-3}$ alkyl, or (c) either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl; $R^5$ is hydrogen, fluorine or $R^5$ and $R^{4a}$ together are $CH_2$—O and together with atoms to which they are attached form a 2,3-dihydrobenzofuran or an indane; $R^6$ is (a) halogen, (b) $C_{1-6}$ alkyl wherein one or two non-adjacent carbon atoms optionally can be replaced by oxygen, (c) $C_{1-3}$ haloalkyl, (d) $C_{1-3}$ alkoxy, (e) $C_{1-6}$ hydroxyalkyl wherein one or two non-adjacent carbon atoms optionally can be replaced by oxygen or (f) cyano-$C_{1-3}$ alkyl; $R^9$ is hydrogen, $CH_2OH$, $CH_2OR^{9a}$ wherein $R^{9a}$ is $(CH_2)_sCO_2H$ wherein s is one to four, $C(O)CHR^{9b}NHR^{9c}$ wherein $R^{9b}$ is hydrogen, methyl, iso-propyl, iso-butyl, sec-butyl, phenyl or 4-hydroxy-phenyl and $R^{9c}$ is hydrogen or $C_{1-6}$ alkoxycarbonyl; m is zero to three; and n is independently in each occurrence zero to two.

In yet another embodiment of the present invention there is provided a compound according to formula I wherein $R^1$ is hydrogen, $C_{1-6}$ alkyl, $C_{1-6}$ haloalkyl, halogen, hydroxy, $C_{1-6}$ alkoxy, $C_{1-6}$ haloalkoxy, cyano, $NR^aR^b$, carboxy, $C_{1-3}$ alkoxycarbonyl, carboxamido, amino $C_{1-3}$alkyl, $C_{1-3}$ acylamino $C_{1-3}$alkyl, $C_{1-6}$ hydroxyalkoxy. $R^2$ is selected from the group consisting of: (a) —$[C(R^8)_2]_p$—$Ar^1$ (b) —$[C(R^8)_2]_p$—$OAr^1$, (c) —$(CH_2)_mC(=O)X$, (d) —$NR^7C(=O)Ar^4$, (e) —$C_{1-6}$ alkyl, (f) —$C_{1-6}$ haloalkyl, (g) $C_{1-6}$ alkoxy, (h) $C_{1-6}$ haloalkoxy, (i) $C_{1-6}$ alkyl, (j) $C_{1-6}$ hydroxyalkyl, (k) hydroxy, (l) halogen, (m) hydrogen, (o) phenoxy, (p) —$O(CH_2)_mAr^1$, (q) —$[C(R^8)_2]_p$—$NR^eR^f$, (r) (E)- or (Z) —$R^{10}C$=$CR^{10}Ar^1$—, (s) hydrogen, (t) —$C\equiv CAr^1$ wherein $R^8$ is hydrogen, carboxyl, $C_{1-3}$ alkoxycarbonyl, carboxamido, $C_{1-3}$ hydroxyalkyl, $C_{1-3}$ alkyl, —$(CH_2)_rNR^gR^h$ or cyano, $R^{10}$ is independently in each occurrence hydrogen, $C_{1-6}$ alkyl, $C_{1-6}$ hydroxyalkyl, cyano, $C_{1-3}$ alkoxycarbonyl, carboxamido, or $C_{1-3}$alkoxy-$C_{1-6}$alkyl, p is zero to four, r is 1 to 3, and $R^g$ and $R^h$ are independently hydrogen or $C_{1-6}$ alkyl or $R^g$ and $R^h$ together with the nitrogen to which they are attached are an optionally substituted cyclic amine. $Ar^1$ is $Ar^1$ is phenyl, naphthyl, pyridinyl, pyrimidinyl, pyrazinyl, pyridazinyl or quinolinyl each optionally independently substituted with one to three substituents selected from the group consisting of (a) hydroxy, (b) $C_{1-6}$ alkoxy, (c) $C_{1-6}$ alkyl, (d) $C_{1-10}$ hydroxyalkyl wherein one or two carbon atoms optionally can be replaced by oxygen provided the replacement does not form a oxygen-oxygen, (e) $C_{1-3}$ alkoxy-$C_{1-6}$ alkyl, (f) halogen, (g) cyano, (h) $C_{1-6}$ alkoxycarbonyl, (i) $C_{1-6}$ alkylsulfonyl, (j) carboxyl, (k) $C_{1-3}$ acylamino-$C_{1-6}$ alkyl, (l) $(CH_2)NR^aR^b$, (m) $(CH_2)_nCONR^aR^b$ and (n) —$O(CH_2)_nCONR^aR^b$.

$R^a$ and $R^b$ are (i) independently in each occurrence (a) hydrogen, (b) $C_{1-6}$ alkyl, (c) $C_{1-3}$ haloalkyl, (d) $C_{1-6}$ acyl, (e) $C_{1-6}$ alkylsulfonyl, (f) $C_{1-6}$ haloalkylsulfonyl, (g) $C_{3-7}$ cycloalkylsulfonyl, (h) $C_{3-7}$ cycloalkyl-$C_{1-3}$ alkyl-sulfonyl, (i) $C_{1-6}$ alkoxy-$C_{1-6}$ alkylsulfonyl, (j) $(CH_2)_{1-3}NR^gR^h$, (k) $SO_2$ $(CH_2)_{1-6}NR^gR^h$ wherein $R^g$ and $R^h$ are as defined above, (l) sulfamoyl $C_{1-3}$ alkylsulfamoyl, (m) $C_{1-3}$ dialkylsulfamoyl, (n) carbamoyl, (o) $C_{1-3}$ alkylcarbamoyl, (p) $C_{1-3}$ dialkylcarbamoyl, or (q) benzoyl said benzoyl optionally independently substituted with one or two groups selected from the group consisting of amino, halogen, $C_{1-6}$ alkyl or $C_{1-3}$ alkylsulfonylamido; or (ii) $R^a$ and $R^b$ taken together with the nitrogen to which they are attached are (a) an optionally substituted cyclic amine (b) $(CH_2)_{2-3}OC(O)$ or (c) 2-oxo-oxazolidine. $R^e$ and $R^f$ when (i) taken independently are selected from (a) hydrogen, (b) $C_{1-3}$ alkyl, (c) $C_{4-7}$ cycloalkyl or (d) phenyl said cycloalkyl and said phenyl optionally independently substituted with one to three groups selected from $C_{1-3}$ alkylsulfonylamido, $C_{1-3}$ alkyl, $C_{1-3}$ alkoxy or halogen or (ii) when taken together along with the nitrogen to which they are attached are a cyclic amine independently substituted with one to three groups selected from $C_{1-3}$ alkylsulfonylamido, $C_{1-3}$ alkyl, $C_{1-3}$ alkoxy or halogen. X is OH, $C_{1-6}$ alkoxy, $NR^cR^d$ or $Ar^3$. $Ar^3$ is phenyl optionally substituted with one to three substitutents selected from the group consisting of: (a) halogen, (b) hydroxy, (c) $C_{1-3}$ hydroxyalkyl, (d) amino, (e) amino-$C_{1-3}$ alkyl, (f) $C_{1-3}$ alkylamino (g) $C_{1-3}$ alkylamino-$C_{1-3}$ alkyl, (h) $C_{1-3}$ dialkylamino, (i) $C_{1-3}$ dialkylamino-$C_{1-3}$ alkyl, (j) carboxamido, (k) $C_{1-6}$ alkylsulfonylamido, (l) $C_{1-6}$ alkylsulfonylamido-$C_{1-3}$ alkyl, (m) $NR^7$—$C_{1-3}$ alkyl-$C_{1-6}$ alkylsulfonamido, (n) $C_{1-6}$ alkyl, (o) $C_{1-6}$ alkoxycarbonyl and (p) carboxyl. $R^c$ and $R^d$ are (i) independently in each occurrence $R^c$ and $R^d$ are (i) independently in each occurrence: (a) hydrogen, (b) $Ar^2$, (c) $Ar^2$—$C_{1-6}$ alkyl, (d) $C_{3-6}$ cycloalkyl optionally substituted $C_{1-3}$ dialkylamino, $C_{1-6}$ alkylsulfonamido or $C_{1-3}$ hydroxyalkyl, (e) $C_{1-6}$ alkyl-$C_{3-7}$ cycloalkyl, (f) $C_{1-3}$ alkoxy-$C_{1-3}$ alkyl, (g) pyridinyl or pyridinyl $C_{1-6}$ alkyl said pyridinyl optionally substituted with amino, $C_{1-3}$ alkylamino, $C_{1-3}$ dialkylamino, $C_{1-6}$ alkylsulfonylamido, sulfamoyl, $C_{1-3}$ alkylsulfamoyl, $C_{1-3}$ dialkylsulfamoyl, (h) thienyl optionally substituted with $C_{1-3}$ alkyl, (i) heterocyclyl or heterocyclyl $C_{1-6}$ alkyl wherein the heterocyclyl group is pyrrolidine or piperidine said heterocyclyl group is optionally substituted with $C_{1-3}$ alkyl or oxo; or (ii) $R^c$ and $R^d$ together with the nitrogen to which they are attached are pyrrolidinyl or piperidinyl both of which are optionally substituted with $C_{1-3}$ alkyl, hydroxy or hydroxy-$C_{1-3}$ alkyl. $Ar^2$ is phenyl optionally substituted with one to three substituents independently selected from the group consisting of (a) $C_{1-3}$ alkyl (b) amino, (c) amino $C_{1-3}$ alkyl, (d) $C_{1-3}$ alkylamino, (e) $C_{1-3}$ alkylamino-$C_{1-3}$ alkyl, (f) $C_{1-3}$ dialkylamino, (g) $C_{1-3}$ alkylamino-$C_{1-3}$ alkyl, (h) $C_{1-3}$ alkylsulfonylamido, (i) $C_{1-3}$ alkylsulfonamido-$C_{1-3}$ alkyl, (j) N—$C_{1-3}$ alkyl-$C_{1-6}$ alkylsulfonamido, (k) $C_{1-3}$ hydroxyalkyl, and (l) hydroxy. $Ar^4$ is phenyl, pyridinyl, pyrazinyl, pyridazinyl or pyrimidinyl each optionally substituted with one to three substituents independently selected in each occurrence from the group consisting of (a) amino, (b) $C_{1-3}$ alkylamino, (c) di-$C_{1-3}$ alkylamino, (d) $C_{1-3}$ haloalkylamino, (e) $C_{1-6}$ alkylsulfonylamido, (f) sulfamoyl, (g) $C_{1-3}$ alkylsulfamoyl, (h) $C_{1-3}$ dialkylsulfamoyl, (i) $C_{1-6}$ alkylsulfonylamido-$C_{1-3}$ alkyl, (j) $NR^7$—$C_{1-3}$ alkyl-$C_{1-6}$ alkylsulfonamido, (k) halogen, (l) $C_{1-3}$ alkyl, (m) $C_{1-3}$ alkoxy, (n) $C_{1-6}$ acylamino, (o) hydroxy, (p) halogen; (q) $(CH_2)_nCONR^aR^b$, (r) —$O(CH_2)_nCONR^aR^b$, (s) —$O(CH_2)_nNR^iR^j$ wherein $R^i$ and $R^j$ are independently hydrogen or $C_{1-3}$ alkyl, (t) —$NR^i$ $(CH_2)_nOR^j$, (u) $C_{1-3}$-haloalkyl, (v) $C_{1-3}$ alkoxy-$C_{1-6}$ alkoxy, (w) $C_{3-6}$ cycloalkylamine. $R^7$ is independently in each occurrence hydrogen or $C_{1-3}$ alkyl. $R^3$ is hydrogen, $C_{1-6}$ alkyl, $C_{1-6}$ haloalkyl, $C_{1-6}$ alkoxy, $C_{1-6}$ haloalkoxy, $C_{1-3}$ alkoxy-$C_{1-6}$ alkoxy, halogen or $R^3$ and $R^{4a}$ together are $CH_2$—O and together with atoms to which they are attached form a 2,3-dihydrobenzofuran or an indane. $R^{4a}$, $R^{4b}$ and $R^{4c}$ (a) when taken independently are each selected independently from (i) $C_{1-3}$ alkyl, (ii) $C_{1-2}$ alkoxy, (iii) $C_{1-2}$ fluoroalkyl, (iv) $C_{1-3}$ hydroxyalkyl (v) hydroxy (vi) cyano or (vii) halogen or (b) when taken together, (i) $R^{4a}$ and $R^{4b}$ together are $C_{2-4}$ methylene and $R^{4c}$ is $C_{1-3}$ alkyl, $C_{1-2}$ alkoxy, halogen, cyano or $C_{1-2}$ fluoroalkyl or (ii) $R^{4a}$ and $R^{4b}$ together with the carbon to which they are attached are 3-oxetanyl $R^{4c}$ is hydrogen, $C_{1-3}$ alkyl, or (c) either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl or (d) $R^{4a}$, $R^{4b}$, $R^{4c}$ together with the carbon to which they are attached are cyclopropyl, trifluoromethyl or 2,2,2-trifluoroethyl. $R^5$ is hydrogen, fluorine or $R^5$ and $R^{4a}$ together are $CH_2$—O and together with atoms to which they are attached form a 2,3-dihydrobenzofuran or an indane. $R^6$ is (a) halogen, (b) $C_{1-6}$ alkyl wherein one or two non-adjacent carbon atoms optionally can be replaced by oxygen, (c) $C_{1-3}$ haloalkyl, (d) $C_{1-3}$ alkoxy, (e) carboxyl, (f) $C_{1-6}$ hydroxyalkyl wherein one or two non-adjacent carbon atoms optionally can be replaced by oxygen, or (f) cyano-$C_{1-3}$ alkyl. $R^9$ is hydrogen, $CH_2OH$, $CHMeOH$, $CH_2OR^{9a}$ or $CHMeOR^{9a}$ wherein $R^{9a}$ is (a) $CO(CH_2)_sCO_2H$ wherein s is one to four, (b) $C(O)$ $CHR^{9b}NHR^{9c}$ wherein $R^{9b}$ is hydrogen, methyl, iso-propyl, iso-butyl, sec-butyl, phenyl or 4-hydroxy-phenyl and $R^{9c}$ is hydrogen or $C_{1-6}$ alkoxycarbonyl or $R^{9b}$ and $R^{9c}$ together are $(CH_2)_3$; (c) $P(O)(OH)_2$. m is zero to three and n is independently in each occurrence zero to two. This embodiment further includes pharmaceutically acceptable salts of the compounds therein.

In a second embodiment of the present invention there is provided a compound according to formula I wherein $R^2$ is —$[C(R^8)_2]_p$—$Ar^1$, $Ar^1$ phenyl, pyridinyl, pyrimidinyl, pyrazinyl, pyridazinyl; p is 2; $R^3$ is hydrogen or $C_{1-6}$ alkoxy; and, $R^9$ is hydrogen.

In a third embodiment of the present invention there is provided a compound according to formula I wherein $R^2$ is —$[C(R^8)_2]_p$—$Ar^1$, $Ar^1$ phenyl, pyridinyl, pyrimidinyl, pyrazinyl, pyridazinyl; p is 2; $R^3$ is hydrogen or $C_{1-6}$ alkoxy; $R^8$ and $R^9$ are hydrogen.

In a fourth embodiment of the present invention there is provided a compound according to formula I wherein $R^1$ is hydrogen or hydroxy, $R^2$ is —$[C(R^8)_2]_p$—$Ar^1$, $Ar^1$ phenyl, pyridinyl, pyrimidinyl, pyrazinyl, pyridazinyl; p is 2; $R^3$ is hydrogen or methoxy; $R^6$ is halogen, $C_{1-6}$ alkyl or $C_{1-6}$ alkoxy; and, $R^5$, $R^8$ and $R^9$ are hydrogen.

In a sixth embodiment of the present invention there is provided a compound according to formula I wherein $R^1$ is hydrogen or hydroxy, $R^2$ is —$[C(R^8)_2]_p$—$Ar^1$, $Ar^1$ phenyl, pyridinyl, pyrimidinyl, pyrazinyl, pyridazinyl; p is 2; $R^3$ is hydrogen or methoxy; $R^{4a}$, $R^{4b}$ and $R^{4c}$ are methyl; $R^5$ is hydrogen; $R^6$ is hydrogen, halogen, $C_{1-6}$ alkyl or $C_{1-6}$ alkoxy and, $R^5$, $R^8$ and $R^9$ are hydrogen.

In a sixth embodiment of the present invention there is provided a compound according to formula I wherein $R^1$ is hydrogen or hydroxy, $R^5$, $R^8$ and $R^9$ are hydrogen, $R^2$ is —$[C(R^8)_2]_p$—$Ar^1$, $Ar^1$ is phenyl or pyridinyl substituted at least by $(CH_2)_nNR^aR^b$, n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; p is 2, $R^3$ is hydrogen or methoxy, either $R^{4a}$, $R^{4b}$ and $R^{4c}$ are methyl, $R^6$ is halogen, $C_{1-6}$ alkyl or $C_{1-6}$ alkoxy. To avoid any ambiguity and the phrase "substituted at least by $(CH_2)_n NR^a R^{b''}$ as used in reference to the compounds herein means that the aryl or heteroaryl ring is substituted by an amine (n=0) or an aminoalkyl group (n>0). Other unsubstituted positions on the aryl or heteroaryl ring are optionally substituted with other groups with the scope of the claims.

In a seventh embodiment of the present invention there is provided a compound according to formula I wherein $R^1$, is hydrogen or hydroxy, $R^5$, $R^8$ and $R^9$ are hydrogen, $R^2$ is $-[C(R^8)_2]_p-Ar^1$, $Ar^1$ is optionally substituted 4-methanesulfonylamino-phenyl, 5-methansulfonylamino-pyridin-2-yl or 2-methansulfonylamino-pyridin-5-yl; p is 2, $R^3$ is hydrogen or methoxy, either $R^{4a}$, $R^{4b}$ and $R^{4c}$ are methyl, $R^6$ is hydrogen, halogen, $C_{1-6}$ alkyl or $C_{1-6}$ alkoxy.

In a eighth embodiment of the present invention there is provided a compound according to formula I wherein $R^1$ is hydrogen or hydroxy, $R^2$ is $-[C(R^8)_2]_p-Ar^1$, $Ar^1$ phenyl, pyridinyl, pyrimidinyl, pyrazinyl, pyridazinyl; p is 2; $R^3$ is hydrogen or methoxy; $R^6$ is halogen, $C_{1-6}$ alkyl or $C_{1-6}$ alkoxy and, $R^5$, $R^8$ and $R^9$ are hydrogen; (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methyl ene and $R^{4c}$ is $C_{1-3}$ alkyl, $C_{1-2}$ alkoxy, halogen, cyano or $C_{1-2}$ fluoroalkyl or (c) $R^{4a}$ and $R^{4b}$ together with the carbon to which they are attached are 3-oxetanyl and $R^{4c}$ is hydrogen or $C_{1-3}$ alkyl, or (c) either (i) $R^5$ and $R^{4a}$ or (ii) $R^3$ and $R^{4a}$ together are $CH_2-O$ or $(CH_2)_2$ and with atoms to which they are attached for a 2,3-dihydro-benzofuran or an indane and $R^{4b}$ and $R^{4c}$ are $C_{1-3}$ alkyl and, $R^8$ and $R^9$ is hydrogen.

In a ninth embodiment of the present invention there is provided a compound according to formula I wherein $R^1$ is hydrogen or hydroxy, $R^2$ is $-[C(R^8)_2]_p-Ar^1$, $Ar^1$ is phenyl or pyridinyl substituted at least with $(CH_2)_n NR^a R^b$ wherein n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; p is 2; $R^3$ is hydrogen or methoxy; $R^6$ is halogen, $C_{1-6}$ alkyl or $C_{1-6}$ alkoxy and, $R^5$, $R^8$ and $R^9$ are hydrogen; (a) $R^{4a}$ and $R^{4b}$ are $C_{1-3}$ alkyl and $R^{4c}$ is from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) $R^{4a}$ and $R^{4b}$ together with the carbon to which they are attached are 3-oxetanyl and $R^{4c}$ is hydrogen or $C_{1-3}$ alkyl, or (c) either (i) $R^5$ and $R^{4a}$ or (ii) $R^3$ and $R^{4a}$ together are $CH_2-O$ or $(CH_2)_2$ and with atoms to which they are attached for a 2,3-dihydro-benzofuran or an indane and $R^{4b}$ and $R^{4c}$ are $C_{1-3}$ alkyl and, $R^8$ and $R^9$ is hydrogen.

In a tenth embodiment of the present invention there is provided a compound according to formula I wherein $R^1$ is hydrogen or hydroxy, $R^2$ is $-[C(R)_2]_p-Ar^1$, $Ar^1$ is optionally substituted 4-methanesulfonylamino-phenyl, 5-methansulfonylamino-pyridin-2-yl or 2-methansulfonylamino-pyridin-5-yl; p is 2; $R^3$ is hydrogen or methoxy; $R^6$ is halogen, $C_{1-6}$ alkyl or $C_{1-6}$ alkoxy and, $R^5$, $R^8$ and $R^9$ are hydrogen; (a) $R^{4a}$ and $R^{4b}$ are $C_{1-3}$ alkyl and $R^{4c}$ is from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) $R^{4a}$ and $R^{4b}$ together with the carbon to which they are attached are 3-oxetanyl and $R^{4c}$ is hydrogen or $C_{1-3}$ alkyl, or (c) either (i) $R^5$ and $R^{4a}$ or (ii) $R^3$ and $R^{4a}$ together are $CH_2-O$ or $(CH_2)_2$ and with atoms to which they are attached for a 2,3-dihydro-benzofuran or an indane and $R^{4b}$ and $R^{4c}$ are $C_{1-3}$ alkyl and, $R^8$ and $R^9$ is hydrogen.

In a eleventh embodiment of the present invention there is provided a compound according to formula I wherein $R^2$ is $-[C(R^8)_2]_p-Ar^1$, $Ar^1$ is naphthyl or quinolinyl substituted at least with $(CH_2)_n NR^a R^b$ wherein n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; p is 0; $R^3$ is hydrogen or $C_{1-6}$ alkoxy.

In a twelfth embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; p is 2; $R^3$ is hydrogen or $C_{1-6}$ alkoxy; and, $R^9$ is hydrogen.

In a thirteenth embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; $R^{10}$ is hydrogen; $R^3$ is hydrogen or $C_{1-6}$ alkoxy; and, $R^9$ is hydrogen.

In a fourteenth embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; $R^{10}$ is hydrogen; $R^3$ is hydrogen or methoxy; $R^6$ is halogen, $C_{1-6}$ alkyl or $C_{1-6}$ alkoxy; and, $R^1$, $R^5$, $R^8$ and $R^9$ are hydrogen.

In a fifteenth embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; $R^{10}$ is hydrogen; $R^3$ is hydrogen or methoxy; $R^{4a}$, $R^{4b}$ and $R^{4c}$ are methyl; $R^6$ is halogen, $C_{1-6}$ alkyl or $C_{1-6}$ alkoxy; and, $R^1$, $R^5$, $R^8$ and $R^9$ are hydrogen.

In a sixteenth embodiment of the present invention there is provided a compound according to formula I wherein $R^2$ is (E) $R^{10}C=CR^{10}Ar^1$; $Ar^1$ is phenyl or pyridinyl substituted at least by $(CH_2)_n NR^a R^b$, n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^3$ is hydrogen or methoxy, either $R^{4a}$, $R^{4b}$ and $R^{4c}$ are methyl, $R^6$ is halogen, $C_{1-6}$ alkyl or $C_{1-6}$ alkoxy; $R^1$, $R^5$, $R^8$ and $R^9$ are hydrogen.

In a seventeenth embodiment of the present invention there is provided a compound according to formula I wherein $R^2$ is (E) $R^{10}C=CR^{10}Ar^1$; $Ar^1$ is optionally substituted 4-methanesulfonylamino-phenyl, 5-methansulfonylamino-pyridin-2-yl or 2-methansulfonylamino-pyridin-5-yl; $R^3$ is hydrogen or methoxy, either $R^{4a}$, $R^{4b}$ and $R^{4c}$ are methyl, $R^6$ is hydrogen, halogen, $C_{1-6}$ alkyl or $C_{1-6}$ alkoxy $R^1$, $R^5$, $R^8$ and $R^9$ are hydrogen.

In a eighteenth embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; $R^{10}$ is hydrogen; $R^3$ is hydrogen or methoxy; (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) $R^{4a}$ and $R^{4b}$ together with the carbon to which they are attached are 3-oxetanyl and $R^{4c}$ is hydrogen or $C_{1-3}$ alkyl, or (c) either (i) $R^5$ and $R^{4a}$ or (ii) $R^3$ and $R^{4a}$ together are $CH_2-O$ or $(CH_2)_2$ and with atoms to which they are attached for a 2,3-dihydro-benzofuran or an indane and $R^{4b}$ and $R^{4c}$ are $C_{1-3}$ alkyl; $R^6$ is halogen, $C_{1-6}$ alkyl or $C_{1-6}$ alkoxy; and, $R^1$, $R^5$, $R^8$ and $R^9$ are hydrogen.

In another embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; $R^{10}$ is hydrogen; $R^3$ is hydrogen or methoxy; $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl; $R^6$ is halogen, $C_{1-6}$ alkyl or $C_{1-6}$ alkoxy; and, $R^1$, $R^5$, $R^8$ and $R^9$ are hydrogen.

In yet another embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; $R^{10}$ is hydrogen; $R^3$ is hydrogen or methoxy; $R^{4a}$ and $R^{4b}$ together with the carbon to which they are attached are 3-oxetanyl and $R^{4c}$ is hydrogen or $C_{1-3}$ alkyl; $R^6$ is halogen, $C_{1-6}$ alkyl or $C_{1-6}$ alkoxy; and, $R^1$, $R^5$, $R^8$ and $R^9$ are hydrogen.

In still another embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; $R^{10}$ is hydrogen; $R^3$ is hydrogen or methoxy; either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl; $R^6$ is halogen, $C_{1-6}$ alkyl or $C_{1-6}$ alkoxy; and, $R^1$, $R^5$, $R^8$ and $R^9$ are hydrogen.

In a nineteenth embodiment of the present invention there is provided a compound according to formula I wherein $R^2$ is (E) $R^{10}C=CR^{10}Ar^1$; $Ar^1$ is phenyl or pyridinyl substituted at least with $(CH_2)_n$ $NR^aR^b$ wherein n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$cycloalkyl-$C_{1-3}$ alkyl-sulfonyl or $C_{1-6}$ alkoxy-$C_{1-6}$ alkylsulfonyl; $R^{10}$ is hydrogen; $R^3$ is hydrogen or methoxy; (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) $R^{4a}$ and $R^{4b}$ together with the carbon to which they are attached are 3-oxetanyl and $R^{4c}$ is hydrogen or $C_{1-3}$ alkyl, or (c) either (i) $R^5$ and $R^{4a}$ or (ii) $R^3$ and $R^4$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl; $R^6$ is halogen, $C_{1-6}$ alkyl or $C_{1-6}$ alkoxy; and, $R^1$, $R^5$, $R^8$ and $R^9$ are hydrogen.

In a twentieth embodiment of the present invention there is provided a compound according to formula I wherein $R^2$ is (E) $R^{10}C=CR^{10}Ar^1$; $Ar^1$ is optionally substituted 4-methanesulfonylamino-phenyl, 5-methansulfonylamino-pyridin-2-yl or 2-methansulfonylamino-pyridin-5-yl; $R^{10}$ is hydrogen; $R^3$ is hydrogen or methoxy; (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) $R^{4a}$ and $R^{4b}$ together with the carbon to which they are attached are 3-oxetanyl and $R^{4c}$ is hydrogen or $C_{1-3}$ alkyl, or (c) either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl; $R^6$ is halogen, $C_{1-6}$ alkyl or $C_{1-6}$ alkoxy; and, $R^1$, $R^5$, $R^8$ and $R^9$ are hydrogen.

In a another embodiment of the present invention there is provided a compound according to formula I wherein $R^2$ is (E) $R^{10}C=CR^{10}Ar^1$; $Ar^1$ is optionally substituted 4-methanesulfonylamino-phenyl, 5-methansulfonylamino-pyridin-2-yl or 2-methansulfonylamino-pyridin-5-yl; $R^{10}$ is hydrogen; $R^3$ is hydrogen or methoxy; either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl; $R^6$ is halogen, $C_{1-6}$ alkyl or $C_{1-6}$ alkoxy; and, $R^1$, $R^5$, $R^8$ and $R^9$ are hydrogen.

In a twenty-first embodiment of the present invention there is provided a compound according to formula I wherein $R^2$ is (E) $R^{10}C=CR^{10}Ar^1$; $Ar^1$ phenyl, pyridinyl, pyrimidinyl, pyrazinyl, pyridazinyl; p is 2; $R^3$ is hydrogen or $C_{1-6}$ alkoxy; and, $R^9$ is $CH_2OH$, $CH_2OR^{9a}$ wherein $R^{9a}$ is $(CH_2)_sCO_2H$ wherein s is one to four, $C(O)CHR^{9b}R^{9c}$ wherein $R^{9b}$ is hydrogen, methyl, iso-propyl, iso-butyl, sec-butyl, phenyl or 4-hydroxy-phenyl and $R^{9c}$ is hydrogen or $C_{1-6}$ alkoxycarbonyl.

In a twenty-second embodiment of the present invention there is provided a compound according to formula I wherein $R^2$ is —$NR^7C(=O)Ar^4$.

In a twenty-third embodiment of the present invention there is provided a compound according to formula I wherein $R^2$ is —$NR^7C(=O)Ar^4$, $R^1$ and $R^5$ are hydrogen and $R^3$ is $C_{1-6}$ alkoxy.

In a twenty-fourth embodiment of the present invention there is provided a compound according to formula I wherein $R^2$ is —$NR^7C(=O)Ar^4$, $Ar^4$ is phenyl substituted with one to three groups independently selected from $C_{1-3}$ alkyl, halogen, $(CH_2)_n$ $NR^aR^b$ and $(CH_2)_nCO_2NR^aR^b$, n is zero, one or two, $R^a$ is hydrogen or $C_{1-3}$ alkyl and $R^b$ is hydrogen, $C_{1-3}$ alkyl, $C_{1-3}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^1$ and $R^5$ are hydrogen and $R^3$ is $C_{1-6}$ alkoxy.

In a twenty-fifth embodiment of the present invention there is provided a compound according to formula I wherein $R^2$ is —$NR^7C(=O)Ar^4$, $Ar^4$ is phenyl substituted with one to three groups independently selected from $C_{1-3}$ alkyl, halogen, $(CH_2)_n$ $NR^aR^b$ and $(CH_2)_nCO_2NR^aR^b$, n is zero, one or two, $R^a$ is hydrogen or $C_{1-3}$ alkyl and $R^b$ is hydrogen, $C_{1-3}$ alkyl, $C_{1-3}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^1$ and $R^5$ are hydrogen; $R^3$ is $C_{1-6}$ alkoxy and $R^{4a}$, $R^{4b}$ and $R^{4c}$ are methyl.

In a twenty-sixth embodiment of the present invention there is provided a compound according to formula I wherein $R^2$ is —$NR^7C(=O)Ar^4$, $Ar^4$ is phenyl substituted with one to three groups independently selected from $C_{1-3}$ alkyl, halogen, $(CH_2)_n$ $NR^aR^b$ and $(CH_2)_nCO_2NR^aR^b$, n is zero, one or two, $R^a$ is hydrogen or $C_{1-3}$ alkyl and $R^b$ is hydrogen, $C_{1-3}$ alkyl, $C_{1-3}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^1$ and $R^5$ are hydrogen; $R^3$ is $C_{1-6}$ alkoxy and (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) $R^{4a}$ and $R^{4b}$ together with the carbon to which they are attached are 3-oxetanyl and $R^{4c}$ is hydrogen or $C_{1-3}$ alkyl, or (c) either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl.

In another embodiment of the present invention there is provided a compound according to formula I wherein $R^2$ is —$NR^7C(=O)Ar^4$, $Ar^4$ is phenyl substituted with one to three groups independently selected from $C_{1-3}$ alkyl, halogen, $(CH_2)$, $NR^aR^b$ and $(CH_2)_nCO_2NR^aR^b$, n is zero, one or two, $R^a$ is hydrogen or $C_{1-3}$ alkyl and $R^b$ is hydrogen, $C_{1-3}$ alkyl, $C_{1-3}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^1$ and $R^5$ are hydrogen; $R^3$ is $C_{1-6}$ alkoxy; $R^{4a}$ and $R^{4b}$ take together are $C_{2-4}$ methylene and $R^{4c}$ is $C_{1-3}$ alkyl, $C_{1-2}$ alkoxy, halogen, cyano or $C_{1-2}$ fluoroalkyl.

In yet another embodiment of the present invention there is provided a compound according to formula I wherein $R^2$ is —$NR^7C(=O)Ar^4$, $Ar^4$ is phenyl substituted with one to three groups independently selected from $C_{1-3}$ alkyl, halogen, $(CH_2)_n NR^aR^b$ and $(CH_2)_nCO_2NR^aR^b$, n is zero, one or two, $R^a$ is hydrogen or $C_{1-3}$ alkyl and $R^b$ is hydrogen, $C_{1-3}$ alkyl, $C_{1-3}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^1$ and $R^5$ are hydrogen; $R^3$ is $C_{1-6}$ alkoxy $R^{4a}$ and $R^{4b}$ together with the carbon to which they are attached are 3-oxetanyl and $R^{4c}$ is hydrogen or $C_{1-3}$ alkyl.

In still another embodiment of the present invention there is provided a compound according to formula I wherein $R^2$ is —$NR^7C(=O)Ar^4$, $Ar^4$ is phenyl substituted with one to three groups independently selected from $C_{1-3}$ alkyl, halogen, $(CH_2)_n NR^aR^b$ and $(CH_2)_nCO_2NR^aR^b$, n is zero, one or two, $R^a$ is hydrogen or $C_{1-3}$ alkyl and $R^b$ is hydrogen, $C_{1-3}$ alkyl, $C_{1-3}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^1$ and $R^5$ are hydrogen; $R^3$ is $C_{1-6}$ alkoxy and either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl.

In a twenty-seventh embodiment of the present invention there is provided a compound according to formula I wherein $R^2$ is —$NR^7C(=O)Ar^4$, $Ar^4$ is pyridinyl substituted with one to three groups independently selected from $C_{1-3}$ alkyl, halogen, $(CH_2)_n NR^aR^b$ and $(CH_2)_nCO_2NR^aR^b$, n is zero, one or two, $R_a$ is hydrogen or $C_{1-3}$ alkyl and $R^b$ is hydrogen, $C_{1-3}$ alkyl, $C_{1-3}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^1$ and $R^5$ are hydrogen and $R^3$ is $C_{1-6}$ alkoxy.

In a twenty-ninth embodiment of the present invention there is provided a compound according to formula I wherein R1 and R5 are hydrogen, R3 is C1-6 alkoxy, R2 is —(CH2)$_m$C(=O)X, m is zero, X is NRcRd, Rc is hydrogen and $R^d$ is Ar2 said Ar2 being phenyl optionally substituted with on to three groups independently selected from hydroxy, C1-6 alkyl, C1-6 hydroxyalkyl, halogen, (CH2)nNRaRb and wherein n is one or two, Ra is hydrogen or C1-3 alkyl and Rb is hydrogen, C1-3 alkyl, C1-3 acyl, C1-3 alkylsulfonyl, C1-6 haloalkylsulfonyl, C3-7 cycloalkylsulfonyl, C3-7 cycloalkyl-C1-3 alkyl-sulfonyl or C1-6 alkoxy-C1-6 alkylsulfonyl.

In a thirtieth embodiment of the present invention there is provided a compound according to formula I wherein $R^2$ is —$(CH_2)_mC(=O)X$, m is zero, X is $NR^cR^d$, $R^c$ is hydrogen and $R^d$ is $Ar^2$ said $Ar^2$ being phenyl optionally substituted with on to three groups independently selected from hydroxy, $C_{1-6}$ alkyl, $C_{1-6}$ hydroxyalkyl, halogen, $(CH_2)_nNR^aR^b$ and wherein n is one or two, $R^a$ is hydrogen or $C_{1-3}$ alkyl, $R^b$ is hydrogen, $C_{1-3}$ alkyl, $C_{1-3}$ acyl, $C_{1-3}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, and $R^{4a}$, $R^{4b}$ and $R^{4c}$ are methyl.

In a thirty-first embodiment of the present invention there is provided a compound according to formula I wherein $R^2$ is —$(CH_2)_mC(=O)X$, m is zero, X is $NR^cR^d$, $R^c$ is hydrogen and $R^d$ is $Ar^2$ said $Ar^2$ being phenyl optionally substituted with on to three groups independently selected from hydroxy, $C_{1-6}$ alkyl, $C_{1-6}$ hydroxyalkyl, halogen, $(CH_2)_nNR^aR^b$ and wherein n is one or two, $R^a$ is hydrogen or $C_{1-3}$ alkyl, $R^b$ is hydrogen, $C_{1-3}$ alkyl, $C_{1-3}$ acyl, $C_{1-3}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl, and ( ) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) $R^{4a}$ and $R^{4b}$ together with the carbon to which they are attached are 3-oxetanyl and $R^{4c}$ is hydrogen or $C_{1-3}$ alkyl, or (c) either (i) $R^5$ and $R^{4a}$ or (ii) $R^3$ and $R^{4a}$ together are $CH_2$—O or $(CH_2)_2$ and with atoms to which they are attached for a 2,3-dihydro-benzofuran or an indane and $R^{4b}$ and $R^{4c}$ are $C_{1-3}$ alkyl.

In a thirty-second embodiment of the present invention there is provided a compound according to formula I wherein $R^2$ is —$[C(R^8)_2]_p$—$NR^eR^f$.

In a thirty-third embodiment of the present invention there is provided a compound according to formula I wherein $R^2$ is —$[C(R^8)_2]_p$—$NR^eR^f$, $R^8$ is hydrogen and p is one or two.

In a thirty-fourth embodiment of the present invention there is provided a compound according to formula I wherein $R^2$ is —$[C(R^8)_2]_p$—$NR^eR^f$, $R^8$ is hydrogen, p is one or two and $R^e$ and $R^f$ together with the nitrogen to which they are attached are a pyrrolidine, a piperidine or an azepinyl ring optionally independently substituted with one to three groups selected from $C_{1-3}$ alkylsulfonylamido, $C_{1-3}$ alkyl, $C_{1-3}$ alkoxy or halogen.

In another embodiment of the present invention there is provided a compound according to formula I wherein $R^{4a}$, $R^{4b}$, $R^{4c}$ together with the carbon to which they are attached are trifluoromethyl or 2,2,2-trifluoroethyl and $R^1$, $R^2$, $R^3$, $R^5$, $R^6$, $R^7$, $R^8$, $R^9$, m, n and p are as described hereinabove. Said compounds can be prepared from 2,6-dibromo-4-trifluoromethyl-aniline (CASRN 72678-19-4) or 4-(2,2,2-trifluoroethyl)-aniline (CASRN 131395-17-0) utilizing the methodology described herein In a thirty-fifth embodiment of the present invention there is provided a compound according to formula I selected from I-1 to I-293 or II-1 to II-9 in TABLE I.

In another embodiment of the present invention there is provided a compound according to formula I-126, I-137 to I-175, I-180 to I-184, I-186 to I-188, I-200 to I-211, I-213, I-219 to I-246, I-248 to I-250, I-261 to I-275, I-288 to I-292, II-1 to II-3 and II-5-II8 in TABLE I.

In a thirty-sixth embodiment of the present invention there is provided a method for treating a disease caused by the Hepatitis C Virus (HCV) virus comprising administering to a patient in need thereof, a therapeutically effective quantity of a compound according to formula I wherein $R^1$, $R^2$, $R^3$, $R^{4a}$, $R^{4b}$, $R^{4c}$, $R^5$, $R^6$, $R^7$, $R^8$, $R^9$, m, n and p are as defined hereinabove.

In an thirty-seventh embodiment of the present invention there is provided a method for treating a disease caused by the Hepatitis C Virus (HCV) virus comprising co-administering to a patient in need thereof, a therapeutically effective quantity of a compound according to formula I wherein $R^1$, $R^2$, $R^3$, $R^{4a}$, $R^{4b}$, $R^{4c}$, $R^5$, $R^6$ $R^7$, $R^8$, m, n and p are as defied hereinabove along with at least one immune system modulator and/or at least one antiviral agent that inhibits replication of HCV.

In an thirty-eighth embodiment of the present invention there is provided a method for treating a disease caused by the Hepatitis C Virus (HCV) virus comprising co-administering to a patient in need thereof, a therapeutically effective quantity of a compound according to formula I wherein $R^1$, $R^2$, $R^3$, $R^{4a}$, $R^{4b}$, $R^{4c}$, $R^5$, $R^6$ $R^7$, $R^8$, m, n and p are as defined here with at least one immune system modulator selected from the group consisting of an interferon, interleukin, tumor necrosis factor or colony stimulating factor.

In an thirty-ninth embodiment of the present invention there is provided a method for treating a disease caused by the Hepatitis C Virus (HCV) virus comprising co-administering to a patient in need thereof, a therapeutically effective quantity of a compound according to formula I wherein $R^1$, $R^2$, $R^3$, $R^{4a}$, $R^{4b}$, $R^{4c}$, $R^5$, $R^6$ $R^7$, $R^8$, m, n and p are as defined hereinabove along with at least one immune system modulator selected from the group consisting of an interferon, or a chemically derivatized interferon.

In an fortieth embodiment of the present invention there is provided a method for treating a disease caused by the Hepatitis C Virus (HCV) virus comprising co-administering to a patient in need thereof, a therapeutically effective quantity of a compound according to formula I wherein $R^1$, $R^2$, $R^3$, $R^{4a}$, $R^{4b}$, $R^{4c}$, $R^5$, $R^6$ $R^7$, $R^8$, m, n and p are as defined hereinabove along with at least one antiviral agent selected from the group consisting of a HCV protease inhibitor, another HCV polymerase inhibitor, a HCV helicase inhibitor, a HCV primase inhibitor and a HCV fusion inhibitor.

In a forty-first embodiment of the present invention there is provided a method for inhibiting replication of HCV in a cell be delivering a compound according to formula I wherein $R^1$, $R^2$, $R^3$, $R^{4a}$, $R^{4b}$, $R^{4c}$, $R^5$, $R^6$ $R^7$, $R^8$, m, n and p are as defined hereinabove.

In a forty-second embodiment of the present invention there is provided a pharmaceutical composition according to formula I R $R^1$, $R^2$, $R^3$, $R^{4a}$, $R^{4b}$, $R^{4c}$, $R^5$, $R^6$ $R^7$, $R^8$, m, n and p are as defined hereinabove admixed with at least one pharmaceutically acceptable The term "alkyl" as used herein without further limitation denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-10}$ alkyl" as refers to an alkyl composed of 1 to 10 carbons. Examples of alkyl groups include, but are not limited to, methyl, ethyl, propyl, i-propyl, n-butyl, i-butyl, t-butyl or pentyl, isopentyl, neopentyl, hexyl, heptyl, and octyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" denotes the radical R'R"—, wherein R' is a phenyl radical, and R" is an alkylene radical as defined herein with the understanding that the attachment point of the phenylalkyl moiety will be on the alkylene radical. Examples of arylalkyl radicals include, but are not limited to, benzyl, phenylethyl, 3-phenylpropyl. The terms "arylalkyl" or "aralkyl" are interpreted similarly except R' is an aryl radical. The terms "(het)arylalkyl" or "(het)aralkyl" are interpreted similarly except R' is optionally an aryl or a heteroaryl radical. The term "pyridinyl $C_{1-6}$ alkyl refers to a group wherein R' is pyridinyl and R" is alkylene.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. "$C_{0-4}$ alkylene" refers to a linear or branched saturated divalent hydrocarbon radical comprising 1-4 carbon atoms or, in the case of $C_0$, the alkylene radical is omitted. "$(CH_2)_{0-4}$" refers to a linear saturated divalent hydrocarbon radical comprising 0-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "aryl" as used herein denotes a phenyl or naphthyl radical which can optionally be substituted with one or more, preferably one or three substituents independently selected from hydroxy, thio, cyano, alkyl, alkoxy, lower haloalkoxy, alkylthio, halogen, haloalkyl, hydroxyalkyl, nitro, alkoxycarbonyl, amino, alkylamino, dialkylamino, aminoalkyl, alkylaminoalkyl, and dialkylaminoalkyl, alkylsulfonyl, arylsulfinyl, alkylaminosulfonyl, arylaminosulfonyl, alkylsulfonylamino, arylsulfonylamino, carbamoyl, alkylcarbamoyl and dialkylcarbamoyl, arylcarbamoyl, alkylcarbonylamino, arylcarbonylamino, unless otherwise indicated. Alternatively two adjacent atoms of the aryl ring may be substituted with a methylenedioxy or ethylenedioxy group. Examples of aryl radicals include, but are not limited to, phenyl, naphthyl, indanyl, anthraquinolyl, tetrahydronaphthyl, 3,4-methylenedioxyphenyl, 1,2,3,4-tetrahydroquinolin-7-yl, 1,2,3,4-tetrahydroisoquinoline-7-yl, and the like. The phrase "substituted at least with $(CH_2)_n NR^a R^b$" in relation to any moiety indicates the moiety is substituted with $(CH_2)_n NR^a R^b$ but additional substitution also is permitted if free sites are present on the moiety after substitution by $(CH_2)_n NR^a R^b$.

The term "$C_{2-6}$ alkenylene" as used herein refers to a straight or branched $C_{2-6}$ alkylene radical as defined herein in which at least one pair of adjacent carbons linked by a double bond. Thus, for example, ethenylene thus refers to —CH═CH—, propenylene refers to —CH2CH═CH— or —CMe═CH—.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl. "$C_{3-7}$ cycloalkyl" as used herein refers to an cycloalkyl composed of 3 to 7 carbons in the carbocyclic ring.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cyclolalkyl and R" is $C_{1-3}$ alkylene as defined herein.

The term "haloalkyl" as used herein denotes a unbranched or branched chain alkyl group as defined above wherein 1, 2, 3 or more hydrogen atoms are substituted with a halogen. Examples are 1-fluoromethyl, 1-chloromethyl, 1-bromomethyl, 1-iodomethyl, difluoromethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "alkoxy" as used herein means an —O-alkyl group, wherein alkyl is as defined above such as methoxy, ethoxy, n-propyloxy, i-propyloxy, n-butoxyl, i-butoxyl, t-butoxyl, pentyloxy, hexyloxy, including their isomers. "Lower alkoxy" as used herein denotes an alkoxy group with a "lower alkyl" group as previously defined. "$C_{1-10}$ alkoxy" as used herein refers to an-O-alkyl wherein alkyl is $C_{1-10}$.

The terms "alkoxycarbonyl" and "aryloxycarbonyl" as used herein denotes a group of formula —C(═O)OR wherein R is alkyl or aryl respectively and alkyl and aryl are as defined herein. For example, $C_1$ alkoxycarbonyl refers to —C(═O)Me.

The term "haloalkoxy" as used herein refers to a group —OR where R is haloalkyl as defined herein. The term "haloalkylthio" as used herein refers to a group —SR where R is haloalkyl as defined herein.

The terms "hydroxyalkyl" and "alkoxyalkyl" as used herein denote an alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The term "$C_{1-6}$ fluoroalkyl" as used herein denotes a unbranched or branched chain alkyl group as defined above wherein 1, 2, 3 or more hydrogen atoms are substituted with a fluorine.

The term "halogen" or "halo" as used herein means fluorine, chlorine, bromine, or iodine.

The term "acyl" as used herein denotes a group of formula —C(═O)R wherein R is hydrogen or lower alkyl as defined herein. The term or "alkylcarbonyl" as used herein denotes a group of formula C(═O)R wherein R is alkyl as defined herein. The term $C_{1-6}$ acyl refers to a group —C(═O)R contain 1 to 6 carbon atoms. The $C_1$ acyl group is the formyl group wherein R═H and a C6 acyl group refers to hexanoyl when the alkyl chain is unbranched. The term "arylcarbonyl" as used herein means a group of formula C(═O)R wherein R is an aryl group; the term "benzoyl" as used herein an "arylcarbonyl" group wherein R is phenyl.

The terms "amino", "alkylamino" and "dialkylamino" as used herein refer to —$NH_2$, —NHR and —$NR_2$ respectively and R is alkyl as defined above. The two alkyl groups attached to a nitrogen in a dialkyl moiety can be the same or different. The terms "aminoalkyl", "alkylaminoalkyl" and "dialkylaminoalkyl" as used herein refer to $NH_2$(alkylene)-, RHN(alkylene)-, and $R_2$N(alkylene)- respectively wherein R is alkyl, and both alkylene and alkyl are as defined herein. "$C_{1-10}$ alkylamino" as used herein refers to an aminoalkyl wherein alkyl is $C_{1-10}$. $C_{1-10}$ alkyl-amino-$C_{2-6}$ alkyl" as used herein refers to a $C_{1-10}$ alkylamino(alkylene)$_{2-6}$ wherein alkyl is $C_{1-10}$ and the alkylene is $(CH_2)_{2-6}$. When the alkylene group contains three or more carbon atoms, the alkylene can be linear, e.g. —$(CH_2)_4$— or branched, e.g., —$(CMe_2CH_2)$—. The term "phenylamino" as used herein refers to —NHPh wherein Ph represents an optionally substituted phenyl group.

The term "$C_{1-3}$ acylamino-$C_{1-3}$ alkyl" as used herein refers a —$(CH_2)_{1-3}$NHC(═O)R where R is hydrogen, methyl or ethyl The terms "alkylsulfonyl" and "arylsulfonyl" as used herein denotes a group of formula —S(═O)$_2$R wherein R is alkyl or aryl respectively and alkyl and aryl are as defined herein. The term $C_{1-3}$ alkylsulfonylamido as used herein refers to a group $RSO_2NH$— wherein R is a $C_{1-3}$ alkyl group as defined herein.

The term "sulfamoyl" as used herein refers to the radical —S(O)$_2NH_2$. The terms "N-alkylsulfamoyl" and "N,N-dialkylsulfamoyl" as used herein refers to the radical —S(O)$_2$NR'R", wherein R' and R" are hydrogen and lower alkyl and R' and R" are independently lower alkyl respectively. Examples of N-alkylsulfamoyl substituents include, but are not limited to methylaminosulfonyl, iso-propylaminosulfonyl. Examples of N,N-dialkylsulfamoyl substituents include, but are not limited to dimethylaminosulfonyl, iso-propylmethylaminosulfonyl. The prefix N-alkyl or N,N-dialkyl can be replaced with aryl, heteroaryl, heterocyclyl or other radical to indicate a case where the amine is substituted with a group other than alkyl. The term "sulfamide" refers to a group $NH_2SO_2NH_2$. Sulfamides can be substituted on either of the nonequivalent nitrogen atoms and are distinguished as N or N' substituted sulfamides. A radical, —$NHSO_2NH_2$, is referred to herein as a "sulfamoylamino" radical. If it is necessary to distinguish specifically, —$NHSO_2N'R_2$ the nitrogen atom which is not linked to the core structure is designated N'. Thus N'-methyl sulfamoylamino refers to —$NHSO_2NHMe$, N-methyl sulfamoylamino refers to —$NMeSO_2NH_2$ and N,N'-dimethyl sulfamoylamino refers to —$NMeSO_2NHMe$. In there is no designation, either nitrogen can be substituted.

The term "alkylsulfonamido" refers to the radical —NH—S(O)$_2$-alkyl. The term alkyl can be replaced by other chemically relevant radicals such as aryl or heteroaryl to indicate, e.g. phenylsulfonamido —NH—S(O)$_2$—Ph. Thus "$C_{1-6}$ alkylsulfonamido" represents —NH—S(O)$_2$—$C_{1-6}$ alkyl "N-alkylalkylsulfonamido" refers to the radical —NR—S(O)$_2$-alkyl where R is a lower alkyl group.

The term "$C_{1-6}$ alkylsulfonamido-$C_{1-3}$ alkyl-" refers to the radical —NRH—S(O)$_2$—$C_{1-6}$ alkyl wherein R represents $(CH_2)_{1-3}$. The term alkyl can be replaced by other chemically relevant radicals such as aryl or heteroaryl to indicate, e.g. phenylsulfonamido —NH—S(O)$_2$—Ph. "N-alkylalkylsulfonamido" refers to the radical —NR—S(O)$_2$-alkyl where R is a lower alkyl group.

The term "aryl sulfinic acid" as used herein refers to a compound with the formula Ar—S(O)OH.

The term "carbamoyl" as used herein means the radical —$CONH_2$. The prefix "N-alkylcarbamoyl" and "N,N-dialkylcarbamoyl" means a the radical CONHR' or CONR'R" respectively wherein the R' and R" groups are independently alkyl as defined herein. The prefix "N-arylcarbamoyl" denotes the radical CONHR' wherein R' is an aryl radical as defined herein.

The term "heterocyclyl" or "heterocycle" as used herein denotes a monovalent saturated cyclic radical, consisting of one or more rings, preferably one to two rings, of three to eight atoms per ring, incorporating one or more ring heteroatoms (chosen from N,O or S(O)$_{0-2}$), and which can optionally be independently substituted with one or more, preferably one or two substituents selected from hydroxy, oxo, cyano, lower alkyl, lower alkoxy, lower haloalkoxy, alkylthio, halo, haloalkyl, hydroxyalkyl, nitro, alkoxycarbonyl, amino, alkylamino, alkylsulfonyl, arylsulfonyl, alkylaminosulfonyl, arylaminosulfonyl, alkylsulfonylamino, arylsulfonylamino, alkylaminocarbonyl, arylaminocarbonyl, alkylcarbonylamino, arylcarbonylamino, unless otherwise indicated. Examples of heterocyclic radicals include, but are not limited to, azetidinyl, pyrrolidinyl, hexahydroazepinyl, oxetanyl, tetrahydrofuranyl, tetrahydrothiophenyl, oxazolidinyl, thiazolidinyl, isoxazolidinyl, morpholinyl, piperazinyl, piperidinyl, tetrahydropyranyl, thiomorpholinyl, quinuclidinyl and imidazolinyl.

The terms "azetidine", "pyrrolidine", "piperidine" and "azepine" refer to a 4-, 5-, 6- or 7-membered cycloalkane respectively wherein one carbon atom is replaced by a nitrogen atom.

The term "cyclic amine" denotes a saturated carbon ring, containing from 3 to 6 carbon atoms as defined above, and wherein at least one of the carbon atoms is replaced by a heteroatom selected from the group consisting of N, O or S and wherein the N-atom is linked to the phenyl ring, for example, piperidine, piperazine, morpholine, thiomorpholine, di-oxo-thiomorpholine, pyrrolidine, pyrazoline, imidazolidine, azetidine wherein the cyclic carbon atoms are optionally substituted by one or more substituents, selected from the group consisting of halogen, hydroxy, phenyl, lower alkyl, lower alkoxy, $C_{1-3}$ alkylsulfonylamido, $C_{1-3}$ alkyl, $C_{1-3}$ alkoxy or 2-hydrogen atoms on a carbon are both replace by oxo (═O). When the cyclic amine is a piperazine, one nitrogen atom can be optionally substituted by $C_{1-6}$ alkyl, $C_{1-6}$ acyl, $C_{1-6}$ alkylsulfonyl.

The term "pyridinyl-$C_{1-6}$ alkyl" refers to a substituent with the following formula:

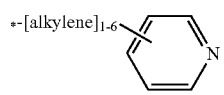

Compounds of the present invention and their isomeric forms and pharmaceutically acceptable salts thereof are also useful in treating and preventing viral infections, in particular, hepatitis C infection, and diseases in living hosts when used in combination with each other and with other biologically active agents, including but not limited to the group consisting of interferon, a pegylated interferon, ribavirin, protease inhibitors, polymerase inhibitors, small interfering RNA compounds, antisense compounds, nucleotide analogs, nucleoside analogs, immunoglobulins, immunomodulators, hepatoprotectants, anti-inflammatory agents, antibiotics, antivirals and antiinfective compounds. Such combination therapy may also comprise providing a compound of the invention either concurrently or sequentially with other medicinal agents or potentiators, such as ribavirin and related compounds, amantadine and related compounds, various interferons such as, for example, interferon-alpha, interferon-beta, interferon gamma and the like, as well as alternate forms of interferons such as pegylated interferons. Additionally combinations of ribavirin and interferon, may be administered as an additional combination therapy with at least one of the compounds of the present invention.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759, GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al. WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. W02005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Examples of the HCV NS3 protease inhibitors include, but are not limited to SCH-503034 (Schering, SCH-7), VX-950 (telaprevir, Vertex), BILN-2065 (Boehringer-Ingelheim, BMS-605339 (Bristo Myers Squibb), and ITMN-191 (Intermune).

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen and actimmune, IFN-omega with DUROS, albuferon, locteron, Albuferon, Rebif, oral interferon alpha, IFNalpha-2b XL, AVI-005, PEG-Infergen, and pegylated IFN-beta.

Ribavirin analogs and the ribavirin prodrug viramidine (taribavirin) have been administered with interferons to control HCV.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), dibenzylideneacetone (DBA), 1,5-diazabicyclo[4.3.0]non-5-ene (DBN), 1,8-diazabicyclo[5.4.0]undec-7-ene (DBU), N,N'-dicyclohexylcarbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$-(mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), satd. (saturated), tert-butyldimethylsilyl or t-BuMe2Si (TBDMS), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or $Me_3Si$ (TMS), p-toluenesulfonic acid monohydrate (TsOH or pTsOH), 4-Me-$C_6H_4SO_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford.).

Compounds and Preparation

Examples of representative compounds encompassed by the present invention and within the scope of the invention are provided in TABLE I. Physical constants are tabulated in TABLE II. These examples and preparations which follow are provided to enable those skilled in the art to more clearly understand and to practice the present invention. They should not be considered as limiting the scope of the invention, but merely as being illustrative and representative thereof.

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted as a Markush structure with generalized substituents; however, one skilled in the art will immediately appreciate that the nature of the R groups as defined in the claims can varied as defined in the appended claims to afford the various compounds contemplated in this invention. Moreover, the reaction conditions are exemplary and alternative conditions can be identified without undue experimentation. The reaction sequences in the following examples are not meant to limit the scope of the invention as set forth in the claims.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it Compounds encompassed by the present invention are substituted 3-phenyl-1H-pyridin-2-one derivatives. The following numbering scheme is used to refer to the substitution sites on the core substructure.

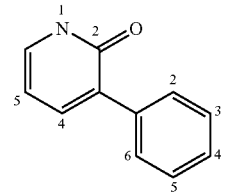

TABLE I

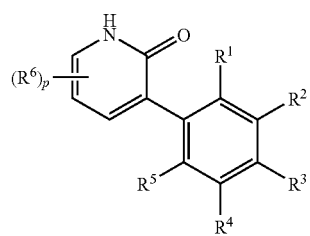

(1)

| Cpd. No. | $R^1$ | $R^2$ | $R^3$ | $R^4$ | $R^5$ | $R^6$ |
|---|---|---|---|---|---|---|
| I-1 | H | H | H | *—$CMe_3$ | H | H |
| I-2 | —OH | H | H | *—$CMe_3$ | H | H |
| I-3 | H | Me | H | *—$CMe_3$ | H | H |
| I-4 | H | H | —OMe | *—$CMe_3$ | H | H |
| I-5 | H | H | —OEt | *—$CMe_3$ | H | H |
| I-6 | H | H | —$OCHF_2$ | *—$CMe_3$ | H | H |
| I-7 | H | Me | H | *—$CMe_3$ | H | 5-Me |
| I-8 | H | Me | H | *—$CMe_3$ | H | 5-Cl |
| I-9 | —OH | Br | H | *—$CMe_2Et$ | H | H |
| I-10 | —OH | *—$CH_2OH$ | H | *—$CMe_3$ | H | H |
| I-11 | —OH | Me | H | *—$CMe_3$ | H | H |
| I-12 | H | Me | H | *—$CMe_3$ | H | 6-$CH_2OH$ |
| I-13 | —OH | Br | H | *—$CMe_3$ | H | H |
| I-14 | —OH | Et | H | *—$CMe_3$ | H | H |
| I-15 | —OH | Ph | H | *—$CMe_3$ | H | H |
| I-16 | —OH | Cl | H | *—$CMe_3$ | H | H |
| I-17 | —OH | —$CH_2Ph$ | H | *—$CMe_3$ | H | H |

TABLE I-continued
| | | | | | | |
|---|---|---|---|---|---|---|
| I-18 | —OH | —(CH₂)₂CO₂H | —OMe | *—CMe₃ | H | H |
| I-19 | H | 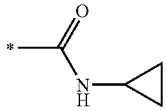 *—C(=O)NH-cyclopropyl | —OMe | *—CMe₃ | H | H |
| I-20 | —OH | 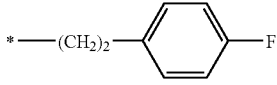 *—(CH₂)₂-C₆H₄-4-F | H | *—CMe₃ | H | H |
| I-21 | H | 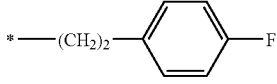 *—(CH₂)₂-C₆H₄-4-F | —OMe | *—CMe₃ | H | H |
| I-22 | H | —(CH₂)₂CO₂H | —OMe | *—CMe₃ | H | H |
| I-23 | H | —OH | —OMe | *—CMe₃ | H | H |
| I-24 | H | 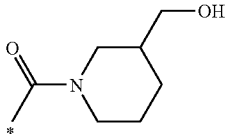 | —OMe | *—CMe₃ | H | H |
| I-25 | H | 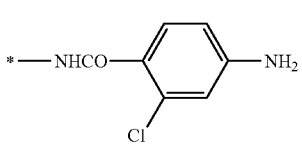 | —OMe | *—CMe₃ | H | H |
| I-26 | H | —OMe | —OMe | *—CMe₃ | H | H |
| I-27 | H | -Me | H | 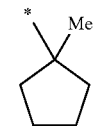 | H | H |
| I-28 | H | -Me | H | 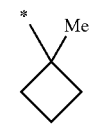 | H | H |
| I-29 | H | -Me | —OMe | *—CMe₃ | H | H |
| I-30 | H | -Et | —OMe | *—CMe₃ | H | H |
| I-31 | H | 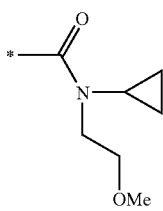 | —OMe | *—CMe₃ | H | H |
| I-32 | H | 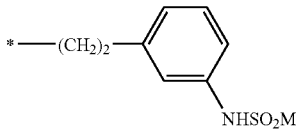 | —OMe | *—CMe₃ | H | H |
| I-33 | H | 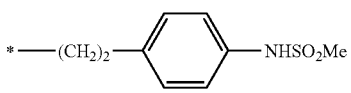 | —OMe | *—CMe₃ | H | H |
| I-34 | H | *—CONH—(CH₂)₂-Ph | —OMe | *—CMe₃ | H | H |
| I-35 | H | *—CONH—CH₂CHMe-Ph | —OMe | *—CMe₃ | H | H |

TABLE I-continued

| | | | | | | |
|---|---|---|---|---|---|---|
| I-36 | H | —CONH—CH₂CHMe-(3-pyridyl) | —OMe | *—CMe₃ | H | H |
| I-37 | H | *—CONH—CH₂-Ph | —OMe | *—CMe₃ | H | H |
| I-38 | H | *—CONH—CH₂-(4-pyridyl) | —OMe | *—CMe₃ | H | H |
| I-39 | H | *—CONH—CH₂-(1-methyl-imidazol-5-yl) | —OMe | *—CMe₃ | H | H |
| I-40 | H | *—CONH—CH₂—C₆H₄—NMe₂ | —OMe | *—CMe₃ | H | H |
| I-41 | H | *—CONH—C₆H₄—NMe₂ | —OMe | *—CMe₃ | H | H |
| I-42 | H | *—CONH—(CH₂)₃—N(pyrrolidinyl) | —OMe | *—CMe₃ | H | H |
| I-43 | H | *—CONH(CH₂)₂—NMe₂ | —OMe | *—CMe₃ | H | H |
| I-44 | H | *—CONH—(CH₂)₃—N(2-oxopyrrolidinyl) | —OMe | *—CMe₃ | H | H |
| I-45 | H | *—O-Ph | H | *—CMe₃ | H | H |
| I-46 | H | *—CH₂-Ph | —H | *—CMe₃ | H | H |
| I-47 | H | *—C(O)-Ph | —OMe | *—CMe₃ | H | H |
| I-48 | H | *—CH₂-Ph | —OMe | *—CMe₃ | H | H |
| I-49 | H | *—C(O)-C₆H₄-3-F | —OMe | *—CMe₃ | H | H |
| I-50 | H | *—C(O)-C₆H₄-4-F | —OMe | *—CMe₃ | H | H |
| I-51 | —OH | *—(CH₂)₂—C₆H₄—NHSO₂Me | H | *—CMe₃ | H | H |

TABLE I-continued
| | | | | | | |
|---|---|---|---|---|---|---|
| I-52 | H | 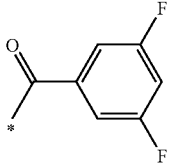 | —OMe | *—CMe₃ | H | H |
| I-53 | H | Me | H | *—CMe₃ | H | 5-F |
| I-54 | H | 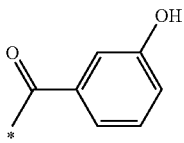 | —OMe | *—CMe₃ | H | H |
| I-55 | H | 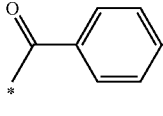 | —OMe | *—CMe₃ | H | H |
| I-56 | H | H | —OMe | *—CMe₃ | F | H |
| I-57 | H | 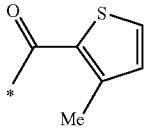 | —OMe | *—CMe₃ | H | H |
| I-58 | H | 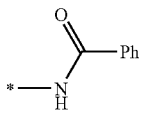 | —OMe | *—CMe₃ | H | H |
| I-59 | H | 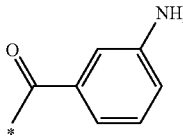 | —OMe | *—CMe₃ | H | H |
| I-60 | H | 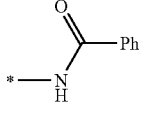 | —F | *—CMe₃ | H | H |
| I-61 | H | H | —OMe |  | H | H |
| I-62 | H | H | —OMe | 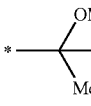 | H | H |
| I-63 | H | 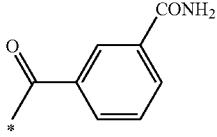 | —OMe | *—CMe₃ | H | H |
| I-64 | H | 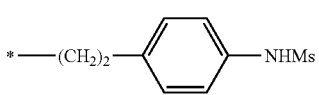 | —OMe | *—CMe₃ | H | 6-Me |

TABLE I-continued

| ID | | | | | | |
|---|---|---|---|---|---|---|
| I-65 | H | 3-(CH₂NHMs)-C₆H₄-C(O)-* | —OMe | *—CMe₃ | H | H |
| I-66 | H | 4-(CH₂NH₂)-C₆H₄-C(O)-* | —OMe | *—CMe₃ | H | H |
| I-67 | H | *—(CH₂)₂—C₆H₄—NHMs | —OMe | *—CMe₃ | H | 5-F |
| I-68 | H | *—CONH-Ph | —OMe | *—CMe₃ | H | H |
| I-69 | H | *—CONH—(2-Me,4-NHMs-C₆H₃) | —OMe | *—CMe₃ | H | H |
| I-70 | H | *—NHCO—C₆H₄—NHMs | —OMe | *—CMe₃ | H | H |
| I-71 | H | *—CH₂O—C₆H₄—NHMs | —OMe | *—CMe₃ | H | H |
| I-72 | H | *—NHCO—C₆H₄—NH₂ | —OMe | *—CMe₃ | H | H |
| I-73 | H | *—NHCO—C₆H₄—NHMs | F | *—CMe₃ | H | H |
| I-74 | H | *—(CH₂)₂—C₆H₄—NHMs | H | *—CMe₃ | H | H |
| I-75 | H | *—(CH₂)₂—C₆H₄—NMeMs | —OMe | *—CMe₃ | H | H |
| I-76 | H | *—CONH—C₆H₄—CH₂NHMs | —OMe | *—CMe₃ | H | H |
| I-77 | H | *—C(O)NH—(1-Me-piperidin-3-yl) | —OMe | *—CMe₃ | H | H |
| I-78 | H | *—CONH—(2-Me,3-CH₂OH-C₆H₃) | —OMe | *—CMe₃ | H | H |

TABLE I-continued

| I-79 | H | 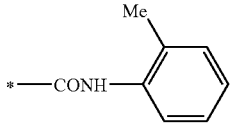 —CONH—(2-Me-phenyl) | —OMe | *—CMe₃ | H | H |
| I-80 | —NHAc | 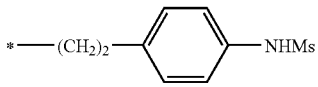 *—(CH₂)₂—(4-NHMs-phenyl) | H | *—CMe₃ | H | H |
| I-81 | H | 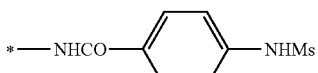 *—NHCO—(4-NHMs-phenyl) | —OMe | *—CMe₃ | H | 5-F |
| I-82 | H | 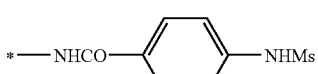 *—NHCO—(4-NHMs-phenyl) | —OMe |  1-Me-cyclopropyl | H | H |
| I-83 | H | 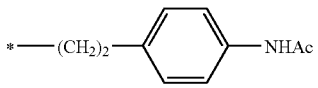 *—(CH₂)₂—(4-NHAc-phenyl) | H | *—CMe₃ | H | H |
| I-84 | H | 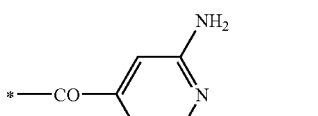 *—CO—(2-amino-pyridin-4-yl) | —OMe | *—CMe₃ | H | H |
| I-85 | H | 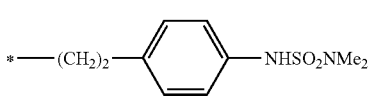 *—(CH₂)₂—(4-NHSO₂NMe₂-phenyl) | H | *—CMe₃ | H | H |
| I-86 | H |  *—(CH₂)₂—(4-NHCONHMe-phenyl) | H | *—CMe₃ | H | H |
| I-87 | CN | 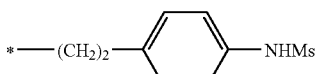 *—(CH₂)₂—(4-NHMs-phenyl) | H | *—CMe₃ | H | H |
| I-88 | H | 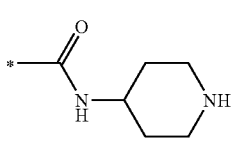 *—CONH-(piperidin-4-yl) | —OMe | *—CMe₃ | H | H |
| I-89 | H | 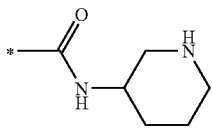 *—CONH-(piperidin-3-yl) | —OMe | *—CMe₃ | H | H |
| I-90 | H | 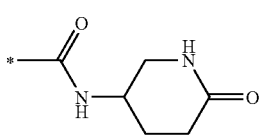 *—CONH-(6-oxo-piperidin-3-yl) | —OMe | *—CMe₃ | H | H |
| I-91 | H | 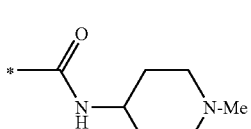 *—CONH-(N-Me-piperidin-4-yl) | —OMe | *—CMe₃ | H | H |

TABLE I-continued

| | | | | | | |
|---|---|---|---|---|---|---|
| I-92 | H | *—C(O)NH—cyclohexyl-NMe₂ | —OMe | *—CMe₃ | H | H |
| I-93 | H | *—C(O)NH—cyclohexyl(CH₂OH) | —OMe | *—CMe₃ | H | H |
| I-94 | H | *—(CH₂)₂—C₆H₄—NHMs | H | *—CMe₃ | H | 5-F |
| I-95 | H | *—(CH₂)₂—C₆H₄—NHMs | H | *—CMe₃ | H | 5-Cl |
| I-96 | H | *—(CH₂)₂—C₆H₄—NHMs | H | *—CMe₃ | H | 5-Br |
| I-97 | H | *—CONH—C₆H₄—CH₂OH | —OMe | *—CMe₃ | H | H |
| I-98 | NH₂ | *—(CH₂)₂—C₆H₄—NHMs | H | *—CMe₃ | H | H |
| I-99 | H | *—(CH₂)₂—C₆H₄—NH₂ | —OMe | *—C(Me)(cyclopropyl) | H | H |
| I-100 | H | *—C(O)—C₆H₄—NHMs | —OMe | *—CMe₃ | H | H |
| I-101 | H | *—C(O)NH—cyclohexyl | —OMe | *—CMe₃ | H | H |
| I-102 | H | *—(CH₂)₂—C₆H₃(F)—NHMs | —OMe | *—CMe₃ | H | H |
| I-103 | H | *—(CH₂)₂—C₆H₃(F)—NHMs | —OMe | *—CMe₃ | H | H |

TABLE I-continued
| | | | | | | |
|---|---|---|---|---|---|---|
| I-104 | H | 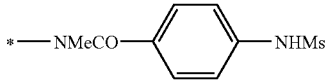 *—NMeCO—⌬—NHMs | —OMe | *—CMe₃ | H | H |
| I-105 | —OMe | H | —OMe | *—CMe₃ | H | 6-Et |
| I-106 | H | 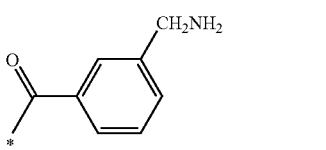 | —OMe | *—CMe₃ | H | H |
| I-107 | H |  | H | *—CMe₃ | H | H |
| I-108 | H | 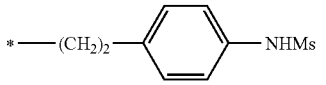 *—(CH₂)₂—⌬—NHMs | —OMe | 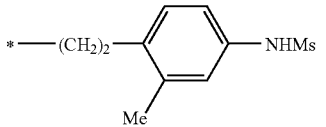 | H | H |
| I-109 | H | 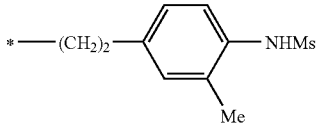 *—(CH₂)₂—⌬(Me)—NHMs | —OMe | *—CMe₃ | H | H |
| I-110 | H | 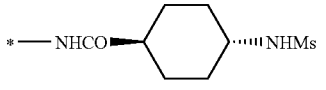 *—(CH₂)₂—⌬—NHMs (Me) | —OMe | *—CMe₃ | H | H |
| I-111 | H | *—NHCO—⌬—NHMs (trans cyclohexyl) | —OMe | *—CMe₃ | H | H |
| I-112 | H | 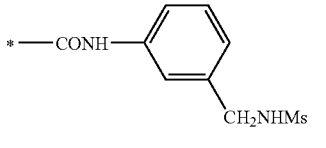 *—CONH—⌬—CH₂NHMs | —OMe | *—CMe₃ | H | H |
| I-113 | H | 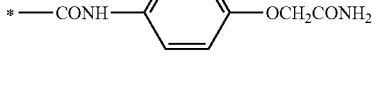 *—CONH—⌬—OCH₂CONH₂ | —OMe | *—CMe₃ | H | H |
| I-114 | —CN | 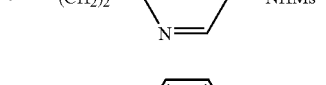 *—(CH₂)₂—pyridyl—NHMs | H | *—CMe₃ | H | H |
| I-115 | H | 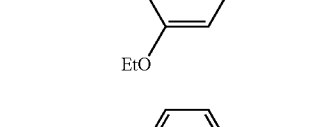 *—NHCO—⌬(EtO)—NHMs | —OMe | *—CMe₃ | H | H |
| I-116 | H | 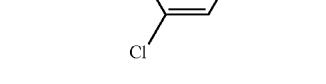 *—NHCO—⌬(Cl)—NHMs | —OMe | *—CMe₃ | H | H |

TABLE I-continued

| ID | | | | | | |
|---|---|---|---|---|---|---|
| I-117 | H | *—(CH₂)₂—N(piperidine)—NHMs | —OMe | *—CMe₃ | H | H |
| I-118 | —O(CH₂)₂OH | *—(CH₂)₂—C₆H₄—NHMs | H | *—CMe₃ | H | H |
| I-119 | H | *—CH₂NH—(trans-cyclohexyl)—NHMs | —OMe | *—CMe₃ | H | H |
| I-120 | H | *—NHCO—C₆H₃(F)—NH₂ | —OMe | *—CMe₃ | H | H |
| I-121 | H | *—NHCO—C₆H₃(F)—NHMs | —OMe | *—CMe₃ | H | H |
| I-122 | —CONH₂ | *—(CH₂)₂—C₆H₄—NHMs | H | *—CMe₃ | H | H |
| I-123 | H | *—(CH₂)₂—(pyridyl)—NHMs | OMe | *—CMe₃ | H | H |
| I-124 | H | *—(CH₂)₂—(pyridyl)—NHMs | —OMe | *—CMe₃ | H | H |
| I-125 | H | *—(CH₂)₂—(pyrimidyl)—NHMs | —OMe | *—CMe₃ | H | H |
| I-126 | H | *—CH=CH—C₆H₄—NHMs | —OMe | *—CMe₃ | H | H |
| I-127 | H | *—(CH₂)₂—(pyridazinyl)—NHMs | —OMe | *—CMe₃ | H | H |
| I-128 | H | *—(CH₂)₂—(pyridazinyl)—NH₂ | —OMe | *—CMe₃ | H | H |
| I-129 | H | *—NHCO—C₆H₃(Me)—NHMs | —OMe | *—CMe₃ | H | H |
| I-130 | H | *—NHCO—C₆H₃(OMe)—NHMs | —OMe | *—CMe₃ | H | H |

TABLE I-continued
| | | | | | | |
|---|---|---|---|---|---|---|
| I-131 | H | 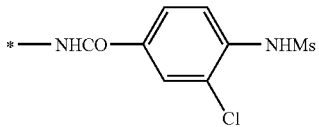 | —OMe | *—CMe$_3$ | H | H |
| I-132 | H | 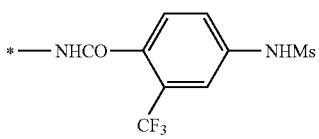 | —OMe | *—CMe$_3$ | H | H |
| I-133 | H | 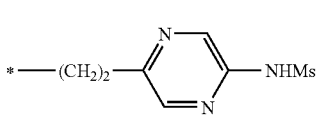 | —OMe | *—CMe$_3$ | H | H |
| I-134 | —CO$_2$Me | 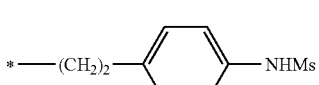 | H | *—CMe$_3$ | H | H |
| I-135 | —CO$_2$H | 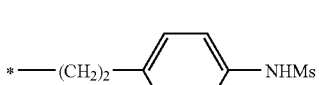 | H | *—CMe$_3$ | H | H |
| I-136 | H | 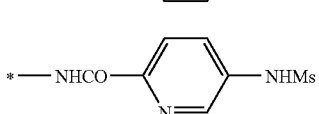 | —OMe | *—CMe$_3$ | H | H |
| I-137 | —OH | 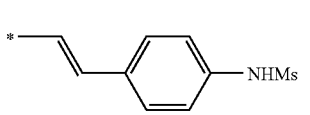 | H | *—CMe$_3$ | H | H |
| I-138 | H | 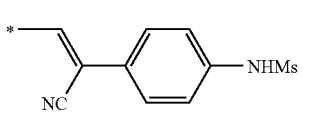 | —OMe | *—CMe | H | H |
| I-139 | H | 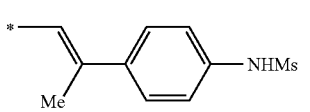 | —OMe | *—CMe$_3$ | H | H |
| I-140 | —OH | 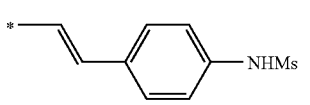 | H | *—CMe$_3$ | H | 6-Me |
| I-141 | H | 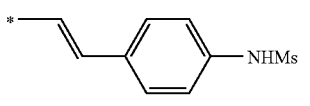 | H | *—CMe$_3$ | H | H |
| I-142 | H | 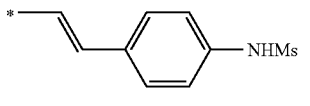 | —OMe | *—CMe$_3$ | H | 5-F |
| I-143 | —OH | 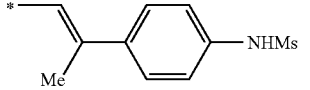 | H | *—CMe$_3$ | H | H |
| I-144 | H | 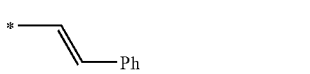 | —OMe | *—CMe$_3$ | H | H |

| | | | | | | |
|---|---|---|---|---|---|---|
| I-145 | H | 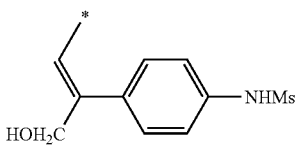 | —OMe | *—CMe₃ | H | H |
| I-146 | H | 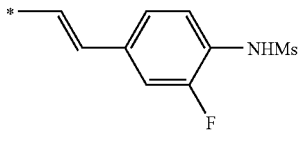 | H | *—CMe₃ | H | H |
| I-147 | H | 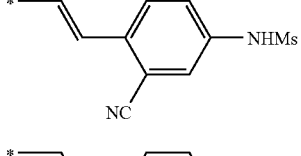 | H | *—CMe₃ | H | H |
| I-148 | H | 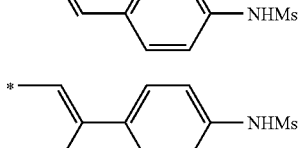 | H | *—CMe₃ | H | 5-F |
| I-149 | H | 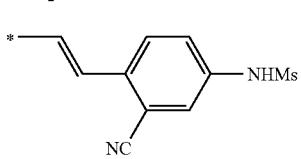 | —OMe | *—CMe₃ | H | H |
| I-150 | H | 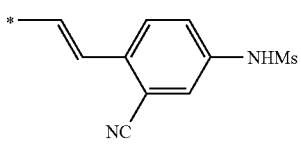 | —OMe | *—CMe₃ | H | H |
| I-151 | H | 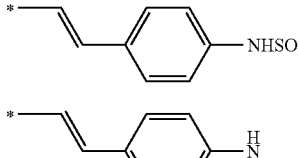 | —OMe | *—CMe₃ | H | 5-F |
| I-152 | H | 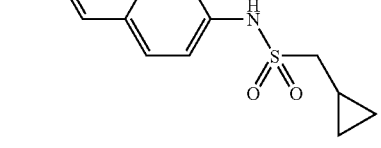 | —OMe | *—CMe₃ | H | 5-F |
| I-153 | H | 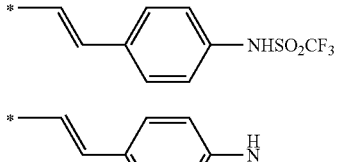 | —OMe | *—CMe₃ | H | 5-F |
| I-154 | H | 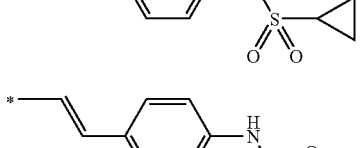 | —OMe | *—CMe₃ | H | 5-F |
| I-155 | H |  | —OMe | *—CMe₃ | H | 5-F |
| I-156 | H |  | —OMe | *—CMe₃ | H | 5-F |

TABLE I-continued
| | | | | | | |
|---|---|---|---|---|---|---|
| I-157 | H | 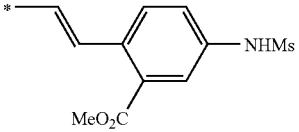 | —OMe | *—CMe₃ | H | H |
| I-158 | H | 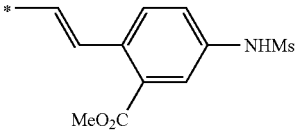 | H | *—CMe₃ | H | H |
| I-159 | H | 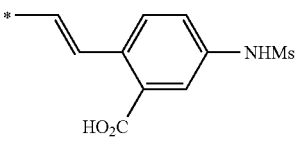 | H | *—CMe₃ | H | H |
| I-160 | H | 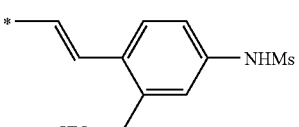 | —OMe | *—CMe | H | H |
| I-161 | H | 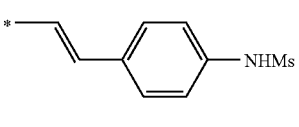 | —OMe | *—CMe₃ | H | 5-Cl |
| I-162 | H | 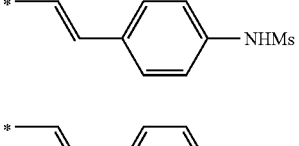 | H | 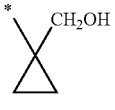 | H | H |
| I-163 | H | 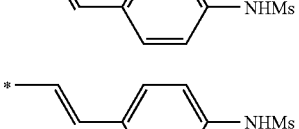 | —OMe | *—CMe₃ | H | 6-CH₂OH |
| I-164 | H | 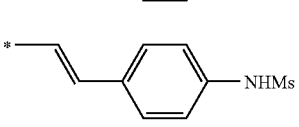 | —OMe | *—CMe | H | 6-CH₂OMe |
| I-165 | H | 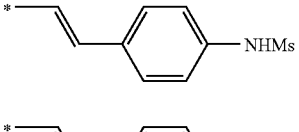 | —OMe | *—CMe₃ | H | 6-MEM |
| I-166 | H | 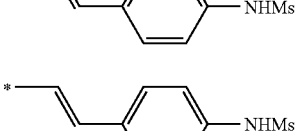 | —OMe | *—CMe₃ | H | H |
| I-167 | —OH | 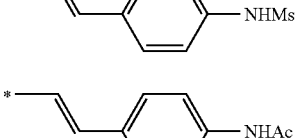 | H | *—CMe₃ | H | H |
| I-168¹ | H | 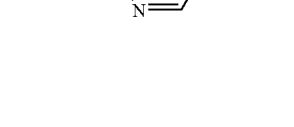 | H | *—CMe₃ | H | H |
| I-169 | H |  | —OMe | *—CMe₃ | H | 5-F |

TABLE I-continued
| | | | | | | |
|---|---|---|---|---|---|---|
| I-170 | H | 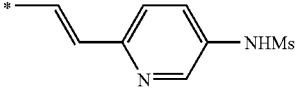 | —OMe | *—CMe₃ | H | 5-F |
| I-171 | H | 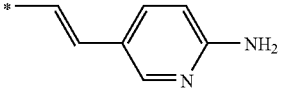 | —OMe | *—CMe₃ | H | H |
| I-172 | H | 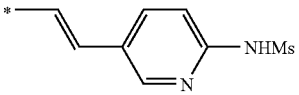 | —OMe | *—CMe₃ | H | H |
| I-174 | H | 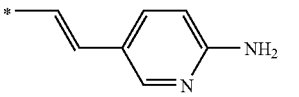 | —OMe | *—CMe₃ | H | H |
| I-175 | H | 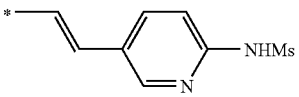 | —OMe | *—CMe₃ | H | 5-F |
| I-176 | H | 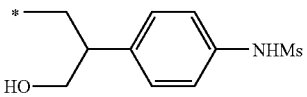 | —OMe | *—CMe₃ | H | H |
| I-177 | H | 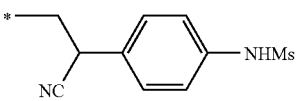 | —OMe | *—CMe₃ | H | H |
| I-178 | H | 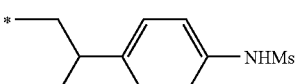 | —OMe | *—CMe₃ | H | H |
| I-179 | H | 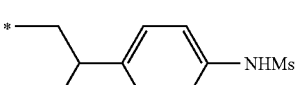 | —OMe | *—CMe₃ | H | H |
| I-180 | H | 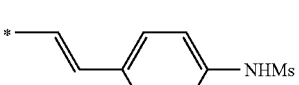 | —OMe | 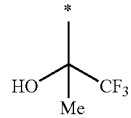 | H | H |
| I-181 | H | 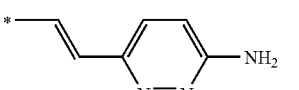 | OMe | *—CMe₃ | H | H |
| I-182 | H | 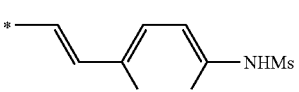 | —OMe | *—CMe₃ | H | H |
| I-183 | H | 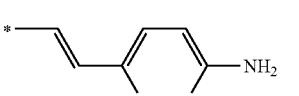 | —OMe | *—CMe₃ | H | 5-F |
| I-184 | H | 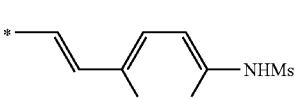 | —OMe | *—CMe₃ | H | 5-F |

TABLE I-continued
| | | | | | | |
|---|---|---|---|---|---|---|
| I-185 | H | 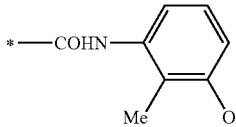 | —OMe | *—CMe₃ | H | H |
| I-186 | H | 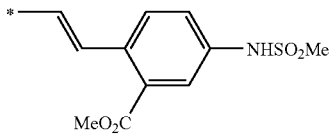 | —OMe | *—CMe₃ | H | 5-F |
| I-187 | H | 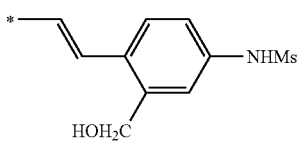 | —OMe | *—CMe₃ | H | 5-F |
| I-188 | H | 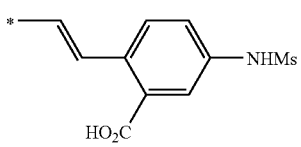 | —OMe | *—CMe₃ | H | 5-F |
| I-189 | H | 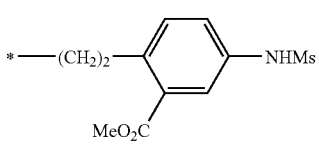 | —OMe | *—CMe₃ | H | 5-F |
| I-190 | H | 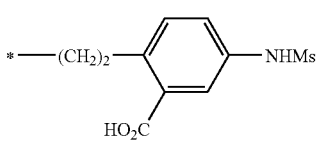 | —OMe | *—CMe₃ | H | 5-F |
| I-191 | H | 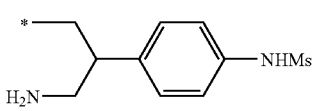 | —OMe | *—CMe₃ | H | H |
| I-192 | H | 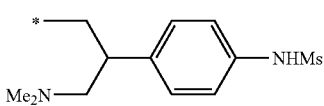 | —OMe | *—CMe₃ | H | H |
| I-193 | H | 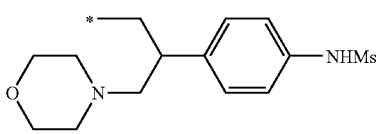 | —OMe | *—CMe₃ | H | H |
| I-194[2] | H | 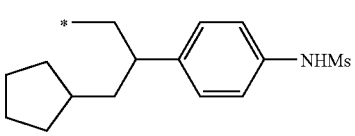 | —OMe | *—CMe₃ | H | H |
| I-195 | H | 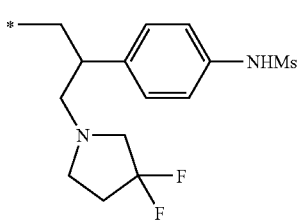 | —OMe | *—CMe₃ | H | H |

TABLE I-continued

| ID | Col1 | Col2 | Col3 | Col4 | Col5 | Col6 |
|---|---|---|---|---|---|---|
| I-196 | H | *—CH₂—C(Me)(CN)—C₆H₄—NHMs | —OMe | *—CMe₃ | H | H |
| I-197 | H | *—CH₂—C(Me)(CH₂NH₂)—C₆H₄—NHMs | —OMe | *—CMe₃ | H | H |
| I-198 | H | *—CH₂—C(Me)(CH₂OH)—C₆H₄—NHMs | —OMe | *—CMe₃ | H | H |
| I-199 | —OH | *—(CH₂)₂—C₆H₄—NHMs | H | *—C(Me)₂—CH₂OH | H | H |
| I-200 | H | *—CH=CH—C₆H₃(2-CN)—NHMs | —OMe | *—CMe₃ | H | 5-F |
| I-201 | H | *—CH=CH—C₆H₃(2-CO₂Me)—NHMs | —OMe | *—CMe₃ | H | 6-Me |
| I-202 | H | *—CH=CH—C₆H₃(2-CONMe₂)—NHMs | —OMe | *—CMe₃ | H | H |
| I-203 | H | *—CH=CH—C₆H₃(2-CO₂H)—NHMs | —OMe | *—CMe₃ | H | H |
| I-204 | H | *—CH=CH—C₆H₃(2-C(Me)₂OH)—NHMs | —OMe | *—CMe₃ | H | H |
| I-205 | H | *—CH=CH—C₆H₃(2-CH₂OH)—NHMs | —OMe | *—CMe₃ | H | H |
| I-206 | H | *—CH=CH—C₆H₃(2-CH₂OMe)—NHMs | —OMe | *—CMe₃ | H | H |

TABLE I-continued
| | | | | | | |
|---|---|---|---|---|---|---|
| I-207 | H | 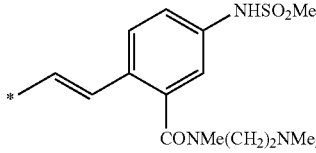 | —OMe | *—CMe₃ | H | 5-F |
| I-208 | H | 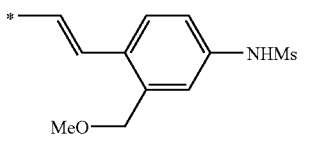 | —OMe | *—CMe₃ | H | 6-Me |
| I-209 | H | 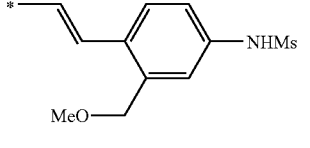 | —OMe | *—CMe₃ | H | 6-OMe |
| I-210 | H | 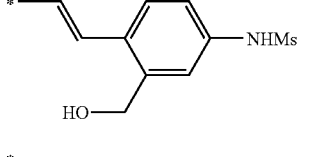 | —OMe | *—CMe₃ | H | 6-OMe |
| I-211 | H | 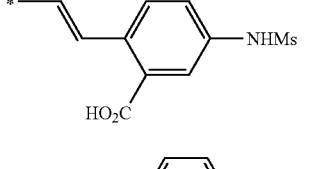 | —OMe | *—CMe₃ | H | 6—OMe |
| I-212 | —CN | 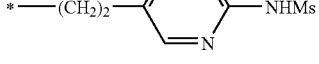 | H | *—CMe₃ | H | H |
| I-213 | H | 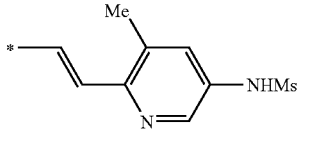 | —OMe | *—CMe₃ | H | H |
| I-214 | —OH | 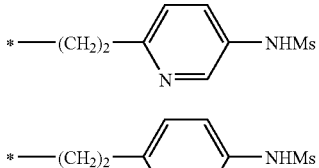 | H | *—CMe₃ | H | H |
| I-215 | —OH | 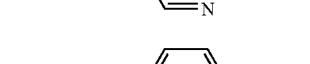 | H | *—CMe₃ | H | H |
| I-216 | —OH | 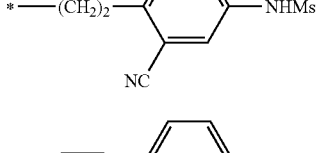 | H | *—CMe₃ | H | H |
| I-217 | —OH | 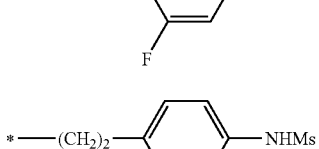 | H | *—CMe₃ | H | H |
| I-218 | —OH |  | —OMe | *—CMe₃ | H | H |

TABLE I-continued

| | | | | | | |
|---|---|---|---|---|---|---|
| I-219 | H | *—CH=CH—C₆H₃(NHMs)(O(CH₂)₂C(OH)Me₂) | —OMe | *—CMe₃ | H | 5-F |
| I-220 | H | *—CH=CH—C₆H₃(NHMs)(CH₂-N-oxazolidinone) | —OMe | *—CMe₃ | H | 5-F |
| I-221 | H | *—CH=CH—C₆H₃(NHMs)(CH₂NMe₂) | —OMe | *—CMe₃ | H | 5-F |
| I-222 | H | *—CH=CH—C₆H₃(NHMs)(CH₂-morpholine) | —OMe | *—CMe₃ | H | 5-F |
| I-223 | H | *—CH=CH—C₆H₄—NHMs | —OMe | *—CMe₃ | H | 6-CH(OH)Me |
| I-224 | H | *—CH=CH—C₆H₄—NHMs | —OMe | *—CMe₃ | H | 6-CH₂CN |
| I-225 | H | *—CH=CH—C₆H₄—NHMs | —OMe | *—CMe₃ | H | 6-MEM |
| I-226 | H | *—CH=CH—C₆H₄—NHMs | —OMe | *—CMe₃ | H | 5-Me |
| I-227 | H | *—CH=CH—C₆H₃(NHMs)(MeO(CH₂)₂) | —OMe | *—CMe₃ | H | 5-F |
| I-228 | H | *—CH=CH—C₆H₄—NHSO₂Et | —OMe | *—CMe₃ | H | 5-F |
| I-229 | H | *—CH=CH—(pyridyl)—NHSO₂CH₂CF₃ | —OMe | *—CMe₃ | H | 5-F |

TABLE I-continued
| | | | | | | |
|---|---|---|---|---|---|---|
| I-230 | H | 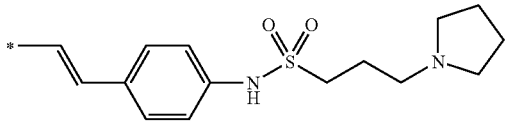 | —OMe | *—CMe₃ | H | 5-F |
| I-231 | H | 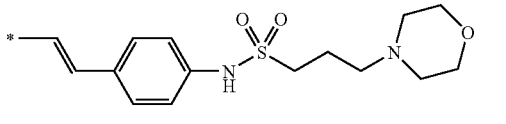 | —OMe | *—CMe₃ | H | 5-F |
| I-232 | H | 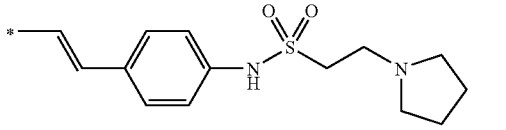 | —OMe | *—CMe₃ | H | 5-F |
| I-233 | H | 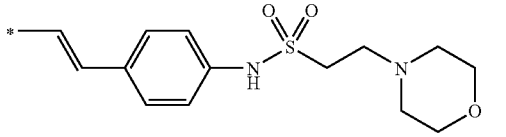 | —OMe | *—CMe₃ | H | 5-F |
| I-234 | H | 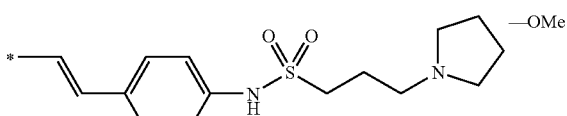 | —OMe | *—CMe₃ | H | H |
| I-235 | H | 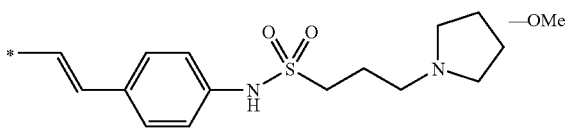 | —OMe | *—CMe₃ | H | 6-Me |
| I-236 | H | 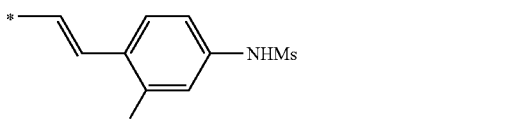 | —OMe | *—CMe₃ | H | 5-F |
| I-237 | H |  | —OMe | *—CMe₃ | H | H |
| I-238 | H | 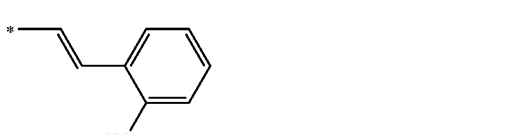 | —OMe | *—CMe₃ | H | H |
| I-239 | H |  | —OMe | *—CMe₃ | H | H |
| I-240 | H | 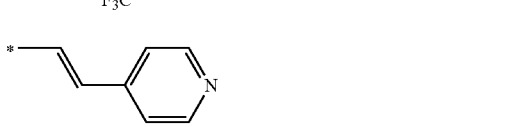 | —OMe | *—CMe₃ | H | H |
| I-241 | H | 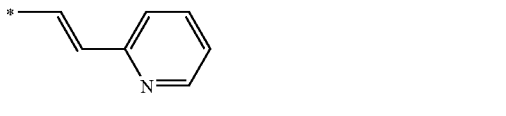 | —OMe | *—CMe₃ | H | H |

TABLE I-continued

| | | | | | | |
|---|---|---|---|---|---|---|
| I-242 | H | *-CH=CH-C6H4-(2-CO2Me) | —OMe | *—CMe3 | H | H |
| I-243 | H | *-CH=CH-C6H4-(3-CO2Me) | —OMe | *—CMe3 | H | H |
| I-244 | H | *-CH=CH-C6H4-(2-SO2Me) | —OMe | *—CMe3 | H | H |
| I-245 | H | *-CH=CH-(3-CN-pyridin-4-yl) | —OMe | *—CMe3 | H | H |
| I-246 | H | *-CH=CH-C6H4-(2-CO2H) | —OMe | *—CMe3 | H | H |
| I-247 | H | MeNHC(O)-(6-NH2-pyridin-3-yl) | —OMe | *—CMe3 | H | H |
| I-248 | H | MeNHC(O)-(6-NHCH2CF3-pyridazin-3-yl) | —OMe | *—CMe3 | H | H |
| I-249 | H | *-CH=CH-C6H4-(4-NHMs) | —OEt | *—CMe3 | H | H |
| I-250 | H | *-CH=CH-C6H4-(4-NHMs) | O(CH2)2OMe | *—CMe3 | H | H |
| I-251 | H | MeNHC(O)-C6H3-(4-NHCH2CF3)(3-F) | —OMe | *—CMe3 | H | H |
| I-252 | H | MeNHC(O)-C6H3-(4-OH)(2-F) | —OMe | *—CMe3 | H | H |
| I-253 | H | MeNHC(O)-C6H4-(4-NHCH2CF3) | —OMe | *—CMe3 | H | H |

TABLE I-continued

| | | | | | | |
|---|---|---|---|---|---|---|
| I-254 | H | 5-(N-methylcarbamoyl)-2-(2-methoxyethylamino)pyridine | —OMe | *—CMe₃ | H | H |
| I-255 | H | 5-(N-methylcarbamoyl)-2-(cyclopropylamino)pyridine | —OMe | *—CMe₃ | H | H |
| I-256 | H | 4-(cyclopropylamino)-N-methylbenzamide | —OMe | *—CMe₃ | H | H |
| I-257 | H | 4-(2-methoxyethylamino)-N-methylbenzamide | —OMe | *—CMe₃ | H | H |
| I-258 | H | *-CH=CH-(5-methylamino-pyridin-2-yl) | —OMe | *—C(CHF₂)(cyclopropyl) | H | H |
| I-259 | H | *—COHN-(3-NHMs-phenyl) | —OMe | *—CMe₃ | H | H |
| I-260 | H | *—COHN-(trans-4-NHMs-cyclohexyl) | —OMe | *—CMe₃ | H | H |
| I-261 | H | *-CH=CH-(5-NHMs-pyridin-2-yl) | —OMe | *—CMe₃ | H | 5-Cl |
| I-262 | H | *-CH=CH-(4-NHMs-phenyl) | —OMe | *—CMe₃ | H | 6-Me |
| I-263 | H | *-CH=CH-(4-NHMs-phenyl) | —OMe | *—C(Cl)(cyclopropyl) | H | 5-F |
| I-264 | H | *-CH=CH-(4-NHMs-phenyl) | —OMe | *—C(Cl)(cyclopropyl) | H | 5-Cl |
| I-265 | H | *-CH=CH-(4-NHMs-phenyl) | —OMe | *—C(Cl)(cyclopropyl) | H | 6-Me |
| I-266 | H | *-CH=CH-(4-NHMs-phenyl) | —OMe | *—C(OMe)(cyclopropyl) | H | H |

TABLE I-continued

| | | | | | | |
|---|---|---|---|---|---|---|
| I-267 | H | *-CH=CH-C6H4-NHMs | —OMe | *-(1-Cl-cyclopropyl) | H | H |
| I-268 | H | *-CH=CH-C6H4-NHMs | —OMe | *-(1-CN-cyclopropyl) | H | H |
| I-269 | H | *-CH=CH-C6H4-NHMs | —OMe | *-(1-CHF2-cyclopropyl) | H | 5-F |
| I-270 | H | *-CH=CH-C6H4-NHMs | —OMe | *-(1-CHF2-cyclopropyl) | H | H |
| I-271 | H | *-CH=CH-C6H4-NHMs | H | *-(1-F-cyclobutyl) | H | H |
| I-272 | H | *-CH=CH-C6H4-NHMs | H | *-C(Me)2CH2OH | H | H |
| I-273 | H | *-CH=CH-C6H4-NHMs | H | *-(1-Cl-cyclopropyl) | H | 5-F |
| I-274 | H | *-CH=CH-C6H4-NHMs | H | *-(1-Cl-cyclopropyl) | H | H |
| I-275 | H | *-CH=CH-C6H4-NHMs | H | *-(1-CHF2-cyclopropyl) | H | H |
| I-276 | H | *-NHCO-C6H3(2-O(CH2)2OMe)(4-NHMs) | —OMe | *—CMe3 | H | H |
| I-277 | H | *-NHCO-C6H4-NHAc | —OMe | *—CMe3 | H | H |
| I-278 | H | *-NHCO-C6H3(3-Me)(4-NH2) | —OMe | *—CMe3 | H | H |
| I-279 | H | *-NHCO-C6H3(3-CF3)(4-NH2) | —OMe | *—CMe3 | H | H |

TABLE I-continued

| | | 71 | | 72 | | |
|---|---|---|---|---|---|---|
| I-280 | H | *—NHCO—(2-F,4-NH₂-phenyl) | —OMe | *—CMe₃ | H | H |
| I-281 | H | *—NHCO—(2-F,4-NHMs-phenyl) | —OMe | *—CMe₃ | H | H |
| I-282 | H | *—NHCO—(2-Me,4-NHMs-phenyl) | —OMe | *—CMe₃ | H | H |
| I-283 | H | *—NHCO—(5-NH₂-pyridin-2-yl) | —OMe | *—CMe₃ | H | H |
| I-284 | H | *—NHCO—(2-O(CH₂)₂NMe₂,4-NH₂-phenyl) | —OMe | *—CMe₃ | H | H |
| I-285 | H | *—NHCO—(2-O(CH₂)₂NMe₂,4-NHMs-phenyl) | —OMe | *—CMe₃ | H | H |
| I-286 | H | *—NHCO—(4-NHMs-phenyl) | —OMe | *—CMe₃ | H | 6-Me |
| I-287 | H | *—(CH₂)₂—(4-NHMs-phenyl) | —OMe | *—CMe₃ | F | H |
| I-288 | H | *—CH=CH—(4-NHMs-phenyl) | —OMe | *—C(Me)₂CH₂OH | H | H |
| I-289 | H | *—CH=CH—(4-NHMs-phenyl) | —OMe | *—C(Me)₂OMe | H | H |
| I-290 | H | *—CH=CH—(4-NHMs-phenyl) | —OMe | *—(3-Me-oxetan-3-yl) | H | H |
| I-291 | H | *—CH=CH—(4-NHMs-phenyl) | —OMe | *—(3-Me-oxetan-3-yl) | H | 5-Cl |
| I-292 | H | *—CH=CH—(5-NHMs-pyridin-2-yl) | —OMe | *—cyclopropyl | H | 5-Cl |

TABLE I-continued
| I-293 | H | *—NMeCO—C₆H₄—NHMs | H | *—CMe₃ | H | H |
II-1 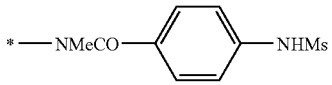
II-2 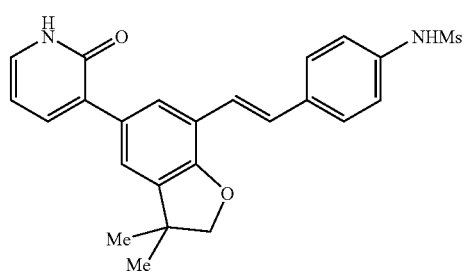
II-3 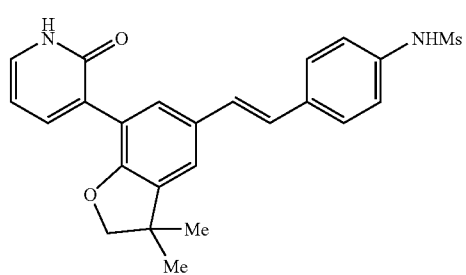
II-4 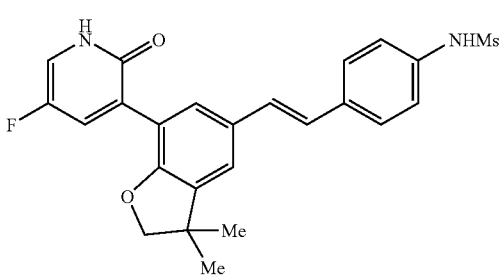
II-5 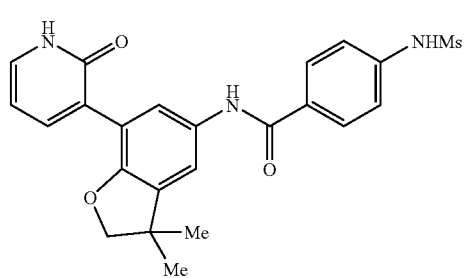

TABLE I-continued

II-6
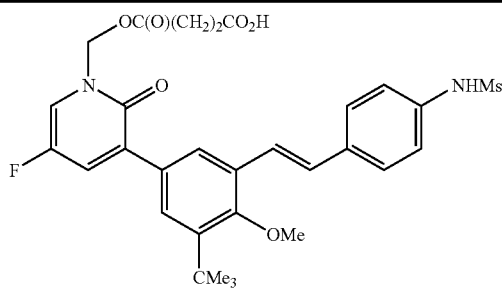

II-7
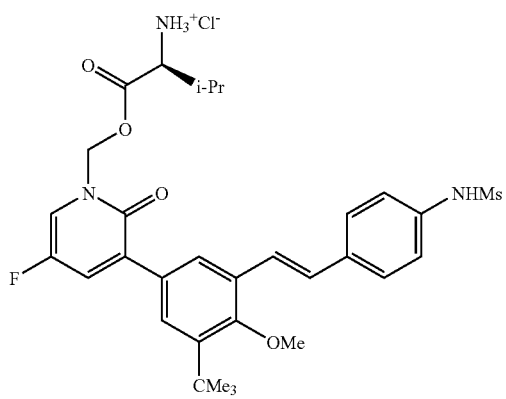

II-8
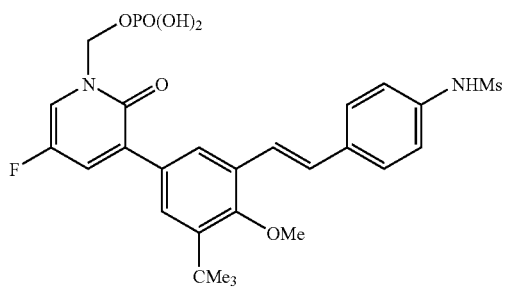

II-9
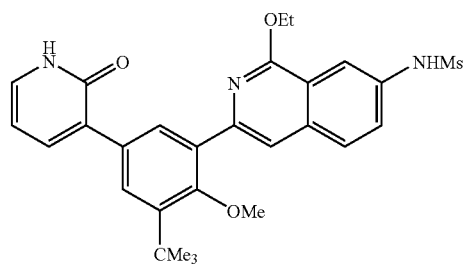

[1]MEM = CH₂O(CH₂)₂OMe
[2]Ms = SO₂Me

Compounds in following schemes are frequently depicted with generalized substituents to exemplify the general nature of the methodology. One skilled in the art will immediately appreciate that the nature of the R groups can varied to afford the various compounds contemplated in this invention. Moreover, the reaction conditions are exemplary and alternative conditions are well known which can be substituted for the conditions described herein. The reaction sequences in the following examples are not meant to limit the scope of the invention as set forth in the claims.

SCHEME A

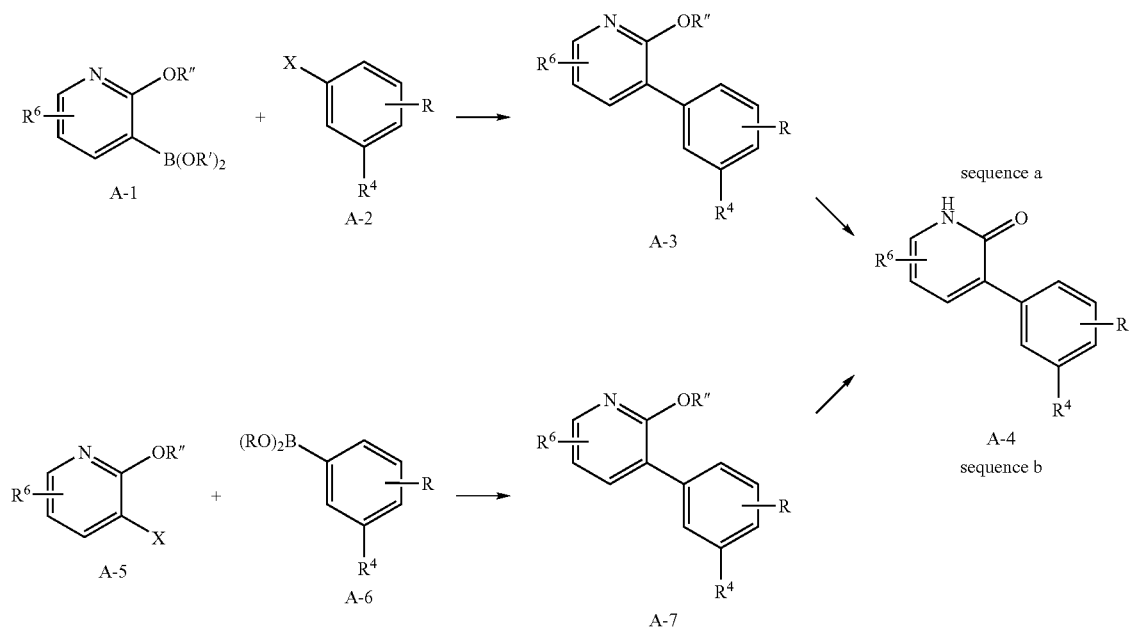

3-Phenyl-1H-pyridin-2-one derivatives were prepared by Suzuki coupling of the 2-alkoxy-pyridin-3-yl boronic acid or boronic acid ester (A-1) an aryl ring substituted with a leaving group as depicted in sequence a of SCHEME A. Subsequent cleavage of the O—R" bond affords the desired pyridone. The coupling can also be accomplished as depicted in sequence b wherein the boronic acid and the leaving group are interchanged. Both between sequence a and sequence b can be adopted and the optimal route frequently is determined by the availability of the requisite starting materials.

The Suzuki reaction is a palladium-catalyzed coupling of a boronic acid with an aryl or vinyl halide or triflate. Typical catalysts include $Pd(PPh_3)_4$, $PdCl_2(dppf)$, $Pd(OAc)_2$ and $PdCl_2(PPh_3)_2$. With $PdCl_2(dppf)$, primary alkyl borane compounds can be coupled to aryl or vinyl halide or triflate without beta-elimination. The reaction can be carried out in a variety of organic solvents including toluene, THF, dioxane, DCE, DMF, DMSO and MeCN, aqueous solvents and under biphasic conditions. Reactions are typically run from about RT to about 150° C. Additives (e.g., CsF, KF, TlOH, NaOEt and KOH) frequently accelerate the coupling. Although there are numerous components in the Suzuki reaction such as the particular palladium catalyst, the ligand, additives, solvent, temperature, numerous protocols have been identified. Highly active catalysts have been described (see, e.g., J. P. Wolfe et al., *J. Am. Chem. Soc.* 1999 121(41):9550-9561 and A. F. Littke et al., *J. Am. Chem. Soc.* 2000 122(17):4020-4028). One skilled in the art will be able to identify a satisfactory protocol without undue experimentation.

SCHEME B

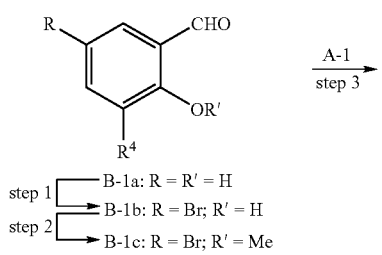

-continued

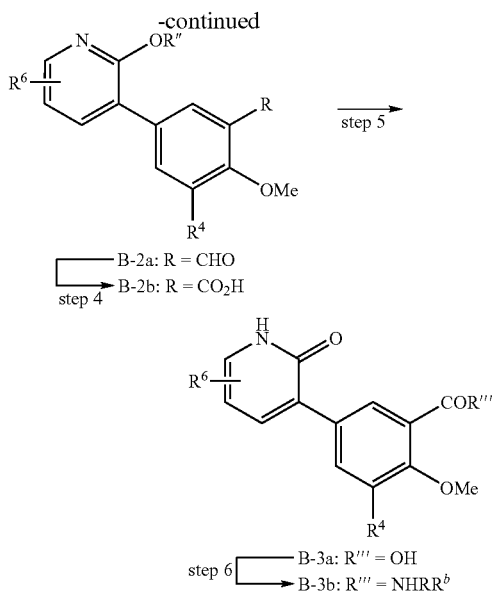

3-Alkyl-2-methoxy-5-(2-oxo-1,2-dihydro-pyridin-3-yl)-benzamide derivatives (B-3b) were prepared by Suzuki coupling (step 3) of A-1 (R'═H, R"═$C_{1-6}$ alkyl or benzyl) and a 2-alkoxy-3-alkyl-5-bromo-benzaldehyde derivative B-1c which is, in turn, available by bromination of a substituted salicylaldehyde (step 1). Oxidation of the aldehyde affords carboxylic acid B-3a which is condensed with an amine to afford the desired amide. Compounds wherein $R^3$ is hydrogen can be prepared from 3-alkyl-benzaldehydes.

Oxidation of an aldehyde to a carboxylic acid is carried out under a variety of conditions is readily accomplished with a variety of oxidizing agents including potassium permanganate, chromic acid, silver oxide. (Haines, Methods for the oxidation of Organic Compounds; Academic Press: New York, 1988, pp 241-263 and 423-428; Houben-Weyl, "Aldehydes" J. Farbe Ed. *Methoden der Organischen Chemie*, Bd E 3, Thieme Verlag, Stuttgart 1983 p 634-635; J. March, *Advanced Organic Chemistry*, John Wiley & Sons: New York, N.Y., 1992, pp. 701-703) Sodium Chlorite has proven to be a useful reagent for oxidation of aldehydes to acids. (B. Lindgren and T. Nilsson, *Acta Chem. Scand.* 1973 27:888; S. B. Balkrishna et al. *Tetrahedron* 1981 37:2091-2096; E. Dalcanale and F. Montanari, *J. Org. Chem.* 1986 51:567-569)

Transformation of a carboxylic acid to an amide can be accomplished utilizing an activated carboxylic acid such as an acid chloride or a symmetrical or mixed acid anhydride and reacting the activated derivative with an amine in a solvent such as DMF, DCM, THF, with or without water as a co-solvent, at temperatures between 0° and 60° C. generally in the presence of a base such as $Na_2CO_3$, $NaHCO_3$, $K_2CO_3$, DIPEA, TEA or pyridine to afford an amide. Carboxylic acids are converted into their acid chlorides using standard reagents well known to those skilled in the art, such as thionyl chloride, oxalyl chloride, phosphoryl chloride. Those reagents can be used in presence of bases such as DIPEA, TEA or pyridine in an inert solvent such as DCM or DMF.

Alternatively a carboxylic acid can be converted in situ into activated acids utilizing peptide coupling protocols known to those skilled in the art. These activated acids were reacted directly with the amines to afford amides. Said activation can involve the use of an activating agent like EDIC or DCC, HOBt, BOP, PyBrOP or 2-fluoro-1-methylpyridinium p-toluenesulphonate (Mukaiyama's reagent), with or without a base such NMM, TEA or DIPEA, in an inert solvent such as DMF or DCM at temperatures between 0° C. and 60° C. The reaction may alternatively be carried out in presence of O-(7-azabenzotriazol-1-yl)-N,N,N',N'-tetramethyluronium hexafluorophosphate (HATU) or 1-hydroxy-7-azabenzotriazole (HOAt) and TEA or DIPEA in DMF, DCM or THF. (Organic Synthesis, E. Winterfeldt, ed., vol. 6, Pergamon Press, Oxford 1991 pp. 381-411; see R. C. Larock, *Comprehensive Organic Transformations—A Guide to Functional Group Preparations,* 1989, VCH Publishers Inc., New York; pp. 972-976)

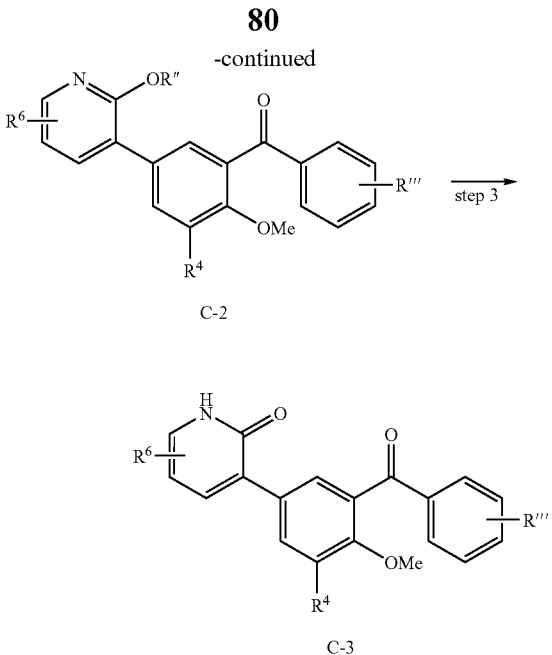

3-(5-Alkyl-3-benzoyl 4-methoxy-phenyl)-1H-pyridin-2-one derivatives C-3 were prepared by contacting an aryl lithium or aryl Grignard reagent with B2a. One skilled in the art will appreciate that, depending upon the nature of the R''' substituent, there may be a need to for a protecting group to permit efficient formation of the aryl organometallic reagent. Oxidation of the resulting secondary alcohol C-1 (step 2) affords the desired ketone followed by dealkylation (step 3) and liberation of the pyridone moiety.

Oxidation of an alcohol to a ketone is typically carried out in solvents such as DMF, NMP, DMSO, THF, dioxane, and DCM at temperatures between 0° C. and 100° C. Typically used reagents are pyridinium dichromate in DCM (E. J. Corey, et al., *Tetrahedron Lett.* 1979 399), DMSO/oxalyl chloride in DCM (Omura, et al., *Tetrahedron* 1978 34:1651), pyridine-sulfur trioxide complex, Dess-Martin periodinane (D. B. Dess, and J. C. Martin, *J. Org. Chem.* 1983 48:4155-4156) or 2-iodoxybenzoic acid (Robert K. Boeckman, Jr., et al. *Collective Volume* 2004 10:696). Benzyl and allylic alcohols are conveniently oxidized with manganese (IV) dioxide.

SCHEME C

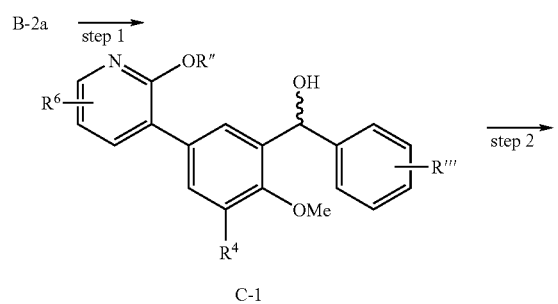

SCHEME D

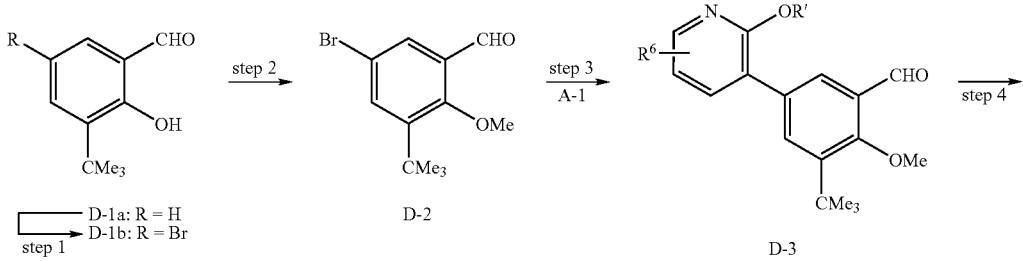

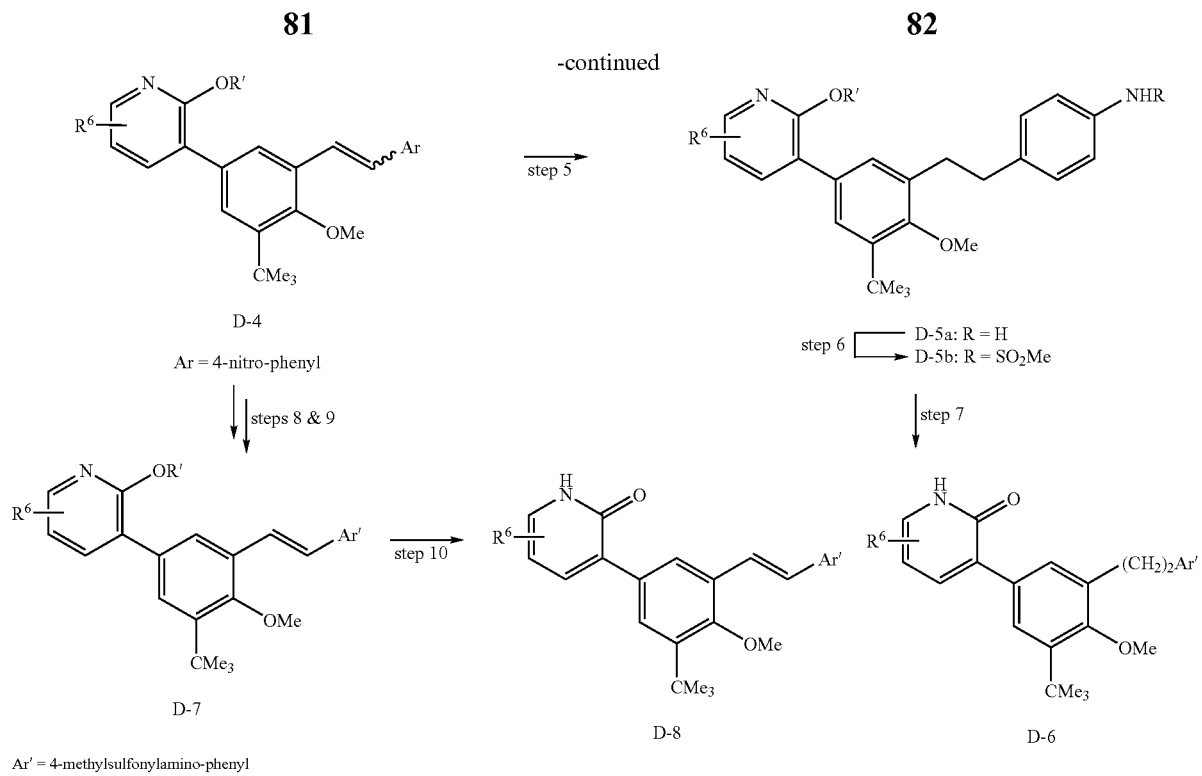

3-(3-tert-Butyl-4-methoxy-5-phenethyl-phenyl)-1H-pyridin-2-ones (e.g., D-6) and 3-[3-tert-butyl-4-methoxy-5-((E)-styryl)-phenyl]-1H-pyridin-2-ones (e.g. D-8) can be prepared from D-2 which in turn is prepared from 3-tert-butyl-2-hydroxy-benzaldehyde (D-1a) by bromination of the 5-position with elemental bromine and alkylation of the phenol to afford D-2. Alkylation of phenol is typically carried out in solvents like DMF, THF, NMP, MeCN, acetone, DCM and DCE, at temperatures between 0° C. and 100° C. Typically used bases are $K_2CO_3$, sodium hydride, lithium hexamethyldisilazide, sodium hexamethyldisilazide and potassium hexamethyldisilazide in conjunction with alkylating agents such as alkyl halides, alkyl mesylates and alkyl triflates to afford D-2. Suzuki coupling of D-2 with a 2-alkoxy- or 2-benxyloxy-pyridin-3-yl boronic acid (A-1) affords D-3.

3-[3-tert-Butyl-4-methoxy-5-((E)-styryl)-phenyl]-1H-pyridin-2-ones (e.g. D-8)1 are prepared from D-3 utilizing a Wittig homologation with benzyl-triphenyl-5-phosphane or a substituted analog thereof (step 4).

The Wittig reaction is the reaction of an aldehyde or ketone with a triphenyl phosphonium ylide to afford an alkene and triphenylphosphine oxide. (A. Maercker, Org. React. 1965, 14, 270-490; A. W. Carruthers, Some Modern Methods of Organic Synthesis, Cambridge University Press, Cambridge, UK, 1971, pp 81-90) Wittig reactions are most commonly used to condense aldehydes or ketones to singly substituted phosphine ylides. The Wittig reagent is usually prepared from a phosphonium salt, which is, in turn, prepared by alkylation of $Ph_3P$ with an alkyl halide. To form the Wittig reagent (ylide), the phosphonium salt is suspended in a solvent such as $Et_2O$ or THF and a strong base such as phenyl lithium or n-butyllithium is added. With simple ylides, the product is usually mainly the Z-isomer, although a lesser amount of the E-isomer also is often formed. This is particularly true when ketones are used. If the reaction is performed in DMF in the presence of LiI or NaI, the product is almost exclusively the Z-isomer. If the E-isomer is the desired product, the Schlosser modification may be used. Alternatively The Horner-Wadsworth-Emmons reaction (B. E. Maryanoff and A. B. Reitz, Chem Rev. 1989 89:863-927) produces predominantly E-alkenes. The Horner-Wadsworth-Emmons reaction (HWE reaction) is the condensation of stabilized phosphonate carbanions with aldehydes (or ketones). In contrast to phosphonium ylides used in the Wittig reaction, phosphonate-stabilized carbanions are more nucleophilic and more basic.

Compounds encompassed by the present invention wherein $R^2$ is an optionally substituted amino-phenylethyl moiety can be prepared from a nitrobenzyl phosphonate. Thus condensation of D-3 and diethyl (4-nitro-benzyl)-phosphonate and subsequent reduction of the nitro substituent (step 5) affords the amine D-5a. Suitable reducing agents include, e.g., $LiAlH_4$, $LiBH_4$, Fe, Sn or Zn, in a reaction inert solvent, e.g. MeOH, EtOH, diglyme, benzene, toluene, xylene, o-dichlorobenzene, DCM, DCE, THF, dioxane, or mixtures thereof. If desired, when the reducing reagent is Fe, Sn or Zn, the reaction is carried out under acidic conditions in the presence of water. Catalytic hydrogen allows concomitant reduction of the styrene and the nitro substituent. Alternatively, an optionally substituted benzyl-triphenyl-$\lambda^5$-phosphane can be condensed with D-3 and similarly converted to an optionally substituted phenylethyl moiety. Sulfonylation or acylation of the resulting amine, if desired, is carried out by treating the amine with an activated carboxylic acid or a sulfonyl halide.

Compounds wherein $R^2$ is an ((E)-styryl)-phenyl moiety also be prepared by condensation of substituted toluene derivatives with D-3. This is most practical when toluene is substituted with electronegativity groups which increase the acidity of protons on the methyl group and allow formation of the which adds to the carbonyl and undergoes subsequent dehydration of the initially formed carbinol. (see e.g., example 38)

SCHEME E

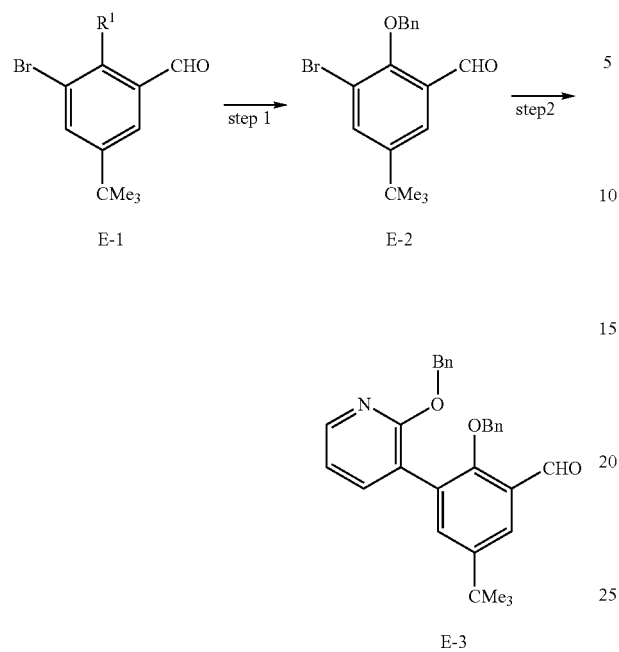

SCHEME F

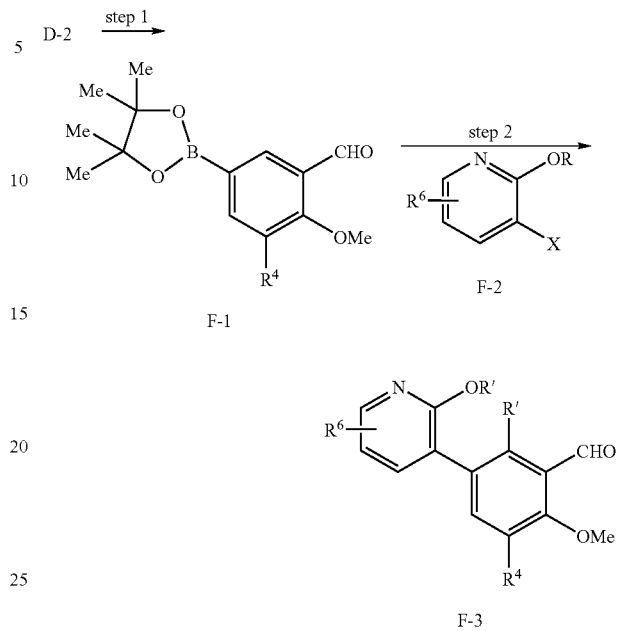

The preparation of compounds of the present invention substituted at the 2-position can be prepared by an analogous sequence starting with E-1. When $R^1$ is a hydroxyl group, the acidic phenol is conveniently protected as a benzyl ether. Incorporation of the latent pyridone as a benzyloxy-pyridine allows concomitant removal of the two benzyl ethers and reduction of the olefin. Alternatively, incorporation of the latent pyridone as a methoxy-pyridine permits stepwise debenzylation and demethylation (see e.g., example 7) One skilled in the art will appreciate other functional groups can be used if desired. Other compounds wherein $R^1$ is alkoxy or substituted alkoxy within the scope of the present invention can be prepared by alkylation of the phenol prior to step 2 with a suitable alkylating agent. Conversion of E-3 to the final product is carried out as depicted in SCHEME D. 3-[3-tert-Butyl-4-methoxy-5-((E)-styryl)-phenyl]-1H-pyridin-2-ones can be prepared by selective hydrogenolysis of the benzyl ethers in the presence of the olefin. (see e.g., example 50).

Introduction of substituents at the 2-position is accomplished starting from 2,6-dibromo-4-tert-butylaniline. An acylamino group is readily prepared by acylation of the amine followed by introduction of the. Introduction of the pyridone and the $R^2$ group can be easily accomplished with step-wise palladium-catalyzed cross-coupling chemistry. The pyridones are introduced as discussed previously and a two-carbon side chain can be incorporated with Sonogashira couplings as illustrated in SCHEME H or Suzuki coupling as illustrated in SCHEME R. Cyano substitution can be introduced by subjecting the aniline to Sandmeyer conditions and displacing the diazonium salt with cyanide. Hydrolysis of the nitrile under standard conditions affords carboxyl, alkoxycarbonyl or carbamoyl substituents.

When it was convenient to incorporate the boronic acid on the benzene ring instead of the pyridine ring (SCHEME A, sequence b), D-2 was contacted with 4,4,5,5,4',4',5',5'-octamethyl-[2,2']bis-[1,3,2]dioxaborolanyl] to afford F-1 which was subject to a Suzuki-type coupling with an appropriately substituted 2-alkoxy-pyridine F-2 wherein X is halo, trifluorosulfonyloxy or toluenesulfonyloxy to afford F-3 which is carried on to the final products as depicted in the disclosed schemes.

SCHEME G

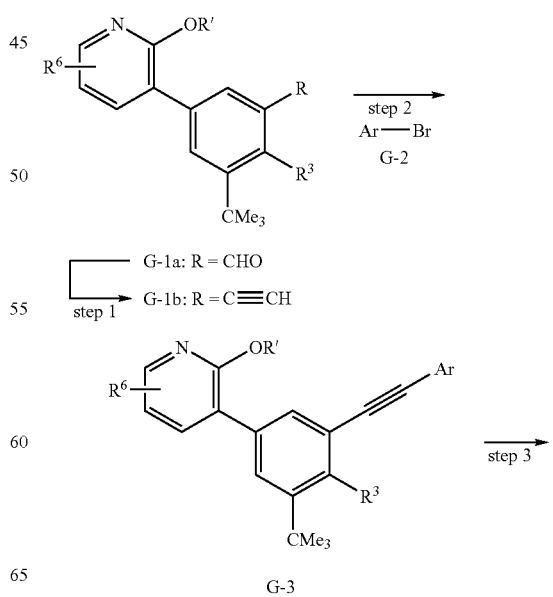

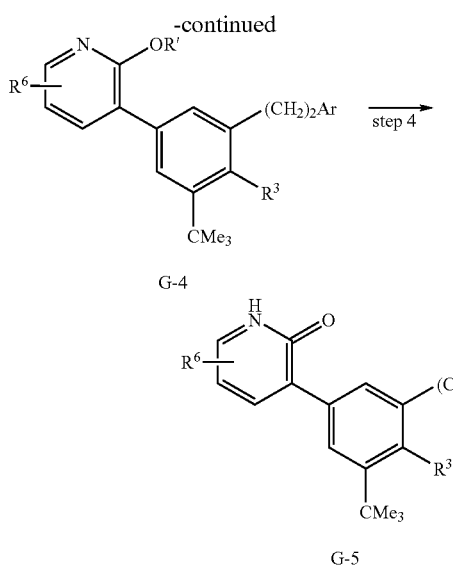

G-4

G-5

Ar = 4-methanesulfonylamino-phenyl

Alternately, the phenylethyl side chain can be elaborated by converting the aldehyde G-1a to the acetylene G1b and coupling an aryl halide such as N-(4-bromo-phenyl)-methanesulfonamide (G-2) or other appropriately substituted halo- or trifluorosulfonyloxy-benzene to afford G3 (i.e., a Sonogashira coupling). Numerous substituted aryl or heteroaryl iodides can be used advantageously. Reduction of the acetylene is carried out by conventional techniques and dealkylation of the pyridinyl ether affords the desired pyridone. The acetylene is prepared by condensing G-1a with (1-diazo-2-oxo-propyl)-phosphonic acid diethyl ester. (R. Muller et al. *Syn Lett* 1996 6:521)

The Sonogashira coupling (K. Sonogashira et al., *Tetrahedron Lett.* 1975 4467-4470; K. Sonogashira, *Comprehensive Organic Synthesis*; B. M. Trost and I. Fleming Eds.; Pergamon Press, Oxford, 1991; Vol. 3, Chapter 2.4, p 521) is typically carried out in the presence of a palladium catalyst such as $Pd(PPh_3)_4$ or $Pd(II)Cl_2(PPh_3)_2$ and a cuprous salt, for example CuI, a dialkyl- or trialkylamine such as diethylamine, diisopropylamine, TEA and the like at temperature from RT to 100° C. The reaction can be carried out using the amine base as the solvent or with other organic solvents including hydrocarbons, ethers, alcohols, aqueous DMA and the like. The existence of alternative procedures affords flexibility in the synthetic planning permitting introduction of a variety of substituted aryl and heteroaryl substituents. The Hiyama coupling is a related palladium catalyzed cross-coupling of a trialkoxysilyl acetylene, a trifluorosilylacetylene or a trialkylsilylacetylene and an aryl halide and an aryl halide which can be utilized to prepare compounds of the present invention. (Y. Hatanaka and T. Hiyama, *J. Org. Chem.* 1988 53(4):918-920; N. A. Strotman et al., *Angew. Chem. Int. Ed.*, 2007, 46:3556-3558).

SCHEME H

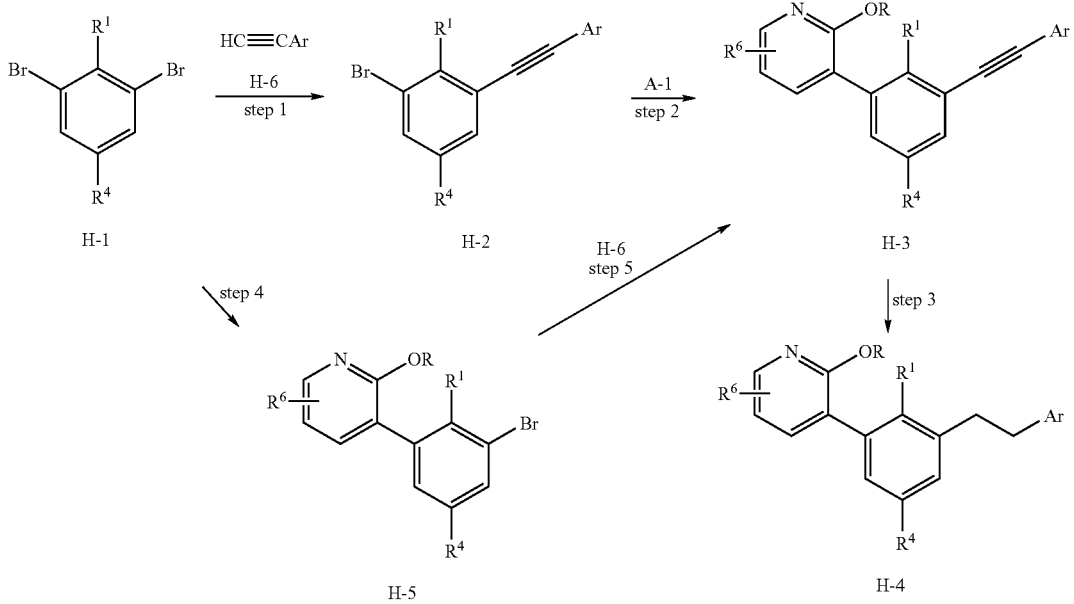

Ar = 4-methanesulfonylamino-phenyl

The phenylethyl side chain can be introduced as a single unit by employing a Sonogashira-type coupling of a phenyl acetylene such as H-6 and the aryl bromide H-1 (SCHEME H). Introduction of the protected pyridone ring by Suzuki-type coupling of A-1 affords H-3 which can be converted to the desired compounds using procedures described previously. The sequence of the steps is flexible and thus the Suzuki coupling can be carried out first to afford H-5 which is then converted to the diaryl acetylene H-3.

SCHEME K

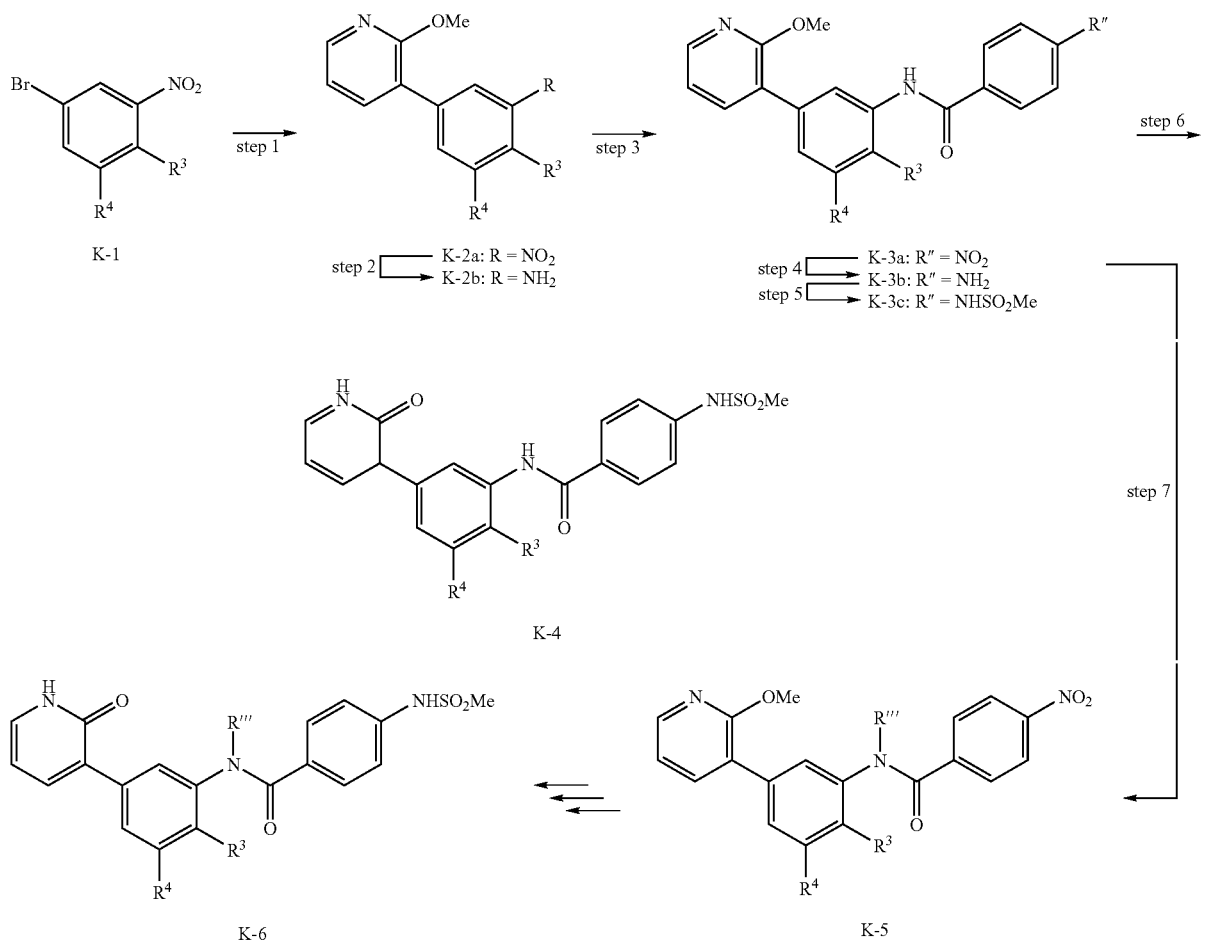

N-[3-(2-Oxo-1,2-dihydro-pyridin-3-yl)-phenyl]-benzamides encompassed by the present can be prepared from invention can be prepared from 3-bromo-nitrobenzenes derivatives such as 1-bromo-3-tert-butyl-5-nitro-benzene (CASRN 156264-79-8) and 5-bromo-1-tert-butyl-2-methoxy-3-nitro-benzene (CASRN 474554-50-2) as depicted in SCHEME K. Introduction of the pyridone ring is accomplished by a Suzuki coupling as described in SCHEME A. Substitution on the benzamide can be introduced prior to the amide coupling step (step 3) or by modification of the benzamide substituents after the coupling. N-substituted compounds can be prepared by alkylation of K-3a to afford K-5 which can be further modified as described previously.

Reduction of a nitro group to an amine is typically carried out with a reducing agent in an inert solvent, e.g. MeOH, EtOH, EtOAc, THF or mixtures thereof. The reduction may be carried out by hydrogenation in the presence of a metal catalyst, e.g. nickel catalysts such as Raney nickel, palladium catalysts such as Pd/C, platinum catalysts such as $PtO_2$, or ruthenium catalysts such as $RuCl_2(Ph_3P)_3$ under $H_2$ atmosphere or in the presence of hydrogen sources such as hydrazine or formic acid. If desired, the reaction is carried out under acidic conditions, e.g. in the presence of HCl or HOAc. The reduction may also be carried out in the presence of a suitable hydride reducing agent, e.g. $LiAlH_4$, $LiBH_4$, Fe, Sn or Zn, in a reaction inert solvent, e.g. MeOH, EtOH, diglyme, benzene, toluene, xylene, o-dichlorobenzene, DCM, DCE, THF, dioxane, or mixtures thereof; or without solvent. If desired, when the reducing reagent is Fe, Sn or Zn, the reaction is carried out under acidic conditions in the presence of water.

SCHEME L

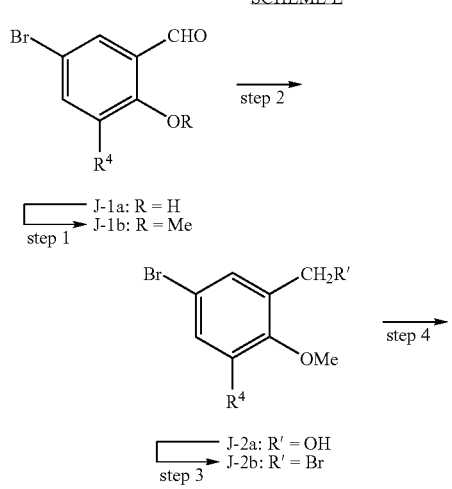

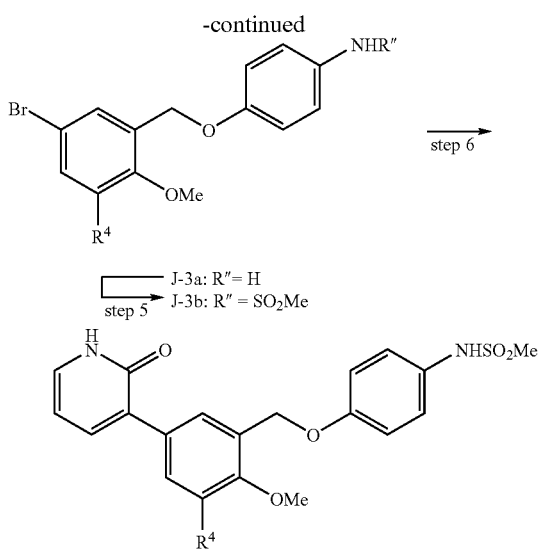

4-[5-(2-Oxo-1,2-dihydro-pyridin-3-yl)-benzyloxy]-phenyl derivatives were prepared by alkylation of a 2-bromobenzyl bromide (J-2b) and subsequent introduction of the pyridone by Suzuki-coupling with 2-oxo-1,2-dihydropyridine-3-boronic acid as depicted in SCHEME L. One skilled in the art will appreciate that a multitude of variously substituted phenols are accessible and can be used in place of N-(4-hydroxy-phenyl)-methanesulfonamide which is shown above as an exemplification, not a limitation of the invention.

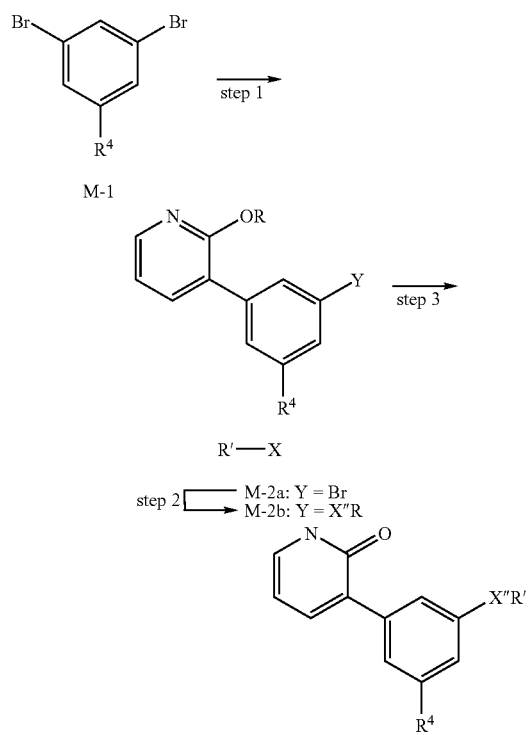

Introduction of an aryl ether or arylsulfone at the 3-position of phenyl-1H-pyridin-2-ones can be accomplished by palladium catalyzed displacement of a halogen or triflate. Palladium-catalyzed C—O coupling of unactivated aryl halides with alcohols and phenols has been reported. (M. Palucki et al., *J. Am. Chem. Soc.* 1997 119(14):3395-96; G. Mann et al., *J. Am. Chem. Soc.* 1999 121(13):3224-3225) Similarly, palladium catalyzed coupling of aryl halides and triflates and aryl sulfinic acids affords diaryl sulfones. (S. Cacchi et al., *J. Org. Chem.* 2004 69(17):5608-14; S. Cacchi et al., *Synlett* 2003 3:361) Introduction of an aralkyl or alkyl group at the 3-position of phenyl-1H-pyridin-2-ones can be accomplished by utilizing the Negishi coupling. (E.-I. Negishi, *Acc. Chem. Res.* 1982 15:340-348) The Negishi reaction is catalyzed by palladium Pd(0) and palladium is preferably ligated to a bidentate ligand including Pd(dppf)Cl$_2$ and Pd(dppe)Cl$_2$. (J. M. Herbert *Tetrahedron Lett.* 2004 45:817-819) Typically the reaction is run an inert aprotic solvent and common ethereal solvents include dioxane, DME and THF are suitable. The reaction is commonly run at elevated temperature.

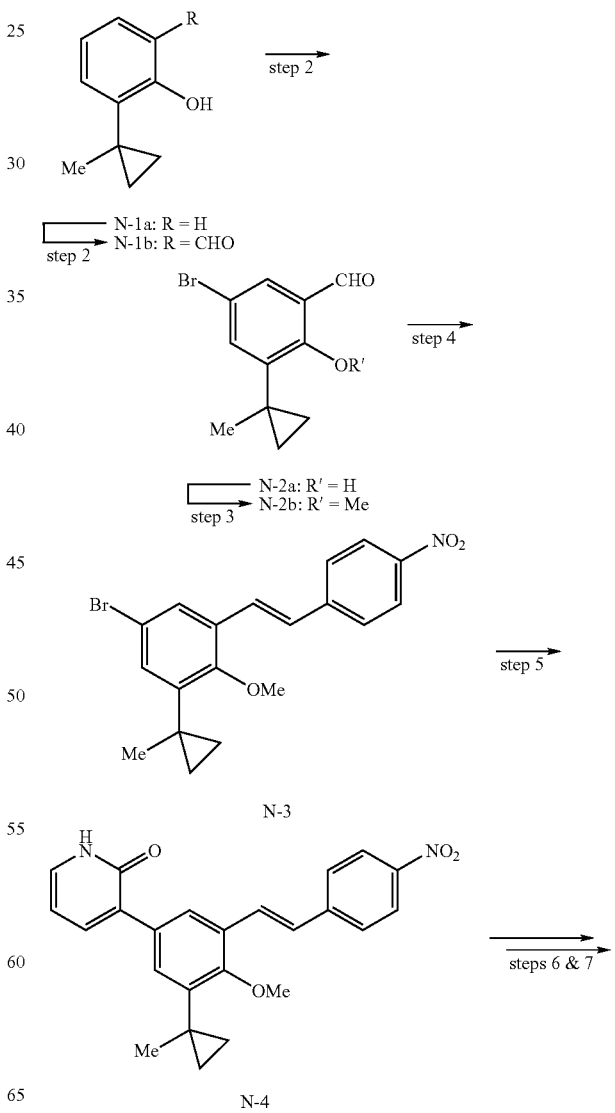

Compounds encompassed by the present invention with a 1-methyl-cyclopropy substituent were prepared from 2-(1-methyl-cyclopropyl)-phenol (CASRN 4333684-77-6) as depicted in SCHEME N. 3-[3-(1-Methyl-cyclobutyl)-phenyl]-1H-pyridin-2-one and 3-[3-(1-methyl-cyclopentyl)-phenyl]-1H-pyridin-2-one compounds encompassed by the present invention are prepared by condensation of an aryl Grignard reagent with a cycloalkanone and conversion of the resulting tertiary alcohol to a tertiary alkane as depicted in SCHEME O. Replacement of the carbinol with an alkyl is carried out with TiCl4 and a dialkylzinc as described in step 1 of example 21. Introduction of a boronic acid ester, palladium-mediated coupling with a 2-benzyloxy-3-bromopyridine and debenzylation of the ether group results in the elaboration of the pyridone ring.

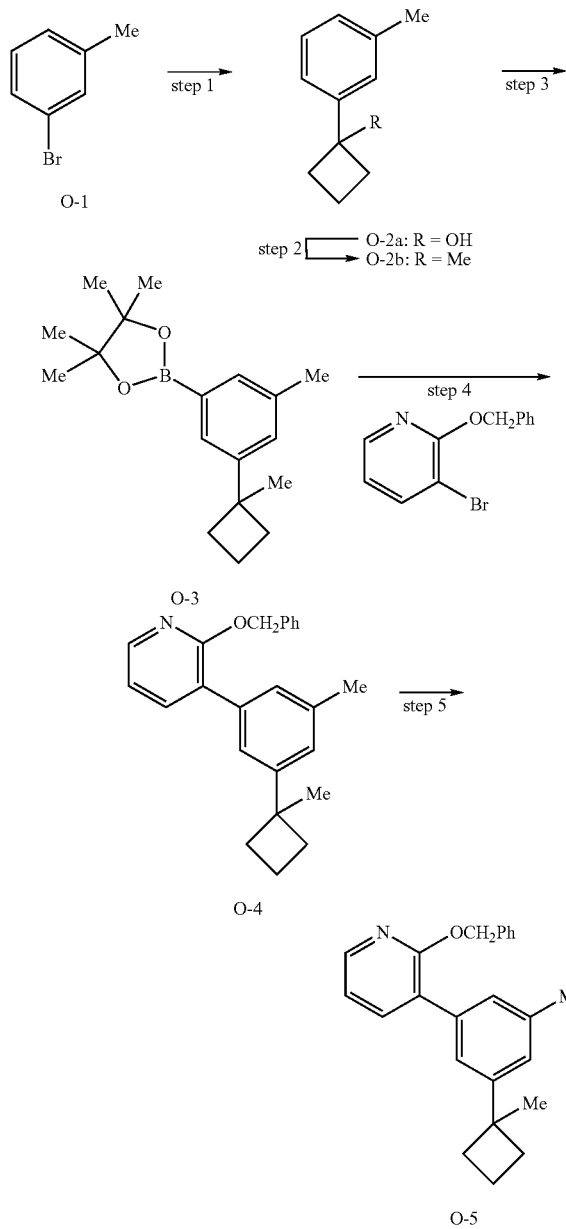

Phenylethyl substituted compounds encompassed by present invention containing substitution on alkylene linkage can be prepared by the condensation of a substituted phenyl-acetonitrile derivative with D-2 to afford P-1. Reduction of the olefin and nitro group, if present, affords P-3a which in the present example is sulfonylated. The cyano substituent can be converted to other functional groups by hydrolysis or reduction to the corresponding carboxyaldeyde which can be converted to the carboxylic acid and subsequently condensed with an amine or reduced to the corresponding primary alcohol. Representative examples are illustrated in TABLE I.

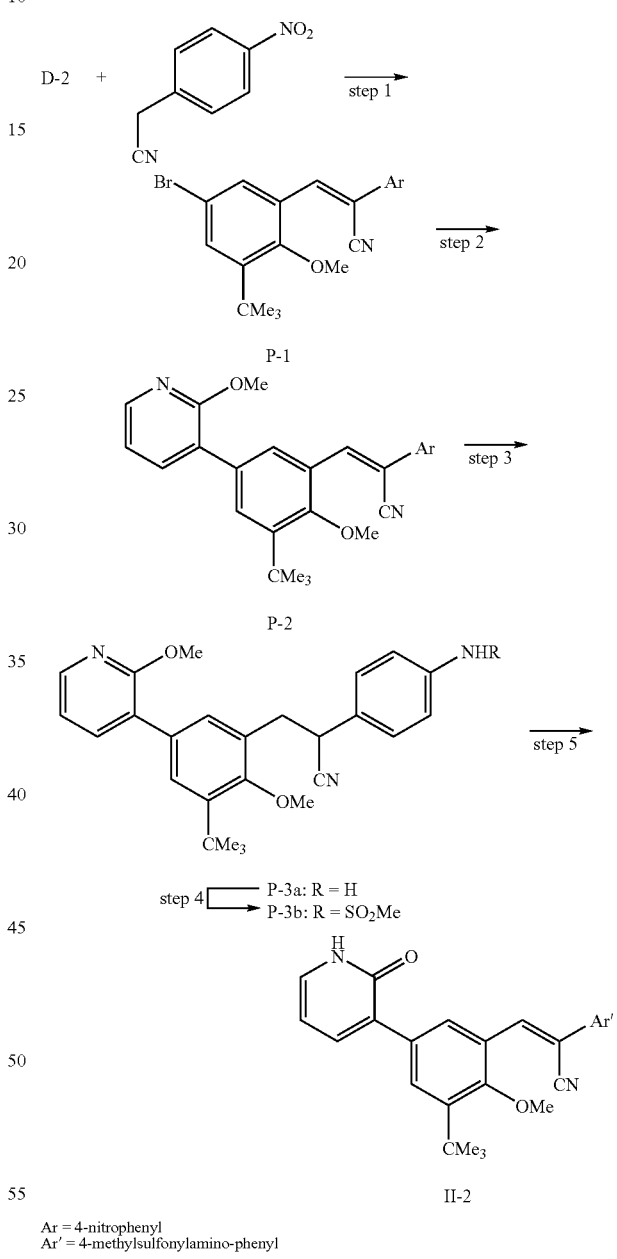

Ar = 4-nitrophenyl
Ar' = 4-methylsulfonylamino-phenyl

Compounds of the present invention with a dialkylaminoethyl substituent are accessible from by reductive amination [5-(2-benzyloxy-pyridin-3-yl)-3-tert-butyl-2-methoxy-phenyl]-acetaldehyde Q-1b which can be prepared by Wittig homologation of D-3 with methoxymethylene-triphenyl-$\lambda^5$-phosphane and hydrolysis of the resulting enol ether Q-1a. Reductive amination with a primary or secondary amine affords Q-1c which can be converted to the pyridone by hydrogenolysis or by acid hydrolysis.

SCHEME Q

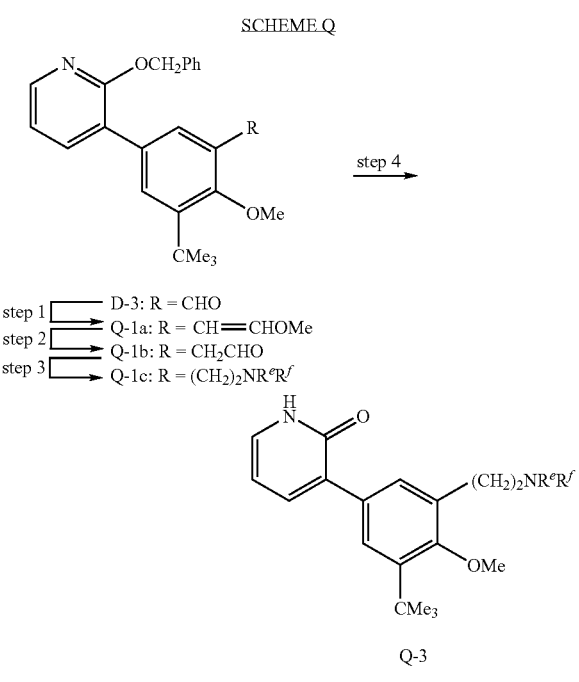

Reductive amination is typically carried out by combining an amine and carbonyl compound in the presence of a complex metal hydride such as $NaBH_4$, $LiBH_4$, $NaBH_3CN$, $Zn(BH_4)_2$, sodium triacetoxyborohydride or borane/pyridine conveniently at a pH of 1-7 optionally in the presence of a dehydrating agent such as molecular sieve or $Ti(IV)(O-i-Pr)_4$ to facilitate formation of the intermediate imine at ambient temperature. Alternatively the imine can be formed under a hydrogen atmosphere in the presence of a hydrogenation catalyst, e.g. in the presence of Pd/C, at a hydrogen pressure of 1 to 5 bar, preferably at temperatures between 20° C. and the boiling temperature of the solvent used. It may also be advantageous during the reaction if reactive groups are protected during the reaction by conventional protecting groups which are cleaved again by conventional methods after the reaction. Reductive amination procedures have been reviewed: R. M. Hutchings and M. K. Hutchings *Reduction of C═N to CHNH by Metal Hydrides in Comprehensive Organic Synthesis* col. 8, I. Fleming (Ed) Pergamon, Oxford 1991 pp. 47-54.

SCHEME R

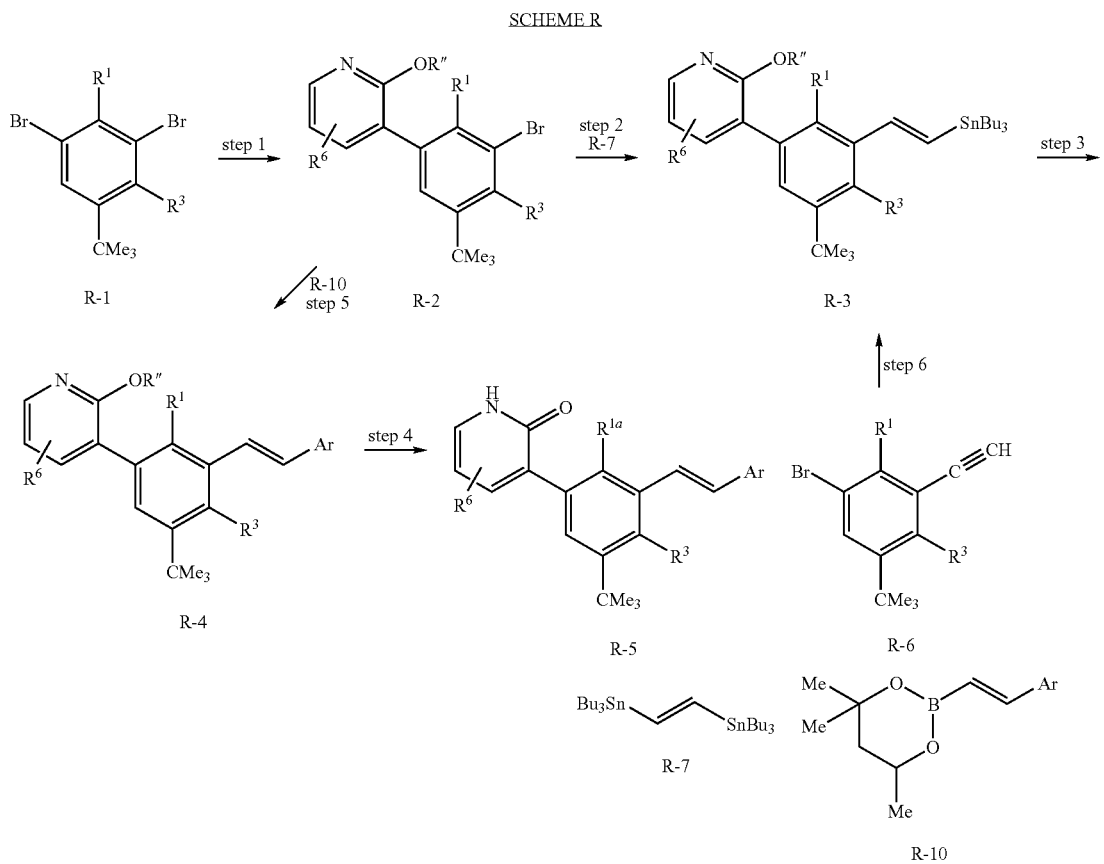

The preparation of 5-((E)-styryl)-phenyl]-1H-pyridin-2-ones using Wittig homologation was depicted in SCHEME D. Alternative routes can employing palladium-catalyzed couplings also can be used. (SCHEME R). Coupling of R-1 and a pyridinyl-boronic acid under conditions described herein affords R-2 (see e.g. example 35 for the case wherein $R^1$ and $R^3$ are hydrogen). Sequential Stille-type couplings with R-7 (step 2) initially afford $R^3$ which is subsequently coupled (step 4) with a substituted haloaryl compound such as N-(2-fluoro-4-iodo-phenyl)-methanesulfonamide or 2-amino-5-iodo-pyridine to afford $R^4$.

The Stille cross-coupling reaction is a palladium-catalyzed coupling of an aryl or vinyl stannanes with aryl or vinyl halides or -sulfonyloxy compounds (J. K. Stille *Angew. Chem. Int. Ed.* 1986 25:508-524; A. F. Littke and G. C. Fu, *Angew. Chem. Int. Ed.* 1999, 38:2411-2413). Commercially available Pd reagents including $Pd(PPh_3)_4$, $Pd(OAc)_2$ and $Pd_2(dba)_3$ can be used. Phosphine ligands are useful rate accelerants if they are not a component of the palladium catalyst. Relatively poorly electron-donating ligands tend to provide the greatest rate acceleration (V. Farina and B. Krishnan, *J. Am. Chem. Soc.* 1991 113:9585-9595). Additives including CuI have been incorporated to provide rate accelerations (V. Farina et al. *J. Org. Chem.* 1994 59:5905-5911). The reaction is typically run in aprotic solvents at elevated temperature.

Alternatively the phenyl acetylene (R-6, see SCHEME G and step 3 of example 9 for the conversion of a benzaldehyde derivative to the corresponding phenylacetylene) can be subjected to free radical hydrostannylation (E. J. Corey and R. H. Wollenberg, *J. Org. Chem.* 1975 40:2265; M. E. Jung and L. A. Light, Tetrahedron Lett. 1982 23:3851) to afford R-3 which can be subjected to Stille-palladium catalyzed coupling as described above. Yet another alternative approach is the Suzuki coupling of R-2 and a vinyl [1,3,2]dioxaborinane (242) to directly afford the aryl styrene (R-4).

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 3. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system. Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays Dosage and Administration The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

A "pharmaceutically acceptable salt" form of an active ingredient may also initially confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

Example 1

3-(3-tert-Butyl-4-difluoromethoxy-phenyl)-1H-pyridin-2-one (1-6)

step 1—To a mixture of 4-bromo-2-tert-butyl-phenol (640 mg, 2.795 mmol) and potassium carbonate (1.20 g, 8.682 mmol) in DMF (8 mL) was added ethyl chlorodifluoroacetate (1.1 mL, 8.687 mmol). The reaction was heated to 80° C. overnight then cooled to RT, and diluted with EtOAc and water. The organic layer was washed with water, with brine, dried ($Na_2SO_4$), filtered and concentrated. The crude residue was purified by $SiO_2$ column eluting with hexane to afford 259 mg (33%) of 4-bromo-2-tert-butyl-difluoromethoxy-benzene (20) as a colorless oil.

step 2—A sealed tube containing 20 (129 mg, 0.464 mmol), 2-methoxy-3-pyridine boronic acid (37, 108 mg, 0.706 mmol, CASRN 163105-90-6), $Pd(PPh_3)_4$ (39 mg, 0.034 mmol) and $Na_2CO_3$ (147 mg, 1.387 mmol) in a mixture of MeOH (3 mL) and DCM (1 mL) was heated in a microwave synthesizer at 115° C. for 30 min. The organic volatiles were removed under reduced pressure. The residue was partitioned between EtOAc and water. The organic layer was washed with brine, dried ($Na_2SO_4$), filtered and concentrated. The crude residue was purified by $SiO_2$ chromatography eluting with a EtOAc/hexane gradient (0 to 5% EtOAc) to afford 82 mg (58%) of 3-(3-tert-butyl-4-difluoromethoxy-phenyl)-2-methoxy-pyridine (22) as an oil.

step 3—A mixture of 22 (82 mg, 0.267 mmol), 48% HBr (90 □L, 0.784 mmol) and HOAc (4 mL) in a sealed tube was heated overnight at 70° C. The reaction mixture was carefully poured into a cold sat'd. aq. $NaHCO_3$ solution, and then extracted with EtOAc. The organic layer was washed with brine dried ($Na_2SO_4$), filtered and concentrated. The crude residue was purified by preparative TLC plate developed with 66% EtOAc in hexanes to afford 39 mg (50% yield) of 1-6 as a light yellow solid.

Example 2

3-(5-tert-Butyl-2-methoxy-phenyl)-6-ethyl-1H-pyridin-2-one (1-109)

step 1—A mixture of 2-bromo-6-methoxypyridine (5.00 g), tributylvinyltin (9.30 mL), and $PdCl_2(PPh)_3$ in dioxane (100 mL) in a sealed tube was heated overnight at 100° C. The reaction was cooled to RT and the volatile organics were removed under reduced pressure. The crude residue was purified by $SiO_2$ chromatography eluting with a EtOAc/hexane gradient (0 to 10% EtOAc) to afford 2.00 g of 2-methoxy-6-vinyl-pyridine (24) as a colorless oil.

step 2—A mixture of 22 (1.95 g) and Pd/C (10% wt. on carbon, 50 mg) in EtOAc (15 mL) and EtOH (15 mL) at RT was stirred under 1 atmosphere of $H_2$ for 45 min. The catalyst was filtered off and the filtrate was concentrated. The crude residue was purified by $SiO_2$ chromatography eluting with a EtOAc/hexane gradient (0 to 5% EtOAc) to afford 560 mg of 2-ethyl-6-methoxypyridine (26) as a colorless oil.

step 3—A mixture of 26 (530 mg), 48% HBr (1.05 mL) and HOAc (10 mL) in a sealed tube was heated at 90° C. overnight. The reaction mixture was cooled to RT, carefully poured into saturated aqueous $NaHCO_3$ solution, and then extracted with EtOAc. The organic layer was washed with brine, dried ($Na_2SO_4$) and concentrated to afford 2-ethyl-6-hydroxypyridine (28) as a light yellow solid.

step 4—To a solution of 28 (250 mg) in CC14 (10 mL) RT was added NBS (730 mg). The reaction was heated at reflux for 2 h then cooled to RT. The solid precipitate was collected by filtration and washed with MeOH to afford give the product (330 mg) of 3,5-dibromo-2-ethyl-6-hydroxypyridine (30) as a white solid.

step 5—To a suspension of 30 (320 mg) in THF (10 mL) at −78° C. was added dropwise a solution of n-BuLi (2.0M in cyclohexane, 1.25 mL). The reaction was stirred at −78° C. for 2 h then quenched with water and extracted with EtOAc. The organic layer was washed with brine, dried ($Na_2SO_4$), filtered and concentrated. The crude residue was purified by $SiO_2$ chromatography eluting with an EtOAc/hexane gradient (10 to 50% EtOAc) to afford 45 mg of 3-bromo-6-ethyl-2-hydroxy-pyridine (32) as a white solid.

step 6—A sealed tube containing 32 (45 mg), 5-tert-butyl-2-methoxybenzene boronic acid (CASRN 128733-85-7, 69 mg), $Na_2CO_3$ (58 mg) and $Pd(PPh_3)_4$ (26 mg) in a mixture of MeOH (4 mL) and DCM (1 mL) was irradiated in a microwave reactor at 120° C. for 30 min. The volatile organics were removed under reduced pressure. The residue was partitioned between EtOAc and water. The organic layer was washed with brine, ($Na_2SO_4$), filtered and concentrated. The crude residue was purified by preparative HPLC to afford 10 mg of I-105 as a white solid.

I-13 can be prepared from 4-tert-butyl-2,6-dibromo-phenol (CASRN 98-22-6) by Suzuki coupling with 37 utilizing a procedure analogous to step 2 of example 1 and demethylating the pyridinyl ether utilizing a procedure analogous to step 3 of example 1. I-9 is prepared analogously except 4-tert-butyl-2,6-dibromo-phenol is replaced with 2,6-dibromo-4-(1,1-dimethyl-propyl)phenol I-4 can be prepared from 2-tert-butyl-4-bromo-anisole (33, CASRN 14804-34-3) by Suzuki coupling with 37 utilizing a procedure analogous to step 2 of example 1 and demethylating the pyridinyl ether utilizing a procedure analogous to step 3 of example 1. 33 can be prepared by Friedel-Crafts alkylation of 4-bromoanisole with tert-butyl chloride and $AlCl_3$.

I-3 can be prepared by Suzuki coupling of 3-bromo-2-hydroxy-pyridine (CASRN 13466-43-8) and 3-tert-butyl-5-methyl-benzeneboronic acid (CASRN 193905-93-0) utilizing a procedure analogous to step 2 of example 1.

I-16 can be prepared by Suzuki coupling of 37 and 2-chloro-6-bromo-4-tert-butyl-phenol (35, CASRN 53751-70-9) and 37 utilizing a procedure analogous to step 2 of example 1 and demethylation of the pyridine with step 3 of example 1. The phenol 35 can be prepared by contacting 2-bromo-4-tert-butyl-phenol with sulfuryl chloride. I-1 and 1-2 can be prepared analogously except 35 is replaced with 4-tert-butyl-bromobenzene (CASRN 3972-64-3) and 2-bromo-4-tert-butyl-phenol (CASRN 2198-66-5), respectively.

I-15 can be prepared from 2,6-dibromo-4-tert-butyl-phenol (CASRN 98-22-6). Sequential Suzuki coupling with 37 and benzeneboronic acid utilizing conditions analogous to those in step 2 of example 1 and demethylation using condition analogous to step 3 of example 1 will afford I-15.

I-7 can be prepared by Suzuki coupling of 3-bromo-5-methyl-1H-pyridin-2-one (CASRN 17282-02-9 and 3-tert-butyl-5-methyl-benzene boronic acid utilizing conditions analogous to those in step 2 of example 1.

Example 3

3-tert-Butyl-N-(4-methanesulfonylamino-2-methyl-phenyl)-2-methoxy-5-(2-oxo-1,2-dihydro-pyridin-3-yl)-benzamide (I-69)

step 1—To a solution of 3-tert-butyl-2-hydroxybenzaldehyde (CASRN 24623-65-2, 5.00 g) DCM (20 mL) at 0° C. was added dropwise a solution of $Br_2$ (1.45 mL) in DCM (15 mL) over a period of 30 min. After the addition was complete the reaction was stirred for 1 h before the organic volatiles were removed under reduced pressure to afford 7.23 g of 5-bromo-3-tert-butyl-2-hydroxybenzaldehyde (B-1b, $R^4$=tert-Bu) as a light yellowish solid.

step 2—A mixture of B-1b ($R^4$=tert-Bu, 3.83 g), MeI (2.32 mL) and $K_2CO_3$ (6.18 g) in DMF (50 mL) was heated at 50° C. for 1 h then cooled to RT and diluted with ether and water. The organic layer was thrice washed with water then brine, dried ($MgSO_4$) and concentrated to afford 3.99 g of 5-bromo-3-tert-butyl-2-methoxybenzaldehyde B-1c ($R^4$=tert-Bu) as a yellow solid.

step 3—A sealed tube containing B-1c (1.08 g), 37 (0.91 g), $Na_2CO_3$ (1.05 g) and $Pd(PPh_3)_4$ (460 mg) in a mixture of MeOH (20 mL) and DCM (5 mL) was irradiated in a microwave reactor at 120° C. for 30 min. The organic volatiles were removed under reduced pressure. The residue was partitioned between EtOAc and water. The organic layer was washed with brine, dried ($Na_2SO_4$), filtered and concentrated. The crude residue was purified by $SiO_2$ chromatography eluting with an EtOAc/hexane gradient (0 to 20% EtOAc) to afford 300 mg of B-2a (R"=Me, $R^4$=tert-Bu and $R^6$=H, 39, CASRN 417715-87-8).

step 4—To a solution of B-2a (1.40 g) in a mixture of tert-BuOH (30 mL) and water (30 mL) was added 2-methyl-2-butene (10 mL), $NaH_2PO_4 \cdot H_2O$ (7.80 g), and $NaClO_2$ (3.80 g). The reaction was stirred at 0° C. and allowed to warm to RT over a period of 1.5 h before 1N aqueous HCl solution was added to adjust the reaction below pH 7. The reaction mixture was then extracted with EtOAc. The organic extract was washed with brine, dried ($Na_2SO_4$), filtered and concentrated. The crude residue was purified by $SiO_2$ chromatography eluting with a MeOH/DCM gradient (0 to 15% MeOH) to afford 720 mg of B-2b (R"=Me, $R^4$=tert-Bu and $R^6$=H) as a white solid.

step 5—A mixture of B-2b (700 mg), 48% HBr (1.23 mL) and HOAc (8 mL) in a sealed tube was heated at 70° C. for 6.5 h. The reaction mixture was cooled to RT, carefully poured into a saturated aqueous $NaHCO_3$ and then extracted with EtOAc. The organic layer was washed with brine, dried ($MgSO_4$), filtered and concentrated. The crude residue was purified by $SiO_2$ chromatography eluting with a MeOH/DCM gradient (0 to 15% MeOH) to afford 600 mg of B-3a (R'''=H, $R^6$=H, $R^4$=tert-Bu; 39) as a white solid.

step 6—To a solution of B-3a (40 mg) in DMF (2 mL) at 0° C. was added sequentially N-(4-amino-3-methylphenyl)-methanesulfonamide (CASRN 108791-97-5, 57 mg), HOBt (27 mg), and EDCI (38 mg). The reaction removed from the cooling bath and stirred for 1.5 h. The reaction mixture was diluted with water and extracted with EtOAc. The organic extract was washed with brine, dried ($MgSO_4$), filtered and concentrated. The crude residue was purified on a preparative $SiO_2$ TLC plate to afford 57 mg of I-69 as a solid.

The following compounds can be prepared analogously except in step 6, N-(4-amino-3-methylphenyl)-methanesulfonamide is replaced with the amine in parenthesis: I-19 (cyclopropylamine, CASRN 765-30-0), I-34 (phenethylamine, CASRN 64-04-0), I-35 (2-phenyl-propylamine, CASRN 582-22-9), I-36 (2-pyridin-3-yl-propylamine, CASRN 20173-24-4), I-37 (benzyl amine), I-38 (C-pyridin-4-yl-methylamine, CASRN 3731-53-1), I-40 ((4-aminomethyl-phenyl)-dimethyl-amine, CASRN 19293-58-4), I-41 (N,N-dimethylamino-aniline, CASRN 99-98-9), I-42 (3-pyrrolidin-1-yl-propylamine, CASRN 23159-07-1), I-43 ($N^1$, $N^1$-dimethyl-ethane-1,2-diamine, CASRN 108-00-9), I-44 (1-(3-amino-propyl)-pyrrolidin-2-one), 1-68 (aniline), I-76 (N-[(4-aminophenyl)methyl]-methanesulfonamide, CASRN 81880-95-7), I-77 (1-methyl-piperidin-3-ylamine, CASRN 42389-57-1), I-78 (2-methyl-3-amino-benzyl alcohol, CASRN 57414-76-3), I-79 (2-methyl aniline, CASRN 95-53-4), I-90 (5-amino-piperidin-2-one, CASRN 154148-70-6), I-91 (1-methyl-piperidin-4-ylamine, CASRN 41838-46-4), I-92 (N,N-dimethyl-cyclohexane-1,4-diamine, CASRN 42389-50-4), I-93 ((2-amino-cyclohexyl)-methanol, CASRN 89854-92-9), I-97 ((3-amino-phenyl)-methanol, CASRN 1877-77-6), I-101 (cyclohexylam CASRN 108-91-4), I-105 (piperidin-3-yl-methanol, CASRN 4606-65-9), I-185 (2-methyl-3-hydroxy-aniline (CASRN 53222-92-7).

I-88 and I-89 can be prepared analogously except in step 6, N-(4-amino-3-methylphenyl)-methanesulfonamide is replaced with 3-(N-Boc-amino)piperidine (CASRN 73874-95-0) and 3-(N-Boc-amino)piperidine (CASRN 172603-05-3) respectively. Removal of the Boc-protecting group is carried out using standard conditions (TFA/DCM or 1N HCl in dioxane).

Example 4

N-{3-[3-tert-Butyl-2-methoxy-5-(2-oxo-1,2-dihydro-pyridin-3-yl)-benzoyl]-phenyl}-methanesulfonamide (I-100, SCHEME C)

step 1—To a solution of 3-tert-butyl-2-methoxy-5-(2-methoxy-pyridin-3-yl)-benzaldehyde (B-2a, $R^4$=tert-Bu, $R^6$=H, 110 mg, 0.368 mmol) in THF (5 mL) at 0° C. was added a solution of 3-(bis-(trimethylsilyl)amino)phenyl magnesium chloride (1.0 M in THF, 0.750 mL, 0.750 mmol). The reaction was gradually warmed RT and stirred overnight. The reaction mixture was quenched with 1N aqueous HCl solution and extracted with EtOAc. The organic layer was washed sequentially with water and brine, dried ($Na_2SO_4$), filtered and concentrated. The crude residue was purified by $SiO_2$ chromatography eluting with an EtOAc/hexane gradient (25 to 50% EtOAc) to afford 79 mg (55%) of (3-amino-phenyl)-[3-tert-butyl-2-methoxy-5-(2-methoxy-pyridin-3-yl)-phenyl]-methanol (34) as a colorless oil.

step 2—To a solution of 34 (79 mg, 0.202 mmol) in DCM (10 mL) at RT was added $MnO_2$ (359 mg, 4.129 mmol). The reaction mixture was vigorously stirred at RT for 3 h before the solid was filtered through a pad of CELITE® and the filtrate was concentrated. The crude residue was purified by $SiO_2$ chromatography eluting with an EtOAc/hexane gradient (5 to 20% EtOAc) to afford the product 69 mg, (88% yield) of (3-amino-phenyl)-[3-tert-butyl-2-methoxy-5-(2-methoxy-pyridin-3-yl)-phenyl]-methanone (36) as a colorless oil.

step 3—A solution of 36 (69 mg, 0.177 mmol), 48% HBr (0.075 mL, 0.654 mmol) and AcOH (3 mL) in a sealed tube was heated overnight at 60° C. The reaction mixture was cooled to RT, carefully poured into a cold saturated aqueous $NaHCO_3$ solution and then extracted with EtOAc. The organic layer was washed with brine, dried (Na$_2$SO$_4$), filtered and concentrated. The crude residue was purified on a preparative SiO$_2$ TLC plate developed with EtOAc/hexanes to afford 44 mg (66% yield) of 3-[3-(3-amino-benzoyl)-5-tert-butyl-4-methoxy-phenyl]-1H-pyridin-2-one (38 [I-59]) as a light yellow solid.

step 4—To a solution of 38 (29 mg, 0.077 mmol) in pyridine (2 mL) at 0° C. was added methanesulfonyl chloride (10 □L, 0.129 mmol). The reaction was gradually warmed to RT and stirred overnight. The reaction was diluted with EtOAc and washed with saturated CuSO$_4$ solution. The organic layer was washed with water and concentrated. The residue was taken up in a mixture of THF (4 mL) and 1N aqueous NaOH (4 mL) and stirred overnight at RT then neutralized with 1N aqueous HCl solution, and extracted with EtOAc. The organic extract was washed sequentially with water and brine, dried (Na$_2$SO$_4$), filtered and concentrated. The crude residue was purified on a preparative SiO$_2$ TLC plate developed with EtOAc/hexanes to afford 27 mg (77% yield) of I-100 as an off-white solid.

I-47, I-49, I-50, I-52, and I-57 are prepared analogously except in step 1, 3-(bis-(trimethylsilyl)amino)phenyl magnesium chloride is replaced with phenyl magnesium bromide, 3-fluorophenyl magnesium bromide (CASRN 17318-03-5), 4-fluorophenyl magnesium bromide (CASRN 352-13-6), 3,5-difluorophenyl magnesium bromide (CASRN 62351-47-7) and 3-methylthien-2-yl magnesium bromide CASRN 95184-07-9) respectively.

I-54 and I-55 can be prepared analogously except in step 1,3-(bis-(trimethylsilyl)amino)phenyl magnesium chloride is replaced with (3-benzyloxy)phenyl magnesium bromide (CASRN36281-96-6) and (4-benzyloxy)phenyl magnesium bromide (CASRN 120186-59-6). The benzyl protecting is removed by catalytic hydrogenolysis.

I-63 is prepared analogously by condensation of B-2a (R$^4$=tert-Bu, R$^6$=H) and 3-cyanophenyl magnesium chloride (CASRN 511903-65-6). Oxidation of the carbinol is accomplished with MnO$_2$ in accord with the procedure in step 2 of this example to afford 3-[3-tert-butyl-2-methoxy-5-(2-oxo-1,2-dihydro-pyridin-3-yl)-benzoyl]-benzonitrile (41). Hydrolysis of the nitrile is carried out with hydrido(dimethyl phosphinous acid-kP)[hydrogen bis-(dimethylphosphinito-kP)]platinum (II) in refluxing EtOH. Demethylation with HBr/HOAc is carried out in accord with the procedure in step 5 of example 3

I-66 is prepared by catalytic hydrogenation of 41 with Raney Nickel (MeOH/NH40H) to afford 3-[3-(3-aminomethyl-benzoyl)-5-tert-butyl-4-methoxy-phenyl]-1H-pyridin-2-one. Conversion of the amine to a sulfonamide and cleavage of the pyridinyl ether are carried out in accord with the procedures in step 3 and 4 of example 6.

Example 5

3-[3-(2-Amino-pyridine-4-carbonyl)-5-tert-butyl-4-methoxy-phenyl]-1H-pyridin-2-one
(I-84, SCHEME C)

step 1—To a solution of 2-chloro-4-iodo-pyridine (1.577 g, 6.586 mmol) in THF (15 mL) at −40° C. under an argon atmosphere was added a solution of iso-propylmagnesium chloride (2.0M in Et$_2$O, 2.6 mL, 5.2 mmol). The reaction was stirred for 30 min at −40° C. then a solution of B-2a (R$^4$=tert-Bu, R"=Me, 787 mg, 2.632 mmol) in THF (15 mL) was added dropwise via syringe. The reaction mixture was gradually warmed to RT and stirred overnight then quenched with 1N aqueous HCl solution (10 mL) and the reaction mixture was extracted with EtOAc. The organic extract was washed with water, brine, dried (Na$_2$SO$_4$), filtered and concentrated. The crude residue was purified by SiO$_2$ chromatography eluting with an EtOAc/hexane gradient (10 to 30% EtOAc) to provide 588 mg (54%) of [3-tert-butyl-2-methoxy-5-(2-methoxy-pyridin-3-yl)-phenyl]-(2-chloro-pyridin-4-yl)-methanol (40) as a white solid.

step 2—To a solution of 40 (124 mg, 0.301 mmol) in DCM (10 mL) at RT was added MnO$_2$ (528 mg, 6.073 mmol). The reaction mixture was vigorously stirred at RT overnight then the solid was filtered through a pad of CELITE. The filtrate was concentrated and the crude residue was purified by SiO$_2$ chromatography eluting with an EtOAc/hexane gradient (5 to 10% EtOAc) to afford 106 mg (86%) of [3-tert-butyl-2-methoxy-5-(2-methoxy-pyridin-3-yl)-phenyl]-(2-chloro-pyridin-4-yl)-methanone (42) as a colorless oil.

step 3—A flask containing 42 (106 mg, 0.259 mmol), benzophenone imine (0.070 mL, 0.417 mmol), Pd$_2$(dba)$_3$ (11.5 mg, 0.013 mmol), racemic BINAP (23.8 mg, 0.038 mmol), and sodium tert-butoxide (35 mg, 0.364 mmol) was purged with argon 3 times before toluene (5 mL) was added. The reaction was heated overnight at 80° C. then cooled to RT. The reaction mixture was diluted with EtOAc, filtered through CELITE, and the filtrate was concentrated. The residue was taken up in a mixture of MeOH (5 mL) and hydroxylamine (50% wt solution in water, 0.5 mL) and stirred overnight at RT before it was concentrated. The crude residue was purified by SiO$_2$ chromatography eluting with an EtOAc/hexane gradient (25 to 75% EtOAc) to afford (2-amino-pyridin-4-yl)-[3-tert-butyl-2-methoxy-5-(2-methoxy-pyridin-3-yl)-phenyl]-methanone (44) as a pale yellow oil.

step 4—A solution of 44 (60 mg, 0.153 mmol), 48% HBr (0.060 mL, 0.523 mmol) and AcOH (4 mL) in a sealed tube was heated overnight at 60° C. The reaction mixture was cooled to RT, carefully poured into a cold saturated aqueous NaHCO$_3$ solution and then extracted with EtOAc. The organic layer was washed with brine, dried (Na$_2$SO$_4$) and concentrated. The crude residue was purified on a preparative TLC plate developed with EtOAc to afford 41 mg (70%) of I-84 as a yellow solid.

Example 6

N-(4-{2-[3-tert-Butyl-2-methoxy-5-(2-oxo-1,2-dihydro-pyridin-3-yl)-phenyl]-ethyl}-phenyl)-methanesulfonamide-(2-oxo-1,2-dihydro-pyridin-3-yl)-phenyl]-ethyl}-3-fluoro-phenyl)-methanesulfonamide
(I-33 SCHEME D)

step 1—To a solution of 4-nitro-benzyltriphenylphosphonium bromide (1.53 g, 3.20 mmol) in DMF (8 mL) at 0° C. was added NaH (60% in oil dispersion, 227 mg, 5.68 mmol). The reaction was stirred for 30 min at 0° C. and followed by addition of a solution of the B2a (R$^4$=tert-Bu, R"=Me, 320 mg, 1.07 mmol) in DMF (7 mL). The resulting solution was gradually warmed to RT and stirred overnight. The reaction was quenched with 1N aqueous HCl solution and diluted with EtOAc. The organic layer was washed with brine, dried (Na$_2$SO$_4$), filtered and concentrated. The crude residue was purified by SiO$_2$ chromatography eluting with an EtOAc/hexane gradient (0 to 8% EtOAc) to afford 351 mg (78%) 3-{3-tert-butyl-4-methoxy-5-[2-(4-nitro-phenyl)-vinyl]-phenyl}-2-methoxy-pyridine (44) of as an orange oil.

step 2—To a solution of the above 44 (351 mg, 0.840 mmol) in EtOAc (15 mL) and MeOH (15 mL), was added Pd(OH)$_2$ (20 wt % on carbon, 166 mg, 0.237 mmol). The reaction was stirred under an atmosphere of hydrogen for 45 min, the catalyst was filtered, and the filtrate concentrated. The residue was re-dissolved in a mixture of MeOH (15 mL) and EtOAc (15 mL) and a fresh batch of Pd(OH)$_2$ (166 mg, 0.237 mmol) was added. The resulting reaction mixture was stirred under an atmosphere of hydrogen overnight, the catalyst was filtered and the filtrate concentrated. The crude residue was purified by SiO$_2$ chromatography eluting with 20% EtOAc/hexanes to afford 106 mg (32%) of 4-{2-[3-tert-butyl-2-methoxy-5-(2-methoxy-pyridin-3-yl)-phenyl]-ethyl}-phenylamine (46) as a colorless oil.

step 3—To a solution of 46 (106 mg, 0.272 mmol) in pyridine (5 mL) cooled to 0° C. was added methanesulfonyl chloride (0.035 mL, 0.450 mmol). The reaction was gradually warmed to RT and stirred for 1.5 h then diluted with EtOAc. The organic layer was washed sequentially with saturated aqueous CuSO$_4$ solution and brine, dried (Na$_2$SO$_4$), filtered and concentrated. The crude residue was purified by SiO$_2$ chromatography eluting with a EtOAc/hexane gradient (10 to 20% EtOAc) to afford 104 mg (82%) of N-(4-{2-[3-tert-butyl-2-methoxy-5-(2-methoxy-pyridin-3-yl)-phenyl]-ethyl}-phenyl)-methanesulfonamide (46) as a colorless oil.

step 4—A mixture of 46 (104 mg, 0.222 mmol), 48% HBr (0.100 mL, 0.871 mmol) and AcOH (3 mL) in a sealed tube was heated overnight at 65° C. The reaction mixture was carefully poured into a cold saturated aqueous NaHCO$_3$ solution and then extracted with EtOAc. The organic layer was washed with brine, dried (Na$_2$SO$_4$), filtered and concentrated. The crude residue was purified on a preparative SiO$_2$ TLC plate developed with EtOAc/hexanes to afford 51 mg (51%) of I-33 as a white solid.

II-21 can be prepared analogously except in step 1, 4-nitro-benzyltriphenyl-phosphonium bromide is replaced with 4-fluoro-benzyltriphenylphosphonium bromide and step 4 is omitted.

I-22 can be prepared analogously except in step 1, condensation with 4-nitro-benzyltriphenylphosphonium bromide is replaced by methyl (dimethoxy-phosphoryl)-acetate (HWE conditions) and the resulting ester is hydrolyzed under basic conditions. I-18 can be prepared analogously except B-2a is replaced with 2-benzyloxy-3-bromo-5-tert-butyl-6-methoxy-benzaldehyde which can be prepared from 47 by alkylation of the phenol with benzyl bromide. Hydrogenation results in concomitant reduction of the olefin and cleavage of the benzyl protecting group which affords 6-tert-butyl-8-(2-methoxy-pyridin-3-yl)-chroman-2-one. Hydrolysis of the lactone affords I-18.

I-32 can be prepared analogously except in step 1, 4-nitro-benzyltriphenyl-phosphonium bromide is replaced with 3-nitro-benzyltriphenylphosphonium bromide.

I-14 can be prepared from 3-bromo-5-tert-butyl-2-hydroxy-benzaldehyde (47) by sequentially converting the aldehyde to a vinyl group by Wittig homologation with methyl-triphenylphosphonium bromide and sodium hexamethyldisilazane, coupling the resulting olefin with 37 utilizing a procedure analogous to step 2 of example 1, reducing the vinyl group with Pd(OH)$_2$ and H$_2$ and finally demethylating the pyridinyl ether utilizing a procedure analogous to step 3 of example 1. I-30 can be prepared analogously except 47 was replaced with B-1c (R$^4$=tert-Bu).

I-11 can be prepared from 47 by analogous procedures. Suzuki coupling of 3-bromo-5-tert-butyl-benzaldehyde with 37 utilizing a procedure analogous to step 2 of example 1, reduction of the aldehyde with sodium borohydride. The resulting intermediate can be dealkylated utilizing a procedure analogous to step 3 of example 1 and hydogenolysis of the benzyl bromide with Pd(OH)$_2$ and H$_2$ affords I-11. I-10 can be prepared analogously except the final hydrogenolysis step is omitted.

I-29 can be prepared from D-2 by Suzuki coupling with 37 and subsequent reduction of the aldehyde to the corresponding benzyl alcohol with sodium borohydride and further hydrogenolysis of the alcohol to the corresponding alkane (H$_2$ and Pd(OH)$_2$). Demethylation of the pyridinyl ether can be accomplished utilizing a procedure analogous to step 3 of example 1.

I-26 can be prepared from D-2 by sequential Baeyer-Villiger oxidation and alkylation of the resulting phenol to afford 2,3-dimethoxy-4-bromo-tert-butyl-benzene and subsequent Suzuki coupling with 37 and demethylating the pyridinyl ether utilizing a procedure analogous to step 3 of example 1. I-23 can be prepared analogously except alkylation of the phenolic product from the Bayer-Williger oxidation is omitted.

Example 7

N-(4-{2-[5-tert-Butyl-2-hydroxy-3-(2-oxo-1,2-dihydro-pyridin-3-yl)-phenyl]-ethyl}-phenyl)-methanesulfonamide (I-51, SCHEME E)

step 1—A sealed tube containing 3-bromo-5-tert-butyl-2-hydroxy benzaldehyde E-1b (R$^1$=OH, R$^4$=tert-Bu, 858 mg, 3.339 mmol), 37 (766 mg, 5.008 mmol), Pd(PPh$_3$)$_4$ (240 mg, 0.208 mmol), and Na$_2$CO$_3$ (891 mg, 8.406 mmol) in a mixture of MeOH (10 mL) and DCM (2 mL) was irradiated in a microwave reactor at 115° C. for 30 min. The organic volatiles were removed under reduced pressure and the residue was partitioned between EtOAc and water. The organic layer was washed with brine, dried (Na$_2$SO$_4$), filtered and concentrated. The crude residue was purified by SiO$_2$ chromatography eluting with an EtOAc/hexane gradient (3 to 5% EtOAc) to afford 737 mg (77%) of 5-tert-butyl-2-hydroxy-3-(2-methoxy-pyridin-3-yl)-benzaldehyde (48) as a pale yellow oil.

step 2—A mixture of 48 (737 mg, 2.59 mmol), benzyl bromide (0.625 mL, 5.26 mmol) and K$_2$CO$_3$ (734 mg, 5.31 mmol) in DMF (10 mL) was stirred overnight at RT then partitioned between EtOAc and water. The organic layer was thrice washed with water, brine, dried (Na$_2$SO$_4$), filtered and concentrated. The crude residue was purified by SiO$_2$ chromatography eluting with an EtOAc/hexane gradient (0 to 10% EtOAc) to afford 812 mg (84%) of 2-benzyloxy-5-tert-butyl-3-(2-methoxy-pyridin-3-yl)-benzaldehyde (50) as a pale yellow oil.

step 3—To a solution of 4-nitro-benzyltriphenylphosphonium bromide (1.07 g, 2.238 mmol) in DMF (8 mL) at 0° C., was added NaH (60% in oil dispersion, 156 mg, 3.90 mmol). The reaction was stirred for 30 min at 0° C. then a solution of 50 (281 mg, 0.749 mmol) in DMF (6 mL) was added. The resulting mixture was gradually warmed to RT and stirred overnight. The reaction was quenched with 1N aqueous HCl solution (6 mL) and diluted with EtOAc. The organic layer was washed with brine, dried (Na$_2$SO$_4$), filtered and concentrated. The crude residue was purified by SiO$_2$ chromatography eluting with an EtOAc/hexane gradient (5 to 10% EtOAc) to afford 311 mg (84%) of 3-{2-benzyloxy-5-tert-butyl-3-[2-(4-nitro-phenyl)-vinyl]-phenyl}-2-methoxy-pyridine (52) as a yellow oil.

step 4—A mixture of 52 (311 mg, 0.630 mmol) and Pd(OH)$_2$ (20% wt. on carbon, 103 mg, 0.146 mmol) in EtOAc (10 mL) and MeOH (10 mL) was stirred under a H$_2$ atmosphere overnight. The catalyst was filtered, and the filtrate was concentrated. The crude residue was purified by SiO₂ chromatography eluting with an EtOAc/hexane gradient (10 to 25% EtOAc) to afford 156 mg (66%) of 2-[2-(4-amino-phenyl)-ethyl]-4-tert-butyl-6-(2-methoxy-pyridin-3-yl)-phenol (54) as a colorless oil.

step 5—To a solution of 54 (156 mg, 0.415 mmol) in pyridine (5 mL) at 0° C. was added methanesulfonyl chloride (0.050 mL, 0.643 mmol). The reaction was gradually warmed to RT and stirred for 1.5 h then diluted with EtOAc. The organic layer was washed sequentially with saturated aqueous CuSO₄, brine, dried (Na₂SO₄), filtered and concentrated. The crude residue was purified by SiO₂ chromatography eluting with an EtOAc/hexane gradient (10 to 50% EtOAc) to afford 115 mg (61%) of N-(4-{2-[5-tert-butyl-2-hydroxy-3-(2-methoxy-pyridin-3-yl)-phenyl]-ethyl}-phenyl)-methanesulfonamide (56) as a colorless oil.

step 6—A mixture of 56 (115 mg, 0.253 mmol), 48% HBr (0.120 mL, 1.046 mmol) and AcOH (4 mL) in a sealed tube was heated overnight at 65° C. The reaction mixture was carefully poured into a cold saturated aqueous NaHCO₃, and then extracted with EtOAc. The organic layer was washed with brine, dried (Na₂SO₄), filtered and concentrated. The crude residue was purified on a preparative SiO₂ TLC plate developed with EtOAc/hexanes to afford 76 mg (68%) pf I-51 as a white solid.

I-20 can be prepared analogously in step 3, 4-nitro-benzyl-triphenylphosphonium bromide is replaced with 4-fluoro-benzyltriphenylphosphonium bromide and step 5 is omitted.

Example 8

N-(4-{2-[3-tert-Butyl-2-methoxy-5-(6-methyl-2-oxo-1,2-dihydro-pyridin-3-yl)-phenyl]-ethyl}-phenyl)-methanesulfonamide (I-64, SCHEME F)

step 1—A mixture of 5-bromo-2-chloro-2-picoline (4.855 g, 23.51 mmol), benzyl alcohol (2.60 mL, 25.12 mmol), KOH (2.93 g, 52.32 mmol), and 18-crown-6 ether (0.34 g, 1.29 mmol) in toluene (30 mL) was refluxed overnight. The reaction was cooled to RT, diluted with ice water and extracted with EtOAc. The organic extract was washed with brine, dried (Na₂SO₄), filtered and concentrated. The crude residue was purified by SiO₂ chromatography eluting with 2% EtOAc/hexanes to afford 5.006 g (78%) of 2-benzyloxy-3-bromo-6-methyl-pyridine (58) as a colorless oil.

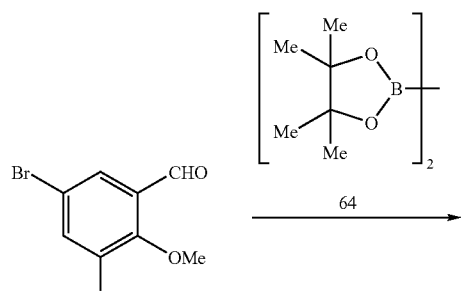

60

-continued

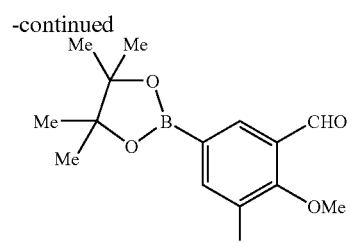

62 step 2—A mixture 60 (0.60 g), bis-(pinacolato)diboron (64, 0.69 g), Pd(dppf)₂Cl₂ (54 mg) and KOAc (542 mg) in DME (30 mL) under an argon atmosphere was heated at 70° C. for 14 h and then at 90° C. for additional 7 h. The reaction was cooled to RT, and diluted with water and ether. The organic layer was washed with brine, dried (MgSO₄), filtered and concentrated. The crude residue was purified by SiO₂ chromatography eluting with a EtOAc/hexane gradient (0 to 12% EtOAc) to afford 478 mg of 62 contaminated with a small amount of 64.

step 3—A mixture of 62 (100 mg, 0.314 mmol), 58 (131 mg, 0.471 mmol), Pd(PPh₃)₄ (36 mg, 0.031 mmol), Na₂CO₃ (88 mg, 0.830 mmol, MeOH (3 mL) and DCM (1 mL) in a sealed tube was irradiated in a microwave reactor at 115° C. for 30 min. The organic volatiles were removed under reduced pressure. The residue was partitioned between EtOAc and water. The organic layer was washed with brine, dried (Na₂SO₄) and concentrated. The crude residue was purified by SiO₂ chromatography eluting with an EtOAc/hexane gradient (0 to 4% EtOAc) to afford 56 mg (45%) of 5-(2-benzyloxy-6-methyl-pyridin-3-yl)-3-tert-butyl-2-methoxy-benzaldehyde (66) as a colorless oil which solidified upon standing.

step 4—To a solution of 4-nitro-benzyltriphenylphosphonium bromide (829 mg, 1.734 mmol) in DMF (5 mL) at 0° C. was added NaH (60% in oil dispersion, 133 mg, 3.32 mmol). The reaction was stirred for 30 min at 0° C. and followed by addition of a solution of 66 (215 mg, 0.553 mmol) in DMF (5 mL). The resulting mixture was gradually warmed to RT and stirred overnight. The reaction was quenched with 1N aqueous HCl solution (6 mL) then diluted with EtOAc. The organic layer was washed with brine, dried (Na₂SO₄), filtered and concentrated. The crude residue was purified by SiO₂ chromatography eluting with an EtOAc/hexane gradient (0 to 4% EtOAc) to afford 180 mg (64%) of 2-benzyloxy-3-{3-tert-butyl-4-methoxy-5-[2-(4-nitro-phenyl)-vinyl]-phenyl}-6-methyl-pyridine (68) as an orange oil.

step 5—A mixture of 68 (180 mg, 0.354 mmol) and Pd(OH)₂ (20 wt % on C, 75 mg, 0.107 mmol) in EtOAc (10 mL) and MeOH (10 mL) was stirred under an atmosphere of hydrogen for 2 h before the catalyst was filtered, and the filtrate was concentrated. The crude residue was purified by SiO₂ chromatography eluting with an EtOAc/hexane gradient (75 to 100% EtOAc) to afford 68 mg (49%) of 3-{3-[2-(4-amino-phenyl)-ethyl]-5-tert-butyl-4-methoxy-phenyl}-6-methyl-1H-pyridin-2-one (70) as a foam.

step 6—To a solution of 70 (68 mg, 0.174 mmol) in pyridine (4 mL) at 0° C. was added methanesulfonyl chloride (0.016 mL, 0.206 mmol). The reaction was gradually warmed to RT and stirred for 1.5 h then diluted with EtOAc. The organic layer was washed sequentially with saturated aqueous CuSO₄, brine, dried (Na₂SO₄), filtered and concentrated. The crude residue was purified on a preparative SiO₂ TLC plate developed with 66% EtOAc/hexanes to afford 28 mg (34% yield) of I-64 as an off-white solid.

I-67 can be prepared analogously except in step 3, 58 is replaced by 2-benzyloxy-3-bromo-5-fluoro-pyridine.

Example 9

N-(4-{2-[3-tert-Butyl-2-methoxy-5-(2-oxo-1,2-dihydro-pyridin-3-yl)-phenyl]-ethyl}-3-fluoro-phenyl)-methanesulfonamide (I-102, SCHEME G)

step 1—To a solution of 4-bromo-3-fluoro-aniline (1.00 g, 5.263 mmol) in pyridine (5 mL) at 0° C. was added methanesulfonyl chloride (0.500 mL, 6.424 mmol). The reaction was gradually warmed to RT and stirred overnight then diluted with EtOAc. The organic layer was washed successively with saturated aqueous $CuSO_4$ solution, brine, dried ($Na_2SO_4$), filtered and concentrated. The crude residue was purified by $SiO_2$ chromatography eluting with an EtOAc/hexane gradient (5 to 20% EtOAc) to afford 1.235 g (88%) of N-(4-bromo-3-fluoro-phenyl)-methanesulfonamide (72) as a white solid.

step 2—A sealed tube containing 5-bromo-3-tert-butyl-2-methoxybenzaldehyde (3.99 g, 14.72 mmol), 2-benzyloxy-3-pyridine boronic acid (5.07 g, 22.14 mmol), $Pd(PPh_3)_4$ (1.32 g, 1.142 mmol) and $Na_2CO_3$ (3.93 g, 37.08 mmol) in a mixture of MeOH (33 mL) and DCM (9 mL) was irradiated in a microwave reactor at 115° C. for 30 min. The organic volatiles were removed under reduced pressure. The residue was partitioned between EtOAc and water. The organic layer was washed with brine, dried ($Na_2SO_4$), filtered and concentrated. The crude residue was purified by $SiO_2$ chromatography eluting with an EtOAc/hexane gradient (0 to 19% EtOAc) to afford 5.506 g (99%) of G-1a ($R^3$=OMe, $R^6$=H, 74) as an orange oil which solidified upon standing.

step 3—To a solution of 74 (1.00 g, 2.667 mmol) in MeOH (20 mL) cooled to −78° C., was added a solution of sodium methoxide (0.5M in MeOH, 11.00 mL, 5.500 mmol) followed by dropwise addition of a solution of dimethyl 1-diazo-2-oxopropylphoshonate (712 mg, 4.000 mmol) in MeOH (10 mL). The resulting reaction mixture was gradually warmed to RT and stirred overnight then quenched with a saturated aqueous $NaHCO_3$. The organic volatiles were removed under reduced pressure. The crude residue was partitioned between EtOAc and saturated aqueous $NaHCO_3$. The organic layer was washed with water, brine, and dried ($Na_2SO_4$), filtered and concentrated. The crude residue was purified by $SiO_2$ chromatography eluting with an EtOAc/hexane gradient (0 to 4% EtOAc) to afford 679 mg (69%) of G-1b 1a ($R^3$=OMe, $R^6$=H, 76) as a colorless oil.

step 4—A mixture of 76 (149 mg, 0.402 mmol), 72 (72 mg, 0.269 mmol), $PdCl_2(PPh_3)_2$ (23 mg, 0.033 mmol), Cu(I)I (2.9 mg, 0.015 mmol) and TEA (4 mL) in THF (4 mL) under an argon atmosphere was heated overnight at 60° C. The reaction mixture was cooled to RT and concentrated. The crude residue was purified by $SiO_2$ chromatography eluting with an EtOAc/hexane gradient (10 to 30% EtOAc) to afford 59 mg (39%) of N-{4-[5-(2-benzyloxy-pyridin-3-yl)-3-tert-butyl-2-methoxy-phenylethynyl]-3-fluoro-phenyl}-methanesulfonamide (78) as a orange oil.

step 5—A Parr bottle containing a mixture of 78 (82 mg, 0.147 mmol) and $Pd(OH)_2$ (20% wt. on carbon, 59 mg, 0.084 mmol) in EtOAc (6 mL) and MeOH (6 mL) at RT was shaken under 35 psi atmosphere of $H_2$ for 4.5 h and then under 43 psi atmosphere for 6 h. The catalyst was filtered and the filtrate was concentrated. The crude residue was purified on a preparative $SiO_2$ TLC plate developed with EtOAc to afford 35 mg (50%) of I-102 as a white solid.

I-103 can be prepared analogously except in step 1, 4-bromo-3-fluoro-aniline is replaced with 4-bromo-2-fluoro-aniline.

Example 10

N-(4-{2-[2-Amino-5-tert-butyl-3-(2-oxo-1,2-dihydro-pyridin-3-yl)-phenyl]-ethyl}-phenyl)-methanesulfonamide (I-98) and N-[4-tert-Butyl-2-[2-(4-methanesulfonylamino-phenyl)-ethyl]-6-(2-oxo-1,2-dihydro-pyridin-3-yl)-phenyl]-acetamide (I-80, SCHEME H)

step 1—To a solution of 4-ethynyl aniline (4.00 g, 34.00 mmol) DCM (60 mL) at 0° C. was added sequentially pyridine (3.32 mL, 40.8 mmol) and dropwise addition of methanesulfonyl chloride (3.17 mL, 40.80 mmol). The reaction was stirred and allowed to warm from 0° C. to RT over 3 h then poured into a saturated aqueous $NaHCO_3$ (150 mL). The aqueous layer was separated and extracted with DCM (2×100 mL). The combined organic extracts were washed with brine, dried ($Na_2SO_4$), filtered and concentrated. The crude residue was purified by $SiO_2$ chromatography eluting with 20% EtOAc/hexanes to afford 5.92 g (88%) of N-(4-ethynyl-phenyl)-methanesulfonamide (80) as a solid.

step 2—A sealed tube containing H-1 ($R^1$=$NH_2$, $R^4$=tert-Bu, 1.00 g, 3.30 mmol), 37 (0.596 g, 3.96 mmol), $Pd(PPh_3)_4$ (0.376 g, 0.16 mmol) and $Na_2CO_3$ (1.036 g, 9.90 mmol) in MeOH (15 mL) and DCM (5 mL) was irradiated in a microwave reactor at 125° C. for 30 min. The organic volatiles were removed under reduced pressure. The residue was partitioned between DCM and water. The aqueous layer was further extracted with DCM. The combined organic extracts were washed with brine, dried ($Na_2SO_4$), filtered and concentrated. The crude residue was purified by $SiO_2$ chromatography eluting with 20% EtOAc/hexanes to afford 0.706 g (62%) of 2-bromo-4-tert-butyl-6-(2-methoxy-pyridin-3-yl)-phenylamine (82) as a light brown solid.

step 3—A mixture of 82 (0.285 g, 0.80 mmol), copper (I) iodide (0.018 g, 0.004 mmol), $Pd(II)Cl_2(PPh_3)_2$ (0.059 g, 0.08 mmol), 80 (0.332, 1.60 mmol) and DIPEA (2 mL) in THF (5 mL) under an argon atmosphere was heated at 80° C. for 5 h. The reaction was cooled to RT then concentrated. The crude residue was purified by $SiO_2$ chromatography eluting with an EtOAc/hexane gradient (0 to 60% EtOAc) to afford 0.137 g (36%) of N-{4-[2-amino-5-tert-butyl-3-(2-methoxy-pyridin-3-yl)-phenylethynyl]-phenyl}-methanesulfonamide (84) as a yellow solid.

step 4—A mixture of 84 (0.131 g, 0.29 mmol) and $Pd(OH)_2$ (20% wt. on carbon, 0.100 g) in EtOAc (20 mL) and MeOH (20 mL) in a Parr bottle at RT was shaken under 40 psi hydrogen atmosphere for 45 min. The catalyst was filtered and the filtrate was concentrated to afford 0.093 g (66%) of N-(4-{2-[2-amino-5-tert-butyl-3-(2-methoxy-pyridin-3-yl)-phenyl]-ethyl}-phenyl)-methanesulfonamide (86) as an off-white solid.

step 5—A mixture of 86 (0.050 g, 0.11 mmol), 48% HBr (0.050 mL) and AcOH (2 mL) in a sealed tube was heated overnight at 70° C. The reaction mixture was cooled to RT, carefully poured into a cold saturated aqueous $NaHCO_3$ and then extracted with EtOAc. The organic layer was washed with brine, dried ($MgSO_4$) and concentrated. The crude residue was purified by $SiO_2$ chromatography and eluted with 10% MeOH/DCM to afford 32 mg (66%) of N-(4-{2-[2-amino-5-tert-butyl-3-(2-oxo-1,2-dihydro-pyridin-3-yl)-phenyl]-ethyl}-phenyl)-methanesulfonamide (88) as a solid.

step 6—To solution of 88 (0.087 g, 0.19 mmol) in DCM (5 mL) at 0° C. was added pyridine (23 □L) and followed by acetic anhydride (0.02 mL, 0.23 mmol). The reaction was allowed to warm to RT and stirred overnight then diluted with DCM and saturated aqueous $NaHCO_3$. The aqueous layer was separated and extracted with DCM. The combined extract was washed with brine, dried ($Na_2SO_4$), filtered and concentrated. The crude product was purified on a preparative $SiO_2$ TLC plate developed with 40% EtOAc/hexanes to afford 0.045 g (46%) of N-[4-tert-butyl-2-[2-(4-methanesulfonylamino-phenyl)-ethyl]-6-(2-methoxy-pyridin-3-yl)-phenyl]-acetamide (90) as an off-white solid.

step 7—A mixture of 90 (44 mg, 0.9 mmol), 48% HBr (0.050 mL) and AcOH (2 mL) in sealed tube was heated overnight at 70° C. The reaction mixture was cooled to ambient temperature and carefully poured into a cold saturated aqueous $NaHCO_3$. The mixture was extracted with EtOAc. The organic layer was washed with brine, dried ($Na_2SO_4$) and concentrated. The crude residue was purified by SiO2 chromatography eluting with 10% $MeOH/CH_2Cl_2$ to afford 16 mg (38%) of (I-80) as an off-white solid.

I-98 was made analogously by subjecting 88 to the demethylation conditions described in step 7. I-74 can be made analogously except in step 2, H-1 ($R^1=NH_2$, $R^4$=tert-Bu) is replaced with H-1 ($R^1=H$, $R^4$=tert-Bu).

Example 11

N-(4-{2-[5-tert-butyl-2-cyano-3-(2-oxo-1,2-dihydro-pyridin-3-yl)-phenyl]-ethyl}-phenyl)-methane-sulfonamide (I-87) (SCHEME H)

step 1—To a stirred mixture of H-1 ($R^1=NH_2$, $R^4$=tert-Bu, 13.08 g, 42.60 mmol, CASRN 10546-67-5) in water (16 mL) and HOAc (26 mL) was added concentrated sulfuric acid (11.20 mL, 119.28 mmol). The mixture was heated to complete to dissolve the solids and then cooled to 10° C. The solution was cooled to 10° C. and an aqueous solution of sodium nitrite (3.08 g, 46.86 mmol) in water (30 mL) over a period of 10 min with vigorous stirring until the mixture became a light brown solution.

To a mixture of $CuSO_4$ (7.68 g, 51.12 mmol) in water (30 mL) and ice (40 g) was added KCN (13.00 g, 213.01 mmol) while maintaining the temperature below 20° C. by adding more ice. The precipitate that initially formed dissolved. Finally, $NaHCO_3$ (26.80 g, 340.81 mmol) and benzene (60 mL) were added to the mixture. The solution containing the diazonium salt was added dropwise to this solution at 50-55° C. over 30 min while stirring vigorously. The mixture was stirred for additional 30 min upon the completion of addition. The reaction mixture was cooled to RT then diluted with benzene (200 mL). The organic layer was washed with 2N aqueous NaOH solution, brine, dried ($Na_2SO_4$), filtered and concentrated. The residue was fractionally recrystallized from a mixture of DCM and ether to afford 7.84 g (58%) of 2,6-dibromo-4-tert-butyl-benzonitrile (92) as a light brown solid.

step 2—A mixture of 92 (0.750 g, 1.90 mmol), Cu(I) (0.027 g, 0.09 mmol), $Pd(II)(PPh_3)_2Cl_2$ (0.203 g, 0.19 mmol), 80 (0.748 g, 2.85 mmol) and DIPEA (5 mL mL) under an argon atmosphere was heated overnight at 80° C. The reaction was cooled to RT then concentrated. The crude residue was purified by $SiO_2$ chromatography eluting with 40% EtOAc/hexanes to afford 0.293 g (24%) of N-[4-(3-bromo-5-tert-butyl-2-cyano-phenylethynyl)-phenyl]-methanesulfonamide (94) as a light brown solid.

step 3—A sealed tube containing 94 (0.290 g, 0.67 mmol), 2-benzyloxy-3-pyridine boronic acid (0.184 g, 0.80 mmol, 141), $Pd(PPh_3)_4$ (0.220 g, 0.07 mmol) and $Na_2CO_3$ (0.609 g, 2.01 mmol) in MeOH (9 mL) and DCM (3 mL) was irradiated in a microwave reactor at 125° C. for 30 min. The organic volatiles were removed under reduced pressure. The residue was partitioned between DCM and water then the aqueous layer was further extracted with DCM. The combined extracts were washed with brine, dried ($Na_2SO_4$), filtered and concentrated. The crude residue was purified by $SiO_2$ chromatography eluting with 20% EtOAc/hexanes to afford 0.230 g (64%) of N-{4-[3-(2-benzyloxy-pyridin-3-yl)-5-tert-butyl-2-cyano-phenylethynyl]phenyl}-methanesulfonamide (96) as a light brown solid.

step 4—A mixture of 96 (0.095 g, 0.18 mmol) and $Pd(OH)_2$ (20 wt % on carbon, 0.100 g) in EtOAc (20 mL) and MEOH (20 mL) in a Parr bottle RT was shaken under 40 psi hydrogen atmosphere. After 30 min, additional $Pd(OH)_2$ (0.100 g) was added and the reaction was shaken for 2 h. The catalyst was filtered and the filtrate was concentrated. The crude residue was purified on a preparative $SiO_2$ TLC plate developed with 10% MeOH/DCM to afford 0.024 g (30%) of I-87 as a light brown solid.

I-94 can be prepared utilizing procedures analogous to those described in steps 2 to 4 except in step 2, 92 is replaced with 3,5-dibromo-tert-butyl benzene and in step 3, 2-benzoxy-3-pyridine boronic acid is replaced with 2-benzoxy-5-fluoro-3-pyridine boronic acid.

I-85 can be prepared utilizing procedures analogous to those described in steps 2 to 4 except in step 2, 92 is replaced with 3,5-dibromo-tert-butyl benzene and N-(4-ethynyl-phenyl)-methanesulfonamide (80) is replaced with N-(4-ethynyl-phenyl)-N',N'-dimethyl-sulfamate.

I-83 can be prepared utilizing procedures analogous to those described in steps 2 to 4 except in step 2, 92 is replaced with 3,5-dibromo-tert-butyl benzene and N-(4-ethynyl-phenyl)-methanesulfonamide (80) is replaced with N-(4-ethynyl-phenyl)-acetamide.

I-86 can be prepared utilizing procedures analogous to those described in steps 2 to 4 except in step 2, 92 is replaced with 3,5-dibromo-tert-butyl benzene and N-(4-ethynyl-phenyl)-methanesulfonamide (80) is replaced with 1-(4-ethynyl-phenyl)-3-methyl-urea.

Example 12

N-[3-tert-Butyl-2-methoxy-5-(2-oxo-1,2-dihydro-pyridin-3-yl)-phenyl]-4-methanesulfonylamino-benzamide (I-70) (SCHEME K)

step 1—A mixture of 5-bromo-1-tert-butyl-2-methoxy-3-nitrobenzene (0.48 g, 1.7 mmol; CASRN 474554-50-2), 37 (0.28 g, 1.8 mmol), $Pd(PPh_3)_3$ (0.19 g, 0.17 mmol) and $Na_2CO_3$ (0.53 g, 5.0 mmol) in DCM/MeOH (3:1, 8 mL) was subjected to microwave heating to 115° C. for 35 min. The reaction mixture was filtered and the filtrate concentrated. The crude residue was purified by $SiO_2$ chromatography eluting with EtOAc/hexane to afford 0.44 g (82%) of 3-(3-tert-butyl-4-methoxy-5-nitrophenyl)-2-methoxypyridine (98) as a yellow solid.

step 2—To a solution of 98 (0.98 g, 3.1 mmol) in EtOAc/MeOH (2:1, 30 mL) was added 10% Pd/C (0.10 g). A stream of hydrogen gas was bubbled through the solution for 20 min then the solution was stirred at RT for 16 h. The reaction mixture was filtered and concentrated to afford 3-tert-butyl-2-methoxy-5-(2-methoxypyridin-3-yl)phenylamine (100).

step 3—To a solution of 100 (0.24 g, 0.85 mmol) and TEA (0.18mL, 1.3 mmol) in DCM (10 mL) at 0° C. was added 4-nitrobenzoyl chloride (0.19 g, 1.0 mmol). The resulting mixture was stirred at 0° C. for 3 h, and then warmed to RT. The mixture was then diluted with additional DCM, washed sequentially with water and brine, dried ($Na_2SO_4$), filtered and concentrated. The crude residue so obtained was purified by $SiO_2$ chromatography eluting with EtOAc/hexane to afford 0.36 g (97%) of N-[3-tert-butyl-2-methoxy-5-(2-methoxypyridin-3-yl)phenyl]-4-nitrobenzamide (102) as a light yellow solid.

step 4—To a solution of 102 (0.36 g, 0.82 mmol) in EtOAc/MeOH (2:1, 15 mL) was added 10% Pd/C (0.035 g). A stream of hydrogen gas was bubbled through the solution for 20 min, and the white solid precipitate that formed was recovered by filtration to afford 4-amino-N-[3-tert-butyl-2-methoxy-5-(2-methoxypyridin-3-yl)phenyl]benzamide (104).

step 5—To a solution of 104 (0.10 g, 0.25 mmol) in pyridine (2 mL) at 0° C. was added methanesulfonyl chloride (0.034 g, 0.30 mmol). Stirring was continued at 0° C. for two h, then at RT for an additional two h. The reaction mixture was diluted with EtOAc, washed sequentially with aqueous CuSO$_4$ and 2N HCl, dried (Na$_2$SO$_4$), filtered and concentrated. The crude residue was purified by SiO$_2$ chromatography (EtOAc/hexane) to afford 0.12 g of N-[3-tert-butyl-2-methoxy-5-(2-methoxypyridin-3-yl)phenyl]-4-methanesulfonylaminobenzamide (106) as a colorless oil.

step 6: A solution of 106 (0.12 g, 0.25 mmol), 48% HBr (40 µL) and HOAc (3 mL) was heated in a sealed tube at 60° C. for 15 h. The reaction mixture was cooled to RT, diluted with EtOAc, and washed with water. Upon addition of saturated aqueous NaHCO$_3$, a white solid precipitated, which was collected and triturated with Et$_2$O to afford I-70.

I-72 can be prepared analogously except step 5 is omitted. I-81 is prepared analogously except in step 1, 37 is replaced with 5-fluoro-2-methoxy-3-pyridineboronic acid (107, CASRN 957120-32-0).

The following compounds can be prepared analogously except in step 3, 4-nitro-benzoic acid is replaced with the benzoic acid in parentheses in parenthesis: I-115 (2-ethoxy-4-nitro-benzoic acid, CASRN 2486-66-0); I-116 (2-chloro-4-nitro-benzoic acid); I-121 (3-fluoro-4-nitro-benzoic acid, CASRN 403-214); I-129 (3-methyl-4-nitro-benzoic acid, CASRN 3113-71-1); I-130 (3-methoxy-4-nitro-benzoic acid, CASRN 5081-36-7); I-131 (3-chloro-4-nitro-benzoic acid, CASRN 39608-47-4); I-132 (4-nitro-2-trifluoromethyl-benzoic acid, CASRN 320-37-3), I-136 (5-nitro-2-pyridinecarboxylic acid, CASRN 30651-24-2), I-281. (2-fluoro-3-nitrobenzoic acid, CASRN 403-24-7), I-282 (2-methyl-4-nitrobenzoic acid, CASRN 1975-51-5) and I-285 (2-[2-(dimethylamino)ethoxy]-4-nitro-benzoic acid, CASRN 99842-09-8). I-277 was prepared analogously except in step 5, methanesulfonyl chloride and pyridine were replaced with acetyl chloride and TEA.

The following compounds were prepared analogously except step 5 was omitted: I-278 (3-methyl-4-nitro-benzoic acid, CASRN 3113-71-1), I-279 (4-nitro-2-trifluoromethyl-benzoic acid, CASRN 320-37-6), I-280 (2-methyl-4-nitrobenzoic acid), I-283 (5-nitro-2-pyridine acid, CASRN 30651-24-2) and I-284 (2-[2-(dimethylamino)ethoxy]-4-nitro-benzoic acid)

Example 13

N-[3-tert-Butyl-2-fluoro-5-(2-oxo-1,2-dihydro-pyridin-3-yl)-phenyl]-4-methanesulfonylamino-benzamide (I-73)

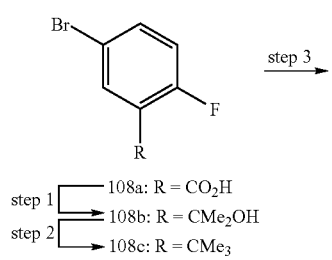

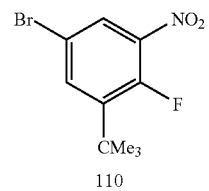

step 1—To a solution of 108a (1.0 g, 4.6 mmol) in toluene (20 mL) at RT was added slowly a solution of Me$_3$Al (2.0 M in toluene, 11.4 mL, 22.8 mmol). The mixture was then stirred and heated at reflux for 8 h, cooled to 0° C., treated dropwise with 2N hydrochloric acid and extracted with EtOAc. The extracts were washed with brine, dried (Na$_2$SO$_4$), filtered and concentrated. The crude residue was purified by SiO$_2$ chromatography eluting with EtOAc/hexane to afford 0.65 g (61%) of 2-(5-bromo-2-fluorophenyl)-2-propanol 108b as a white solid.

step 2—To a solution of 108b (0.65 g, 2.8 mmol) in DCM (20 mL) cooled to −78° C. was added TiCl$_4$ (0.61 mL, 5.6 mmol), and the resulting mixture was stirred for 90 min at −78° C. Me$_2$Zn (1.0M in heptane, 11.1 mL, 11.1 mmol) was added, and the reaction mixture allowed to warm to RT. After 2 h, the reaction mixture was poured onto ice and extracted with DCM. The extracts were washed with brine, dried (Na$_2$SO$_4$), filtered and concentrated to afford 108c.

step 3—The crude material was treated with concentrated H$_2$SO$_4$ (2 mL) with stirring and cooled to 0° C. HNO$_3$ (69%) was added dropwise and the reaction mixture was stirred at 0° C. for 10 min. The reaction mixture was partitioned between water and Et$_2$O, and the organic layer was concentrated. The crude material was purified by SiO$_2$ chromatography eluting with hexane to afford 0.68 g (88%) of 110 as a yellow solid.

The conversion of 110 to N-[3-tert-butyl-2-methoxy-5-(2-oxo-1,2-dihydro-pyridin-3-yl)-phenyl]-4-methanesulfonylamino-benzamide (I-73) was carried out using procedures analogous to those described in steps 1 to 6 of example 12.

I-60 can be prepared analogously except in step 3 of example 12, 4-nitro-benzoyl chloride is replaced with benzoyl chloride.

Example 14

N-{4-[3-tert-Butyl-2-methoxy-5-(2-oxo-1,2-dihydropyridin-3-yl)-benzyloxy]-phenyl}-methanesulfonamide (I-71) (SCHEME L)

Preparation of 2-oxo-1,2-dihydropyridine-3-boronic acid (112)—To a solution of 3-bromo-2-oxo-1,2-dihydropyridine (3.3 g, 19 mmol) in THF (200 mL) cooled to −76° C. was added dropwise over 15 min TMEDA (6.5 g, 56 mmol), followed by n-butyllithium (2.5M in hexane, 58 mmol). The resulting mixture was stirred for 15 min at −76° C. and then warmed to RT. Upon reaching an internal temperature of 19° C., the reaction mixture was cooled to 0° C., and B(OMe)$_3$ (4.0 g, 39 mmol) was added dropwise over 15 min. After the addition was complete, the reaction mixture was warmed to RT and was stirred for 15 h. The mixture was then cooled to 0° C. and a small amount of ice was added followed by 2M aqueous HCl (100 mL). The THF was removed under reduced pressure, and the aqueous solution was washed twice with DCM. Concentrated aqueous NaOH was added slowly until pH 5 was attained and a precipitate formed. The mixture was cooled to 0° C. and stirred for 10 min. The solid was collected by filtration, washed with cold water, and dried under vacuum to afford 1.83 g (69%) of 112 as a yellow solid step 1: To a solution of 5-bromo-3-tert-butyl-2-methoxy-benzaldehyde (0.30 g, 1.1 mmol; CASRN 417715-87-8) in EtOH (5 mL) at 0° C. was added NaBH4 (0.042 g, 1.1 mmol). The mixture was stirred for 1 h, and partitioned between 1N HCl and Et$_2$O. The ether layer was evaporated, and the crude benzyl alcohol was dissolved in DCM and treated sequentially with CBr$_4$ (0.55 g, 1.7 mmol) and PPh$_3$ (0.45 g, 1.7 mmol). After stirring 2 h at RT, the reaction mixture was concentrated, and the crude product was purified by SiO$_2$ chromatography eluting with EtOAc/hexane to afford 0.34 g (90%) 5-bromo-1-bromomethyl-3-tert-butyl-2-methoxybenzene (114).

step 2—A mixture of 114 (0.20 g, 0.59 mmol), 4-nitrophenol (0.082 g, 0.59 mmol) and K$_2$CO$_3$ (0.12 g, 0.89 mmol) in DMF was stirred at 50° C. for 2 h. The mixture was cooled to RT and partitioned between water and Et$_2$O. The ether layer was concentrated, and the crude residue was purified by SiO$_2$ chromatography eluting with EtOAc/hexane to afford 0.19 g (83%) of 5-bromo-1-tert-butyl-2-methoxy-3-(4-nitro-phenoxymethyl)benzene (116) as a white solid.

step 3 To a solution of 116 (0.19 g, 0.49 mmol) in MeOH-water (1:1, 20 mL) was added NH$_4$Cl (0.26 g, 4.9 mmol) and iron powder (0.14 g, 2.5 mmol). The resulting mixture was heated at reflux and stirred for 1 h. After cooling to RT, the mixture was filtered through a pad of diatomaceous earth which was washed with MeOH. The filtrate was concentrated under reduced pressure and the resulting aqueous fraction was extracted with EtOAc. The extracts were washed with brine, dried (Na$_2$SO$_4$), filtered and concentrated. The crude residue was purified by SiO$_2$ chromatography eluting with EtOAc/hexane to afford 0.24 g (64%) of 4-(5-bromo-3-tert-butyl-2-methoxybenzyloxy)phenylamine (118) as a yellow oil.

step 4—To a solution of 118 (0.20 g, 0.55 mmol) in pyridine (3 mL) cooled to 0° C. was added methanesulfonyl chloride (0.081 g, 0.71 mmol). Stirring was continued at 0° C. for 30 min then at RT for 3 h. The reaction mixture was diluted with EtOAc, washed sequentially with aqueous CuSO$_4$ and 2N HCl, dried (Na$_2$SO$_4$), filtered and concentrated. The crude residue was purified by SiO$_2$ chromatography eluting with EtOAc/hexane to afford 0.20 g (84%) of N-[4-(5-bromo-3-tert-butyl-2-methoxybenzyloxy)phenyl]methanesulfonamide (120) as a white solid.

step 5—A mixture of 120 (0.20 g, 0.46 mmol), 112 (0.095 g, 0.69 mmol), Pd(PPh$_3$)$_4$ (0.053 g, 0.046 mmol) and Na$_2$CO$_3$ (0.15 g, 1.4 mmol) in DCM/MeOH (3:1, 8 mL) was irradiated in microwave synthesizer at 115° C. for 35 min. The reaction mixture was filtered and the filtrate concentrated. The crude residue was purified by SiO$_2$ chromatography eluting with DCM/MeOH/NH$_4$OH and the recovered product triturated with ether to afford I-71 as a solid.

Example 15

3-(3-Benzenesulfonyl-5-tert-butyl-phenyl)-1H-pyridin-2-one (I-107)(SCHEME I)

step 1—A sealed tube containing 3,5-dibromo-tert-butylbenzene (1.00 g, 3.425 mmol, CASRN 129316-09-2), 37 (522 mg, 3.413 mmol), Pd(PPh$_3$)$_4$ (194 mg, 0.168 mmol) and Na$_2$CO$_3$ (942 mg, 8.888 mmol) and a mixture of MeOH/DCM (8/2 10 mL) was irradiated in a microwave synthesizer at 100° C. for 10 min. The organic volatiles were removed under reduced pressure. The residue was partitioned between EtOAc and water. The organic layer was washed with brine, dried (Na$_2$SO$_4$), filtered and concentrated. The crude residue was purified by SiO$_2$ chromatography eluting with a EtOAc/hexane gradient (0 to 2% EtOAc) to afford 0.633 g (58%) of 3-(3-bromo-5-tert-butyl-phenyl)-2-methoxy-pyridine (122) as a colorless oil.

step 2—A mixture of 122 (150 mg, 0.469 mmol), benzene sulfinic acid sodium salt (94 mg, 0.573 mmol), Pd$_2$(dba)$_3$ (45 mg, 0.049 mmol), 4,5-bis-(diphenylphosphine)-9,9-dimethylxanthine (56 mg, 0.097 mmol, xantphos, CASRN 161265-03-8), tetrabutylammonium chloride (156 mg, 0.561 mmol), and Cs$_2$CO$_3$ (234 mg, 0.718 mmol) in a Schlenk flask was purged with argon 3 times before toluene (5 mL) was added. The reaction mixture was heated at 120° C. under an argon atmosphere overnight. The reaction mixture was cooled to RT, diluted with EtOAc and water. The organic layer was washed sequentially with water and brine, dried (Na$_2$SO$_4$), filtered and concentrated. The crude residue was purified by SiO$_2$ column chromatography eluting with an EtOAc/hexane gradient (10 to 20% EtOAc) to afford 0.119 g (67%) of I-107 as a light brown oil.

Example 16

3-(3-tert-Butyl-5-phenoxy-phenyl)-1H-pyridin-2-one (I-45)

step 1—A mixture of 3-(3-bromo-5-tert-butyl-phenyl)-2-methoxy-pyridine (123 mg, 0.384 mmol), phenol (46 mg, 0.489 mmol), Pd(OAc)$_2$ (4.1 mg, 0.018 mmol), 2-di-tert-butylphosphino-2',4',6'-tri-isopropyl-1,1'-biphenyl (9.9 mg, 0.023 mmol) and K$_3$PO$_4$ (167 mg, 0.787 mmol)) in a Schlenk flask was purged with argon before toluene (5 mL) was added. The reaction under an argon atmosphere was heated overnight at 115° C. The reaction was cooled to RT, filtered through CELITE, and the filtrate was concentrated. The crude residue was purified by SiO$_2$ chromatography eluting with an EtOAc/hexane gradient (0 to 2% EtOAc) to afford 40 mg (41%) of 3-(3-tert-butyl-5-phenoxy-phenyl)-2-methoxy-pyridine (124).

step 2—A solution of 124 (52 mg, 0.157 mmol), 48% HBr (50 □L, 0.436 mmol) and HOAc (3 mL) in sealed tube was heated at 70° C. overnight. The reaction mixture was cooled to RT, carefully poured into a cold saturated aqueous NaHCO$_3$ and then extracted with EtOAc. The organic layer was washed with brine, dried (Na$_2$SO$_4$), filtered and concentrated. The crude residue was purified on a preparative SiO$_2$ TLC plate developed with 66% EtOAc/hexanes to afford 48 mg (96%) of I-45 as a foam.

Example 17

3-(3-Benzyl-5-tert-butyl-phenyl)-1H-pyridin-2-one (146)

step 1—A mixture of 3-(3-bromo-5-tert-butyl-phenyl)-2-methoxy-pyridine (184 mg, 0.575 mmol) and PdCl$_2$(dppf)$_2$ (40 mg, 0.049 mmol) in a Schlenk flask was purged with argon 3 times before THF (5 mL) was added followed by benzylzinc bromide (0.5M in THF, 2.3 mL, 1.150 mmol). The reaction was then heated at 70° C. overnight then cooled to RT, filtered through a pad of CELITE and the filtrate was concentrated. The crude residue was purified by SiO$_2$ chromatography eluting with an EtOAc/hexane gradient (0 to 4% EtOAc) to afford 156 mg (82%) of 3-(3-benzyl-5-tert-butyl-phenyl)-2-methoxy-pyridine (126) as a colorless oil.

step 2—A solution of 126 (156 mg, 0.471 mmol), 48% HBr (150 □L, 1.30 mmol) and HOAc (4 mL) in sealed tube was heated overnight at 70° C. The reaction mixture was cooled to RT, carefully poured into a cold saturated aqueous NaHCO$_3$ and then extracted with EtOAc. The organic layer was washed with brine, dried (Na$_2$SO$_4$), filtered and concentrated. The crude residue was purified on a preparative SiO$_2$ TLC plate developed with 66% EtOAc/hexanes to afford 124 mg (83%) of I-46 as a white solid.

Example 18

N-(4-{2-[2-Methoxy-3-(1-methyl-cyclopropyl)-5-(2-oxo-1,2-dihydro-pyridin-3-yl)-phenyl]-ethyl}-phenyl)-methanesulfonamide (I-108) and 3-[3-[2-(4-amino-phenyl)-ethyl]-4-methoxy-5-(1-methyl-cyclopropyl)-phenyl]-1H-pyridin-2-one (I-99) (SCHEME N)

step 1—To a solution of 2-(1-methylcyclopropyl)phenol (0.55 g, 3.4 mmol; CASRN 433684-77-6) in MeCN (7 mL) was added paraformaldehyde (0.68 g, 23 mmol), MgCl$_2$ (0.48 g, 0.051 mmol) and TEA (1.3 g, 13 mmol). The mixture was stirred and heated at reflux for 5 h. After cooling to RT, the reaction mixture was partitioned between DCM and 1M aqueous HCl, and the organic extracts were dried (Na$_2$SO$_4$), filtered and concentrated. The crude residue was purified by SiO$_2$ chromatography eluting with EtOAc/hexane to afford 0.34 g (58%) of 2-hydroxy-3-(1-methylcyclopropyl)-benzaldehyde (128) as a light yellow oil.

step 2: To a solution 128 (0.34 g, 1.9 mmol) in DCM-MeOH (3:2, 20 mL) was added tetrabutylammonium tribromide (0.98 g, 2.0 mmol) and the resulting mixture was stirred at RT for 75 min. The solvent was removed under reduced pressure and the residue was partitioned between EtOAc and water. The EtOAc layer was washed sequentially with water and brine, dried (Na$_2$SO$_4$), filtered and concentrated. The crude residue was purified by SiO$_2$ chromatography eluting with EtOAc/hexane to afford 0.45 g (91%) of 5-bromo-2-hydroxy-3-(1-methylcyclopropyl)benzaldehyde (130) as a light yellow solid.

step 3—To a solution of 130 (0.44 g, 1.7 mmol) in DMF (4 mL) was added K$_2$CO$_3$ (0.60 g, 4.4 mmol) and iodomethane (0.32 g, 2.3 mmol). The resulting mixture was stirred at 60° C. for 2 h. The reaction mixture was cooled to RT and partitioned between water and Et$_2$O. The organic layer was washed sequentially with water and brine, dried (Na$_2$SO$_4$), filtered and concentrated to afford 0.47 g (96%) of 5-bromo-2-methoxy-3-(1-methylcyclopropyl)benzaldehyde (132) as a light yellow solid.

step 4: Sodium hydride (60% dispersion, 0.10 g, 2.6 mmol) and 15-crown-5 (0.038 g, 0.17 mmol) were added to THF (5 mL) at 0° C. and stirred for 5 min. To the reaction mixture was then added dropwise over 5 min a solution of diethyl (4-nitrobenzyl)phosphonate (0.52 g, 1.9 mmol) in THF (5 mL), and stirring was continued at 0° C. for 5 min. To this reaction mixture was then added dropwise over 10 min a solution of 132 (0.47 g, 1.7 mmol) in THF (10 mL). The reaction mixture was stirred for 30 min at 0° C. then for 90 min at RT. Water was carefully added, and the mixture was partitioned between water and EtOAc. The EtOAc layer was washed sequentially with water and brine, dried (Na$_2$SO$_4$), filtered and concentrated. The crude residue was purified by SiO$_2$ chromatography eluting with EtOAc/hexane to afford 0.67 g (94%) of 5-bromo-2-methoxy-1-(1-methylcyclopropyl)-3-[(E)-2-(4-nitrophenyl)vinyl]benzene(134) as a yellow solid (0.67 g, 94%).

step 5—A mixture of 134 (0.17 g, 0.44 mmol), 112 (0.073 g, 0.53 mmol), Pd(PPh$_3$)$_4$ (0.051 g, 0.044 mmol) and Na$_2$CO$_3$ (0.14 g, 1.3 mmol) in DCM/MeOH (3:1, 6 mL) was irradiated in a microwave synthesizer at 115° C. for 30 min. The reaction mixture was partitioned between DCM and water and the DCM layer was then washed with brine, dried (Na$_2$SO$_4$), filtered and concentrated. The crude residue obtained was purified by SiO$_2$ chromatography eluting with EtOAc/hexane to afford 0.15 g (79%) of 3-{4-methoxy-3-(1-methylcyclopropyl)-5-[(E)-2-(4-nitrophenyl)vinyl]phenyl}-1H-pyridin-2-one (136) as a yellow solid.

step 6: To a suspension of 136 (0.14 g, 0.35 mmol) in MeOH-EtOAc (2:1, 7.5 mL) was added 10% Pd/C (0.014 g), and the reaction mixture was stirred under a hydrogen atmosphere maintained by a balloon for 16 h. The reaction mixture was filtered through diatomaceous earth and the pad was rinsed successively with EtOAc, MeOH and DCM. The combined filtrates were concentrated under reduced pressure, and the crude residue was purified by SiO$_2$ chromatography eluting with EtOAc/hexane to afford 0.095 g (76%) of 3-[3-[2-(4-amino-phenyl)-ethyl]-4-methoxy-5-(1-methylcyclopropyl)phenyl]-1H-pyridin-2-one (I-99) as a light yellow powder.

step 7: To a solution of I-99 (0.081 g, 0.22 mmol) in pyridine (2 mL) at 0° C. was added methanesulfonyl chloride (0.030 g, 0.26 mmol). The reaction mixture was stirred 10 min at 0° C. then for 135 min at RT. The mixture was partitioned between DCM and aqueous CuSO$_4$ and organic extract was concentrated. The crude residue was purified by SiO$_2$ chromatography eluting with EtOAc/hexane to afford 0.076 g (78%) of N-(4-{2-[2-methoxy-3-(1-methylcyclopropyl)-5-(2-oxo-1,2-dihydropyridin-3-yl)phenyl]ethyl}phenyl)methanesulfonamide (I-108) as an off-white powder.

Example 19

N-(4-{2-[3-tert-Butyl-5-(5-chloro-2-oxo-1,2-dihydro-pyridin-3-yl)-2-methoxy-phenyl]-ethyl}-phenyl)-methanesulfonamide (I-95) (SCHEME N)

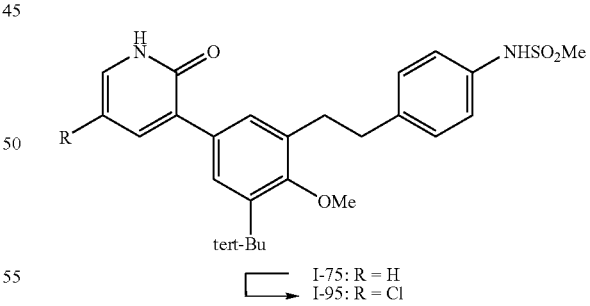

To a mixture I-75 (0.10 g, 0.22 mmol) and N-chlorosuccinimide (0.030 g, 0.23 mmol) in MeCN was stirred and heated at reflux for 2 h. The mixture was concentrated and the crude residue purified by SiO$_2$ chromatography eluting with EtOAc/hexane and then washed with water to remove succinimide to afford I-95 as a solid.

I-96 was prepared analogously except N-chlorosuccinimide was replace with N-bromosuccinimide (88%) as a yellow solid.

Example 20

N-[3-tert-Butyl-2-methoxy-5-(2-oxo-1,2-dihydro-pyridin-3-yl)-phenyl]-4-methanesulfonylamino-N-methyl-benzamide (I-104)

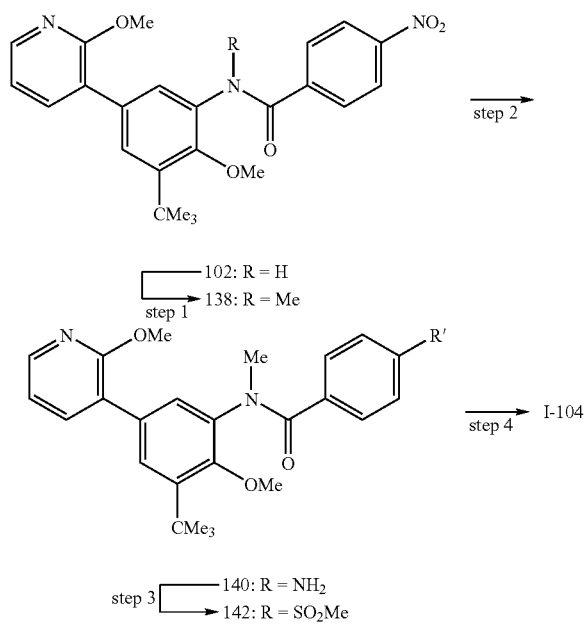

steps 1 & 2—To a solution of 102 (0.24 g, 0.55 mmol) in THF (5 mL) was added sodium hydride (0.033 g, 0.83 mmol). The mixture was stirred at RT until the evolution of gas subsided, and iodomethane (0.069 mL, 1.1 mmol) was added. The resulting mixture was stirred for 3 h and then quenched with water and the mixture extracted with EtOAc. The solvent was evaporated, and the crude residue was dissolved in EtOAc/hexane (2:1, 10 mL) to which was added 10% Pd/C (0.025 g). A stream of hydrogen gas was bubbled through the solution for 20 min, and the resulting solution was stirred at RT for 3 h. The solution was filtered, the filtrate concentrated, and the crude residue purified by $SiO_2$ chromatography eluting with EtOAc/hexane to afford 0.23 g (97%) of 4-amino-N-[3-tert-butyl-2-methoxy-5-(2-methoxypyridin-3-yl)phenyl]-N-methylbenzamide (140) as a white foam.

step 3—To a solution of 140 (0.15 g, 0.36 mmol) in pyridine (3 mL) cooled to 0° C. was added methanesulfonyl chloride (0.053 g, 0.46 mmol) and the resulting solution stirred at 0° C. for 2 h, followed by 2 h at RT. The reaction mixture was diluted with EtOAc, washed sequentially with aqueous $CuSO_4$ and 2N HCl, dried ($Na_2SO_4$), filtered and concentrated. The crude residue was purified by $SiO_2$ chromatography eluting with an EtOAc/hexane gradient to afford 0.17 g (97%) of N-[3-tert-butyl-2-methoxy-5-(2-methoxypyridin-3-yl)phenyl]-4-methanesulfonylamino-N-methylbenzamide (142) as a white foam (0.17 g, 94% step 4: To a solution of 142 (0.17 g, 0.33 mmol) in HOAc (3 mL) was added concentrated aqueous HBr (48%, 0.11 mL), and the solution was heated in a sealed tube at 60° C. for 15 h. The reaction mixture was cooled to RT, diluted with EtOAc, and washed sequentially with water and saturated aqueous $NaHCO_3$. The organic layer was dried ($Na_2SO_4$), filtered and concentrated. The crude residue was purified by $SiO_2$ chromatography eluting with DCM/MeOH/$NH_4$OH to afford 0.15 g (93%) of N-[3-tert-butyl-2-methoxy-5-(2-oxo-1,2-dihydropyridin-3-yl)phenyl]-4-methanesulfonylamino-N-methylbenzamide (I-104) as a white powder.

Example 21

3-(3-tert-Butyl-2-fluoro-4-methoxy-phenyl)-1H-pyridin-2-one (I-56)

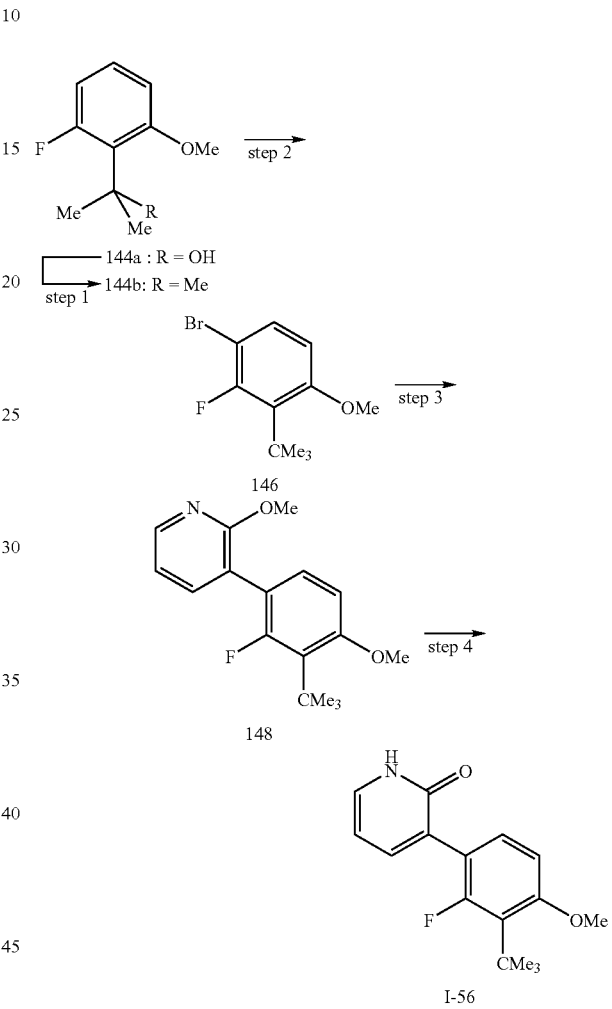

step 1—To a solution of 144a (0.30 g, 1.6 mmol; CASRN 935285-84-0) in DCM (5 mL) at −76° C. was added dropwise $TiCl_4$ (0.62 g, 3.3 mmol) over 10 min. The resulting solution was stirred 90 min at −76° C. then a solution of $Me_2Zn$ (1.0M in heptane, 6.5 mmol) was added dropwise over 15 min and the reaction mixture was warm to RT and stirred for 4 h. The reaction mixture was then poured into ice/water (20 mL), stirred for 30 min, and extracted with DCM. The organic extracts were washed with brine, dried ($Na_2SO_4$), filtered and concentrated. The residue was purified by $SiO_2$ chromatography eluting with hexane to afford 0.13 g (45%) of 144b as a yellow oil.

step 2—To a solution of 144b (0.12 g, 0.66 mmol) in MeCN (4 mL) was added NBS (0.13 g, 0.72 mmol), and the resulting mixture stirred at RT for 1 h. The reaction mixture was concentrated, and then partitioned between $Et_2O$ and water. The organic layer was washed sequentially with water and brine, dried ($Na_2SO_4$), filtered and concentrated. The residue was purified by SiO₂ chromatography eluting with hexane to afford 0.16 g (93%) of 146 as a light yellow oil.

step 3—A mixture of 146 (0.15 g, 0.59 mmol), 37 (0.13 g, 0.88 mmol), Pd(PPh₃)₄ (0.068 g, 0.059 mmol) and Na₂CO₃ (0.19 g, 1.8 mmol) in DCM/MeOH (3:1, 6 mL) was irradiated in a microwave synthesizer at 115° C. for 35 min. The reaction mixture was concentrated, partitioned between EtOAc and water, and then the organic layer was washed sequentially with water and brine, dried (Na₂SO₄), filtered and concentrated. The residue was purified by SiO₂ chromatography eluting with EtOAc/hexane to afford 0.15 g (87%) of 148 as a colorless oil.

step 4—To a solution of 148 (0.14 g, 0.49 mmol) in HOAc (3 mL) was added concentrated aqueous HBr (0.17 mL), and the mixture was stirred at 70° C. in a sealed tube for 15 h. The reaction mixture was cooled to RT, poured into ice/water (5 mL), brought to pH 4 with saturated aqueous NaHCO₃ and extracted with EtOAc. The extracts were washed sequentially with water and brine, dried (Na₂SO₄), filtered and concentrated. The residue was purified by SiO₂ chromatography eluting with EtOAc/hexane to afford 0.13 g (93%) of I-56 as an off-white powder.

I-61 can be prepared analogously except the stating material is 2-(1-methyl-cyclopropyl)-phenol which is O-methylated (see, e.g., step 3 of example 18). Steps 2-4 of the present example can then be utilized.

I-53 can be prepared from 3,5-dibromo-tert-butylbenzene by palladium-mediated coupling with 107 to afford 3-(3-bromo-5-tert-butyl-phenyl)-5-fluoro-1H-pyridin-2-one which is converted to I-53 by palladium-catalyzed Negishi coupling with Me₂Zn.

I-62 can be prepared analogously by omitting step 1 and replacing 144b with 1-methoxy-2-(1-methoxy-1-methyl-ethyl)-benzene.

Example 22

N-(4-{2-[3-tert-Butyl-2-methoxy-5-(2-oxo-1,2-dihydro-pyridin-3-yl)-phenyl]-ethyl}-3-methyl-phenyl)-methanesulfonamide (I-109)

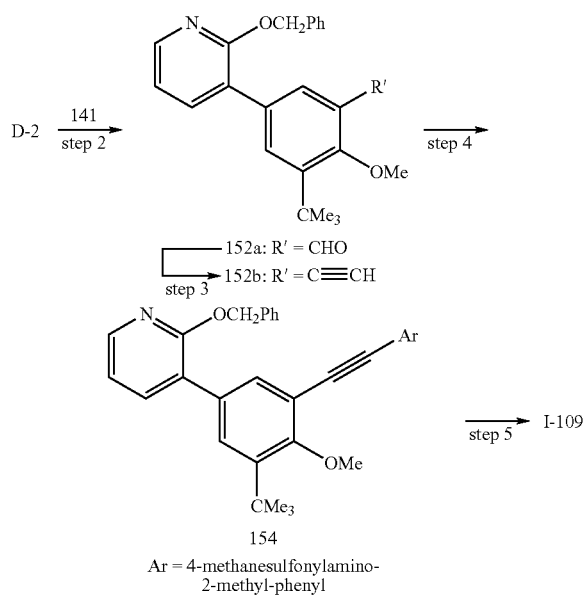

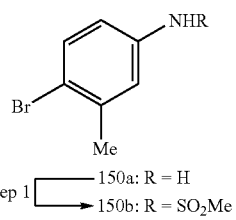

2-benzyloxy-pyridin-3-yl boronic acid (141)—A solution of 2-benzyloxy-3-bromo-pyridine (2.50 gq, 9.47 mmol), Pd(II)Cl₂(PPh₃)₂ (232 mg, 0.28 mmol), KOAc (2.32 g, 23.67 mmol), bis-(pinacolato)diborane (2.95 g, 11.36 mmol) and DME (75 mL) was heated at 70° C. for 26 h. The reaction mixture was cooled and partitioned between Et₂O and water. The organic phase was separated, dried and evaporated. The crude product was purified by SiO₂ chromatography eluting with an EtOAc/hexane gradient (0 to 5% EtOAc to afford 1.81 g of 2-benzyloxy-pyridin-3-yl boronic acid containing a small amount of bis-(pinacolato)diborane.

step 1—To a solution of 150a (2.00 g, 10.749 mmol) in pyridine (10 mL) at 0° C., was added methanesulfonyl chloride (1.00 mL, 12.868 mmol). The reaction was gradually warmed to RT and stirred overnight. The solution was diluted with EtOAc, washed sequentially with saturated CuSO₄ solution, 1N HCl solution twice, and dried (Na₂SO₄), filtered and evaporated. The crude product was purified by SiO₂ chromatography eluting with an EtOAc/hexane gradient (15% to 30% EtOAc) to afford 2.4 g (85%) of 150b as a white solid.

step 2—A sealed tube containing D-2 (3.99 g, 14.72 mmol), 141 (5.07 g, 22.14 mmol), Pd(PPh₃)₄, (1.32 g, 1.142 mmol), Na₂CO₃ (3.93 g, 37.08 mmol) in a mixture of MeOH (33 mL) and DCM (9 mL) was irradiated in a microwave synthesizer at 115° C. for 30 min. The reaction mixture was concentrated, diluted with EtOAc, washed with brine, and dried (Na₂SO₄), filtered and evaporated. The crude product was purified by SiO₂ chromatography eluting with an EtOAc/hexane gradient (0 to 10% EtOAc) to afford 5.506 g (99%) of 142a as an orange oil, which solidified on standing.

step 3—To a solution of 152a (1.00 g, 2.667 mmol) in MeOH (20 mL) at −78° C., added sodium methoxide (0.5M in MeOH, 11 mL, 5.5 mmol). A solution of dimethyl 1-diazo-2-oxopropylphoshonate (712 mg, 4.00 mmol) in MeOH (10 mL) was dropwise and the resulting white suspension was gradually warmed to RT and stirred overnight. The reaction was quenched with saturated NaHCO₃ solution and concentrated. The crude residue was diluted with EtOAc, washed with saturated NaHCO₃, water, brine, dried (Na₂SO₄), filtered and evaporated. The crude product was purified by SiO₂ chromatography eluting with an EtOAc/hexane gradient (0 to 4% EtOAc) to afford 679 mg (69%) of 152b as a colorless oil.

step 3—A solution of 152b (150 mg, 0.404 mmol), 150b (75 mg, 0.282 mmol), PdCl₂(PPh₃)₂ (20 mg, 0.028 mmol), CuI (2.3 mg, 0.012 mmol) in DMF (4 mL) and TEA (4 mL) was purged 3 times with argon. The suspension was heated at 60° C. overnight under an argon atmosphere. The reaction mixture was concentrated, diluted with EtOAc, thrice washed with 1N HCl, dried (Na₂SO₄), filtered and concentrated. The crude product was purified by SiO₂ chromatography eluting an EtOAc/hexane gradient (10% to 30% EtOAc) to afford 30 mg (19%) of 154 as a orange oil.

125 step 4—To a solution of 154 (60 mg, 0.108 mmol) in EtOAc (20 mL) and MeOH (20 mL), was added 20% Pd(OH)₂/C (23 mg, 0.033 mmol). The reaction was transferred to a Parr bottle and hydrogenated with shaking at 45 psi for 6 h. LCMS indicated incomplete reaction. The reaction mixture was filtered and the filtrate transferred to a Parr bottle and fresh 20% Pd(OH)₂/C (21 mg, 0.030 mmol) was added. The reaction was hydrogenated with a Parr shaker at 45 psi overnight, filtered, concentrated, and purified on a preparative SiO₂ TLC plate developed with 2:1 EtOAc/hexane to afford 26 mg (52%) of I-109 a white solid.

I-110 can be prepared analogously except in step 1, 150a is replaced with N-(4-bromo-2-methyl-phenyl)-methanesulfonamide.

Example 23

N-(4-{2-[3-tert-Butyl-2-methoxy-5-(2-oxo-1,2-dihydro-pyridin-3-yl)-phenyl]-1-cyano-ethyl}-phenyl)-methanesulfonamide (I-177, SCHEME P)

step 1—To a solution of potassium phosphate (106 mg, 0.499 mmol) in EtOH (5 mL), was added a solution of D-2 (272 mg, 1.004 mmol) and 4-nitrophenylacetonitrile (190 mg, 1.173 mmol) in EtOH (10 mL). The reaction mixture was stirred overnight at RT, concentrated, and purified by SiO₂ chromatography eluting with a EtOAc/hexane gradient (0 to 10% EtOAc) to afford 295 mg (71%) of P-1 as a yellow foam.

step 2—A sealed tube containing P-1 (667 mg, 1.607 mmol), 37 (370 mg, 2.419 mmol), Pd(PPh₃)₄ (149 mg, 0.129 mmol), Na₂CO₃ (448 mg, 4.227 mmol) in a mixture of MeOH (7 mL) and DCM (3 mL) was irradiated in a microwave synthesizer at 115° C. for 30 min. The reaction mixture was concentrated, diluted with DCM, washed with brine, dried (Na₂SO₄), filtered and evaporated. The crude product was purified by SiO₂ chromatography eluting with an EtOAc/hexane gradient (0 to 10% EtOAc) to afford 658 mg (92%) of P-2 as a pale yellow oil.

step 3—To a solution of P-2 (658 mg, 1.485 mmol) in EtOAc (30 mL) and MeOH (30 mL), was added 20% Pd/C (173 mg, 0.247 mmol). The reaction was stirred at RT under an atmosphere of hydrogen overnight. The reaction mixture was filtered, concentrated, and purified by SiO₂ chromatography eluting with an EtOAc/hexane gradient (20 to 30% EtOAc) to afford 270 mg (44%) of P-3a as a colorless oil.

step 4—To a solution of amine P-3a (270 mg, 0.651 mmol) and pyridine (0.150 mL, 1.855 mmol) in DCM (5 mL) cooled to 0° C., was added methanesulfonyl chloride (0.060 mL, 0.772 mmol). The reaction was gradually warmed to RT and stirred overnight. The solution was diluted with DCM, washed sequentially with saturated CuSO₄ and 1N HCl solution, dried (Na₂SO₄), filtered and evaporated. The crude product was purified by SiO₂ chromatography eluting with an EtOAc/hexane gradient (30 to 50% EtOAc) to afford 281 mg (88%) of P-3b as a white foam.

step 5—A solution of P-3b (91 mg, 0.185 mmol), HBr 48% (0.090mL, 0.784 mmol) in HOAc (3 mL) was heated at 60° C. overnight in a sealed tube. The reaction mixture was carefully poured into a mixture of saturated NaHCO₃ and ice, extracted with EtOAc, and dried (Na₂SO₄), filtered and evaporated. The crude product was purified on a preparative SiO₂ TLC plate developed with 2:1 EtOAc/hexane to afford 44 mg (50%) of I-177 as an off-white solid.

126

Example 24

3-[3-tert-Butyl-2-methoxy-5-(2-oxo-1,2-dihydro-pyridin-3-yl)-phenyl]-2-(4-methanesulfonylamino-phenyl)-propionic acid (I-179)

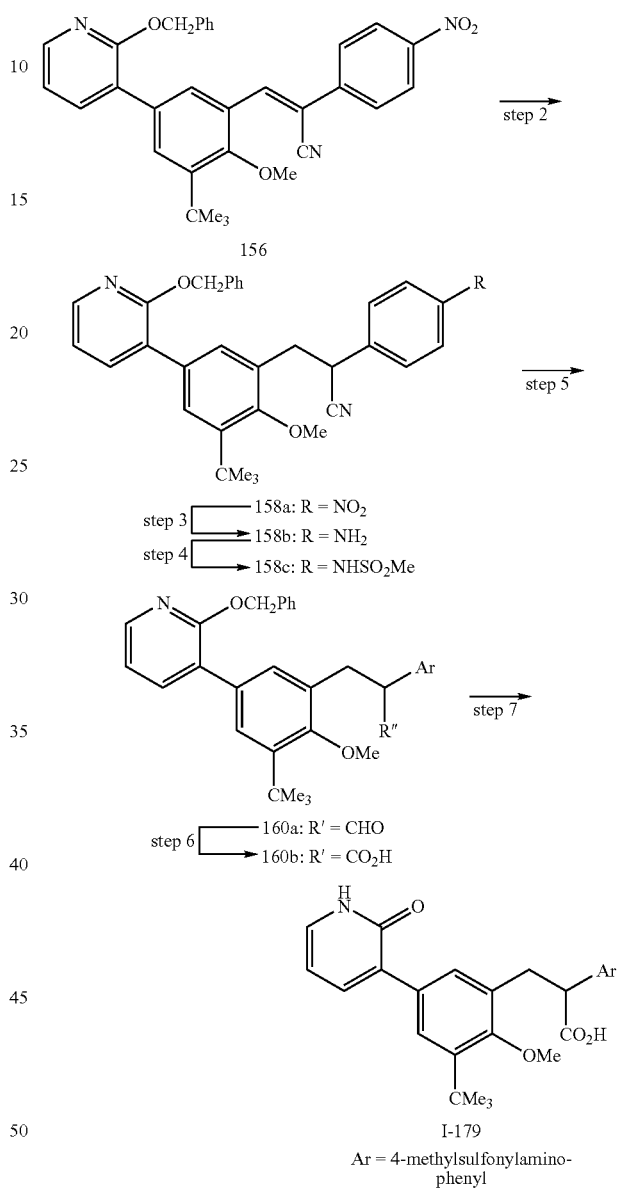

step 1—A sealed tube containing P-1 (934 mg, 2.251 mmol), 141 (773 mg, 3.376 mmol), Pd(PPh₃)₄ (182 mg, 0.157 mmol), Na₂CO₃ (600 mg, 5.661 mmol) in a mixture of MeOH (11 mL) and DCM (3 mL) was irradiated in a microwave synthesizer at 115° C. for 30 min. The reaction mixture was concentrated, diluted with EtOAc, washed with brine, and dried (Na₂SO₄), filtered and evaporated. The crude product was purified by SiO₂ chromatography eluting with an EtOAc/hexane gradient (0 to 10% EtOAc) to afford 943 mg (81%) of 156 as a yellow foam.

step 2—To a solution of 156 (943 mg, 1.817 mmol) in MeOH (2 mL) and THF (10 mL) at 0° C., was added NaBH₄ (105 mg, 2.776 mmol). The reaction was gradually warmed to RT for 2 h then quenched with aqueous NHCl. The organic solvents were concentrated and resulting residue was extracted with EtOAc. The extracts were dried (Na₂SO₄), filtered and evaporated to afford 899 mg (95%) of 158a as a white foam that was used without further purification.

step 3—To a solution of 158a (793 mg, 1.52 mmol) in DMF (30 mL) and EtOAc (30 mL), was added tin chloride dihydrate (1.72 g, 7.62 mmol). The reaction mixture was stirred overnight at RT partitioned between EtOAc and saturated NaHCO₃ and filtered through CELITE. The organic layer was separated, thrice washed with water, dried (Na₂SO₄), filtered and evaporated. The crude product was purified by SiO₂ chromatography eluting with a EtOAc/hexane gradient (20 to 50% EtOAc) to afford 472 mg (63%) of 158b as a white foam step 4—To a solution of 158b (537 mg, 1.094 mmol) and pyridine (0.220 mL, 2.720 mmol) in DCM (10 mL) at 0° C., was added methanesulfonyl chloride (0.110 mL, 1.415 mmol). The reaction was gradually warmed to RT and stirred overnight. The solution was diluted with DCM, washed with 1N HCl solution, dried (Na₂SO₄), filtered and evaporated. The crude product was purified by SiO₂ chromatography eluting with an EtOAc/hexane gradient (20 to 30% EtOAc) to afford 534 mg (86%) of 158c as a white foam.

step 5—To a solution of 158c (534 mg, 0.938 mmol) in DCM (8 mL), was added a solution of DIBAL (2.05 mL, 1.0M in DCM, 2.05 mmol). After 1 h at RT, the reaction mixture was cooled to 0° C. and diluted with diethyl ether (20 mL). 1N HCl (6 mL) was added and the suspension was stirred for 2 h. The reaction mixture was extracted with EtOAc, dried (Na₂SO₄), filtered and evaporated. The crude product was purified by SiO₂ chromatography eluting with an EtOAc/hexane gradient (20 to 75% EtOAc) to afford 282 mg (53%) of 160a as a white foam.

step 6—A solution of 160a (172 mg, 0.301 mmol), sodium chlorite (69 mg, 0.763 mmol), NaH₂PO₄ (52 mg, 0.377 mmol), 2-methyl-2-butene (0.640 mL, 6.050 mmol) in tert-butanol (3 mL), water (3 mL), THF (3 mL) was stirred at 0° C. and gradually warmed to RT overnight. The 22 reaction mixture was diluted with EtOAc, washed with NH₄Cl solution, dried (Na₂SO₄), filtered and evaporated. The crude product was purified by SiO₂ chromatography eluting with an EtOAc/hexane gradient (50 to 100% EtOAc) to afford 72 mg (41%) of 160b as a white foam.

step 7—To a solution of 160b (72 mg, 0.122 mmol) in EtOAc (15 mL) and MeOH (15 mL) was added 20% Pd(OH)₂/C (29 mg, 0.041 mmol). The reaction was transferred to a Parr bottle and hydrogenated with a Parr shaker for 2 h. The reaction mixture was filtered, concentrated, and purified on a preparative SiO₂ TLC plate developed with EtOAc to afford 20 mg (33%) of I-177 as a white solid.

Example 25

N-(1-{2-[3-tert-Butyl-2-methoxy-5-(2-oxo-1,2-dihydro-pyridin-3-yl)-phenyl]-ethyl}-piperidin-4-yl)-methanesulfonamide (I-117, SCHEME Q)

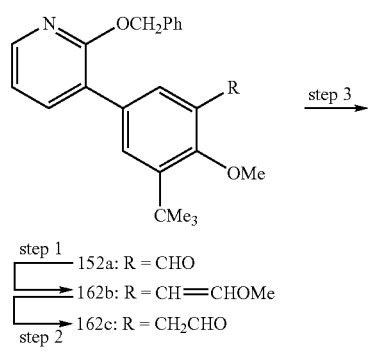

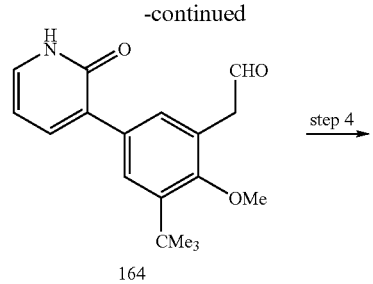

164

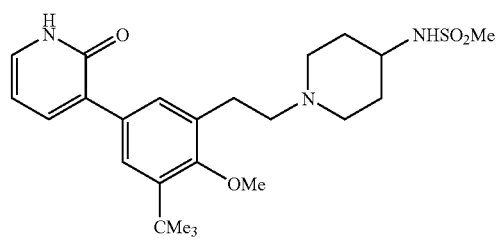

I-117 step 1—To a solution of methoxymethyl triphenylphosphonium chloride (1.71 g, 4.988 mmol) in THF (10 mL) was added a solution of sodium bis(trimethylsilyl)amide (5.5 mL, 1.0M in THF, 5.5 mmol) at −78° C. After 35 min, a solution of 152a (362 mg, 0.965 mmol) in THF (10 mL) was added and the reaction mixture was gradually warmed to RT and stirred overnight. The reaction was quenched with NH₄Cl solution and concentrated. The crude residue was diluted with EtOAc, washed with brine and dried (Na₂SO₄), filtered and evaporated. The product was purified by SiO₂ chromatography eluting with an EtOAc/hexane gradient (0 to 5% EtOAc) to afford 82 mg of Q-1a as a colorless oil which was determined by NMR to be the trans olefin. A further 245 mg of mixed fractions were re-purified using an Et₂O/hexane gradient (0 to 5% Et₂O) to give 215 mg of a colorless oil as a mixture of cis and trans olefins. Both isomers were combined together and used in step 2.

step 2—A solution of Q-1a (303 mg, 0.752 mmol), 1N HCl (8 mL) in dioxane (10 mL) was heated for 6 h at 60° C. The volatiles were removed in vacuo and the crude residue was diluted with EtOAc, washed with aqueous NaHCO₃, dried (Na₂SO₄), filtered and evaporated to afford 137 mg of Q-1b as a colorless oil that was used without further purification.

step 3—To a solution of Q-1b (187 mg, 0.625 mmol) and N-(4-piperidinyl)methanesulfonamide (145 mg, 0.815 mmol, CASRN 70724-72-0) in DCE (10 mL) was added HOAc (5 drops). After one h, sodium triacetoxyborohydride (265 mg, 1.25 mmol) was added. After 3 h, the reaction mixture was quenched with 1N NaOH and stirred for 30 min. The reaction mixture was extracted with DCM and dried (Na₂SO₄), filtered and evaporated. The crude product was purified on a preparative SiO₂ TLC plate developed with MeOH/DCM to afford 34 mg (12%) of Q-1c as an off-white solid.

Debenzylation is carried out by hydrogenolysis as described in step 7 of example 24.

Example 26

N-{4-[3-tert-Butyl-2-methoxy-5-(2-oxo-1,2-dihydro-pyridin-3-yl)-benzylamino]-cyclohexyl}-methane-sulfonamide (I-119)

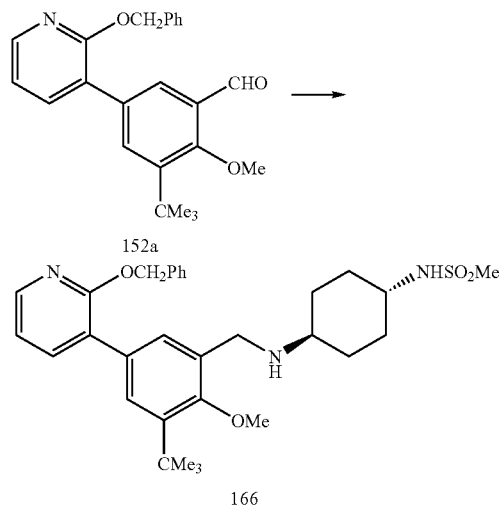

step 1—To a solution of N-(trans-4-aminocyclohexyl)-methanesulfonamide, (91 mg, 0.474 mmol, CASRN 264608-37-9) and 152a (128 mg, 0.341 mmol) in DCE (15 mL) was added HOAc (5 drops) and MeOH (2 mL). After 1 h, IPA (2 mL) and 3 Å molecular sieves were added and the reaction mixture was heated to 50° C. After 1 h, sodium triacetoxyborohydride (149 mg, 0.703 mmol) was added and the reaction mixture was stirred overnight. The reaction was quenched with NaHCO$_3$ solution and concentrated. The crude residue was diluted with EtOAc, washed with NaHCO$_3$, dried (Na$_2$SO$_4$), filtered and evaporated. The crude product was purified by SiO$_2$ chromatography eluting with a MeOH/DCM gradient (0 to 5 to 10% MeOH) to afford 88 mg (47%) of 166 as a colorless oil.

step 2—A solution of 166 (56 mg, 0.102 mmol), HBr 48% (0.050 mL, 0.436 mmol) in HOAc (4 mL) was heated at 60° C. for 3 h in a sealed tube. The reaction mixture was carefully poured into a mixture of saturated NaHCO$_3$ and ice, extracted with EtOAc, dried (Na$_2$SO$_4$), filtered and evaporated. The crude product was purified on a preparative SiO$_2$ TLC plate developed with 10% MeOH/DCM to afford 20 mg (17% yield) of product that was further purified by reverse phase HPLC to afford 8 mg of I-119 a white solid.

Example 27

N-(6-{2-[5-tert-Butyl-2-cyano-3-(2-oxo-1,2-dihydro-pyridin-3-yl)-phenyl]-ethyl}-pyridin-3-yl)-methane-sulfonamide (I-114)

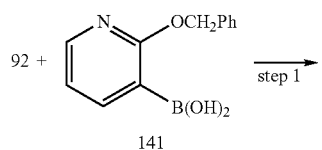

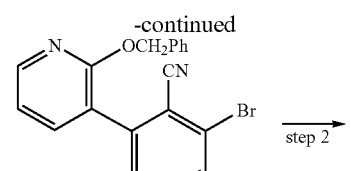

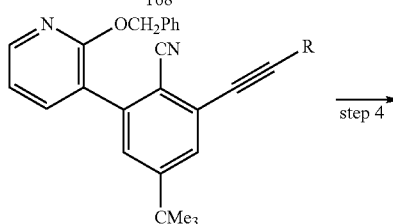

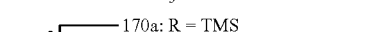

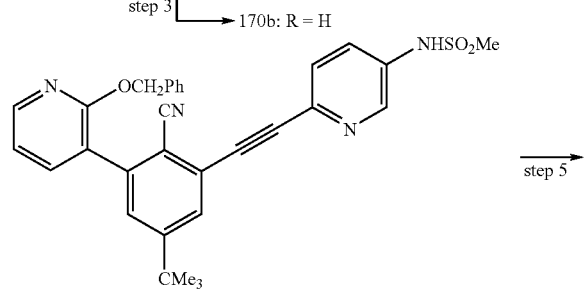

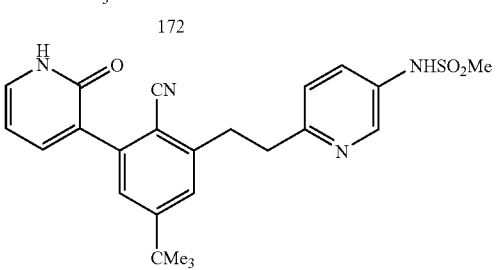

step 1—To the 92 (0.500 g, 1.9 mmol) in a microwave tube was added sequentially 141 (0.526 g, 2.3 mmol), Pd(PPh$_3$)$_4$ (0.220 g, 0.1 eq.), Na$_2$CO$_3$ (0.609 g, 3 eq.), and MeOH/DCM (9 mL/3 mL). The reaction was irradiated in the microwave synthesizer at 125° C. for 30 min, then cooled, concentrated and partitioned between DCM and water (25 mL/25 mL). The aqueous layer was twice washed with DCM (25 mL). The combined organic layers were washed with brine, dried (Na$_2$SO$_4$), filtered and evaporated. The residue was purified by SiO$_2$ chromatography eluting with 20% EtOAc/hexane to afford 0.402 g (50%) of 168 as a light brown solid.

step 2—To a solution of 168 (0.788 g, 1.9 mmol) and THF was added CuI (0.018 g, 0.05 eq.), PdCl$_2$(PPh$_3$)$_2$ (0.131 g, 0.1 eq.), trimethylsilyl acetylene (0.8mL, 3 eq) and DIPEA (5 mL). The reaction was heated at 80° C. for 3 h, then additional copper iodide (0.05 eq.), PdCl$_2$(PPh$_3$)$_2$ (0.1 eq), and trimethylsilyl acetylene (3 eq) were added and the reaction stirred at 80° C. over night. The reaction mixture was partitioned between EtOAc and water and the aqueous layer twice washed with EtOAc (25 mL). The combined extracts were washed with brine, dried (Na$_2$SO$_4$), filtered and evaporated. The crude product was purified by SiO$_2$ chromatography eluting with an EtOAc/hexane gradient (0 to 10% EtOAc) to afford 0.497 g (60%) of 170a as a glassy yellow solid.

step 3—To a solution of 170a (0.450 g, 1 mmol) and in MeOH (5 mL) was added $K_2CO_3$ (0.045 g, 0.32 eq). The reaction was stirred over night at RT. The reaction mixture was concentrated and purified by $SiO_2$ chromatography eluting with 10% EtOAc/hexane to afford 0.165 g (44%) of 170b as a light yellow glassy solid.

step 4—To a solution of 170b (0.160 g, 0.44 mmol) and 165 (0.195 g, 1.5 eq.) and THF (15 mL) was added CuI (0.004 g, 0.05 eq.), PdCl2(PPh$_3$)$_2$ (0.031 g, 0.1 eq.) and DIPEA. The reaction was heated overnight at 80° C., concentrated and partitioned between EtOAc/water (25 mL/25 mL). The aqueous layer was separated and twice washed with EtOAc (25 mL). The combined extracts were washed with brine, dried ($Na_2SO_4$), filtered and concentrated to give a yellow/brown oil. The oil was purified by $SiO_2$ chromatography eluting with an EtOAc/hexane gradient (20 to 100% EtOAc) to afford 0.070 g (30%) of 172 as a light brown solid.

step 5—To a solution of 172 (0.070 g, 0.13 mmol) and EtOAc/MeOH (20 mL/20 mL) was added 20% Pd(OH)$_2$/C (0.100 g). The reaction was shaken under 40 psi of hydrogen in a Parr Shaker. After 3 h, additional Pd(OH)$_2$/C (0.100 g) was added shaking continued for 1 h then filtered through glass filter paper on a Hirsch funnel to remove the catalyst. The filtrate was concentrated, and the recovered product purified on a preparative $SiO_2$ TLC plate. The plate was developed half-way with 80% EtOAc/hexane then quickly dried under a nitrogen stream and re-developed with 40% EtOAc/hexane to afford 0.028 g (48%) of I-114 as an off-white powder.

Preparation of N-(6-iodo-pyridin-3-yl)-methanesulfonamide (165)—To a solution of 2-iodo-5-aminopyridine (2.0 g, 9 mmol, CASRN 29958-12-1) and DCM (15 mL) cooled to 0° C. was added pyridine (0.88 mL, 1.2 eq) followed by methanesulfonyl chloride. The reaction was stirred for 3 h and then warmed to RT and partitioned between saturated $NaHCO_3$ (20 mL) and DCM (20 mL). The aqueous layer was thrice washed with DCM (25 mL). The combined extracts were washed with brine, dried ($Na_2SO_4$), filtered and concentrated. The resulting yellow-brown oil was triturated with dichloromethane to afford 1.299 g (48%) of 165 a white powder.

Example 28

4-tert-Butyl-2-[2-(4-methanesulfonylamino-phenyl)-ethyl]-6-(2-oxo-1,2-dihydro-pyridin-3-yl)-benzamide (I-122)

To a solution of I-87 (0.067 g) and ethanol (5 mL) was added a catalytic amount of hydrido(dimethyl phosphinous acid-kP)[hydrogen bis-(dimethylphosphinito-kP)]platinum (II) and the reaction was stirred over night at RT. Additional platinum (II) catalyst was added and the reaction stirred for an additional two h then the solution was concentrated. The resulting brown oil was partitioned between EtOAc/hexane (20 mL/20 mL) and the aqueous layer was twice washed with EtOAc (20 mL). The combined organic extracts were washed with brine, dried ($Na_2SO_4$), filtered and concentrated. The crude product was purified on a preparatory $SiO_2$ TLC plate developed with 40% EtOAc/hexane to afford 0.008 g (12%) of I-122.

Example 29

3-tert-Butyl-N-[3-(methanesulfonylamino-methyl)-phenyl]-2-methoxy-5-(2-oxo-1,2-dihydro-pyridin-3-yl)-benzamide (I-112)

To B-3a (R'''=$R^6$=H, 0.040 g, 0.14 mmol) dissolved in DMF (3 mL) was added N-[(3-aminophenyl)methyl]-methanesulfonamide (0.055 g, 2 eq., CASRN 856193-46-9), EDCI (0.038 g, 2 eq.) and HOBt (0.053 g, 2 eq.). The reaction was stirred overnight at RT and then concentrated. The crude mixture was taken up in EtOAc and water (25 mL/25 mL) and the aqueous layer twice washed with EtOAc (20 mL). The combined organic layers were washed with brine, dried ($Na_2SO_4$), filtered and evaporated. The crude product was purified on a preparatory $SiO_2$ TLC plate developed with 80% EtOAc/hexane to afford 0.019 g (28%) of I-112.

Example 30

3-tert-Butyl-N-(4-carbamoylmethoxy-phenyl)-2-methoxy-5-(2-oxo-1,2-dihydro-pyridin-3-yl)-benzamide (I-113)

To a solution of B-3a (R'''=$R^6$=H, 0.040 g, 0.14 mmol) dissolved in DMF (3 mL) was added 2-(3-aminophenoxy)-acetamide (0.046 g, 2 eq., CASRN 62877-06-9), EDCI (0.038 g, 2 eq.) and HOBt (0.053 g, 2 eq.). The reaction was stirred overnight at RT and then concentrated. The crude mixture was partitioned between EtOAc and water (25 mL/25 mL) and the aqueous layer twice washed with EtOAc (20 mL). The combined extracts were washed with brine, dried ($Na_2SO_4$), filtered and concentrated. The crude product was purified on a preparatory $SiO_2$ TLC plate developed with 80% EtOAc/hexane to afford 0.005 g (8%) of I-132.

Example 31

4-tert-Butyl-2-[2-(4-methanesulfonylamino-phenyl)-ethyl]-6-(2-oxo-1,2-dihydro-pyridin-3-yl)-benzoic acid (I-135) and 4-tert-Butyl-2-[2-(4-methanesulfonylamino-phenyl)-ethyl]-6-(2-oxo-1,2-dihydro-pyridin-3-yl)-benzoic acid methyl ester (I-134)

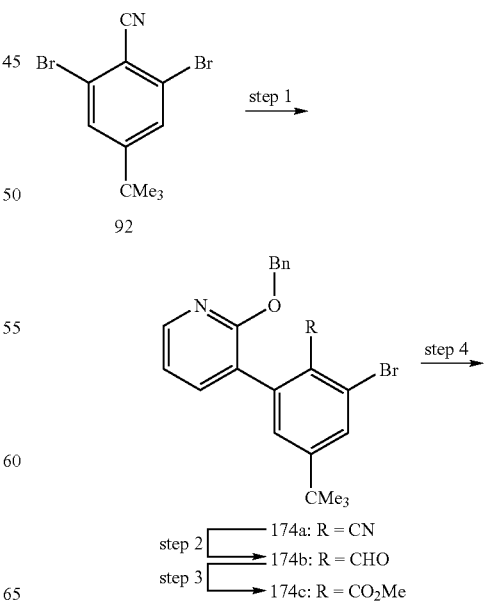

-continued

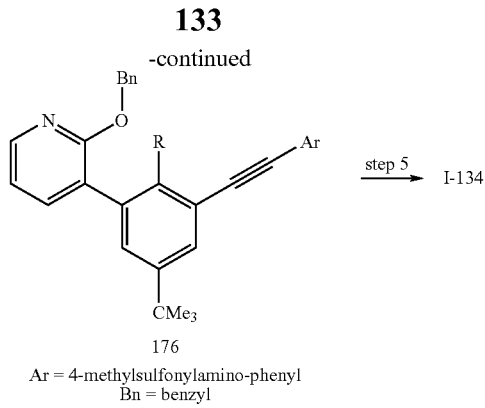

176

Ar = 4-methylsulfonylamino-phenyl
Bn = benzyl step 1—A sealed tube containing 141 (0.72 g, 3.15 mmol), 92 (1.00 g, 3.15 mmol), $Na_2CO_3$ (1.00 g, 9.45 mmol) and $Pd(PPh_3)_4$ (0.36 g, 0.315 mmol) in a mixture of MeOH (12 mL) and DCM (4 mL) was irradiated in a microwave synthesizer at 100° C. for 30 min. The reaction mixture was diluted with DCM, filtered through a pad of CELITE and the filtrate was concentrated. The crude residue was purified by $SiO_2$ chromatography eluting with an EtOAc/hexane gradient (2 to 25% EtOAc) to afford 1.00 g (75%) of 174a.

step 2—To a solution of the 174a (1.00 g, 2.4 mmol) in toluene (20 mL) cooled to −78° C. was added dropwise a solution of DIBAL (2.9 mL, 1M in DCM). The reaction mixture was stirred at −78° C. for 3 h then poured into ice cold aqueous 5% $H_2SO_4$. The layers were separated and the aqueous layer was extracted with EtOAc. The combined extracts were washed with brine and dried ($MgSO_4$) and concentrated. The crude residue was purified by $SiO_2$ chromatography eluting with an EtOAc/hexane gradient (5 to 35% EtOAc) to afford 0.73 g (72%) of 174b.

step 3—To a mixture of 174b (0.73 g, 1.72 mmol), $Na_2HPO_4.H_2O$ (2.85 g 2.06 mmol), 2-methyl-2-butene (2.40 g, 3.70 mL, 3.44 mmol) in tert-BuOH (30 mL), $H_2O$ (30 mL) and THF (10 mL) cooled to 5° C. was added $NaClO_2$ (0.39 g, 4.30 mmol). The mixture was stirred at RT overnight then poured into an ice-1N HCl mixture. The resulting mixture was extracted with EtOAc. The extracts were washed with brine and dried ($MgSO_4$), filtered and concentrated to afford 0.76 g (100%) of the desired acid. To a solution of the acid and MeOH (5 mL) and DCM (15 mL) cooled to 5° C. was added dropwise trimethylsilyl diazomethane (1.29 mL, 2N in hexanes, 2.58 mmol). After 30 minutes, the solvent was evaporated and the crude residue was purified by $SiO_2$ chromatography eluting with an EtOAc/hexane gradient (2 to 15% EtOAc) to afford 0.674 g (86%) of 174c.

step 4—To a mixture of 174c (0.17 g, 0.37 mmol), 4-methanesulfonylphenyl-acetylene (0.11 g, 0.56 mmol), CuI (7.0 mg, 0.037 mmol) in DMF (3 mL) was added TEA (1.5 mL). The mixture was heated at 75° C. for 3 h, cooled and diluted with EtOAc. The EtOAc solution was washed sequentially with 1N HCl, water, brine, dried ($MgSO_4$), filtered and concentrated. The crude residue was purified by $SiO_2$ chromatography eluting with an EtOAc/hexane gradient (10 to 65% EtOAc) to afford 39 mg (19%) of 176.

step 5—A suspension 176 (39 mg, 0.068 mmol) and 20% $Pd(OH)_2$/C (16 mg) in MeOH (20 mL) and EtOAc (10 mL) was shaken (Parr Hydrogenator) under 60 psi of $H_2$ at RT for 4 h. The catalyst was filtered off and the filtrate was concentrated. The crude residue was purified by on a preparative $SiO_2$ TLC plate developed with 5% MeOH/DCM to afford 26 mg (80%) of I-134.

A solution of I-134 (19 mg, 0.039 mmol), 1N LiOH (0.5 mL), THF (1 mL), MeOH (1 mL) and water (0.5 mL) was stirred at RT overnight. The solvent was evaporated the residue diluted with water and made basic. The resulting mixture was with ether and the aqueous solution was acidified to pH 1 with 1N HCl and extracted with EtOAc. The EtOAc solution was washed with brine, dried ($MgSO_4$), filtered and concentrated to afford 14.6 mg (80%) of I-135.

Example 32

N-(4-{(E)-2-[3-tert-Butyl-2-methoxy-5-(2-oxo-1,2-dihydro-pyridin-3-yl)-phenyl]-vinyl}-phenyl)-methanesulfonamide (I-126)

step 1—To a slurry of sodium hydride (0.17 g, 4.159 mmol, 60% in mineral oil) in THF—5 (5 mL) containing 0.1 equivalent of 15-crown cooled to 0° C. was added a solution of diethyl (4-nitro-benzyl)-phosphonate (1.14 g, 4.159 mmol) in THF (5 mL). When gas evolution ceased, a slurry of 74 (1.132 g, 3.781 mmol) was added and stirred at RT overnight. An additional equivalent of NaH was added to the partially reacted mixture and stirring continued for 1 h. The reaction mixture is partitioned between water and $Et_2O$ and the organic extract was sequentially washed with water and brine, dried ($Na_2SO_4$), filtered and evaporated. The crude product was purified by $SiO_2$ chromatography eluting with 1:1 EtOAc/hexane to afford 3-{3-tert-butyl-4-methoxy-5-[(E)-2-(4-nitro-phenyl)-vinyl]-phenyl}-2-methoxy-pyridine (178)

Conversion of 178 to I-126 by reduction of the nitro group, mesylation and dealkylation of the methyl ether can be carried out in analogy to the procedures described in steps 2 to 4 of example 6. Alternatively, selective reduction of the nitro group can be carried out with $SnCl_2.2H_2O$ in accord with step 3 of example 24.

Example 33

N-(6-{2-[5-tert-Butyl-2-cyano-3-(2-oxo-1,2-dihydro-pyridin-3-yl)-phenyl]-ethyl}-pyridin-3-yl)-methanesulfonamide (I-114)

step 1—To a mixture of 5-amino-2-iodo-pyridine (0.447 g, 2.031 mmol), G-1b ($R^3$=OMe, $R^6$=H, 0.3 g, 1.016 mmol), $Pd(II)Cl_2(PPh_3)_2$ (0.071 g, 0.102 mmol), CuI (9.67 mg, 0.051 mmol), DIPEA (1.774 mL, 10.16 mmol) and THF (5 ml) was degassed by 3 cycles of vacuum and Ar flushes. The reaction mixture was heated to 80° C. overnight. The reaction mixture was partitioned between EtOAc and water. The EtOAc extract was washed with water, dried ($MgSO_4$), filtered and evaporated. The crude product was purified by $SiO_2$ chromatography eluting with a EtOAc/hexane gradient (0 to 70% EtOAc) to afford 0.322 g of 6-[3-tert-butyl-2-methoxy-5-(2-methoxy-pyridin-3-yl)-phenylethynyl]-pyridin-3-ylamine (180) as a yellow gum.

step 2—A suspension of 180 (0.322 g, 0.831 mmol) 20% $Pd(OH)_2$/C (0.146 g) and EtOAc/MeOH (1:1, 40 mL) was hydrogenated in a Parr Shaker under 50 psi of hydrogen for 2 h. The resulting suspension was filtered through CELITE and evaporated. The crude product was purified by $SiO_2$ chromatography eluting with a EtOAc/hexane gradient (0 to 90% EtOAc) to afford 0.183 g of 6-{2-[3-tert-butyl-2-methoxy-5-(2-methoxy-pyridin-3-yl)-phenyl]-ethyl}-pyridin-3-ylamine (182) as a yellow foam.

step 3—To a solution of 182 (0.183 g, 0.467 mmol), pyridine (0.076 mL, 0.935 mmol) and DCM (5 mL) was added dropwise methanesulfonyl chloride (0.268 g, 2.337 mmol).

The reaction was stirred overnight at RT then evaporated and taken up in EtOAc, washed with water, dried (MgSO4), filtered and evaporated. The crude product was purified by SiO₂ chromatography eluting with an EtOAc/hexane gradient to afford 0.099 g of N-(6-{2-[3-tert-butyl-2-methoxy-5-(2-methoxy-pyridin-3-yl)-phenyl]-ethyl}-pyridin-3-yl)-methanesulfonamide (184) along with the bis-mesylated byproduct.

step 4—A solution of 184 (0.099 g, 0.211 mmol), 48% HBr (0.096 mL) and HOAc (4 mL) in a microwave tube was heated at 70° C. 5 h. The crude product was purified by SiO₂ chromatography eluting with a DCM/MeOH gradient (0 to 10% MeOH) to afford 0.037 g of I-114 as a colorless foam.

I-128 was prepared analogously except in step 1, 5-amino-2-iodo-pyridine was replaced with 6-bromo-pyridazin-3-ylamine.

I-133 was prepared analogously except in step 1, 5-amino-2-iodo-pyridine was replaced with 5-bromo-pyrazin-2-ylamine.

Example 34

N-(4-{2-[5-tert-Butyl-2-(2-hydroxy-ethoxy)-3-(2-oxo-1,2-dihydro-pyridin-3-yl)-phenyl]-ethyl}-phenyl)-methanesulfonamide (I-118)

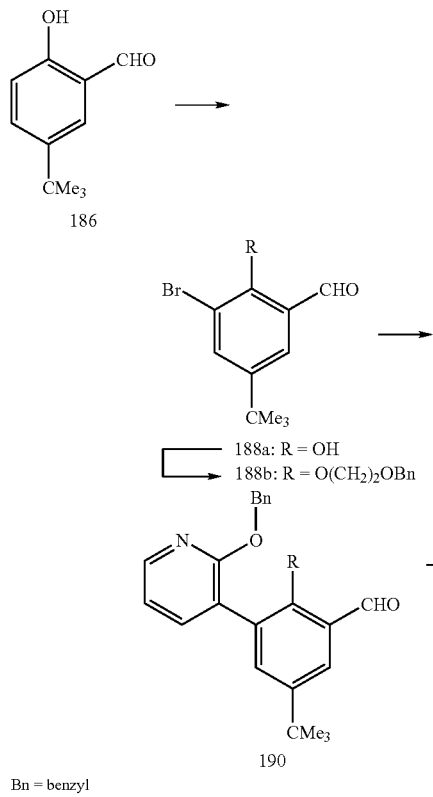

Bn = benzyl step 1—To a solution 186 (10.0 g, 56.1 mmol) and KOAc (13.75 g, 140.3 mmol) dissolved in HOAc (120 mL) was added dropwise a solution of bromine (2.99 mL, 61.72 mmol) and the resulting solution was heated at 50° C. overnight. The reaction mixture was cooled and poured into water. The precipitate was filtered, washed with water (2×500 mL) and dried in an oven overnight at 65° C. to afford 14.0 g of 188a.

step 2—To a solution of 188a (1.0 g, 3.89 mmol) in DMF (10 mL) cooled to 0° C. was added NaH (0.187 g, 4.67 mmol, 60% mineral oil dispersion). The resulting mixture was stirred for 15 min and then benzyl 2-bromoethyl ether (1.54 g, 9.72 mmol) was added and the reaction removed from the cooling bath. After reaching RT the mixture was heated at 65° C. for 3 h. The reaction was cooled to RT and partitioned between water and ether. The organic phase was washed twice with water, then with brine, dried and concentrated to afford 1.92 g of 188b.

Condensation of 188b and 141 to afford 190 was carried out by the procedure described in step 1 of example 7. Wittig homologation of 190 with p-nitrobenzyl-phosphonium bromide, reduction of the nitro substituent to an amino group (192) and sulfonylation of the amine with mesyl chloride (194) was carried out as described in steps 3 to 5 of example 7. The procedure for the reduction was modified as described below to achieve selective reduction of the nitro group. Final debenzylation was carried out as described below.

4-{2-[2-(2-benzyloxy-ethoxy)-3-(2-benzyloxy-pyridin-3-yl)-5-tert-butyl-phenyl]-vinyl}-phenylamine (192)—A suspension of 2-benzyloxy-3-{2-(2-benzyloxy-ethoxy)-5-tert-butyl-3-[2-(4-nitro-phenyl)-vinyl]-phenyl}-pyridine (0.78 g), Ra—Ni in water (1.5 mL) in MeOH (10 mL), THF (90 mL) and NH₄OH (0.1 mL) was stirred under 1 atm of hydrogen for 1.5 h. The catalyst was filtered and the solution concentrated. The residue was dissolved in EtOAc, washed with water and brine, dried and concentrated. The crude product was purified by SiO₂ chromatography eluting with an EtOAc/hexane gradient (10 to 40% EtOAc) to afford 627 mg of the title compound as an oil which solidified upon standing.

N-(4-{2-[3-tert-Butyl-6-(2-hydroxy-ethoxy)-5-(2-hydroxy-pyridin-3-yl)-2-methoxy-phenyl]-ethyl}-phenyl)-methanesulfonamide (I-118)—To a solution of N-(4-{2-[2-(2-benzyloxy-ethoxy)-3-(2-benzyloxy-pyridin-3-yl)-5-tert-butyl-phenyl]-vinyl}-phenyl)-methanesulfonamide (194, 159 mg), Pd(OH)₂/C (35 mg) and EtOAc (15 mL) were stirred under 1 atmosphere of hydrogen for 1 h. The catalyst was filtered and the filtrate evaporated. The crude product was purified by SiO₂ chromatography eluting with 10% MeOH/DCM to afford 0.102 g of I-118 as a white solid.

Example 35

N-(4-{(E)-2-[3-tert-Butyl-5-(2-oxo-1,2-dihydro-pyridin-3-yl)-phenyl]-vinyl}-2-fluoro-phenyl)-methanesulfonamide (I-146)

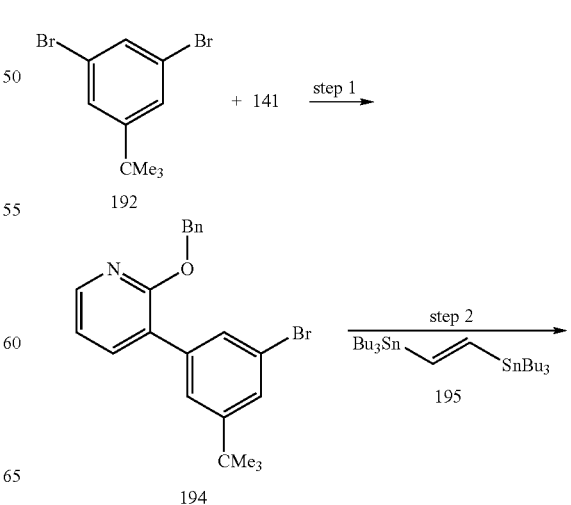

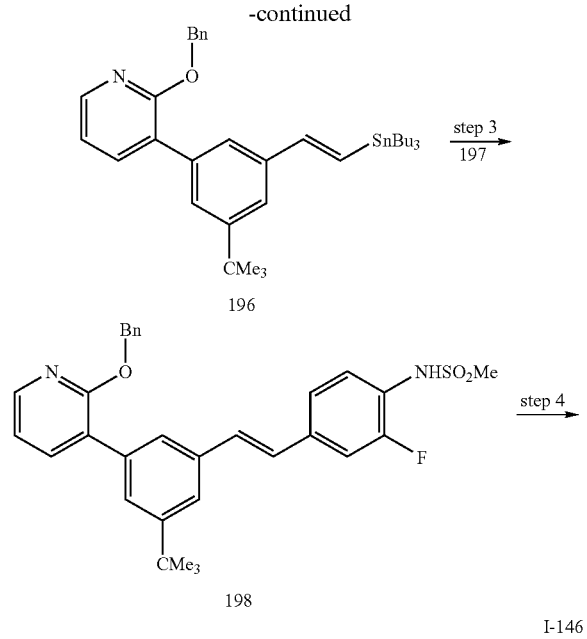

N-(2-Fluoro-4-iodo-phenyl)-methanesulfonamide (197)—To a solution of 2-fluoro-4-iodo-aniline (2.0 g, 8344 mmol) and pyridine (10 mL) cooled to 0° C. was added mesyl chloride (0.800 mL, 10.29 mmol) and the resulting solution allowed to warm to RT and stir overnight. The solution was diluted with EtOAc and the washed sequentially with saturated $CuSO_4$ and 1N HCl, dried ($Na_2SO_4$), filtered and evaporated. The crude product was purified by $SiO_2$ chromatography eluting with an EtOAc/hexane gradient (stepwise elution with 5, 10 and 15% EtOAc) to afford 2.32 g of 197.

step 1—A tube was charged with 192 (2.50 g, 8.56 mmol), 141 (2.35 g, 10.27 mmol), $Pd(PPh_3)_4$ (0.494 g, 0.43 mmol), $Na_2CO_3$ (1.36 g, 12.84 mmol), MeOH (15 mL) and DCM (2 mL), sealed and irradiated in a microwave synthesizer at 115° C. for 30 min. The reaction mixture was concentrated and the crude product purified by $SiO_2$ chromatography eluting with a EtOAc/hekane gradient (1 to 10% EtOAc) to afford 3.78 g of 194 as a viscous colorless oil along 1.02 g of the bis-arylated byproduct.

step 2—A mixture of 194 (0.503 g, 1.27 mmol), 1-[dibutyl-((E)-2-tributylstannanyl-vinyl)-stannanyl]-butane (195, 1.00 g) $Pd(PPh_3)_4$ (0.073 g, 0.06 mmol), TEA (0.442 mL, 3.17 mmol) and toluene (10 mL) was maintained under an Ar atmosphere and heated to 90° C. for 3.5 h. The reaction was cooled to RT and concentrated. The crude product was purified on a preparative $SiO_2$ TLC plate which afforded 0.469 g of 196 contaminated with small quantities of 195. The product was used in the next step without further purification.

step 3—A solution of 196 (0.19 mmol), 197 (0.072 g, 0.23 mmol), $Pd(PPh_3)_4$ (11 mg, 0.01 mmol), TEA and toluene (1.5 mL) was heated at 90° C. for 24 h. The reaction mixture was cooled, concentrated and purified by $SiO_2$ chromatography eluting with a EtOAc/hexane gradient (10 to 30% EtOAc) followed by preparative TLC to afford 31 mg of 198 as a yellow oil.

step 4—A tube was charged with 198 (0.028 g), 48% HBr (20 µL) and HOAc (1 mL), sealed and heated at 50° C. for 1.5 h. The reaction mixture was cooled to RT and partitioned between EtOAc and saturated aq. $NaHCO_3$. The organic phase was washed sequentially with $H_2O$ and brine, dried, filtered and concentrated. The crude product was purified by $SiO_2$ chromatography eluting with a MeOH/DCM gradient (1 to 10% MeOH) to afford 13 mg of I-146 as a white solid.

I-158 was prepared in an analogous manner except in step 3, 197 was replaced with methyl 2-bromo-5-methanesulfonylamino-benzoate to afford 2-{(E)-2-[3-(2-benzyloxy-pyridin-3-yl)-5-tert-butyl-phenyl]-vinyl}-5-methanesulfonylamino-benzoic acid methyl ester (199) which was demethylated as described in step 4 of this example.

2-{(E)-2-[3-tert-Butyl-5-(2-oxo-1,2-dihydro-pyridin-3-yl)-phenyl]-vinyl}-5-methanesulfonylamino-benzoic acid (I-159) was prepared from 199 as follows:

step a—A solution of 199 (0.042 g) in 1 N LiOH (1 mL), MeOH (1 mL) and THF (1 mL) was stirred at 50° C. for 3 h, cooled and concentrated in vacuo. The solution was acidified and extracted with EtOAc. The extracts were washed with brine, dried, filtered and evaporated to afford 2-{(E-2-[3-(2-benzyloxy-pyridin-3-yl)-5-tert-butyl-phenyl]-vinyl}-5-methanesulfonylamino-benzoic acid (199a).

step b—A solution of 199a, TFA (3 mL), $H_2O$ (1 mL) and DCM (10 mL) was heated at reflux for 3 h, cooled and diluted with a ice-water mixture. The pH of the solution was adjusted to ca. 3 with sat'd. $NaHCO_3$ and extracted with EtOAc. The combined extracts were washed with brine, dried, filtered and evaporated to afford N-{3-[3-(2-benzyloxy-pyridin-3-yl)-5-tert-butyl-phenyl]-1-oxo-isochroman-7-yl}-methanesulfonamide (199b)

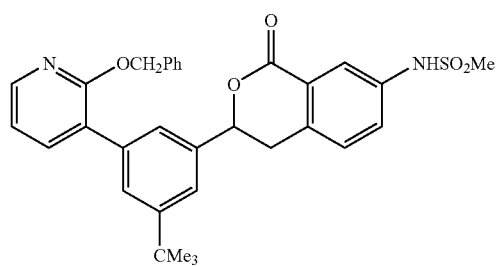

step c—Debenzylation of 199b as described in step 4 of this example afforded I-159.

Example 36

N-(4-{(E)-2-[3-tert-Butyl-5-(2-oxo-1,2-dihydro-pyridin-3-yl)-phenyl]-vinyl}-3-cyano-phenyl)-methanesulfonamide (I-147)

N-(4-Bromo-3-cyano-phenyl)-methanesulfonamide (200)—The sulfonamide was prepare by the procedure described for 197 in example 35 except 2-fluoro-4-iodo-aniline was replaced with 4-bromo-3-cyano-aniline.

I-147 was prepared by palladium-catalyzed of 196 and 200 followed by HBr-mediated cleavage of the benzyl ether as described in steps 3 and 4 of example 35.

Example 37

N-(4-{(E)-2-[3-tert-Butyl-5-(5-fluoro-2-oxo-1,2-dihydro-pyridin-3-yl)-2-methoxy-phenyl]-vinyl}-phenyl)-methanesulfonamide (I-142)

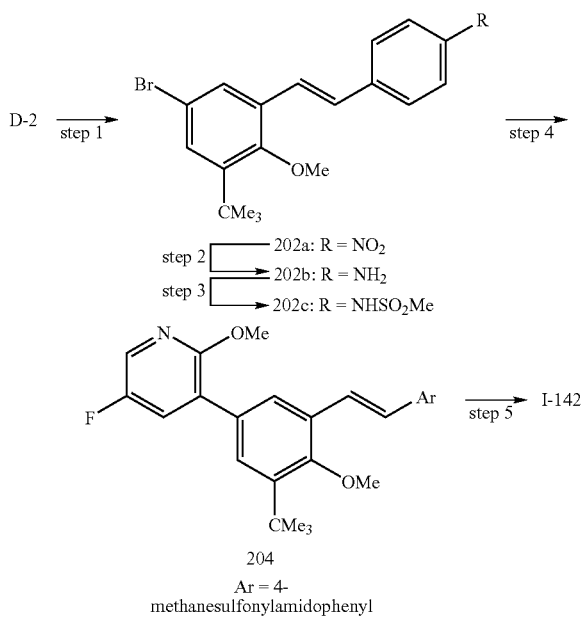

step 1—To a suspension of NaH (0.3493 g, 8.73 mmol, 60% mineral oil dispersion) and dry THF (9 mL) was added 15-crown-5 (0.27 mL, 1.36 mmol) and the resulting mixture cooled to 0° C., A solution of diethyl (4-nitro-benzyl)-phosphonate (2.33 g, 8.53 mmol) in dry THF (10.5 mL) was added slowly while maintaining the temperature at 0° C. The reaction was stirred for 15 min then a solution of D-2 (1.93 g, 7.12 mmol) and dry THF (21 mL) was added. The reaction mixture was stirred at 0° C. for 2 h then allowed to warm to RT and stirred overnight. The reaction mixture was quenched with H₂O (50 mL) and the resulting solution thrice extracted with Et₂O (3×60 mL). The combined extracts were washed with brine, dried (Na₂SO₄), filtered and concentrated in vacuo. The crude product was purified by SiO₂ chromatography eluting with 5% EtOAc/hexane to afford 2.70 g (98%) of 202a.

step 2—A mixture of 202a (0.7883, 2.02 mmol), iron (0.471 g, 8.44 mmol), NH₄Cl (0.8667 g, 16.2 mmol), MeOH (25 mL) and H₂O (25 mL) was heated at reflux for 4 h. The reaction mixture was cooled to RT and filtered. The filtrate was thrice extracted with EtOAc and the combined extracts washed with brine, dried (Na₂SO₄), filtered and concentrated in vacuo to afford 0.709 g (95%) of 202b as a yellow solid which was used without further purification.

step 3—The conversion of 202b to the sulfonamide 202c in accord with the procedure described in step 3 of example 6.

step 4—A microwave vial was charged with 202c (0.193 g, 0.442 mmol), 5-fluoro-2-methoxy-pyridin-3-yl boronic acid (0.0771 g, 0.451 mmol), Na₂CO₃ (0.1228, 1.16 mmol), Pd(PPh₃)₄ (0.027 g, 0.023 mmol), MEOH (1.2 mL) and DCM (0.3 mL), sealed and irradiated in a microwave synthesizer at 115° C. for 35 min. The vial was cooled to RT, filtered and the solid washed with EtOAc. The filtrate was washed sequentially with H₂O and brine, dried (Na₂SO₄), filtered and concentrated in vacuo. The crude product was purified by SiO₂ chromatography eluting with a EtOAc/hexane gradient (20 to 50% EtOAc) to afford 0.127 g (59%) of 204 as a yellow oil.

step 5—A vial was charged with 204 (0.087 g, 0.18 mmol), HOAc (2 mL) and 48% HBr (38 µL), sealed and heated at 60° C. overnight. The reaction was cooled to RT and added to a mixture of ice and sat'd. aqueous NaHCO₃. The resulting mixture was thrice extracted with EtOAc and the combined extracts washed sequentially with sat'd. aqueous NaHCO₃ and brine, dried (Na₂SO₄), filtered and concentrated in vacuo to afford 0.0706 g (84%) of I-142.

I-126 was prepared analogously except diethyl (4-nitro-benzyl)-phosphonate was condensed with 214 in the presence of NaH and 15-crown-5 (see, e.g., step 1 of example 41). Reduction of the nitro group with iron/NH₄Cl, conversion of the amine to the sulfonamide with mesyl chloride and demethylation of the pyridinyl ether with HBr/HOAc were carried out in accord with steps 2, 3 and 5 of this example.

I-236 was prepared analogously except in step 4, 5-fluoro-2-methoxy-pyridin-3-yl boronic acid was replaced with 2,6-dimethoxy-pyridin-3-yl boronic acid. The crude material was purified by trituration in 10% methanol in ethyl acetate (10 mL). The solid was filtered and dried to give the 6-methoxy pyridone.

I-249 and I-250 were prepared analogously except in step 1 D-2 was replaced with 5-bromo-3-tert-butyl-2-ethoxy-benzaldehyde and 5-bromo-3-tert-butyl-2-(2-methoxy-ethoxy)-benzaldehyde which were, in turn, prepared by alkylation of 5-romo-3-tert-butyl-2-hydroxy-benzaldehyde with iodoethane and 2-bromoethyl methyl ether in accord with the procedure described in step 2 of Example 3.

Example 38

N-(4-{(E)-2-[3-tert-Butyl-5-(5-fluoro-2-oxo-1,2-dihydro-pyridin-3-yl)-2-methoxy-phenyl]-vinyl}-3-cyano-phenyl)-methanesulfonamide (I-151)

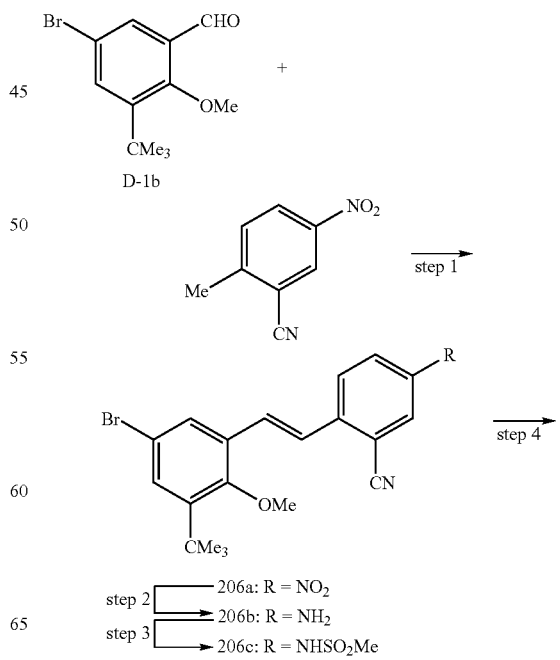

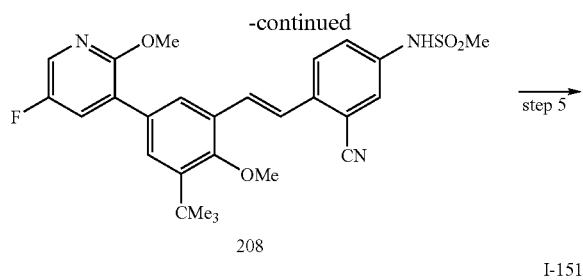

step 1—A solution of D-1b (4.0 g, 14.76 mmol), 3-cyano-4-methyl-nitrobenzene (2.44 g, 15.06 mmol), piperidine (22 mL) and pyridine (20 mL) was heated overnight at reflux. The solution was cooled to RT and concentrated in vacuo. The residue was diluted with EtOAc and the solution washed sequentially with saturated CuSO₄ and 1N HCl, dried (Na₂SO₄), filtered and evaporated. The crude product was purified by SiO₂ chromatography eluting with a EtOAc/hexane gradient (0 to 3% EtOAc) which afforded 1.34 g of 206a and 2.75 of impure 206a was purified by rechromatography (0 to 5% EtOAc).

step 2—To a solution of 206a (0.671 g, 1.617 mmol) in DMF (10 mL) and EtOAc (10 mL) was added SnCl₂.2H₂O and the resulting solution was stirred at RT overnight. The reaction mixture was cooled to 0° C. and quenched with aqueous NaHCO₃ and the resulting solution was stirred for 30 min then filtered through CELITE. The pad was washed with EtOAc and the filtrate thrice washed with brine, dried (Na₂SO₄), filtered and concentrated in vacuo. The crude product was purified by SiO₂ chromatography eluting with 15% EtOAc/hexane to afford 206b.

step 3—The methansulfonamide was prepared by treatment of 206b with mesyl chloride according to the procedure described in step 3 of example 6.

step 4—A vial was charged with 206b (0.097 g, 0.210 mmol), 107 (0.055 g, 0.0322 mmol, CASRN 957120-32-0), Pd(PPh₃)₄ (0.028 g, 0.024 mmol), Na₂CO₃ (0.057 g, 0.538 mmol), MeOH (3 mL) and DCM (1 mL), sealed and irradiated in a microwave synthesizer at 115° C. for 30 min. The solution was cooled to RT, concentrated. The residue was diluted with EtOAc and the organic solution washed with brine, dried (MgSO₄), filtered and evaporated. The crude product was purified by SiO₂ chromatography eluting with a EtOAc/hexane gradient (20 to 30% EtOAc) to afford 0.089 g (83%) of 208.

step 5—Cleavage of the methyl ether was carried out in accord with the procedure described in step 5 of example 37 to afford I-151.

N-(4-{(E)-2-[3-tert-Butyl-2-methoxy-5-(2-oxo-1,2-dihydro-pyridin-3-yl)-phenyl]-vinyl}-3-cyano-phenyl)-methanesulfonamide (I-150) was prepared analogously except in step 4, 107 was replaced with B-(1,2-dihydro-2-oxo-3-pyridinyl)-boronic acid CASRN 951655-49-5) and step 5 was omitted.

I-161 was prepared analogously except in step 4, 107 was replaced by 5-chloro-2-methoxy-pyridin-3-yl boronic acid (CASRN 943153-22-8).

Example 39

N-(2-{(E)-2-[3-tert-Butyl-2-methoxy-5-(2-oxo-1,2-dihydro-pyridin-3-yl)-phenyl]-vinyl}-5-methanesulfonylamino-benzyl)-acetamide (I-160)

step 1—To a solution of 206c (0.834 g, 1.801 mmol) and DCM (10 mL) cooled to −78° C. was added a solution of DIBAL and DCM (5.4 mL, 1.0 M solution in DCM) and the resulting solution stirred at −78° C. for 3 h. Starting material remained and the solution was allowed to stir at RT overnight. An addition aliquot of DIBAL (5.0 mL) was added and stirring continued for 2 h. The reaction was cooled to 0° C., Et₂O (20 mL) and 6N HCl (2 mL) were added and the resulting solution stirred for 30 min. The reaction was diluted with Et₂O, washed with 1N HCl and brine, dried, filtered and concentrated in vacuo. The resulting solid was dried with high vacuum overnight, then diluted with ethyl acetate and washed with saturated Rochelle Salt solution. The organic extract was concentrated to give a highly insoluble solid, which was then partitioned between 2N NaOH solution and EtOAc. The organic layer was separated and dried (Na₂SO₄), filtered and evaporated to afford 859 mg of N-{2-aminomethyl-4-[(E)-2-(5-bromo-3-tert-butyl-2-methoxy-phenyl)-vinyl]-phenyl}-methanesulfonamide (210).

step 2—To a solution of 210 (0.150 g, 0.321 mmol), pyridine (100 L) and DCM (10 mL) cooled to 0° C. was added acetic anhydride (70 µL). The reaction mixture was allowed to warm to RT and stirred overnight. The reaction mixture was diluted with DCM, washed with sat'd. CuSO₄ and twice with 1N HCl, dried (Na₂SO₄), filtered and concentrated in vacuo. The crude product was purified by SiO₂ chromatography eluting with a EtOAc/hexane gradient (50 to 75% EtOAc) to afford 45 mg of N-{5-[(E)-2-(5-bromo-3-tert-butyl-2-methoxy-phenyl)-vinyl]-2-methanesulfonylamino-benzyl}-acetamide (212).

step 3—Palladium-catalyzed coupling of 212 and B-(1,2-dihydro-2-oxo-3-pyridinyl)-boronic acid (213, CASRN 951655-49-5) was carried out in accord with the procedure in step 4 of example 38 to afford the title compound. The product was purified on a SiO₂ preparative TLC plate developed with 5% MeOH/DCM to afford 17.5 mg of I-160

Example 40

N-(4-{(Z)-2-[3-tert-Butyl-2-methoxy-5-(2-oxo-1,2-dihydro-pyridin-3-yl)-phenyl]-1-cyano-vinyl}-phenyl)-methanesulfonamide (I-138)

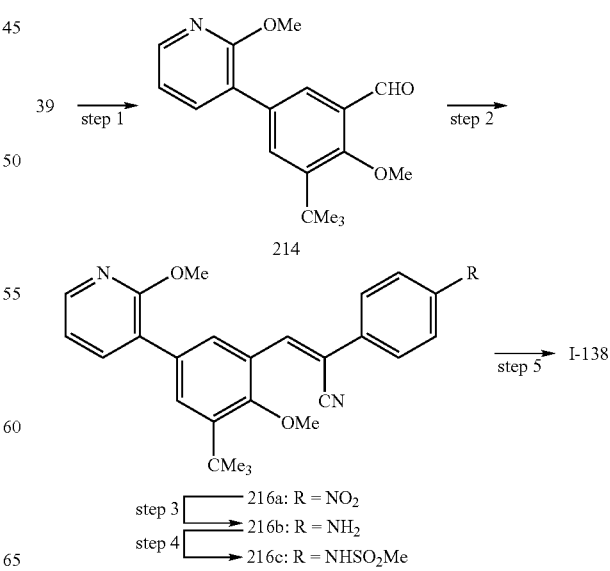

step 1—The Suzuki coupling of 5-bromo-3-tert-butyl-2-methoxy-benzaldehyde (39 example 3, step 3) and B-(2-methoxy-3-pyridinyl)-boronic acid was carried out in accord with the procedure in step 3 of example 3 to afford 214.

step 2—A oven-dried flask maintained under an $N_2$ atmosphere was charged with (4-nitro-phenyl)-acetonitrile (597.3 mg, 3.68 mmol) was added a solution of 214 (1.1 g, 3.68 mmol) and anhydrous EtOH (5 mL). The suspension was stirred and an ethanolic solution of NaOEt (5.7 mL, 0.656 M solution) was added and the resulting solution stirred at RT for 5 h. The solution was diluted with $H_2O$ (20 mL) and thrice extracted with DCM (3×35 mL). The combined extracts were sequentially washed with $H_2O$ and brine, dried ($Na_2SO_4$), filtered and concentrated in vacuo. The crude product was purified by $SiO_2$ chromatography eluting with a EtOAc/hexane gradient (12 to 25% EtOAc) to afford 1.11 g (68%) of 216a.

Reduction of the nitro group with iron and $NH_4Cl$ (step 3) and conversion to the sulfonamide with mesyl chloride (step 4) were carried out in accord with the procedures described in steps 3 and 4 of example 14. Cleavage of the pyrindinyl methyl ether was accomplished with HBr/HOAc in accord with the procedure described in step 4 of example 35 to afford I-138.

Example 41

N-(4-{(E)-2-[3-tert-Butyl-2-methoxy-5-(2-oxo-1,2-dihydro-pyridin-3-yl)-phenyl]-1-methyl-vinyl}-phenyl)-methanesulfonamide (I-139)

step 1—An oven-dried round bottom flask maintained under a $N_2$ atmosphere was charged with NaH (119.8 mg, 0.246 mmol 60% dispersion in mineral oil) and dry THF (3 mL) and 15-crown-5 (55 μL) were added. The suspension was cooled to 0° C. and a solution of diethyl [1-(4-nitro-phenyl)-ethyl]-phosphonate (0.850 g, 2.96 mmol) and THF (3.5 mL) was added dropwise. The solution was stirred for 15 min then a solution of 39 (0.7393 g, 2.49 mmol) and THF (7.0 mL) was slowly added. The resulting solution was stirred for 5 h at 0° C. then allowed to warm to RT. The reaction was quenched by the addition of $H_2O$ (1.5 mL) and the solution thrice extracted with $Et_2O$ (3×20 mL). The combined extracts were washed with brine, dried ($Na_2SO_4$), filtered and concentrated in vacuo. The crude product was purified by $SiO_2$ chromatography eluting with a EtOAc/hexane gradient (12 to 25% EtOAc) to afford 0.806 g (76%) of 5-bromo-1-tert-butyl-2-methoxy-3-[(E)-2-(4-nitro-phenyl)-propenyl]-benzene (218).

Reduction of the nitro group with iron and $NH_4Cl$ (step 2) and conversion to the sulfonamide with mesyl chloride (step 3) were carried out in accord with the procedures described in steps 3 and 4 of example 14. Cleavage of the pyrindinyl methyl ether was accomplished with HBr/HOAc in accord with the procedure described in step 4 of example 35 to afford I-139.

I-143 was prepared analogously except 39 was replaced with 37 (step 2 of example 7) and diethyl [1-(4-nitro-phenyl)-ethyl]-phosphonate was replaced with diethyl [(S)-1-(4-nitro-phenyl)-ethyl]-phosphonate to afford 3-{2-benzyloxy-5-tert-butyl-3-[(E)-2-(4-nitro-phenyl)-propenyl]-phenyl}-2-methoxy-pyridine. Reduction of the amine, sulfonylation of the amine were carried out in accord with the procedures described in steps 3 and 4 of example 14. Cleavage of both the pyrindinyl methyl ether and the benzyl ether was accomplished with HBr/HOAc in accord with the procedure described in step 4 of example 35 to afford I-143.

I-144 was prepared analogously except diethyl [1-(4-nitrophenyl)-ethyl]-phosphonate was replaced with diethyl [1-phenyl-ethyl]-phosphonate to afford 3-[3-tert-butyl-4-methoxy-5-((E)-styryl)-phenyl]-2-methoxy-pyridine. Cleavage of the pyrindinyl methyl ether was accomplished with HBr/HOAc in accord with the procedure described in step 4 of example 35 to afford I-144.

Example 42

N-(6-{(E)-2-[3-tert-Butyl-2-methoxy-5-(2-oxo-1,2-dihydro-pyridin-3-yl)-phenyl]-vinyl}-pyridin-3-yl)-methanesulfonamide (I-166)

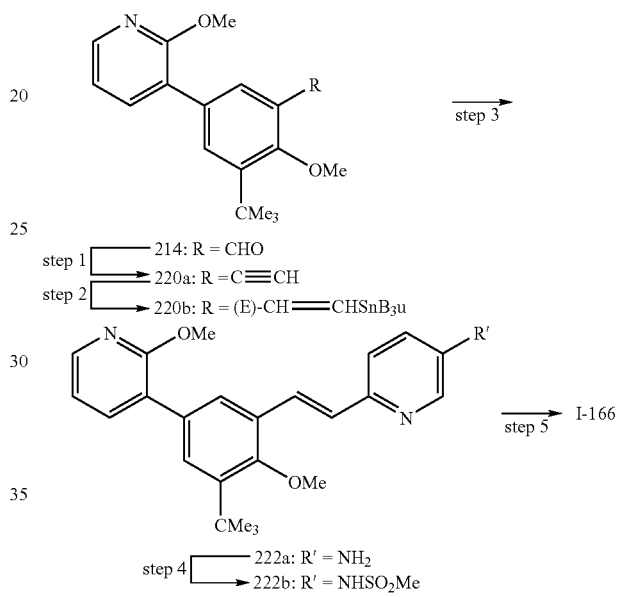

step 1—A solution of 214 (1.12 g, 4 mmol) and dimethyl (1-diazo-2-oxopropyl)phosphonate (1.158 g, 6 mmol, CASRN90965-06-3) in anhydrous MEOH (26 mL) was cooled to 0° C. and a methanolic NaOMe solution (4 mL, 2.0 M in MeOH) was added over 5 min and the resulting mixture was stirred at 0° C. for 15 min then stirred at RT overnight. The reaction was quenched by the addition of sat'd aq. $NaHCO_3$ (40 mL) and the solution was thrice extract with $Et_2O$ (3×10 mL). The combined extracts were was sequentially with $H_2O$ and brine, dried ($Na_2SO_4$), filtered and concentrated in vacuo. The crude product was purified by $SiO_2$ chromatography eluting with a EtOAc/hexane gradient (5 to 10% EtOAc) to afford 1.01 g (92%) of 220a as a clear oil.

step 2—To a solution of 220a (0.390 g, 1.32 mmol) dissolved in THF (4 mL) and benzene (4 mL) maintained under an Ar atmosphere at RT was added AIBN (0.0882 g, 0.53 mmol) followed by dropwise addition of $Bu_3SnH$ (0.46 mL, 0.528 mmol). The reaction mixture was heated at 90° C. for 2 h, cooled to RT and concentrated in vacuo. The crude product was purified by $SiO_2$ chromatography eluting with 5% EtOAc/hexane to afford 0.649 g (84%) of 220b.

step 3—To a solution of $Pd_2(dba)_3$ (0.033 g, 0.027 mmol), tris-(2-furyl)phosphine (0.0323 g, 0.107 mmol) in DMF (2.0 mL) was stirred for 10 min at RT. To this solution was added via cannula a solution of 220b (0.783 g, 1.33 mmol), 5-amino-2-iodo-pyridine (0.3541 g, 1.6 mmol, CASRN 29958-12-1) and DMF (6 mL). To the resulting solution at RT was added LiCl (0.1182 g, 2.67 mmol) and the resulting solution was heated at 110° C. for 18 h. The reaction was cooled to RT, poured into H₂O (80 mL) and the solution thrice extracted with EtOAc. The combined extracts were washed sequentially with H₂O and brine, dried, filtered and evaporated. The crude product was purified by SiO₂ chromatography eluting with a EtOAc/hexane gradient (37 to 100% EtOAc) to afford 0.432 g (83%) of 222a as a yellow oil.

Conversion of the amino group to the sulfonamide with mesyl chloride (step 4) was carried out in accord with the procedures described in step 4 of example 14. Cleavage of the pyrindinyl methyl ether was accomplished with HBr/HOAc in accord with the procedure described in step 4 of example 35 to afford I-166.

I-171 and I-172 were prepared analogously except in step 3, 5-amino-2-iodo-pyridine was replaced with 2-amino-5-iodo-pyridine to afford 5-{(E)-2-[3-tert-butyl-2-methoxy-5-(2-methoxy-pyridin-3-yl)-phenyl]-vinyl}-pyridin-2-ylamine (224). Cleavage of the pyrindinyl methyl ether in 224 was accomplished with HBr/HOAc in accord with the procedure described in step 4 of example 35 to afford I-171. Sulfonylation of 224 according to the procedure described in step 4 of example 14 followed by HBr/HOAc mediated ether cleavage affords I-172. I-174 and I-176 were prepared analogously except 3-tert-butyl-5-(5-fluoro-2-methoxy-pyridin-3-yl)-2-methoxy-benzaldehyde was used as the starting material in place of 214

I-181 was prepared analogously except in step 3, 5-amino-2-iodo-pyridine was replaced with 6-bromo-pyridazin-3-ylamine (CASRN 88497-27-2) to afford 6-{(E)-2-[3-tert-butyl-2-methoxy-5-(2-methoxy-pyridin-3-yl)-phenyl]-vinyl}-pyridazin-3-ylamine (225). Conversion of the 225 to the corresponding sulfonamide with mesyl chloride (step 4) was carried out in accord with the procedure described in step 4 of example 14. Cleavage of the pyrindinyl methyl ether was accomplished with HBr/HOAc in accord with the procedure described in step 4 of example 35 to afford I-181 and I-182. I-183 and I-184 were prepared analogously except in step 1, 214 was replaced with 226.

Example 43

N-(6-{(E)-2-[3-tert-Butyl-5-(5-fluoro-2-oxo-1,2-dihydro-pyridin-3-yl)-2-methoxy-phenyl]-vinyl}-pyridin-3-yl)-methanesulfonamide (I-170)

3-tert-butyl-5-(5-fluoro-2-methoxy-pyridin-3-yl)-2-methoxy-benzaldehyde (226)—A vial was charged with 39 (1.029 g, 3.9 mmol), 107 (0.667 g, 3.9 mmol, CASRN 957120-32-0), Pd(PPh₃)₄ (0.2301 g, 0.199 mmol), Na₂CO₃ (1.088 g, 10.12 mmol), MeOH (8 mL) and DCM (2 mL) sealed and irradiated in a microwave synthesizer at 115° C. for 1 h. The solution was cooled to RT then concentrated in vacuo. The residue was diluted with EtOAc and filtered. The filtrate was washed sequentially with H₂O and brine, dried (MgSO₄), filtered and evaporated. The crude product was purified by SiO₂ chromatography eluting with EtOAc/hexane to afford 0.096 g (78%) of 226.

The conversion of 226 to 6-{(E)-2-[3-tert-butyl-5-(5-fluoro-2-methoxy-pyridin-3-yl)-2-methoxy-phenyl]-vinyl}-pyridin-3-yl-amine (228) was carried out in accord with the procedures in steps 1 to 3 of example 42.

N-(6-{(E)-2-[3-tert-Butyl-5-(5-fluoro-2-oxo-1,2-dihydro-pyridin-3-yl)-2-methoxy-phenyl]-vinyl}-pyridin-3-yl)-acetamide (I-169)—A tube was charged with 228 (0.089 g, 0.211 mmol), 48% HBr (50 μL) and HOAc (2.5 mL) sealed and heated over night at 60° C. The reaction was cooled to RT, poured into sat'd. aq. NaHCO₃ and the resulting solution extracted with EtOAc. The combined extracts were washed sequentially with sat'd. NaHCO₃ and brine, dried (Na₂SO₄), filtered and evaporated 49.8 mg of the acetamide I-169

N-(6-{(E)-2-[3-tert-Butyl-5-(5-fluoro-2-oxo-1,2-dihydro-pyridin-3-yl)-2-methoxy-phenyl]-vinyl}-pyridin-3-yl)-methanesulfonamide (I-170) was prepared by sulfonylation of the amine in accord with the procedure described in step 3 of example 6. Demethylation with HBr/HOAc as described above afforded I-170.

Example 44

2-{(E)-2-[3-tert-Butyl-2-methoxy-5-(2-oxo-1,2-dihydro-pyridin-3-yl)-phenyl]-vinyl}-5-methanesulfonylamino-benzoic acid methyl ester (I-157)

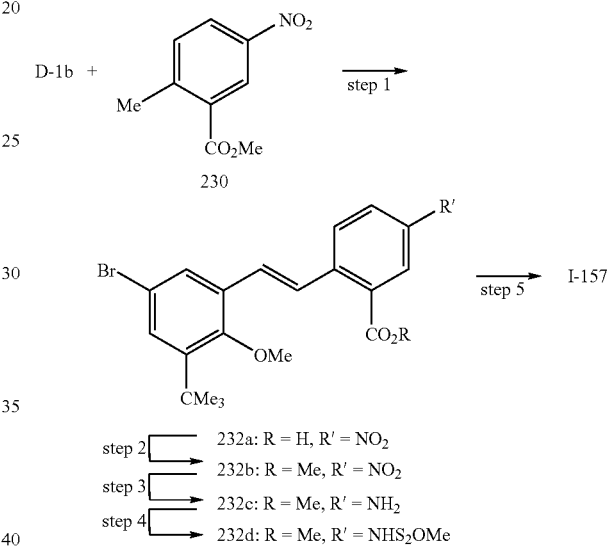

step 1—A solution of D-1b (4.17 g, 15.39 mmol), 230 (2.00 g, 10.26 mmol), DBU (3.1 mL, 20.73 mmol) and DMSO (10 mL) was stirred overnight at RT then heated to 50° C. for 1 h. To the solution was added 1N NaOH and the resulting solid filtered. The filtrate was acidified with 6N HCl extracted with EtOAc and the combined extracts dried (Na₂SO₄), filtered and evaporated to afford 2.51 g of 232a.

step 2—A solution of 232a (2.00 g, 4.608 mmol) iodomethane (1.05 mL, 16.87 mmol), K₂CO₃ (1.92 g, 13.89 mmol) and DMF (10 mL) was stirred overnight at RT. The resulting solution was filtered and the filtrate was diluted with EtOAc and washed with 1N HCl, H₂O and brine. The organic phase was dried (Na₂SO₄), filtered and concentrated in vacuo to afford 1.94 g (94%) of 232b.

step 3—To a solution of 232b (1.42 g, 3.18 mmol) in DMF (10 mL) and EtOAc (10 mL) was added SnCl₂ (2.87 g, 12.72 mmol) and the resulting solution stirred at RT overnight. The reaction mixture was cooled to 0° C. and quenched by slow addition of aq. NaHCO₃ (4 mL). The resulting suspension was filtered through a pad of CELITE and the filtrate diluted with EtOAc, thrice washed with brine, dried (Na₂SO₄), filtered and concentrated in vacuo. The crude product was purified by SiO₂ chromatography eluting with a EtOAc/hexane gradient (10 to 20% EtOAc) to afford 843 mg (64%) of 232c as a yellow foam.

step 4—The methanesulfonamide was prepared by treatment of 232c with mesyl chloride in accord with the procedure in step 3 of example 6. The crude product was purified by SiO₂ chromatography eluting with a EtOAc/hexane gradient (10 to 30% EtOAc) to afford 697 mg (704%) of 232d.

step 5—The palladium-catalyzed coupling of 232d and 213 was carried out in accord with the procedure in step 4 of example 38 to afford the title compound. The product was purified on a SiO₂ preparative TLC plate developed with EtOAc/hexane (2:1) to afford 19.4 mg of I-157.

I-186 is prepared by palladium-catalyzed coupling of 232d

Example 45

N-(4-{(Z)-2-[3-tert-Butyl-2-methoxy-5-(2-oxo-1,2-dihydro-pyridin-3-yl)-phenyl]-1-hydroxymethyl-vinyl}-phenyl)-methanesulfonamide (I-149)

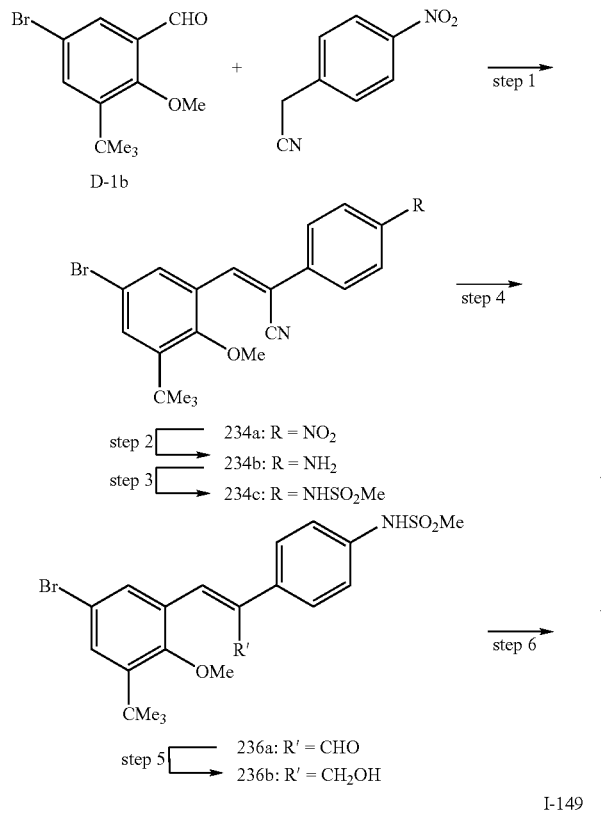

step 1—To a solution of D-1b (15.0 g, 55.35 mmol) and K₃PO₄ (5.87 g, 27.65 mm EtOH (150 mL) was added a slurry of (4-nitro-phenyl)acetonitrile (10.76 g, 66.42 mmol) in EtOH (150 mL) and the resulting solution stirred RT overnight. The solid was filtered and the filtrate was concentrated in vacuo and purified by SiO₂ chromatography eluting with a EtOAc/hexane gradient to afford 16.12 g (70%) of 234a.

Reduction of the nitro group with SnCl₂ (step 2) was carried out in accord with the procedure described in step 3 of example 44 and conversion of the amine to the sulfonamide 234c with mesyl chloride (step 3) in accord with the procedure described in step 3 of example 6.

step 4—To a solution of 234c (0.207 g, 0.447 mmol) in DCM cooled to 0° C. was added a solution of DIBAL and DCM (1.4 mL, 1.4 mmol, 1.0 M solution in DCM). The solution was allowed to warm to RT and stirred overnight. The solution was recooled to 0° C. and quenched by addition of H₂O followed by 1M HCl (2 mL). The organic phase was separated, dried (Na₂SO₄), filtered and purified by SiO₂ chromatography eluting with a EtOAc/hexane gradient (20 to 30% EtOAc) to afford 236a and the corresponding E-isomer as a 3:1 mixture.

step 5—To a solution of 236a (0.147 g, 0.315 mmol) cooled to −78° C. was added a solution of DIBAL (0.95 mL, 0.950 mmol, 1.0M solution in DCM). The reaction was stirred for 1.5 h then warmed to 0° C. and the reaction quenched with MeOH (1 mL) and a solution of Rochelle's salt (5 mL) was added. The reaction was filtered and the filtrate dried (Na₂SO₄), filtered and evaporated. The crude product was purified by SiO₂ chromatography eluting with a EtOAc/hexane gradient (30 to 40% EtOAc) to afford 236b and the corresponding E isomer 237.

step 6—The palladium-catalyzed coupling of 236b and 213 was carried out in accord with the procedure in step 4 of example 38. The product was purified on a SiO₂ preparative TLC plate developed with EtOAc/hexane (2:1) to afford I-149. The E isomer 237 was converted to I-145 in similar fashion.

Example 46

N-(4-{(E)-2-[3-(1-Hydroxymethyl-cyclopropyl)-5-(2-oxo-1,2-dihydro-pyridin-3-yl)-phenyl]-vinyl}-phenyl)-methanesulfonamide (I-162)

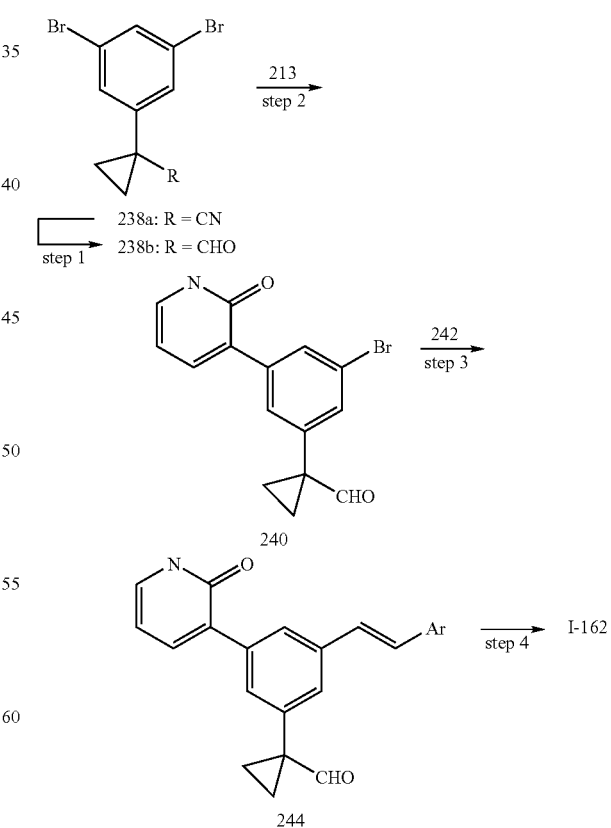

Ar = 4-methanesulfonylamino-phenyl

N-{4-[(E)-2-(4,4,6-Trimethyl-[1,3,2]dioxaborinan-2-yl)-vinyl]-phenyl}-methanesulfonamide (242) To a solution of Pd(OAc)$_2$ (0.076 g), tris-(ortho-tolyl)-phosphine (0.246 g, 1 mmol) and toluene (16 mL) were added sequentially N-(4-iodo-phenyl)-methanesulfonamide (2.00 g, 7 mmol, CASRN 102294-59-7), tributyl amine (1.92 mL) and 4,4,6-trimethyl-2-vinyl-[1,3,2]dioxaborinane (1.244 g, 8 mmol, CASRN 4627-10-5). The reaction was heated at reflux for 72 h, cooled to RT and partitioned between Et$_2$O (100 mL) and 1M HCl (20 mL). The aqueous layer was withdrawn and re-extracted with Et$_2$O. The organic phases were washed sequentially with H$_2$O and brine. The extracts were combined, dried (Na$_2$SO$_4$), filtered and evaporated. The residue was purified by SiO$_2$ chromatography eluting with an EtOAc/hexane gradient (0 to 30% EtOAc) to afford 1.4 g (58%) of 242.

step 1—To a solution of 238a (0.180 g, 0.598 mmol) in DCM 8 mL) cooled to −78° C. was added a solution of DIBAL and toluene (0.9 mL, 0.897 mmol, 1.0 M solution in toluene) and the resulting solution stirred at −78° C. for 2 h. The reaction was quenched with 2 N HCl and extracted with DCM. The combined extracts were washed with sat'd. NaHCO$_3$, dried (Na$_2$SO$_4$), filtered and evaporated. The crude product was purified by SiO$_2$ chromatography eluting with a EtOAc/hexane gradient (0 to 10% EtOAc) to afford 0.13 g (71.5%) of 238b.

step 2—Suzuki coupling of 238b and 213 was carried out in accord with the procedure in step 4 of example 38 to afford 240. The product was purified by chromatography eluting with a solution contain 50% DCM and 50% of a mixture of DCM/MeOH/NH$_4$OH (10:10:1) to afford 240.

step 3—A tube was charged with 240 (0.08 g, 0.251 mmol), 242 (0.097 g, 0.30 mmol), Na$_2$CO$_3$ (0.08 mmol, 0.754 mmol), Pd(PPh$_3$)$_4$ (0.03 g, 0.026 mmol), DCM (1 mL) and MeOH (3 mL), sealed and irradiated in a microwave synthesizer at 115° C. for 40 min. The solution was filtered and concentrated in vacuo. The crude product was purified by SiO$_2$ chromatography eluting with a solution contain 50% DCM and 50% of a mixture of DCM/MeOH/NH$_4$OH (10:10:1) to afford 60 mg 244.

step 4—To a solution of 244 (0.060 g, 0.138 mmol) and MeOH (3 mL) cooled to 0° C. was added NaBH$_4$ (0.026 g, 0.69 mmol). After 1 h the reaction was quenched with sat'd. NH$_4$Cl and the resulting solution concentrated in vacuo. The crude product was purified by SiO$_2$ chromatography eluting with a solution contain 50% DCM and 50% of a mixture of DCM/MeOH/NH$_4$OH (10:10:1) to afford 40 mg of I-162 as a white powder.

Example 47

N-(4-{(E)-2-[3-tert-Butyl-5-(2-oxo-1,2-dihydro-pyridin-3-yl)-phenyl]-vinyl}-phenyl)-methane-sulfonamide (I-141)

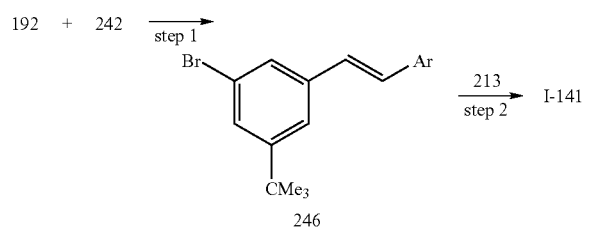

step 1—A tube was charged with 242 (0.600, 0.002 mmol), 192 (0.569 g, 0.002 mmol), Pd(PPh$_3$)$_4$ (0.107 g), K$_3$PO$_4$ (1.282 g, 0.006 mmol). The tube was evacuated, backfilled with argon, closed and DMF (9 mL) was added. The reaction was heated at 100° C. for 3 h. The reaction was cooled and partitioned between Et$_2$O (100 mL) and H$_2$O (15 mL). The aqueous layer was extracted with Et$_2$O (100 mL) and the combined organic extracts washed twice with H$_2$O and once with brine, dried (Na$_2$SO$_4$), filtered and concentrated in vacuo. The crude product was purified by SiO$_2$ chromatography eluting with a EtOAc/hexane gradient (0 to 30% EtOAc) to afford 0.4880 g (64.4%) of 246.

step 2—A microwave tube was charged with 246 (0.290 g, 0.001 mmol), 213 (0.109 g, 0.001 mmol), Pd(PPh$_3$)$_4$ (0.082 g), Na$_2$CO$_3$ (0.228, 0.002 mmol), MeOH (6 mL) and DCM (2 mL), flushed with argon, sealed and heated at 115° C. for 30 min. The reaction mixture was cooled and partitioned between DCM (50 mL) and H$_2$O (10 mL). The organic phase was washed with brine. The aqueous layers were washed with DCM. The extracts were combined, dried (Na$_2$SO$_4$), filtered and concentrated in vacuo. The residue was purified by SiO$_2$ chromatography eluting with a EtOAc/hexane gradient (30 to 100% EtOAc) to afford 0.179 g of I-141 as a yellow powder which was triturated with 2:1 EtOAc/hexane, filtered and dried.

Example 48

N-(4-{(E)-2-[3-tert-Butyl-5-(6-hydroxymethyl-2-oxo-1,2-dihydro-pyridin-3-yl)-2-methoxy-phenyl]-vinyl}-phenyl)-methanesulfonamide (I-163)

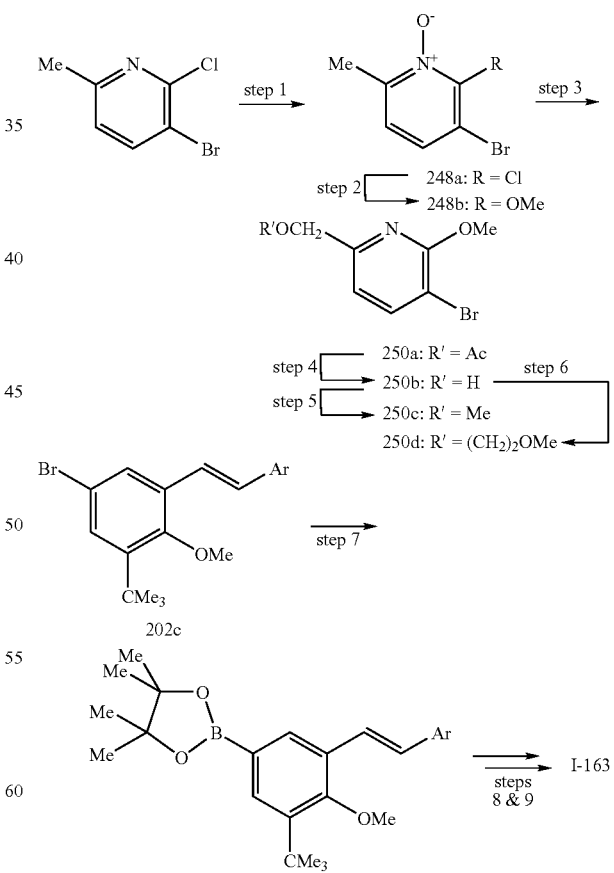

step 1—To a solution of 3-bromo-2-chloro-6-methyl-pyridine (2.0 g, 0.687 mmol) in CHCl₃ was added MCPBA (3.3 g, 19.1 mmol) and the resulting solution was heated at 50° C. overnight, The resulted solution was cooled and partitioned between DCM and sat'd. aq. NaHCO₃. The organic layer was dried (Na₂SO₄), filtered and concentrated in vacuo. The crude product was purified by SiO₂ chromatography eluting with an EtOAc/hexane gradient (30 to 80% EtOAc) to afford 1.88 g (87%) of 248a as a white solid.

step 2—A solution of 248a (0.5 g) and 0.5 M NaOMe/MeOH (4.9 mL) was stirred at RT overnight. The reaction mixture was concentrated in vacuo and the residue loaded on a SiO₂ column and eluted with 5% MeOH/DCM to afford 248b.

step 3—A solution of 248b (0.47 g) and acetic anhydride (4.0 mL) was heated at 120° C. for 2 h, The reaction mixture was concentrated in vacuo and purified on a SiO₂ column eluting with 5% EtOAc/hexane to afford 250a.

step 4—A solution of 250a (0.060 g), 5% aq. NaHCO₃ (2 mL) and MeOH (2 mL) was heated at reflux for 2 h. The reaction mixture was partitioned between H₂O and EtOAc and the combined EtOAc extracts were dried, filtered and evaporated in vacuo. The crude product was purified by SiO₂ chromatography eluting with 25% EtOAc/hexane to afford 250b.

step 5—To a solution of 250b (0.054 g, 0.25 mmol) and DMF (1.0 mL) was added NaH (0.015 g, 0.37 mmol, 60% mineral oil dispersion). The solution was stirred for 20 min at RT then iodomethane (370 µL). The reaction mixture was stirred at RT for 2 h then partitioned between EtOAc and H₂O. The combined extracts were dried, filtered and concentrated in vacuo. The crude product was purified by SiO₂ chromatography eluting with a 5% EtOAc/hexane to afford 250c.

step 6—The preparation of 250d from 250b was carried out in accord with step 5 except iodomethane was replaced with 1-bromo-2-methoxy-ethane. The product was purified by SiO₂ chromatography eluting with 10% EtOAc/hexane.

step 7—A flask was charged with 202c (0.125 g, 0.29 mmol), bis-pinacolato-diboron (0.109 g, 0.44 mmol), Pd(PPh₃)₂Cl₂ (0.0204 g, 0.029 mmol), KOAc (0.0854 g) and dioxane (3.0 mL) and the resulting solution heated at reflux for 2 h under a Ar atmosphere. The solution was cooled, dried, filtered and concentrated in vacuo. The crude product was purified by SiO₂ chromatography eluting with 30% EtOAc/hexane to afford 252.

step 8—A vial was charged with 252 (0.145 g), 250b (0.050 g), Pd(PPh₃)₄ (0.0267 g), Na₂CO₃ (0.0721 g), sealed and flushed with Ar. MeOH (0.9 mL) and toluene (0.3 mL) were added and the vial was irradiated in a microwave synthesizer at 120° C. for 35 min. The reaction was cooled to RT, filtered and purified by SiO₂ chromatography to afford N-(4-{(E)-2-[3-tert-butyl-5-(6-hydroxymethyl-2-methoxy-pyridin-3-yl)-2-methoxy-phenyl]-vinyl}-phenyl)-methanesulfonamide.

step 9—The methyl ether from step 8 was cleaved with HBr/HOAc in accord with the procedure described in step 5 of example 37. The crude product was purified by SiO₂ chromatography eluting with 6% MeOH/DCM to afford I-163.

I-164 and I-165 were prepared analogously except in step 8, 250b was replaced with 250c and 250d respectively. I-164 and I-165 both were purified on a preparative SiO₂ plate developed with 5% MeOH/DCM.

Example 49

Cyclopropanesulfonic acid (4-{(E)-2-[3-tert-butyl-5-(5-fluoro-2-oxo-1,2-dihydro-pyridin-3-yl)-2-methoxy-phenyl]-vinyl}-phenyl)-amide (I-155)

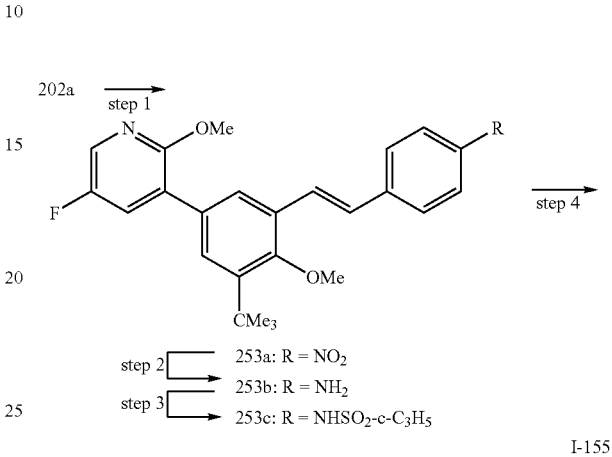

253a: R = NO₂
253b: R = NH₂
253c: R = NHSO₂-c-C₃H₅

I-155

Suzuki coupling of 202a and 107 (step 1) was carried out in accord with the procedure in step 1 of example 35. 253a product was purified by SiO2 chromatography eluting with 5% EtOAc/hexane. Reduction of nitro group (step 2 was carried out with SnCl₂.2H₂O in accord with the procedure in step 2 of example 38 except no DMF was used. 253b was purified by SiO₂ chromatography eluting with 5% EtOAc/hexane. Sulfonylation (step 3) was carried out in analogy to the procedure in step 3 of example 6 except mesyl chloride was replaced with cyclopropylsulfonyl chloride. Demethylation of 253c (step 4) was carried out in accord with the procedure described in step 4 of example 6 to afford I-155 which was purified on a preparative SiO₂ plate developed with 5% MeOH/DCM.

The following can be prepared analogously except in step 3, mesyl chloride is replaced by the sulfonylating agent in parentheses: I-152 (2,2,2-trifluoro-ethanesulfonyl chloride, CASRN 1648-99-3), I-153 (cyclopropyl-methanesulfonyl chloride, CASRN 114132-26-2), I-154 anhydride), and I-156 (3-methoxy-propane-1-sulfonyl chloride, CASRN 64297-55-8)

3-Methoxy-propane-1-sulfonyl chloride—[1,2]Oxathiolane 2,2-dioxide (0.122 g) was dissolved in MeOH (3 mL) then a solution of MeONa and MeOH was added (2.4 mL, 0.5 M solution) and the reaction stirred at RT for 72 h. The reaction was concentrated in vacuo, dissolved in DMF (2.0 mL). To this solution cooled to 0° C. was added dropwise SOCl₂ (71.1 µL). The solution was stirred at 0° C. for 10 min then allowed to warm to RT and stirred for 3 h. The reaction was partitioned between EtOAc and 1 N HCl. The aqueous layer was extracted with EtOAc and the combined extracts were dried, filtered and concentrated in vacuo. The sulfonyl chloride was purified by SiO₂ chromatography eluting with 20% EtOAc/hexane.

Example 50

N-(6-{(E)-2-[5-tert-Butyl-2-hydroxy-3-(2-oxo-1,2-dihydro-pyridin-3-yl)-phenyl]-vinyl}-pyridin-3-yl)-methanesulfonamide (I-167)

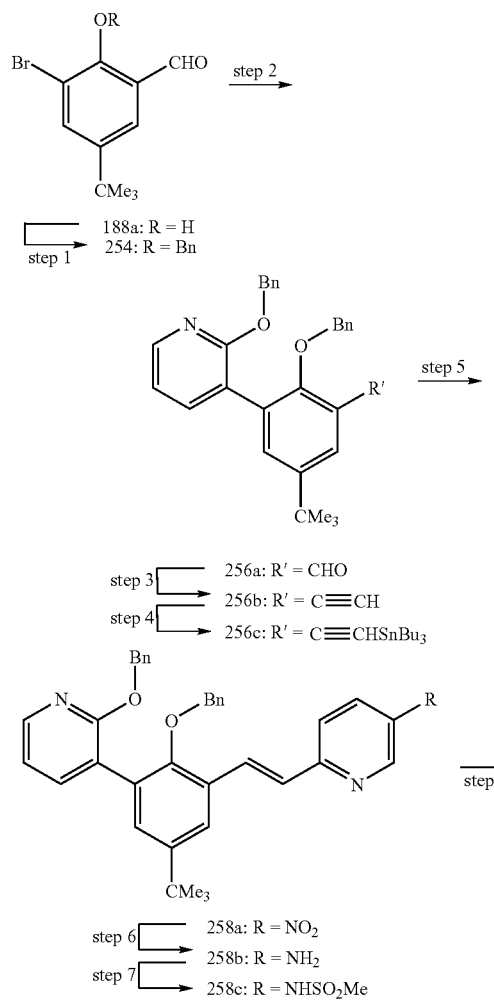

step 1—Alkylation of 188a with benzyl bromide is accomplished treating 188a with benzyl bromide and tetrabutylammonium hydroxide in a biphasic system comprised of MeOH and DCM.

step 2—Condensation of 254 and 141 to afford 256a was carried out in accord with the procedure described in step 1 of example 7. The crude product was purified by $SiO_2$ chromatography eluting with 5% EtOAc/hexane.

step 3—The conversion of 256a to 256b was carried out in accord with the procedure described in step 1 of example 42. The crude product was purified by $SiO_2$ chromatography eluting with 5% EtOAc/hexane.

step 4—Hydrostannylation of 256b to afford 256c was carried out as described in step 2 of example 42. The crude product was purified by $SiO_2$ chromatography eluting with 5% EtOAc/hexane.

step 5—To a solution of $Pd_2(dba)_3$ (0.104 g, 0.11 mmol) and DMF (10 mL) under Ar was added, tri-(2-furyl)phosphine (0.106 g, 0.45 mmol). After stirring for 10 min at RT the solution was added to a solution of 256c (2.8 g, 3.79 mmol), 2-iodo-5-nitro-pyridine (1.14 g, 4.55 mmol) and DMF (10 mL) maintained under an Ar atmosphere. The resulting reaction mixture was heated at 90° C. overnight, cooled and partitioned between EtOAc and aq. $NH_4Cl$. The aqueous phase was extracted with EtOAc and the combined organic extracts dried, filtered and concentrated in vacuo. The crude product was eluted with a EtOAc/hexane gradient (5 to 10% EtOAc) to afford 258a.

step 6—A suspension of 258a (0.050 g), RaNi (0.3 mL of an aqueous slurry of Rainey nickel) in EtOH (2.5 mL) was stirred overnight under an $N_2$ atmosphere (balloon). The catalyst was filtered and the filtrate concentrated. The crude product was purified by $SiO_2$ chromatography eluting with 50% EtOAc/hexane to afford 258b.

steps 7 & 8—Sulfonylation of 258b with mesyl chloride and debenzylation with HBr/HOAc was carried out in accord with the procedures in steps 5 and 6 of example 6. The crude product was purified on a preparative TLC plate developed with 10% MeOH/DCM to afford I-167.

Example 51

N-(4-{(E)-2-[3,3-Dimethyl-5-(2-oxo-1,2-dihydro-pyridin-3-yl)-2,3-dihydro-benzofuran-7-yl]-vinyl}-phenyl)-methanesulfonamide (II-1)

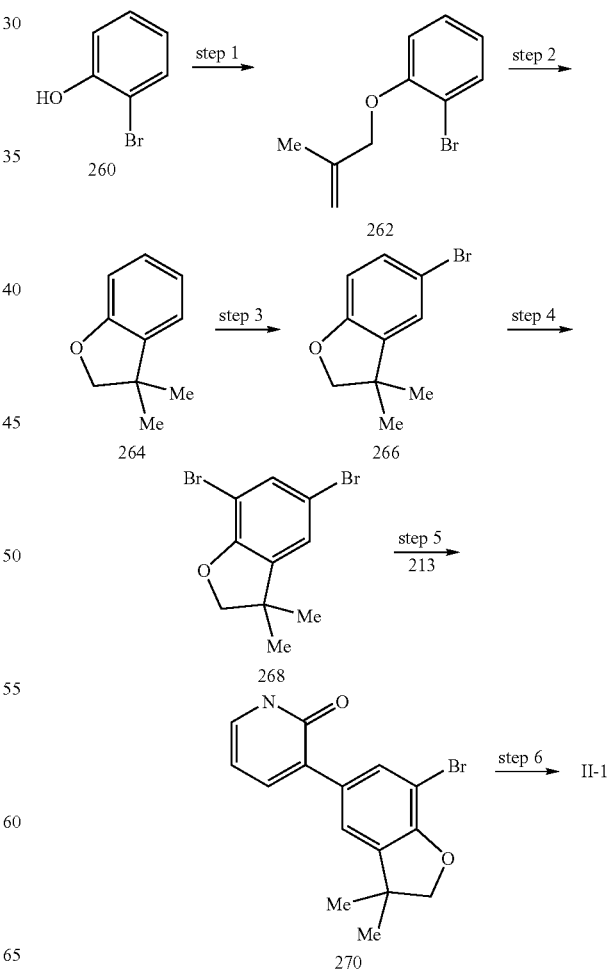

step 1—To a solution of 260 (2.457 g, 14 mmol) and acetone (75 mL) was added $K_2CO_3$ (4.907 g, 36 mmol) and 3-bromo-1-methyl propene (2.0 mL, 20 mmol) and the resulting solution was heated at reflux overnight. The reaction mixture was cooled and concentrated in vacuo. The residue was partitioned between EtOAc (150 mL) and $H_2O$ (40 mL) The aqueous phase was extracted with EtOAc and the combined organic extracts were sequentially washed with $H_2O$ and brine, dried ($Na_2SO_4$), filtered and concentrated in vacuo. The residue was purified by $SiO_2$ chromatography eluting with a EtOAc/hexane gradient (0 to 5% EtOAc) to afford 3.34 g (98.5%) of 262.

step 2—To a solution of 262 (3.33 g, 15 mmol) and benzene (150 mL) in a dried flask was added sequentially $Bu_3SnH$ (6.625 g, 22 mmol) and AIBN (0.241 g) and the resulting solution heated at reflux overnight. The reaction mixture was cooled to RT, a 10% KF solution was added and the resulting two-phase mixture stirred vigorously for 2 h. The phases were separated and the organic phase was sequentially washed with sat'd $NaHCO_3$ (50 mL) and brine. The combined organic extracts were dried ($Na_2SO_4$), filtered and evaporated. The crude product was purified by $SiO_2$ chromatography eluting with a DCM/hexane gradient (0 to 10% DCM to afford 1.855 g (85%) of 264.

step 3—To a solution of 264 (0.700 g, 5 mmol) and DMF (50 mL) in a dried flask was added NBS (1.765 g, 10 mmol) and the reaction was stirred overnight at RT. The reaction mixture was partitioned between $H_2O$ (30 mL) and $Et_2O$ (150 mL). The aqueous layer was separated and extracted with $Et_2O$ (150 mL). The organic extracts were thrice washed with $H_2O$ than once with brine. The combined organic extracts were dried ($Na_2SO_4$), filtered and concentrated in vacuo. The residue was adsorbed on $SiO_2$, added to the top of a $SiO_2$ column and eluted with hexanes to afford 0.9260 (90%) of 266.

step 4—To a solution of 266 (0.956 g, 4 mmol) and HOAc (8.0 mL) cooled to 0° C. added a dropwise solution of $Br_2$ (320 µL, 6 mmol) and HOAc (2 mL) over a 10 min period. The reaction mixture was stirred overnight at RT. The reaction was quenched by addition of 10% $Na_2S_2O_3$ (10 mL) then HOAc was removed in vacuo. The residue was partitioned between $Et_2O$ (100 mL) and sat'd. aq.$NaHCO_3$ (20 mL). The aqueous layer was separated and extracted with $Et_2O$ (100 mL). The organic extracts were washed twice with sat'd. $NaHCO_3$ (20 mL) and once with $H_2O$. The combined extracts were dried ($Na_2SO_4$), filtered and evaporated. The residue was adsorbed on $SiO_2$, added to the top of a $SiO_2$ column and eluted with hexanes to afford 1.22 (95%) of 268.

step 5—The palladium-catalyzed coupling of 268 and 213 was carried out in accord with the procedure in step 4 of example 38. The product was purified by $SiO_2$ chromatography eluting with a EtOAc/hexane gradient (0 to 80% EtOAc) to afford 270 wherein coupling occurred selectively at the 5-bromo substituent.

step 6—The palladium-catalyzed coupling of 270 and 242 was carried out in accord with the procedure in step 3 of example 46. The residue was adsorbed on $SiO_2$, added to the top of a $SiO_2$ column and eluted with a DCM/MeOH gradient (0 to 5% MeOH). The product collected 2 from the column was further purified by HOLC to afford II-1.

II-2 was prepared analogously except the sequence of the coupling steps was reversed such that coupling with 242 was carried out prior to coupling with 213. The residue was adsorbed on $SiO_2$, added to the top of a $SiO_2$ column and eluted with a DCM/MeOH gradient (0 to 5% MeOH). The product collected from the column was further purified by HOLC to afford II-2.

II-3 was prepared analogous by the procedure used to prepare II-2 except in step 5, 213 was replaced with 107 and after step 6 the methyl ether on the pyridine was cleaved with HBr/HOAc as described in step 5 of example 37. The crude product was purified by $SiO_2$ chromatography eluting with a EtOAc/hexane gradient (0 to 100% EtOAc), The residue was triturated with 1.5 mL of DCM/heptane (2:1) and the residue collected to afford 29.0 mg of II-3.

Example 52

N-(4-{(E)-2-[3-tert-Butyl-5-(5-fluoro-2-oxo-1,2-dihydro-pyridin-3-yl)-2-methoxy-phenyl]-vinyl}-3-hydroxymethyl-phenyl)-methanesulfonamide (I-187)

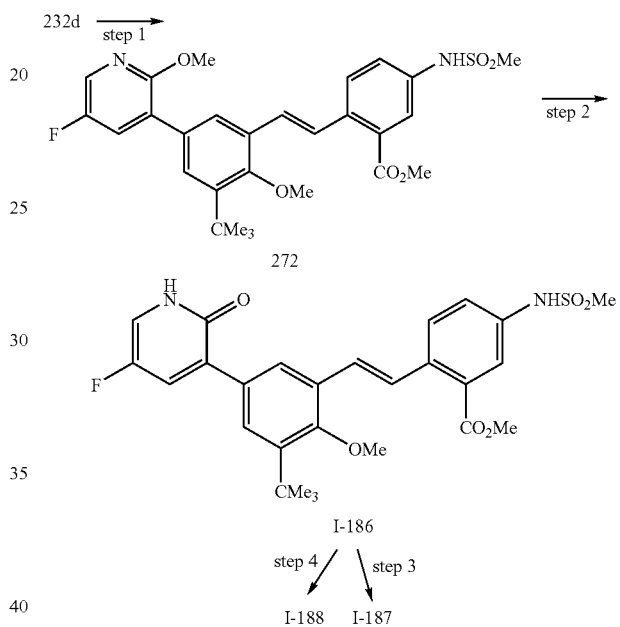

step 1—The cross-coupling of 232d and 107 was carried out in accord with the procedure described in step 6 of example 2 except $Pd(PPh_3)_4$ was replaced with $Pd(dppf)_2Cl_2 \cdot CH_2Cl_2$. The crude product was purified by $SiO_2$ chromatography eluting with an EtOAc/hexane gradient (I0-40% EtOAc) to afford 272 as an amorphous solid.

step 2—Demethylation of 272 to afford I-186 was carried out in accord with the procedure described in step 3 of Example 1 to afford the product as a white solid.

step 3—To a solution of I-186 (25 mg, 0.05 mmol) in THF (5 mL) cooled to −20° C. was added dropwise a solution of $LiAlH_4$ (945 µL. 0.95 mmol, 1.0 M solution in THF). The resulting mixture was stirred at −20° C. for 1 h and then warmed to −10° C. over a period of 1 h before it was quenched with IPA (ca. 0.5 mL). To the resulting mixture was added sequentially $H_2O$ (0.5 mL), 3.0 N aq. NaOH (0.5 mL) and $H_2O$ (0.5 mL). The mixture was diluted with EtOAc and stirred vigorously at RT for 1 h. The organic layer was separated, washed with $H_2O$, brine, dried ($MgSO_4$), filtered and concentrated. The crude was purified by $SiO_2$ chromatography eluting with a MeOH/DCM gradient (1 to 10% MeOH) to afford 0.012 g of I-187 as a light yellow solid.

step 4—A mixture I-186 (150 mg, 0.28 mmol) and 1N aq. LiOH (1.5 mL) in THF (2 mL), MeOH (2 mL) and $H_2O$ (2 mL) was heated at 70° C. for 5 h. The reaction mixture was cooled to RT and the organic volatiles were removed in vacuo. The aqueous layer was acidified at 0° C. with 1 N aq. HCl to pH 6.5 and the resulting white precipitate was collected by suction filtration and dried to afford 0.078 g of I-188 as a white solid. The filtrate was further extracted with EtOAc. The organic layer was washed with H$_2$O, brine, dried (MgSO$_4$), filtered and concentrated to afford a second batch of 0.033 g of I-188.

Example 53

2-{2-[3-tert-Butyl-5-(5-fluoro-2-oxo-1,2-dihydro-pyridin-3-yl)-2-methoxy-phenyl]-ethyl}-5-methane-sulfonylamino-benzoic acid (I-190)

step 1—A mixture of 272 (78 mg, 0.14 mmol) and Pd(OH)$_2$/C (25 mg) in a mixture of EtOAc (8 mL) and EtOH (1 mL) under 1 atmosphere of H$_2$ was stirred at RT for 40 min. The catalyst was filtered off and the filtrate was concentrated to afford 75 mg of 2-{2-[3-tert-butyl-5-(5-fluoro-2-methoxy-pyridin-3-yl)-2-methoxy-phenyl]-ethyl}-5-methanesulfony-lamino-benzoic acid methyl ester (276) as an amorphous solid.

step 2—Demethylation of 276 was carried out in accord with the procedure described in step 3 of Example 1. The crude was purified by SiO$_2$ chromatography eluting with a MeOH/DCM gradient (1 to 10% MeOH) to afford 24 mg of I-189 as a white solid.

step 3—A mixture of I-189 (60 mg, 0.11 mmol) and 1N aq. LiOH (1 mL) in a mixture of THF (2 mL), MeOH (2 mL) and H$_2$O (1 mL) was heated at 80° C. for 2 h. The reaction mixture was cooled to RT and the organic volatiles were removed in vacuo. The aqueous layer was acidified at 0° C. with 1 N aq. HCl to pH 6.5 and twice extracted with EtOAc. The combined extracts were washed with H$_2$O, brine, dried (MgSO$_4$), filtered and concentrated to afford 47 mg I-190 as a white solid.

Example 54

N-(4-{1-Aminomethyl-2-[3-tert-butyl-2-methoxy-5-(2-oxo-1,2-dihydro-pyridin-3-yl)-phenyl]-ethyl}-phenyl)-methanesulfonamide (I-191)

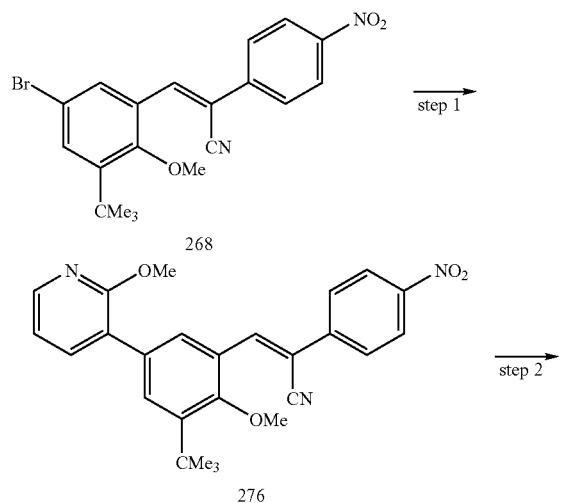

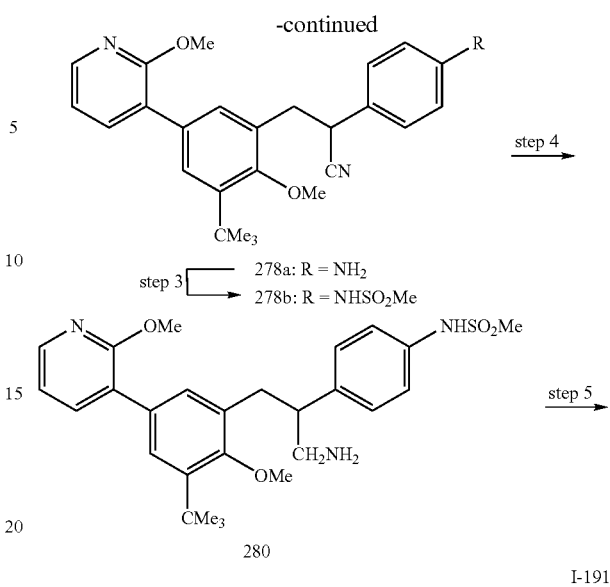

Condensation of D-1b and (4-nitro-phenyl)-acetonitrile to afford 268 was carried out in accord with the procedure described in step 2 of Example 40.

step 1—A tube was charged with sealed tube containing 268 (1.322 g, 3.186 mmol), 37 (0.730 g, 4.773 mmol), Pd(PPh$_3$)$_4$ (0.295 g, 0.255 mmol), Na$_2$CO$_3$ (0.85 g, 8.02 mmol), MeOH (7 mL) and DCM (3 mL), sealed and irradiated in a microwave reactor at 115° C. for 30 min. The reaction mixture was concentrated, diluted with EtOAc, washed with brine, and dried (Na$_2$SO$_4$), filtered and concentrated in vacuo. The crude product was purified by SiO$_2$ chromatography eluting with an EtOAc/hexane gradient (0 to 5% EtOAc) to afford 0.61 g (43%) of 276 as a yellow foam.

step 2—To a solution of 276 (1.144 g, 2.582 mmol) in EtOAc (25 mL) and MeOH (25 mL), was added Pd(OH)$_2$ (20% on carbon, 0.36 g, 0.514 mmol). The reaction was stirred overnight under an atmosphere of hydrogen, filtered through CELITE, and concentrated. The crude residue was purified by SiO$_2$ chromatography eluting with a EtOAc/hexane gradient (20% to 40% EtOAc) to afford 0.624 g (58%) of 278a as an off-white foam.

step 3—Conversion of 278a to the sulfonamide 278b was carried out in accord with the procedure in step 4 of Example 4 step 4—To a solution of 278b (300 mg, 0.609 mmol) in MeOH (40 mL), was added Raney Nickel (50% solution in water, 2 mL) and NH$_4$OH (0.5 mL). The reaction was stirred under an atmosphere of hydrogen overnight, filtered through CELITE, concentrated, and purified by SiO$_2$ chromatography eluting with a EtOAc/hexane gradient (5% to 10% EtOAc) to afford 260 mg (86%) of 280 as a white foam.

step 5—Demethylation of 280 to afford I-191 was carried out in accord with the procedure described in step 3 of Example 1. The crude was purified on preparative SiO$_2$ TLC plate developed with 10% MeOH/DCM to afford I-191 as a white solid.

Example 55

N-(4-{2-[3-tert-Butyl-2-methoxy-5-(2-oxo-1,2-dihydro-pyridin-3-yl)-phenyl]-1-dimethylaminomethyl-ethyl}-phenyl)-methanesulfonamide (I-192)

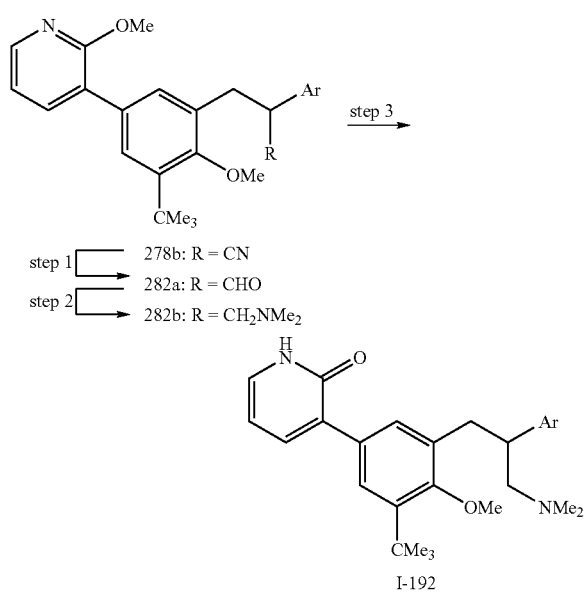

Ar = 4-methanesulfonylaminophenyl step 1—To a solution of 278b (1.455 g, 2.95 mmol) in DCM (20 mL) cooled 0° C. was added DIBAL (1.5M in toluene, 4.4 mL, 6.6 mmol). After 1 h, LCMS indicated incomplete conversion. Additional DIBAL (4.4 mL, 6.6 mmol) was added and the reaction mixture was stirred overnight. Additional DIBAL (4.4 mL, 6.6 mmol) was added and stirred for 3 additional h. The reaction mixture was cooled to 0° C. and diluted with ether (40 mL). 6N HCl (6 mL) was carefully added to the reaction mixture. The resulting suspension was extracted with EtOAc and the organic extracts were dried ($Na_2SO_4$), filtered and concentrated in vacuo. The crude residue was purified by $SiO_2$ chromatographed eluting with an EtOAc/hexane gradient (20% to 40% EtOAc) to afford 545 mg (37%) of 282a as a tan oil (37%).

step 2—To a solution of 282a (130 mg, 0.262 mmol) in DCE (10 mL), was added dimethylamine hydrochloride (45 mg, 0.262 mmol). After 1 h, sodium triacetoxy borohydride (116 mg, 0.547 mmol) was added and the reaction mixture was stirred overnight. The solution was quenched with $NaHCO_3$ solution and extracted with DCM. The combined organic extracts were dried ($Na_2SO_4$), filtered and concentrated. The crude product as purified by $SiO_2$ chromatograph eluting with a MeOH/DCM gradient (0 to 10% MeOH) to afford 81 mg (59%) of 282b as a colorless oil.

step 3—Demethylation of 280 to afford I-191 was carried out in accord with the procedure described in step 3 of Example 1. The crude was purified on preparative $SiO_2$ TLC plate developed with 10% MeOH/DCM to afford 15 mg (19%) I-192 as a white solid.

I-193, I-194 and I-195 were prepared analogously except in step 2, dimethylamine hydrochloride was replaced with morpholine, pyrrolidine and 3,3-difluoro-pyrrolidine, respectively. I-193 was purified on a preparative $SiO_2$ TLC plate developed with 2% MeOH/DCM). I-194 was purified on a preparative $SiO_2$ TLC plate developed with 5% MeOH/DCM) and further purified by HPLC. I-195 was purified on a preparative $SiO_2$ TLC plate developed with 2:1 EtOAc/hexane.

Example 55

N-(4-{2-[3-tert-Butyl-2-methoxy-5-(2-oxo-1,2-dihydro-pyridin-3-yl)-phenyl]-1-cyano-1-methyl-ethyl}-phenyl)-methanesulfonamide (I-196)

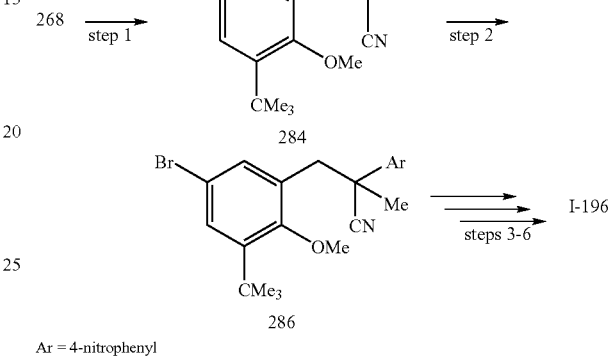

Ar = 4-nitrophenyl step 1—To a solution of 268 (4.0 g, 9.639 mmol) in THF (50 mL) and MeOH (10 mL) at 0° C., was added $NaBH_4$ (0.46 g, 14.803 mmol). The solution was gradually warmed to RT over 2.5 h. The reaction was quenched with aq. $NH_4Cl$ and extracted with EtOAc. The combined extracts were dried ($Na_2SO_4$), filtered and evaporated. The crude residue was purified by $SiO_2$ chromatography eluting with an EtOAc/hexane gradient (0 to 20% EtOAc) to afford 3.33 g (83%) of 284 as a light brown oil.

step 2—To a solution of 284 (1.884 g, 4.518 mmol) in DMF (20 mL) cooled to 0° C., was added sodium hydride (219 mg, 5.475 mmol, 60% mineral oil dispersion). After 15 min, methyl iodide (2.8 mL, 44.977 mmol) was added and the reaction mixture was stirred for 2 h. The resulting suspension was quenched with $NH_4Cl$ and diluted with EtOAc. The crude mixture was thrice washed with 1N HCl, dried ($Na_2SO_4$), filtered and concentrated. The crude product was purified by $SiO_2$ chromatography eluting with an EtOAc/hexane (10% to 20% EtOAc) to afford 1.593 g (82%) of 286 as a pale yellow oil.

steps 3 and 4—Reduction of the nitro substituent (step 3) to the corresponding amine 287 was carried out with $SnCl_2 \cdot 2H_2O$ was carried out as described in step 3 of Example 24. Conversion of the amine to the sulfonamide was carried out in accord with the procedure in step 4 of Example 3 to afford N-{4-[2-(5-bromo-3-tert-butyl-2-methoxy-phenyl)-1-cyano-1-methyl-ethyl]-phenyl}-methanesulfonamide (288).

step 5—A sealed tube containing 288 (69 mg, 0.144 mmol), 112 (30 mg, 0.216 mmol), $Pd(PPh_3)_4$ (16 mg, 0.014 mmol), $Na_2CO_3$ (41 mg, 0.387 mmol) in a mixture of MeOH (3 mL) and DCM (1 mL) was irradiated in a microwave reactor at 115° C. for 30 minutes. The reaction mixture was concentrated, diluted with EtOAc, washed with brine, and dried na2so4, filtered and concentrated. The crude product was purified on a SiO$_2$ preparative TLC plate developed with 20% EtOAc/hexane to afford 33 mg (49%) of I-196 a white solid (49% yield).

Example 56

N-(4-{1-Aminomethyl-2-[3-tert-butyl-2-methoxy-5-(2-oxo-1,2-dihydro-pyridin-3-yl)-phenyl]-1-methyl-ethyl}-phenyl)-methanesulfonamide (I-197)

step 1—To a solution of 288 (150 mg, 0.313 mmol) in MeOH (20 mL) in a Parr bottle was added Raney Nickel (50% solution in water, 1 mL) and NH$_4$OH (0.5 mL) and the mixture was hydrogenated at 45 psi on a Parr shaker overnight. LCMS indicated some remaining starting material. Additional Raney Nickel (1 mL) and NH$_4$OH (0.5 mL) were added and the hydrogenation was continued for another day. The crude mixture was filtered through CELITE and the filtrate was concentrated. The crude product was purified by SiO$_2$ chromatography eluting with 10% MeOH/DCM to afford 127 mg (84%) of N-{4-[1-aminomethyl-2-(5-bromo-3-tert-butyl-2-methoxy-phenyl)-1-methyl-ethyl]-phenyl}-methanesulfonamide (290).

step 2—Conversion of 290 to I-197 was carried out in accord with the procedure in step 5 of Example 55. The product was purified on a preparative SiO$_2$ TLC plate developed with 5% MeOH/DCM to afford I-197 as an off-white solid.

Example 57

N-(4-{2-[3-tert-Butyl-2-methoxy-5-(2-oxo-1,2-dihydro-pyridin-3-yl)-phenyl]-1-hydroxymethyl-1-methyl-ethyl}-phenyl)-methanesulfonamide (I-198)

To a solution of 288 (766 mg, 1.599 mmol) in DCM (10 mL) at 0° C. was added DIBAL (3.2 mL, 3.2 mmol, 1.0M in DCM). The reaction mixture was gradually warmed to RT overnight. LCMS indicated incomplete conversion. Additional DIBAL (3.2 mL, 3.2 mmol) was added and the reaction mixture was stirred for an additional 5 h. The reaction mixture was cooled to 0° C. and diluted with ether (20 mL). The reaction was quenched by careful addition of 6N HCl (1.5 mL). The resulting suspension was extracted with EtOAc and the organic extracts were dried (Na$_2$SO$_4$), filtered and concentrated in vacuo. The crude residue was purified by SiO$_2$ chromatograph eluting with an EtOAc/hexane gradient (20% to 30% EtOAc) to afford 263 mg (34%) of N-{4-[2-(5-bromo-3-tert-butyl-2-methoxy-phenyl)-1-formyl-1-methyl-ethyl]-phenyl}-methanesulfonamide (292) as a tan oil.

step 2—To a solution of 292 (117 mg, 0.243 mmol) in MeOH (5 mL) at 0° C. was added sodium borohydride (44 mg, 1.163 mmol). The solution was gradually warmed to RT over 3 h. The reaction was quenched with NH$_4$Cl solution and extracted with EtOAc. The combined extracts were dried (Na$_2$SO$_4$), filtered and concentrated in vacuo to afford 111 mg of N-{4-[2-(5-bromo-3-tert-butyl-2-methoxy-phenyl)-1-hydroxymethyl-1-methyl-ethyl]-phenyl}-methanesulfonamide (294) a white foam (94%).

step 3—Conversion of 294 to I-198 was carried out in accord with the procedure in step 5 of Example 55. The product was purified on a preparative SiO$_2$ TLC plate developed with 2:1 EtOAc/hexane to afford I-197 as an off-white solid.

Example 58

N-(4-{2-[2-Hydroxy-5-(2-hydroxy-1,1-dimethyl-ethyl)-3-(2-oxo-1,2-dihydro-pyridin-3-yl)-phenyl]-ethyl}-phenyl)-methanesulfonamide (I-199)

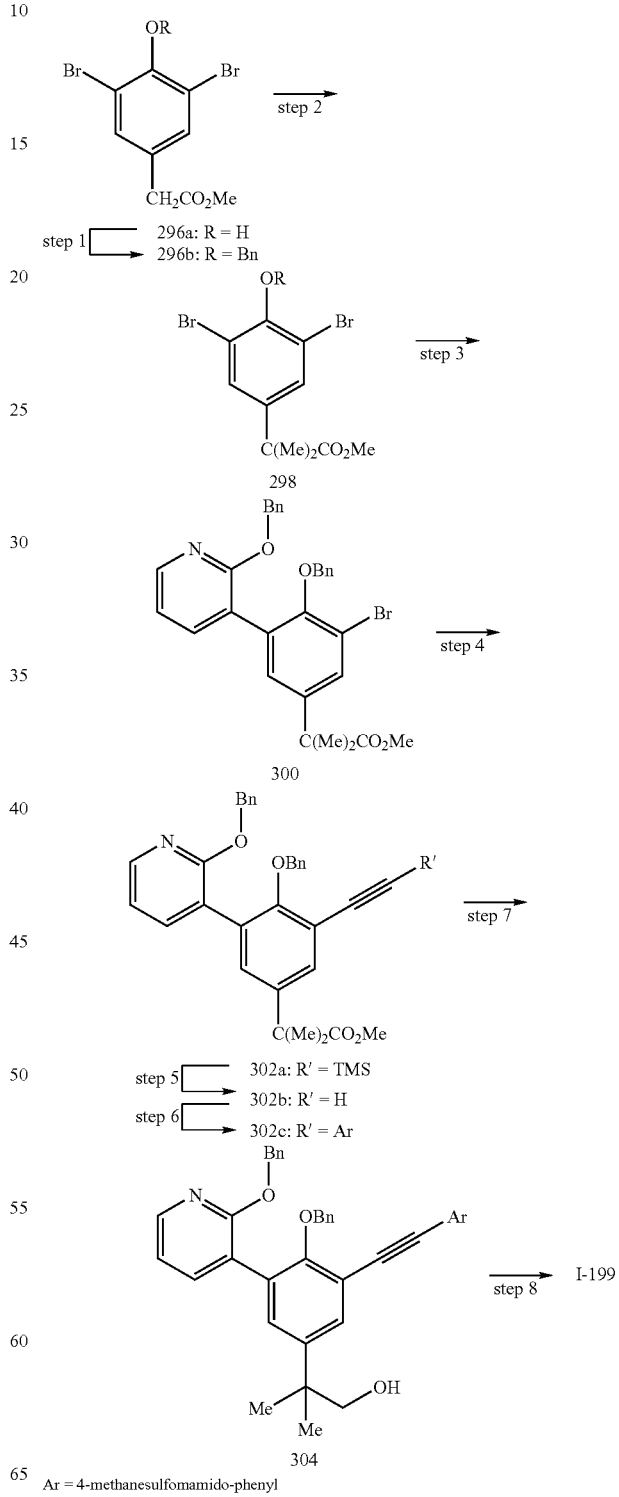

Ar = 4-methanesulfonamido-phenyl step 1—To a solution of 296a (2.23 g, 6.88 mmol) and $K_2CO_3$ (1.90 g, 13.75 mmol) in DMF (10 mL), was added benzyl bromide (1.60 mL, 13.47 mmol). The reaction mixture was stirred at RT overnight, then diluted with EtOAc and thrice washed with $H_2O$ and once with brine. The combined extracts were dried ($Na_2SO_4$), filtered and concentrated in vacuo. The crude residue was purified by $SiO_2$ chromatography eluting with an EtOAc/hexane gradient (0 to 10% EtOAc) to afford 2.339 g (82%) of 296b as a colorless oil.

step 2—To a solution of 296b (2.339 g, 5.65 mmol) in THF (15 mL) was added sodium hydride (0.65 g, 16.25 mmol, 60% mineral oil dispersion). After 15 min, methyl iodide (0.80 mL, 12.85 mmol) was added and the resulting suspension was stirred overnight. An additional aliquot of methyl iodide (0.40 mL, 6.43 mmol) was added. After 3 h, the reaction mixture was quenched with $H_2O$ and the THF was evaporated. The crude residue was then extracted with EtOAc, the extracts dried ($Na_2SO_4$), filtered and concentrated. The crude product was purified by $SiO_2$ chromatography eluting with an EtOAc/hexane gradient (0 to 10% EtOAc) to afford 1.084 g (43%) of 298 as a colorless oil.

step 3—Coupling of 298 and 141 was carried out in accord with the procedure in step 2 of Example 22. The crude product was purified by $SiO_2$ chromatography eluting with an EtOAc/hexane gradient (0 to 10% EtOAc) to afford 300 as a colorless oil.

step 4—A round bottom flask was charged with 300 (428 mg, 0.784 mmol), $Pd(PPh_3)_2Cl_2$ (110 mg, 0.157 mmol) and CuI (28 mg, 0.147 mmol). The flask was purged three times with argon/vacuum cycles. TMS acetylene (1.1 mL, 7.784 mmol), TEA (1.1 mL, 7.892 mmol) and THF (5 mL) were added in succession and the resulting mixture was heated at 65° C. under an atmosphere of argon overnight. The following morning An additional aliquot of TMS acetylene (1.1 mL, 7.784 mmol), $Pd(PPh_3)_2Cl_2$ (110 mg, 0.157 mmol) and CuI (28 mg, 0.147 mmol) we added and the reaction was continued at 65° C. for 6 hours. A third aliquot of TMS acetylene (1.1 mL, 7.784 mmol) was added and the reaction was stirred at RT over the weekend. A fourth aliquot of TMS acetylene (1.1 ML, 7.784 mmol), $Pd(PPh_3)_2Cl_2$ (110 mg, 0.157 mmol) and CuI (28 mg, 0.147 mmol) were added and heated at 65° C. for 6 h. The reaction was cooled and filtered through CELITE. The filtrate was concentrated, diluted with EtOAc and washed with 1N HCl. The organic extract was dried ($Na_2SO_4$), filtered and concentrated. The crude product was purified by $SiO_2$ chromatography eluting with a EtOAc/hexane gradient (0 to 10% EtOAc) to afford 387 mg of a colorless oil which was a mixture of 302a and starting material.

step 5—To a solution of 302a (387 mg, 0.687 mmol) in THF (5 mL) was added tetrabutylammonium fluoride (1.0M in THF, 0.850 mL, 0.850 mmol). After stirring at RT for 1 h, the reaction mixture was quenched with aq. $NH_4Cl$ and extracted with EtOAc. The organic extract was dried ($Na_2SO_4$), filtered and concentrated. The crude product was purified by $SiO_2$ chromatography eluting with an EtOAc/hexane gradient (5% to 10% EtOAc) to afford 123 mg of 302b as an orange oil.

4-iodo-phenyl-methanesulfonamide (303)—To a solution of 4-iodoaniline (4.00 g, 18.26 mmol) in pyridine (20 mL) at 0° C., was added methanesulfonyl chloride (1.7 mL, 21.88 mmol). The reaction was gradually warmed RT and stirred overnight. The solution was diluted with EtOAc, washed with sat'd. aq. $CuSO_4$, twice with 1N HCl solution, and dried ($Na_2SO_4$), filtered and concentrated. NMR indicated a mixture of desired product and bis-sulfonylated byproduct. The crude residue was diluted with THF (20 mL) and 1N NaOH (20 mL) and stirred overnight at RT. The solution was diluted with EtOAc, washed with 6N HCl solution, dried ($Na_2SO_4$), filtered and concentrated. The crude product was purified by $SiO_2$ chromatography eluting with an EtOAc/hexane gradient (10% to 40% EtOAc) to afford 2.13 g of 303 as a white solid (39%).

step 6—A round bottom flask was charged with 302b (123 mg, 0.251 mmol), 303 (112 mg, 0.377 mmol), $PdCl_2(PPh_3)_2$ (18 mg, 0.026 mmol), CuI (2.9 mg, 0.015 mmol) and purged 3 times with argon. THF (5 mL) and TEA (2 mL) were added and the reaction mixture was heated at 65° C. overnight under an argon atmosphere. The reaction mixture was concentrated and purified by $SiO_2$ chromatography eluting with an EtOAc/hexane gradient (20% to 40% EtOAc) to afford 130 mg (78%) of 302c as an orange oil.

step 7—To a solution of 302c (130 mg, 0.197 mmol) in DCM (10 mL) cooled to 0° C., was added DIBAL (0.700 mL, 0.700 mmol, 1.0 M solution in DCM). The reaction mixture was gradually warmed to RT over 3 h, then quenched with a solution of Rochelle's salt and stirred vigorously for 1 h. The organic layer was separated, dried ($Na_2SO_4$), filtered and concentrated to afford 114 mg (92%) of 304 as a colorless oil.

step 8—Hydrogenolytic debenzylation and reduction of the acetylene to afford 199 was carried out in accord with the procedure in step 5 of example 31. The reaction mixture was filtered, concentrated, and purified on a preparative $SiO_2$ plate developed with 2:1 EtOAc/hexane to afford 29 mg of I-199 as a white solid.

Example 59

N-(4-{(E)-2-[3-tert-Butyl-5-(5-fluoro-2-oxo-1,2-dihydro-pyridin-3-yl)-2-methoxy-phenyl]-vinyl}-3-cyano-phenyl)-methanesulfonamide (I-200)

A solution of D-2 (1.00 g, 3.69 mmol), 2-methyl-5-nitro-benzonitrile (0.60 g, 3.70 mmol), and piperidine (0.550 mL, 5.56 mmol) in pyridine (7 mL) was heated at reflux overnight. The reaction mixture was concentrated, diluted with EtOAc, washed sequentially with $CuSO_4$ solution and 1N HCl, and dried ($Na_2SO_4$). The crude residue was purified by $SiO_2$ chromatography eluting with an EtOAc/hexane gradient (0 to 5% EtOAc) to give 0.79 g (52%) of N-{4-[(E)-2-(5-bromo-3-tert-butyl-2-methoxy-phenyl)-vinyl]-3-cyano-phenyl}-methanesulfonamide (306) as a yellow solid.

Reduction of the nitro group (step 2) was carried out in accord with the procedure described in step 3 of Example 24. Conversion of the amine to the sulfonamide (step 4) was carried out in accord with the procedure described in step 4 of Example 24. Cross coupling of the bromide and 107 was carried out in accord with the procedure described in step 4 of Example 37. Cleavage of the methyl ether was carried out in accord with the procedure described in step 5 of Example 37. The final product was purified on a preparative $SiO_2$ TLC plate developed with 2:1 EtOAc/hexane to afford 1-200 as an off-white solid.

Example 60

2-{(E)-2-[3-tert-Butyl-2-methoxy-5-(6-methyl-2-oxo-1,2-dihydro-pyridin-3-yl)-phenyl]-vinyl}-5-methanesulfonylamino-benzoic acid methyl ester (I-201)

Cross coupling of 232d and 2-methoxy-6-methyl-pyridin-3-yl boronic acid (CASRN 1000802-75-4) was carried out as described in step 2 of Example 1 except 141 was replaced with 2-methoxy-6-methyl-pyridin-3-yl boronic acid to afford methyl 2-{(E)-2-[3-tert-butyl-2-methoxy-5-(2-methoxy-6-methyl-pyridin-3-yl)-phenyl]-vinyl}-5-methanesulfonylamino-benzoate (308).

step 1—A solution of 308 (89 mg, 0.165 mmol), HBr 48% (0.090 mL, 0.784 mmol) in HOAc (4 mL) was heated at 50 overnight in a sealed tube. The reaction mixture was carefully poured into a mixture of saturated NaHCO$_3$ and ice, extracted with EtOAc, and dried (Na$_2$SO$_4$). The crude product was purified on a preparative SiO$_2$ TLC plate developed with 2:1 EtOAc/hexane to afford 51 mg of a white solid that was further purified by HPLC to afford 33 mg of I-201 as a white solid.

Example 61

2-{(E)-2-[3-tert-Butyl-2-methoxy-5-(2-oxo-1,2-dihydro-pyridin-3-yl)-phenyl]-vinyl}-methanesulfonylamino-N,N-dimethyl-benzamide (I-202)

step 1—To a solution 232a (400 mg, 0.922 mmol), and dimethylamine hydrochloride (153 mg, 1.876 mmol) in DMF (10 mL) cooled to 0° C., was added TEA (0.500 mL, 3.587 mmol), HOBt (190 mg, 1.406 mmol) and EDCI (263 mg, 1.372 mmol). The solution was gradually warmed to RT and stirred for 72 h. The reaction mixture was diluted with EtOAc, washed sequentially with 1N HCl and brine (twice), dried (Na$_2$SO$_4$), filtered and concentrated. The crude product was purified by SiO$_2$ chromatography eluting with an EtOAc/hexane gradient (5% to 15% EtOAc) to afford 315 mg (74%) of 2-[(E)-2-(5-bromo-3-tert-butyl-2-methoxy-phenyl)-vinyl]-N,N-dimethyl-5-nitro-benzamide (309) as a cream colored solid.

Reduction of the nitro group (step 2) was carried out in accord with the procedure described in step 3 of Example 24. Conversion of the amine to the sulfonamide (step 4) was carried out in accord with the procedure described in step 4 of Example 24. Cross coupling of the bromide and 112 was carried out in accord with the procedure in step 4 of example 38 to afford I-202. The crude product was purified on a preparative SiO$_2$ TLC plate developed with 3% MeOH/DCM to afford a light yellow solid.

I-207 was prepared from I-188 in accord with the procedure in step 1 of the present example except dimethylamine hydrochloride was replaced with N,N,N'-trimethylethylenediamine. The crude product was purified on a preparative SiO$_2$ TLC plate developed with 10% MeOH/DCM to afford I-207 as an off-white solid.

Example 62

2-{(E)-2-[3-tert-Butyl-2-methoxy-5-(2-oxo-1,2-dihydro-pyridin-3-yl)-phenyl]-vinyl}-5-methanesulfonylamino-benzoic acid (I-203)

To a solution of I-201 (78 mg, 0.153 mmol) in THF (2 mL), MeOH (2 mL) and H$_2$O (2 mL) was added lithium hydroxide monohydrate (67 mg, 1.59 mmol). The solution was stirred at RT overnight and concentrated. 1N HCl (2 mL) was added and the resulting white precipitate was filtered and purified by HPLC to afford 31 mg (41%) of I-203 as a white solid (41%).

Example 63

N-[4-{(E)-2-[3-tert-Butyl-2-methoxy-5-(2-oxo-1,2-dihydro-pyridin-3-yl)-phenyl]-vinyl}-3-(1-hydroxy-1-methyl-ethyl)-phenyl]-methanesulfonamide (I-204)

To a solution of I-201 (45 mg, 0.088 mmol) in THF (5 mL) at 0° C., was added MeMgBr (0.200 mL, 0.600 mmol, 3.0 M in THF). The solution was stirred at RT for 6 h and an additional aliquot of MeMgBr (0.600 mL, 1.800 mmol, 3.0 M in THF) was added and the reaction stirring continued overnight. A further aliquot of MeMgBr (0.800 mL, 2.400 mmol) was added and the reaction was stirred for an additional 8 h. The reaction mixture was cooled to 0° C. and quenched with aq. NH$_4$Cl. The resulting suspension was extracted with EtOAc and the combined organic extracts were dried (Na$_2$SO$_4$), filtered and concentrated. The crude product was purified on a preparative SiO$_2$ TLC plate developed with 2:1 EtOAc/hexane to afford 8 mg (18%) of I-204 as a white solid.

Example 64

N-(4-{(E)-2-[3-tert-Butyl-2-methoxy-5-(2-oxo-1,2-dihydro-pyridin-3-yl)-phenyl]-vinyl}-3-hydroxymethyl-phenyl)-methanesulfonamide (I-205)

step 1—To a solution of 232d (184 mg, 0.371 mmol) in THF (10 mL) at 0° C., was added LiAlH$_4$ (0.750 mL, 0.750 mmol, 1.0 M solution in THF). The reaction was gradually warmed to RT over 1.5 hr, then cooled down to 0° C. and quenched with 1N NaOH (2 mL). The suspension was extracted with EtOAc and the combined extracts dried (Na$_2$SO$_4$), filtered and concentrated in vacuo. The crude product was purified by SiO$_2$ chromatography eluting with an EtOAc/hexane gradient (30% to 50% EtOAc) to afford 73 mg (42%) of N-{4-[(E)-2-(5-bromo-3-tert-butyl-2-methoxy-phenyl)-vinyl]-3-hydroxymethyl-phenyl}-methanesulfonamide (310).

Cross coupling of the bromide and 112 and 310 was carried out in accord with the procedure in step 5 of example 14. The crude product was purified on a SiO$_2$ preparative TLC plate developed with 2:1 EtOAc/hexane and further purified by HPLC to afford 15 mg (20%) of I-205 as a white solid.

Example 65

N-(4-{E-2-[3-tert-Butyl-2-methoxy-5-(2-oxo-1,2-dihydro-pyridin-3-yl)-phenyl]-vinyl}-3-methoxymethyl-phenyl)-methanesulfonamide (I-206)

step 1—To a solution of 232b (500 mg, 1.12 mmol) in THF (10 mL) cooled to 0° C., was added LiAlH$_4$ (1.7 mL, 1.7 mmol, 1.0 M solution in THF). The reaction was gradually warmed to RT over 45 min, then re-cooled down to 0° C. and quenched with NaHSO$_4$ solution. The suspension was concentrated, diluted with EtOAc, and washed with 1N HCl and brine. The organic extract was dried (Na$_2$SO$_4$), filtered and concentrated in vacuo. The crude product was purified by SiO$_2$ chromatography eluting with an EtOAc/hexane gradient (5% to 10% EtOAc) to afford 129 mg (28%) of {2-[(E)-2-(5-bromo-3-tert-butyl-2-methoxy-phenyl)-vinyl]-5-nitro-phenyl}-methanol (312) as a yellow oil.

step 2—To a solution of 312 (116 mg, 0.276 mmol) in DMF (5 mL) was added sodium hydride (0.022, 0.550 mmol, 60% mineral oil dispersion). After 20 min, methyl iodide (0.040 mL, 0.643 mmol) was added and the resulting suspension was stirred overnight. The reaction mixture was diluted with EtOAc, thrice washed with brine, dried (Na$_2$SO$_4$), filtered and concentrated in vacuo. The crude product was purified by SiO$_2$ chromatography eluting with an EtOAc/hexane gradient (5% to 15% EtOAc) to afford 81 mg (68%) of 5-bromo-1-tert-butyl-2-methoxy-3-[(E)-2-(2-methoxymethyl-4-nitro-phenyl)-vinyl]-benzene (314) as an orange oil.

Reduction of the nitro group (step 2) was carried out in accord with the procedure described in step 3 of Example 24. Conversion of the amine to N-{4-[(E)-2-(5-bromo-3-tert-butyl-2-methoxy-phenyl)-vinyl]-3-methoxymethyl-phenyl}-methanesulfonamide (315, step 3) was carried out in accord with the procedure described in step 4 of Example 24. Cross coupling of the bromide and 107 was carried out in accord with the procedure in step 4 of example 38. The crude product was purified on a preparative SiO₂ TLC plate developed with 2:1 EtOAc/hexane to afford I-206 as a light yellow solid.

Example 66

N-(4-{(E)-2-[3-tert-Butyl-2-methoxy-5-(6-methyl-2-oxo-1,2-dihydro-pyridin-3-yl)-phenyl]-vinyl}-3-methoxymethyl-phenyl)-methanesulfonamide (I-208)

step 1—Cross coupling of 315 and 6-methyl-2-methoxy-3-pyridine boronic acid (316, CASRN 1000802-754) was carried out in accord with the procedure in step 4 of example 38 except 107 was replaced with 316 which afforded N-(4-{(E)-2-[3-tert-butyl-2-methoxy-5-(2-methoxy-6-methyl-pyridin-3-yl)-phenyl]-vinyl}-3-methoxymethyl-phenyl)-methanesulfonamide (318).

step 2—A solution of 318 (72 mg, 0.137 mmol), HBr 48% (0.100 mL, 0.871 mmol) in HOAc (4 mL) was heated at 60° C. overnight in a sealed tube. The reaction mixture was carefully poured into a mixture of saturated NaHCO₃ and ice, extracted with EtOAc, dried (Na₂SO₄), filtered and concentrated to afford 70 mg (91%) of N-(3-bromomethyl-4-{(E)-2-[3-tert-butyl-2-methoxy-5-(6-methyl-2-oxo-1,2-dihydro-pyridin-3-yl)-phenyl]-vinyl}-phenyl)-methanesulfonamide (320) as an orange oil.

step 3—To a solution of 320 (70 mg, 0.125 mmol) in MeOH (10 mL) was added sodium methoxide (10 mL, 5 mmol, 0.5 M MeOH solution). The reaction was stirred at RT overnight. The reaction mixture was concentrated, diluted with EtOAc and acidified with 6N HCl (1 mL). The organic extract was dried (Na₂SO₄), filtered and concentrated. The crude product was purified on a preparative SiO2 TLC plate developed with 2:1 EtOAc/hexane to afford 28 mg of I-208 as an off-white solid.

Example 67

N-(4-{(E)-2-[3-tert-Butyl-2-methoxy-5-(6-methoxy-2-oxo-1,2-dihydro-pyridin-3-yl)-phenyl]-vinyl}-3-methoxymethyl-phenyl)-methanesulfonamide (I-209)

step 1—A sealed tube containing 315 (117 mg, 0.243 mmol), 2,6-dimethoxy-pyridin-3-yl boronic acid (53 mg, 0.290 mmol, CASRN 221006-70-8), Pd(PPh₃)₄ (28 mg, 0.024 mmol), Na₂CO₃ (76 mg, 0.717 mmol) in a mixture of MeOH (3 mL) and DCM (1 mL) was irradiated in a microwave reactor at 115° C. for 30 minutes. The reaction mixture was concentrated, diluted with EtOAc, washed with brine and dried (Na₂SO₄), filtered and concentrated. The crude product was purified by SiO₂ chromatography eluting with an EtOAc/hexane gradient (20% to 30% EtOAc) to afford 104 mg (79%) of N-(4-{(E)-2-[3-tert-butyl-5-(2,6-dimethoxy-pyridin-3-yl)-2-methoxy-phenyl]-vinyl}-3-methoxymethyl-phenyl)methanesulfonamide (322) as a colorless oil.

step 2—A solution of 322 (104 mg, 0.193 mmol), HBr 48% (0.100 mL, 0.871 mmol) in HOAc (4 mL) was heated at 75° C. for 4 h in a sealed tube. The reaction mixture was carefully poured into a mixture of saturated NaHCO₃ and ice, extracted with EtOAc, dried (Na₂SO₄), filtered and concentrated to afford 93 mg (84%) of N-(3-bromomethyl-4-{(E)-2-[3-tert-butyl-2-methoxy-5-(6-methoxy-2-oxo-1,2-dihydro-pyridin-3-yl)-phenyl]-vinyl}-phenyl)-methanesulfonamide (324) as a purple oil.

step 3—A solution of 324 (93 mg, 0.162 mmol) in MeOH (10 mL) and sodium methoxide (10 mL, 5 mmol, 0.5 M methanol solution) was stirred at RT overnight. The reaction mixture was concentrated, diluted with EtOAc and acidified with 6N HCl (1 mL). The organic extract was dried (Na₂SO₄),
filtered and concentrated. The crude product was purified on a preparative TLC plate developed with 2:1 EtOAc/hexane to afford 26 mg (31%) of I-209 as an off-white solid.

Example 68

N-(4-{(E)-2-[3-tert-Butyl-2-methoxy-5-(6-methoxy-2-oxo-1,2-dihydro-pyridin-3-yl)-phenyl]-vinyl}-3-hydroxymethyl-phenyl)-methanesulfonamide (I-210)

Cross coupling of 232d and 316 (CASRN 1000802-75-4) was carried out in accord with the procedure in step 4 of example 38 except 107 was replaced with 316 which afforded methyl 2-{(E)-2-[3-tert-butyl-5-(2,6-dimethoxy-pyridin-3-yl)-2-methoxy-phenyl]-vinyl}-5-methanesulfonylaminobenzoate (326). Cleavage of the methyl ether to produce the pyridone was carried out in accord with the procedure in step 3 of Example 1 to afford methyl 2-{(E)-2-[3-tert-butyl-2-methoxy-5-(6-methoxy-2-oxo-1,2-dihydro-pyridin-3-yl)-phenyl]-vinyl}-5-methanesulfonylamino-benzoate (328).

step 1—To a solution of 328 (1.376 g, 2.5 mmol) and THF (40 mL) cooled to 0° C. (ice bath) was added lithium borohydride (0.166 g, 7.6 mmol). The reaction was stirred at 0° C. then warmed to RT and stirred over night. Additional lithium borohydride (0.166 g, 7.6 mmol) was added and the reaction heated at 80° C. for 4 h. The reaction was cooled and partitioned between EtOAc (100 mL) and sat'd. aq. NH₄Cl (100 mL). The aqueous layer was separated and twice washed with EtOAc (50 mL). The combined organic extracts were washed with brine (50 mL), dried (Na₂SO₄), filtered and concentrated. The crude product was purified by SiO₂ chromatography eluting with 5% MeOH/DCM to afford 0.470 g (36%) of I-210.

Example 69

N-(5-{2-[5-tert-Butyl-2-cyano-3-(2-oxo-1,2-dihydropyridin-3-yl)-phenyl]-ethyl}-pyridin-2-yl)-methanesulfonamide (I-212)

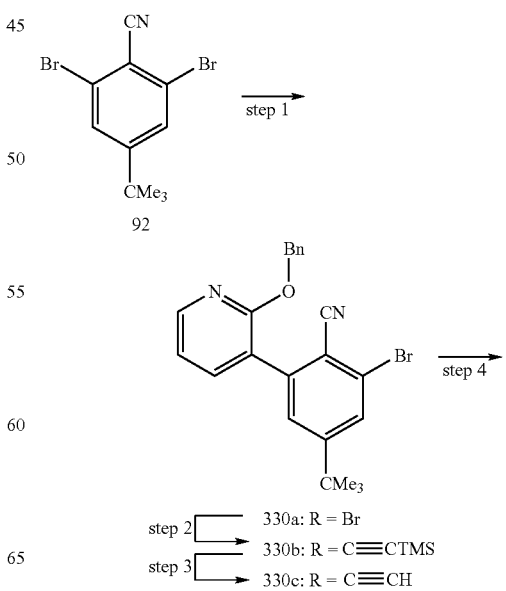

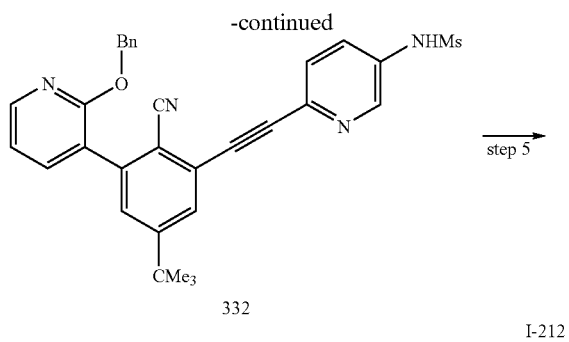

332

I-212 step 1—To each of two 20 mL microwave tubes was added 92 (0.500 g, 1.9 mmol), 141 (0.351 g, 1.5 mmol), Pd(PPh₃)₄ (0.220 g, 0.19 mmol), Na₂CO₃ (0.609 g, 5.7 mmol), and MeOH/DCM (9 mL/3 mL). The tubes were irradiated in the microwave synthesizer at 115° C. for 30 min. The reactions were combined, concentrated then partitioned between EtOAc and H₂O (25 mL/25 mL). The aqueous layer was separated and twice washed with EtOAc (25 mL). The combined organic layers were washed with brine (25 mL), dried (Na₂SO₄), filtered, and concentrated. The crude product was purified by SiO₂ chromatography eluting with an EtOAc/hexane gradient (stepwise 0, 20 and 40% EtOAc) to afford 0.805 g (50%) of 330a.

step 2—To a solution of 330a (0.788 g, 1.9 mmol) and THF (15 mL) was added CuI (0.018 g, 0.09 mmol), Pd(PPh₃)₂Cl₂ (0.131 g, 0.19 mmol), DIPEA (0.5 mL), and trimethylsilyl acetylene (0.8 mL, 5.6 mmol). The reaction was heated at 80° C. for 3 h, then more trimethylsilyl acetylene (0.8 mL, 5.6 mmol), CuI (0.018 g. 0.09 mmol), and Pd(PPh₃)₂Cl₂ (0.131 g, 0.19 mmol) were added and the reaction stirred over night at 80° C. The reaction was concentrated and partitioned between EtOAc and sat'd. aq. NH₄Cl (25 mL/25 mL). The aqueous layer was separated and twice washed with EtOAc (25 mL). The combined organic extracts were washed with brine (25 mL), dried (Na₂SO₄), filtered, and concentrated to give a brown residue. The crude product was purified by SiO₂ chromatography eluting with an EtOAc/hexane gradient (stepwise 0, 20, 40 and 60% EtOAc) to afford 0.497 g (61%) of 330b as a brown solid.

step 3—To a solution of 330b (0.495 g, 1.1 mmol) in MeOH (5 mL) was added K₂CO₃ (0.049 g, 0.36 mmol). The reaction was stirred over night at RT, concentrated and partitioned between EtOAc and H₂O (25 mL/25 mL). The aqueous layer was separated and twice washed with EtOAc (25 mL). The combined organic layers were washed with brine (25 mL), dried (Na₂SO₄), filtered and concentrated. The crude product was purified by SiO₂ chromatography eluting with an EtOAc/hexane gradient (stepwise 0, 20 and 40% EtOAc) to afford 0.147 g (41%) of 330c.

step 4—To a solution of 330c (0.147 g, 0.40 mmol) and THF (5 mL), was added 165 (0.179 g, 0.60 mmol), followed by CuI (0.004 g, 0.02 mmol), Pd(PPh₃)₂Cl₂ (0.028 g, 0.04 mmol), and DIPEA (0. mL). The reaction was heated at 80° C. for 2 h, whereupon more CuI (0.004 g, 0.02 mmol) and Pd(PPh₃)₂Cl₂ (0.028 g, 0.04 mmol) were added. The reaction was heated at 80° C. for an additional 3 h and then stirred overnight at RT. The reaction mixture was partitioned between EtOAc and H₂O (25 mL/25 mL). The aqueous layer was separated and twice washed with EtOAc (25 mL). The combined extracts were washed with brine (25 mL), dried (Na₂SO₄) filtered and concentrated. The crude product was purified by SiO₂ chromatography eluting with an EtOAc/hexane gradient (stepwise 0, 10, 20 and 40% EtOAc) to afford 0.072 g, (33%) of 332.

step 5—To a suspension of 332 (0.072 g, 0.13 mmol, EtOAc (10 mL) and MeOH (10 mL), was added 10% Pd(OH)₂ on carbon. The reaction was shaken in a Parr Shaker under 40 psi of hydrogen for 3 h. The reaction was filtered to remove palladium catalyst and the filtrate concentrated. The crude product was purified sequential preparative SiO₂ chromatography. The first plate was developed with 5% MeOH/DCM and a second plate was developed with 40% EtOAc/hexane to afford 0.005 g (8%) of I-211.

Example 70

N-(6-{(E)-2-[3-tert-Butyl-2-methoxy-5-(2-oxo-1,2-dihydro-pyridin-3-yl)-phenyl]-vinyl}-5-methyl-pyridin-3-yl)-methanesulfonamide (I-213)

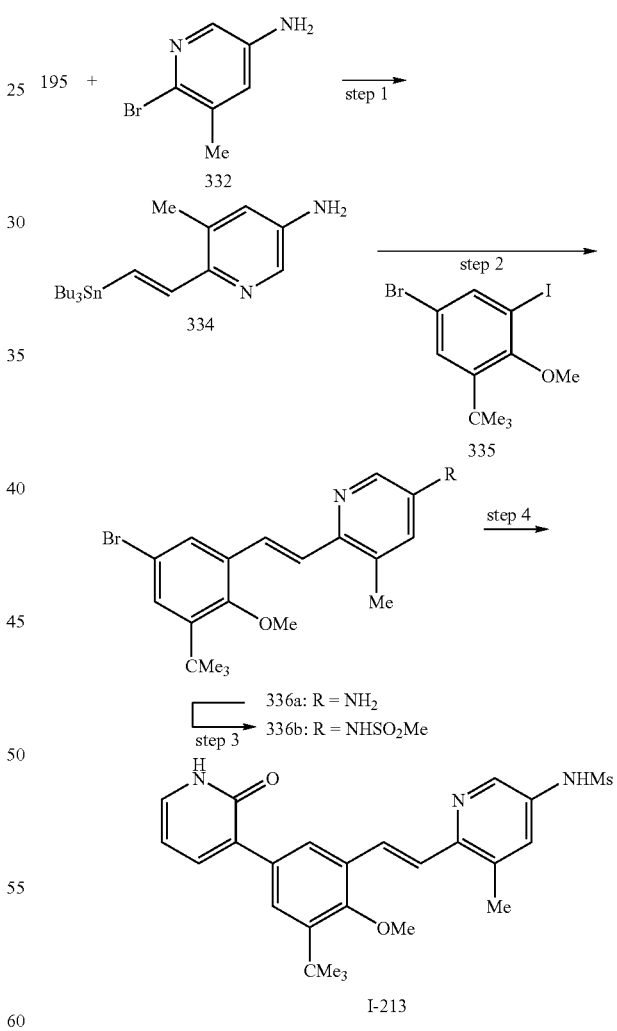

step 1—A mixture of 332 (475 mg, 2.54 mmol), 195 (2.00 g, 3.30 mmol), Pd(PPh₄ (147 mg, 0.13 mmol) and TEA (885 μL, 6.35 mmol) in toluene (20 mL) was degassed under argon for 15 min and then heated at 90° C. for 26 h. The reaction mixture was allowed to cool to RT and concentrated. The crude was purified by SiO₂ chromatography eluting with an EtOAc/hexane gradient (0 to 40% EtOAc containing 0.5% Et₃N) to afford 0.382 g of 334 as a yellow oil.

step 2—A round bottom flask was charged with 335 (413 mg, 1.119 mmol), 334 (473 mg, 1.118 mmol), Pd(PPh₃)₄ (65 mg, 0.056 mmol), TEA (0.400 mL, 2.870 mmol) and toluene (10 mL) and purged with argon three times. The reaction mixture was heated at 75° C. overnight under an Ar atmosphere. An additional portion of Pd(PPh₃)₄ (60 mg, 0.052 mmol) was added and the reaction was heated to 90° C. for an additional 6 h. The reaction was diluted with EtOAc, washed with brine, dried, filtered and concentrated. The crude product was purified by SiO₂ chromatography eluting with an EtOAc/hexane gradient (20% to 30% EtOAc) to give 152 mg (36%) of 336a as an orange oil.

step 3—To a solution of 336a (152 mg, 0.405 mmol) in DCM (7 mL) cooled to 0° C. was added pyridine (100 µL, 1.236 mmol) and methanesulfonyl chloride (60 µL, 0.772 mmol). The reaction was gradually warmed to RT and stirred overnight. The solution was diluted with DCM, washed with sat'd. aq. CuSO4, twice with brine, dried (Na₂SO₄), filtered and concentrated. The crude product was purified by SiO₂ chromatography eluting with an EtOAc/hexane gradient (20% to 25% EtOAc) to afford 88 mg (48%) of 336b as an orange oil.

step 4—Cross-coupling of 336b and 112 was carried out in accord with the procedure described in step 5 of Example 14. The crude product was purified on a preparative SiO₂ TLC plate developed with 3:1 EtOAc/hexane to afford 23 mg (26%) of I-213 as a white solid.

Example 70b

N-(6-{2-[5-tert-butyl-2-hydroxy-3-(2-oxo-1,2-dihydro-pyridin-3-yl)-phenyl]-ethyl}-pyridin-3-yl)-methanesulfonamide (I-214)

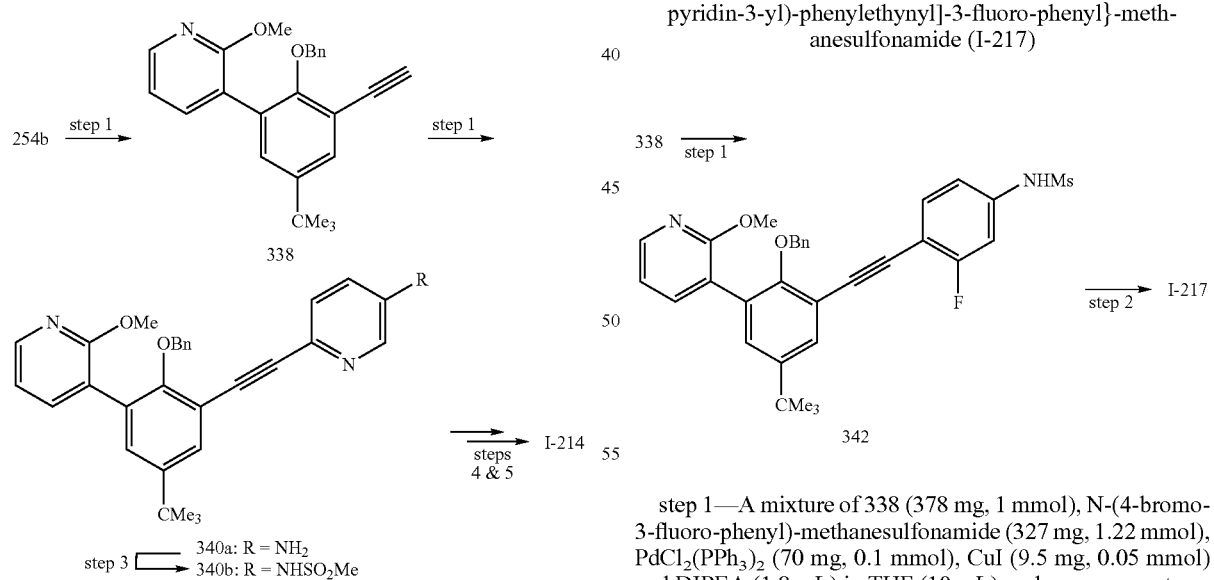

The aldehyde 254b was coupled with 37 then converted to 338 with dimethyl 1-diazo-2-oxopropylphoshonate in accord with the procedure in step 3 of Example 9. Cross-coupling with 5-amino-2-iodo-pyridine (step 2) was carried out in accord with the procedure described step 5 of Example 14. Formation of the sulfonamide (step 3) was carried out in accord with the procedure described in step 4 of Example 4. Debenzylation and reduction of the acetylene (step 4) was carried out in accord with the procedure described in step 8 of Example 58. Cleavage of the methyl ether (step 5) was carried out in accord with the procedure described in step 3 of Example 1. The crude residue was purified on a preparative SiO₂ TLC plate developed with 9:1 DCM/MeOH to afford I-214 as a white solid: MS m/z (ES): (M+H)=442.

N-(4-{2-[5-tert-Butyl-2-hydroxy-3-(2-oxo-1,2-dihydropyridin-3-yl)-phenyl]-ethyl}-3-cyano-phenyl)-methanesulfonamide (I-215) was prepared analogously except step 2, -amino-2-iodo-pyridine was replaced by 2-amino-5-iodopyridine. The crude residue was purified on a preparative SiO₂ TLC plate developed with DCM/MeOH to afford I-215 as a white solid: MS m/z (ES(M+H)=442.

N-(4-{2-[5-tert-Butyl-2-hydroxy-3-(2-oxo-1,2-dihydropyridin-3-yl)-phenyl]ethyl}-3-cyano-phenyl)-methanesulfonamide (I-216) was prepared analogously except step 2, -amino-2-iodo-pyridine was replaced by 2-bromo-5-nitrobenzonitrile. The crude residue was purified on a preparative SiO₂ TLC plate developed with EtOAc/hexanes to afford 25 mg (18%) of pyridone as a white solid. MS m/z (ES)=466 (M+H)⁺.

Example 71

2-{(E)-2-[3-tert-Butyl-2-methoxy-5-(6-methoxy-2-oxo-1,2-dihydro-pyridin-3-yl)-phenyl]-vinyl}-5-methanesulfonylamino-benzoic acid (I-211)

The title compound was prepared by saponification of 328 with LiOH.H₂O. The product was purified by SiO₂ chromatography eluting with 5% MeOH/DCM to afford I-211.

Example 72

N-{4-[5-tert-Butyl-2-hydroxy-3-(2-oxo-1,2-dihydropyridin-3-yl)-phenylethynyl]-3-fluoro-phenyl}-methanesulfonamide (I-217)

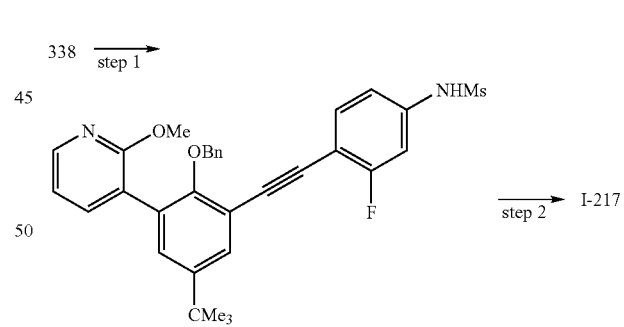

step 1—A mixture of 338 (378 mg, 1 mmol), N-(4-bromo-3-fluoro-phenyl)-methanesulfonamide (327 mg, 1.22 mmol), PdCl₂(PPh₃)₂ (70 mg, 0.1 mmol), CuI (9.5 mg, 0.05 mmol) and DIPEA (1.8 mL) in THF (10 mL) under an argon atmosphere was heated overnight at 60° C. The reaction mixture was cooled to RT and concentrated. The crude residue was purified by SiO₂ chromatography eluting with a 1:4 EtOAc/hexane to afford 230 mg (41%) of 342 as a yellow oil.

step 2—A mixture of 342 (17 mg, 0.03 mmol), 48% aqueous HBr (2 mL) and HOAc (10 mL) in a sealed tube was heated overnight at 65° C. The reaction mixture was carefully poured into a cold sat'd. aq. NaHCO₃, and then extracted with EtOAc. The organic layer was washed with brine, dried (MgSO₄), filtered and concentrated. The crude residue was purified on a preparative SiO₂ TLC plate developed with EtOAc/hexanes to afford 5 mg (37%) of I-217 as an off white semisolid: MS m/z (ES)(M+H)=455.

Example 73

N-(4-{2-[3-tert-Butyl-6-hydroxy-2-methoxy-5-(2-oxo-1,2-dihydro-pyridin-3-yl)-phenyl]-ethyl}-phenyl)-methanesulfonamide (I-218)

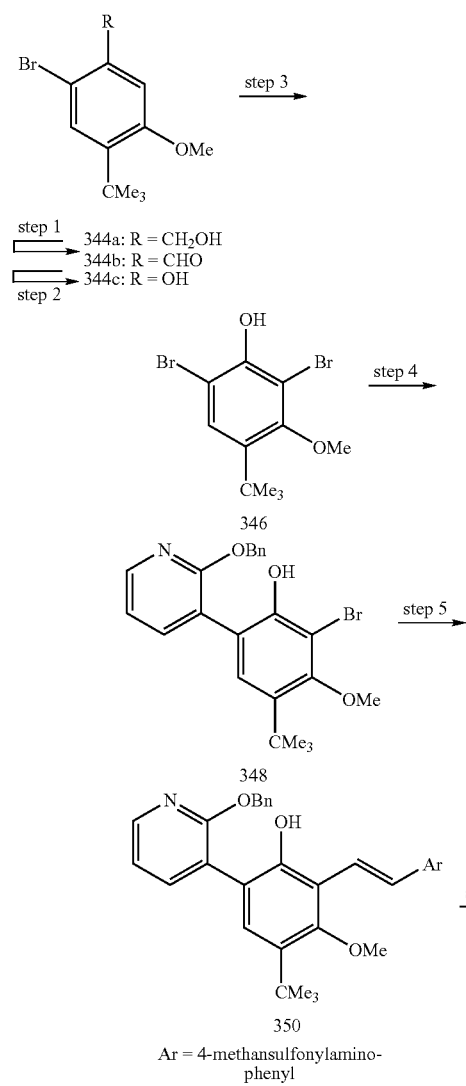

(2-Bromo-4-tert-butyl-5-methoxy-phenyl)-methanol (344a)

step a—To a solution of 4-tert-butyl-3-methoxybenzoic acid (3.00 g, 14.40 mmol, CASRN 79822-46-1) in THF (60 mL) cooled to 5° C. was added dropwise a solution of BH3-Me₂S (2.0M in THF, 16.60 mL, 33.10 mmol). The reaction was allowed to stir for 24 h at RT then cooled to −50° C. and quenched by dropwise addition of MeOH (20 mL). The reaction mixture was warmed to RT and concentrated in vacuo. The residue was taken up in MeOH (3×20 mL) and concentrated in vacuo. The final residue partitioned between EtOAc and sat'd. aq. NaHCO₃. The organic layer was washed with water, brine, dried (MgSO₄), filtered and concentrated to afford 2.64 g (95%) of (4-tert-Butyl-3-methoxy-phenyl)-methanol (345) as a colorless oil.

step b—To a solution of 345 (2.08 g, 10.70 mmol) in CCl₄ (75 mL) was added NBS (2.10 g, 11.80 mmol). The reaction was stirred for 15 min then diluted with a cold 10% aqueous NaHSO₃. The reaction mixture was extracted with DCM. The organic extract was washed with brine, dried (MgSO₄), filtered and concentrated. The residue was taken up in hexanes (80 mL) and then concentrated to afford 2.9 g (100%) of 344a as a white solid.

step 1—A mixture of 344a (7 g, 25.6 mmol) and MnO₂ (30 g) in DCM (50 mL) was stirred overnight at RT. The reaction mixture was diluted with DCM and filtered through CELITE. The solvent was evaporated to afford 6 g (85%) of 344b as a colorless oil.

step 2—A mixture of 344b (6 g, 22.14 mmol) and MCPBA (10 g) in DCM (50 mL) was heated overnight at 40° C. The reaction mixture was diluted with a 1:1 solution of hexanes/EtOAc and washed with sat'd. aq. Na₂S₂O₃ and sat'd. aq. NaHCO₃. The organic phase was separated, dried (NgSO₄), filtered and concentrated to afford 4.7 g (82%) of 344c as a brown oil.

step 3—A mixture of 344c (825 mg, 3.18 mmol) and NBS (680 mg, 3.82 mmol) in DMF (10 mL) was stirred overnight at RT. The reaction mixture was diluted with hexanes. The organic layer was washed with 1N NaHSO₄, dried (MgSO₄), filtered and concentrated to afford 955 mg (89%) of 346 as a brown oil.

step 4—A sealed tube containing 346 (880 mg, 2.6 mmol), 141 (366 mg, 2.86 mmol), Pd(PPh₃)₄ (150 mg, 0.129 mmol), and Na₂CO₃ (828 mg, 7.81 mmol) in a mixture of MeOH (1 mL) and DCM (5 mL) was irradiated in a microwave reactor at 115° C. for 90 min. The organic volatiles were removed under reduced pressure and the residue was partitioned between EtOAc and water. The organic layer was washed with brine, dried (MgSO₄), filtered and concentrated. The crude residue was purified by SiO₂ chromatography eluting with an EtOAc/hexane gradient to afford 235 mg (20%) of 348 as a brown semisolid.

step 6—A sealed tube containing 348 (230 mg, 0.523 mmol), 242 (180 mg, 0.746 mmol), Pd(PPh₃)₄ (31 mg, 0.026 mmol), and Na₂CO₃ (166 mg, 1.56 mmol) in a mixture of MeOH (4 mL) and DCM (1 mL) was irradiated in a microwave reactor at 115° C. for 90 min. The organic volatiles were removed under reduced pressure and the residue was partitioned between EtOAc and water. The organic layer was washed with brine, dried (MgSO₄), filtered and concentrated. The crude residue was purified by SiO₂ chromatography eluting with an EtOAc/hexane gradient to afford 80 mg (27%) of 350 as a brown oil.

step 7—A Parr bottle containing a mixture of 350 (40 mg, 0.072 mmol) and Pd(OH)₂ (20% wt. on carbon, 100 mg) in MeOH (15 mL) at RT was shaken under 60 psi atmosphere of H₂ for 5 h. The catalyst was filtered and the filtrate was concentrated. The crude residue was purified on a preparative SiO₂ TLC plate developed with hexanes/EtOAc to afford 6 mg (9%) of I-128 as a yellow oil: MS m/z (ES)(M+H)=471.

Example 74

N-[4-{(E)-2-[3-tert-Butyl-5-(5-fluoro-2-oxo-1,2-dihydro-pyridin-3-yl)-2-methoxy-phenyl]-vinyl}-3-(3-hydroxy-3-methyl-butoxymethyl)-phenyl]-methanesulfonamide (I-219)

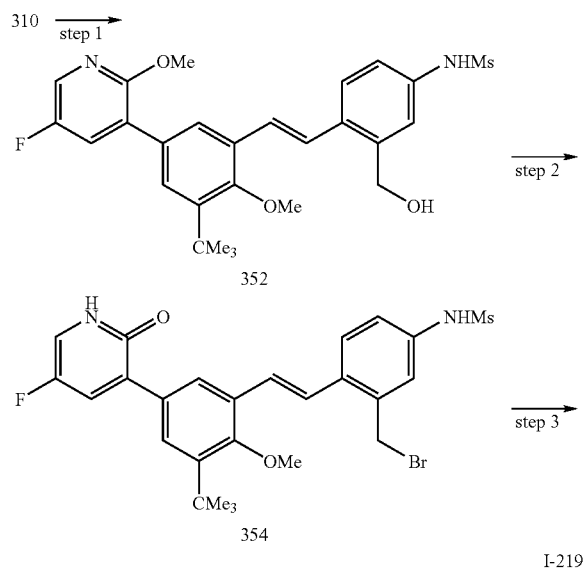

step 1—A sealed tube containing 310 (660 mg, 1.41 mmol), 107 (313 mg, 1.83 mmol Pd(PPh₃)₄ (163 mg, 0.141 mmol), and Na₂CO₃ (448 mg, 4.23 mmol) in a mixture of MeOH (2 mL) and DCM (0.5 mL) was irradiated in a microwave reactor at 115° C. for 1 h. The organic volatiles were removed under reduced pressure and the residue was partitioned between EtOAc and water. The organic layer was washed with brine, dried (MgSO₄), filtered and concentrated. The crude residue was purified by SiO₂ chromatography eluting with an EtOAc/hexane gradient to afford 350 mg (48%) of 352 as a white solid.

step 2—A mixture of 352 (300 mg, 0.583 mmol), 48% aqueous HBr (2 mL) and HOAc (20 mL) in a sealed tube was heated overnight at 65° C. The reaction mixture was carefully poured into a cold sat'd. aq. NaHCO₃, and then extracted with EtOAc. The organic layer was washed with brine, dried (MgSO₄), filtered and concentrated to afford 325 mg (99%) of 354 as a yellow foam.

step 3—THF (8 mL) was added to a mixture of 3-methyl-butane-1,3-diol (240 µL, 2.31 mmol) and NaH (71 mg, 1.85 mmol 60% in mineral oil). The reaction mixture was carefully stirred at RT for 15 min. A solution of 354 (130 mg, 0.23 mmol) in THF was then added. The reaction mixture was stirred at RT overnight and then poured into water, and then extracted with EtOAc. The organic layer was dried (MgSO₄), filtered and concentrated. The crude residue was purified on a preparative SiO₂ TLC plate developed with DCM/MeOH to afford 45 mg (40%) of I-219 as a white solid: MS m/z (ES) (M+H)=587.

Example 75

N-[4-{(E)-2-[3-tert-Butyl-5-(5-fluoro-2-oxo-1,2-dihydro-pyridin-3-yl)-2-methoxy-phenyl]-vinyl}-3-(2-oxo-oxazolidin-3-ylmethyl)-phenyl]-methanesulfonamide (I-220)

THF (1 mL) was added to a mixture of oxazolidinone (91 mg, 1.05 mmol) and NaH (33 mg, 0.86 mmol, 60% in mineral oil). The reaction mixture was carefully stirred at RT for 15 min. A solution of 354 (98 mg, 0.174 mmol) in THF (2 mL) was then added. The reaction mixture was stirred at RT for 2 days and then poured into water, and extracted with EtOAc. The organic layer was washed with sat'd. aq. NaHCO₃, dried (MgSO₄), filtered and concentrated. The crude residue was purified on a preparative SiO₂ TLC plate developed with EtOAc to afford 33 mg (33%) of I-220 as a white solid: MS m/z (ES): 570 (M+H)⁺.

Example 76

N-(4-{(E)-2-[3-tert-Butyl-5-(5-fluoro-2-oxo-1,2-dihydro-pyridin-3-yl)-2-methoxy-phenyl]-vinyl}-3-dimethylaminomethyl-phenyl)-methanesulfonamide (I-221)

A 2M solution of NHMe₂ in MeOH (3 mL) was added to a solution of 354 (50 mg, 0.088 mmol) in THF (3 mL) at RT. The reaction mixture was stirred at RT overnight. The reaction mixture was diluted with EtOAc. The organic layer was washed with sat'd. aq.NaHCO₃, dried (MgSO₄), filtered and concentrated. The crude residue was purified on a preparative SiO₂ TLC plate developed with 9:1 DCM/MeOH to afford 32 mg (69%) of I-221 as a white solid: MS m/z (ES): 528 (M+H)⁺.

N-(4-{(E)-2-[3-tert-Butyl-5-(5-fluoro-2-oxo-1,2-dihydro-pyridin-3-yl)-2-methoxy-phenyl]-vinyl}-3-morpholin-4-yl-methyl-phenyl)-methanesulfonamide (I-222) was prepared analogously except dimethylamine was replaced with morpholine. The crude residue was purified on a preparative SiO₂ TLC plate developed with 9:1 DCM/MeOH to afford 35 mg (70%) of I-222 as a white solid: MS m/z (ES) (M+H)=570.

Example 77

N-[4-((E)-2-{3-tert-Butyl-5-[6-(1-hydroxy-ethyl)-2-oxo-1,2-dihydro-pyridin-3-yl]-2-methoxy-phenyl}-vinyl)-phenyl]-methanesulfonamide (I-223), N-(4-{(E)-2-[3-tert-Butyl-5-(6-cyanomethyl-2-oxo-1,2-dihydro-pyridin-3-yl)-2-methoxy-phenyl]-vinyl}-phenyl)-methanesulfonamide (I-224) and N-[4-((E)-2-{3-tert-Butyl-5-[6-(2-hydroxy-ethoxymethyl)-2-oxo-1,2-dihydro-pyridin-3-yl]-2-methoxy-phenyl}-vinyl)-phenyl]-methanesulfonamide (I-225)

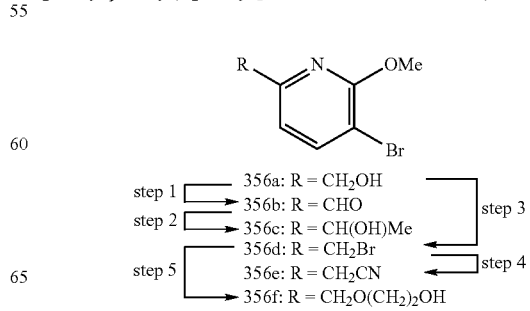

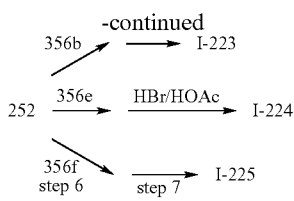

(5-Bromo-6-methoxy-pyridin-2-yl)-methanol (356a)

step a—To a solution of 3-bromo-2-chloro-6-methyl-pyridine (2.0 g, 0.687 mmol) in CHCl₃ was added MCPBA (3.3 g, 19.1 mmol) and the resulting solution was heated at 50° C. overnight. The resulted solution was cooled and partitioned between DCM and sat'd. aq. NaHCO₃. The organic layer was dried (Na₂SO₄), filtered and concentrated in vacuo. The crude product was purified by SiO₂ chromatography eluting with an EtOAc/hexane gradient (30 to 80% EtOAc) to afford 1.88 g (87%) of 3-bromo-2-chloro-6-methyl-pyridine 1-oxide (357a) as a white solid.

step b—A solution of 357a (0.5 g) and 0.5 M NaOMe/MeOH (4.9 mL) was stirred at RT overnight. The reaction mixture was concentrated in vacuo and the residue loaded on a SiO₂ column and eluted with 5% MeOH/DCM to afford 3-bromo-2-methoxy-6-methyl-pyridine 1-oxide (357b).

step c—A solution of 357b (0.47 g) and acetic anhydride (4.0 mL) was heated at 120° C. for 2 h, The reaction mixture was concentrated in vacuo and purified on a SiO₂ column eluting with 5% EtOAc/hexane to afford methyl 5-bromo-6-methoxy-pyridin-2-yl-acetate (357c).

step d—A solution of 357c (0.060 g), 5% aq. NaHCO₃ (2 mL) and MeOH (2 mL) was heated at reflux for 2 h. The reaction mixture was partitioned between H₂O and EtOAc and the combined EtOAc extracts were dried, filtered and evaporated in vacuo. The crude product was purified by SiO₂ chromatography eluting with 25% EtOAc/hexane to afford 356a.

step 1—Dess-Martin periodane (265 mg, 0.625 mmol) was added to a solution of 356a (68 mg, 0.313 mmol) in DCM (1.5 mL) at RT and stirred at RT for 4 h. The reaction mixture was diluted with ether and treated with 1:1 solution of sat'd. aq. NaHCO₃ and 0.5M aq. Na₂S₂O₃. The organic phase was separated, dried (MgSO₄), filtered and concentrated to afford 60 mg (89%) of 356b as white solid.

step 2—A 3.2M solution of MeMgBr (0.17 mL, 0.54 mmol) in THF was added to a solution of 356b (65 mg, 0.302 mmol) in THF (3 mL) cooled to 0° C. The reaction mixture was stirred at RT for 3 h and then diluted with EtOAc and treated with water. The organic phase was separated, dried (MgSO₄), filtered and concentrated to afford 55 mg (79%) of 356c as a white solid.

step 6—A sealed tube containing 356c (55 mg, 0.239 mmol), 252 (170 mg, 0.35 mmol), Pd(PPh₃)₄ (28 mg, 0.024 mmol), and Na₂CO₃ (80 mg, 0.75 mmol) in a mixture of MeOH (1.5 mL) and toluene (0.3 mL) was irradiated in a microwave reactor at 115° C. for 1 h. The organic volatiles were removed under reduced pressure and the residue was partitioned between EtOAc and water. The organic layer was washed with brine, dried (MgSO₄), filtered and concentrated. The crude residue was purified by SiO₂ chromatography eluting with an EtOAc/hexane gradient to afford 60 mg (49%) of N-[4-((E)-2-{3-tert-Butyl-5-[6-(1-hydroxy-ethyl)-2-methoxy-pyridin-3-yl]-2-methoxy-phenyl}-vinyl)-phenyl]-methanesulfonamide (358).

step 7—Cleavage of the methyl ether was out in accord with the procedure in step 3 of Example 1. The crude residue was purified on a preparative SiO₂ TLC plate developed with EtOAc to afford I-223 as a white solid: MS m/z (ES): 497 (M+H)⁺.

step 3—A mixture of 356b (300 mg, 1.38 mmol), CBr₄ (686 mg, 2.07 mmol) and PPh₃ (5.43 mg, 2.07 mmol) in DCM (2 mL) was stirred at RT for 3 h. The reaction mixture was concentrated and then purified by SiO₂ chromatography eluting with an EtOAc/hexane gradient (0 to 10% EtOAc) to afford 160 mg (41%) of 356d as a colorless oil.

step 4—Potassium cyanide (10 mg, 0.154 mmol) was added to a solution of 356d (29 mg, 0.104 mmol) in EtOH (0.9 mL) and H₂O (0.1 mL). The reaction mixture was stirred at RT overnight and then partitioned between EtOAc and water. The organic layer was separated, dried (MgSO₄), filtered and concentrated. The crude residue was purified by SiO₂ chromatography eluting with a 5:95 EtOAc/hexane mixture to afford 20 mg (57%) of 356e as a colorless oil.

Conversion of 356e to I-224 was carried out in accord with the procedures described in steps 6 and 7 above.

step 5—Ethylene glycol (0.177 mL, 3.17 mmol) was added to a tube containing a solution of 356d (80 mg, 0.286 mmol) in THF (2 mL) at RT. A catalytic amount of Bu₄N⁺I⁻ was added. The tube was sealed and the stirred solution heated at 65° C. overnight and then cooled and partitioned between EtOAc and water. The organic layer was separated, dried (MgSO₄), filtered and concentrated to afford 120 mg of 356f.

Conversion of 356f to I-225 was carried out in accord with the procedures described in steps 6 and 7 above.

Example 78

N-(4-{(E)-2-[3-tert-Butyl-2-methoxy-5-(5-methyl-2-oxo-1,2-dihydro-pyridin-3-yl)-phenyl]-vinyl}-phenyl)-methanesulfonamide (I-226)

A sealed tube containing 3-bromo-5-methyl-1H-pyridin-2-one (20 mg, 0.106 mmol, CASRN 17282-02-9), 252(51.6 mg), Pd(PPh₃)₄ (12.7 mg, 0.011 mmol), and Na₂CO₃ (35 mg, 0.330 mmol) in a mixture of MeOH (0.9 mL) and toluene (0.3 mL) was irradiated in a microwave reactor at 120° C. for 35 min. The organic volatiles were removed under reduced pressure and the residue was partitioned between EtOAc and water. The organic layer was washed with brine, dried (MgSO₄), filtered and concentrated. The crude residue was purified on a preparative SiO₂ TLC developed with 95:5 DCM/MeOH to afford 18 mg (36%) of I-226 as a white powder: MS m/z (ES) (M+H)=467.

Example 79

N-[4-{(E)-2-[3-tert-Butyl-5-(5-fluoro-2-oxo-1,2-dihydro-pyridin-3-yl)-2-methoxy-phenyl]-vinyl}-3-(2-methoxy-ethyl)-phenyl]-methanesulfonamide (I-227)

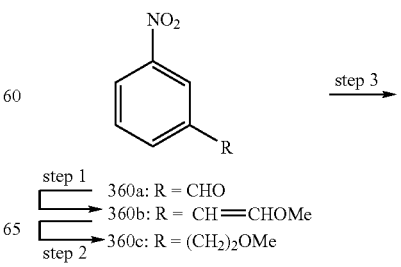

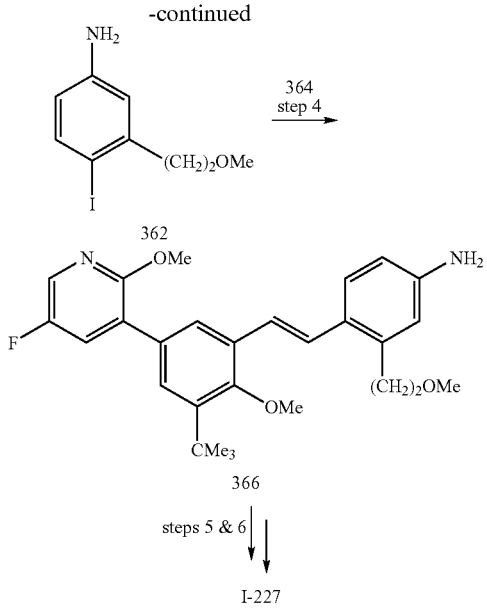

3-[3-tert-Butyl-4-methoxy-5-((E)-2-tributylstannanyl-vinyl)-phenyl]-5-fluoro-2-methoxy-pyridine (364) was prepared in accord with the procedures described steps 2 to 4 of Example 50 except in step 2, the cross coupling was carried out with D-2 107.

step 1—Methoxymethyl phosphonium chloride (10.3 g, 30 mmol) was suspended in anhydrous THF (60 mL) and the suspension was cooled to 0° C. Potassium tert-butoxide (2.27 g, 20 mmol) was added forming a red mixture. After 15 min at 0° C., a solution of 3-nitrobenzaldehyde in 60 mL of THF was added slowly via cannula. After 15 min the reaction mixture was warmed to RT and stirred overnight. The reaction mixture was quenched by addition of H$_2$O (150 mL) and thrice extracted with EtOAc (125 mL). The combined extracts were washed with brine (150 mL), dried (Na$_2$SO$_4$), filtered, and concentrated. The crude product was purified by SiO$_2$ chromatography eluting with an EtOAc/hexane gradient (5 to 10% EtOAc) to afford 1.28 g (71%) of 360b as a yellow oil, which was a ca. 1:1 mixture of E and Z isomers.

step 2—A mixture of 360b (1.02 g, 5.84 mmol) and 10% Pd/C in 85 mL of MeOH was hydrogenated at 50 psi in a Parr apparatus. After 3 h, mixture was filtered through CELITE and the filter bed washed with MeOH. The filtrate was concentrated to afford 0.762 g (90%) of 360c as a yellow-orange liquid, which was used in the next step without further purification.

step 3—To a solution of 360c (549 mg, 3.63 mmol) in DCM (34 mL) and MeOH (14 mL) at RT was added benzyltrimethylammonium dichloroiodate (1.26 g, 3.63 mmol) and CaCO$_3$ (475 mg). After 45 min, the reaction mixture was quenched with aq. NaHSO$_3$ (100 mL) and thrice extracted with diethyl ether (60 mL). The combined extracts were dried (MgSO$_4$), filtered, and concentrated. The crude product was purified by SiO$_2$ chromatography eluting with an EtOAc/hexane gradient (10 to 40% EtOAc) to afford 0.704 g (70%) of 362 and (contaminated with unreacted 360c) as a brown oily liquid.

step 4—In a 25 mL 2-neck round-bottom flask was charged with Pd$_2$(dba)$_3$ (21.4 mg, 0.022 mmol), tris-(2-furyl)phosphine (21.9 mg, 0.089 mmol) and anhydrous DMF (3 mL) and stirred at RT for 15 minutes under argon. To this green solution was added via cannula a solution of 364 (605 mg, 1.01 mmol) and 362 (445 mg, 1.2 mmol) in anhydrous DMF (6 mL). Lithium chloride (88.4 mg, 2.03 mmol) was then added under argon. The brown reaction mixture was then heated at 110° C. for 18 h. After cooling to RT, the reaction mixture was poured into 100 mL of water and thrice extracted with EtOAc (70 mL). The combined extracts were washed with H$_2$O (120 mL) and 120 mL of brine, dried (Na$_2$SO$_4$), filtered, and concentrated. The crude product was purified by SiO$_2$ chromatography eluting with an EtOAc/hexane gradient (25 to 50% EtOAc) to afford 300 mg (65%) of 366 as a yellow solid (85% purity by NMR) and which was without further purification.

Conversion of 366 to the corresponding methanesulfonamide was carried out in accord with the procedure described in step 4 of Example 3. Cleavage of the methyl ether to produce the pyridone was carried out in accord with the procedure in step 3 of Example 1 to afford I-227: MS (ESI) found (M+H)=529.

Example 80

Ethanesulfonic acid (4-{(E)-2-[3-tert-butyl-5-(5-fluoro-2-oxo-1,2-dihydro-pyridin-3-yl)-2-methoxy-phenyl]-vinyl}-phenyl)-amide (I-228)

step 1—A solution of 202b (535 mg, 1.49 mmol) in pyridine (14 mL) was cooled to 0° C. Ethane sulfonyl chloride (0.20 mL, 2.11 mmol) was then added and reaction mixture stirred at 0° C. for 30 min and then at RT overnight. The reaction mixture was quenched with 1N HCl (125 mL) and thrice extracted with EtOAc (70 mL). The combined extracts were washed with sat'd. aq. CuSO$_4$ (50 mL) and brine, dried (Na$_2$SO$_4$), filtered and concentrated to afford 645 g (96%) of ethanesulfonic acid {4-[(E)-2-(5-bromo-3-tert-butyl-2-methoxy-phenyl)-vinyl]-phenyl}-amide (368) as a light brown solid which was used in next step without further purification.

Cross-coupling of 368 and 107 was carried out in accord with the procedure in step 4 of Example 37. Cleavage of the methyl ether to produce the pyridone was carried out in accord with the procedure in step 3 of Example 1 to afford I-228 as a light yellow solid: MS (ESI) (M+H)=485.

Example 81

2,2,2-Trifluoro-ethanesulfonic acid (6-{(E)-2-[3-tert-butyl-5-(5-fluoro-2-oxo-1,2-dihydro-pyridin-3-yl)-2-methoxy-phenyl]-vinyl}-pyridin-3-yl)-amide (I-229)

step 1—A solution of Pd$_2$(dba)$_3$ (27.8 mg, 0.030 mmol) and tris-(2-furyl)phosphine (28.0 mg, 0.121 mmol) in anhydrous DMF (3 mL) was stirred at RT for 15 min under argon. To the resulting solution was added via cannula a solution of 364 (672 mg, 1.11 mmol) and 2-iodo-5-aminopyridine (294 mg, 1.33 mmol) in anhydrous DMF (6 mL) at RT. Lithium chloride (97.1 mg, 2.23 mmol) was then added under argon. The reaction mixture was heated at 110° C. for 18 h. After cooling to RT, the reaction mixture was poured into H$_2$O (90 mL) and thrice extracted with EtOAc (60 mL). The combined extracts were washed with H$_2$O (130 mL) and brine (130 mL), dried (Na$_2$SO$_4$), filtered and concentrated. The crude product was purified by SiO$_2$ chromatography eluting with an EtOAc/hexane gradient (37 to 100% EtOAc) to afford 0.394 g (85%) of 6-{(E)-2-[3-tert-butyl-5-(5-fluoro-2-methoxy-pyridin-3-yl)-2-methoxy-phenyl]-vinyl}-pyridin-3-ylamine (370).

step 2—To a solution of 370 (90.0 mg, 0.221 mmol) in pyridine (3 mL) cooled to 0° C. was added 2,2,2 trifluoroethane sulfonyl chloride (40 μL, 0.364 mmol). After 20 min the reaction mixture was warmed to RT and stirred overnight. The reaction mixture was quenched with 30 mL of 1N HCl and thrice extracted with EtOAc (20 mL). The combined extracts were washed with sat'd. aq. CuSO$_4$ (3×30 mL) and brine, dried (Na$_2$SO$_4$), filtered, and concentrated. The crude product was purified by SiO$_2$ chromatography eluting with an EtOAc/hexane gradient (25 to 35% EtOAc) to afford 88.1 mg (72%) of 2,2,2-trifluoro-ethanesulfonic acid (6-{(E)-2-[3-tert-butyl-5-(5-fluoro-2-methoxy-pyridin-3-yl)-2-methoxy-phenyl]-vinyl}-pyridin-3-yl)-amide (372).

Cleavage of the methyl ether (step 3) to produce the pyridone was carried out in accord with the procedure in step 3 of Example 1 to afford I-229: MS (ESI) found (M+H)=540.

Example 82

3-Pyrrolidin-1-yl-propane-1-sulfonic acid (4-{(E)-2-[3-tert-butyl-5-(5-fluoro-2-oxo-1,2-dihydro-pyridin-3-yl)-2-methoxy-phenyl]-vinyl}-phenyl)-amide (I-230)

dried (Na$_2$SO$_4$), filtered, and concentrated. The desired compound 374 was recovered as brown solid (1.05 g, 66%) in an inseparable mixture with unreacted starting material and was used without further purification.

step 2—A solution of 374 (474 mg, 0.948 mmol) and pyrrolidine (5 mL, 2.37 g, 33.3 mmol) was heated at 80° C. overnight. After cooling to RT the reaction mixture was poured in 80 mL of water and thrice extracted with EtOAc (60 mL). The combined extracts were twice washed with water (100 mL), brine (100 mL), dried (Na$_2$SO$_4$), filtered, and concentrated. The crude product was purified by SiO$_2$ chromatography eluting with a MeOH/DCM gradient (4 to 17% MeOH) to afford 0.227 g (45%) of 376 as a white solid.

step 3—A 20 mL microwave vial was charged with 376 (214 mg, 0.40 mmol), 107 (87.0 mg, 0.509 mmol), Na$_2$CO$_3$ (115 mg, 1.13 mmol), and Pd(PPh$_3$)$_4$ (39.1 mg, 0.034 mmol) in MeOH (4 mL) and DCM (1 mL). The tube was sealed and reaction mixture was irradiated in a microwave synthesizer at 115° C. for 60 min. After cooling to RT, the reaction mixture was filtered and washed with EtOAc. The filtrate was poured into sat'd. aq. NaHCO$_3$ and extracted with EtOAc. The combined extracts were washed with brine, dried (Na$_2$SO$_4$), filtered, and concentrated. The crude product was purified by SiO$_2$ chromatography eluting with a MeOH/DCM gradient (4 to 10% MeOH) to afford 0.135 g (58%) of 378.

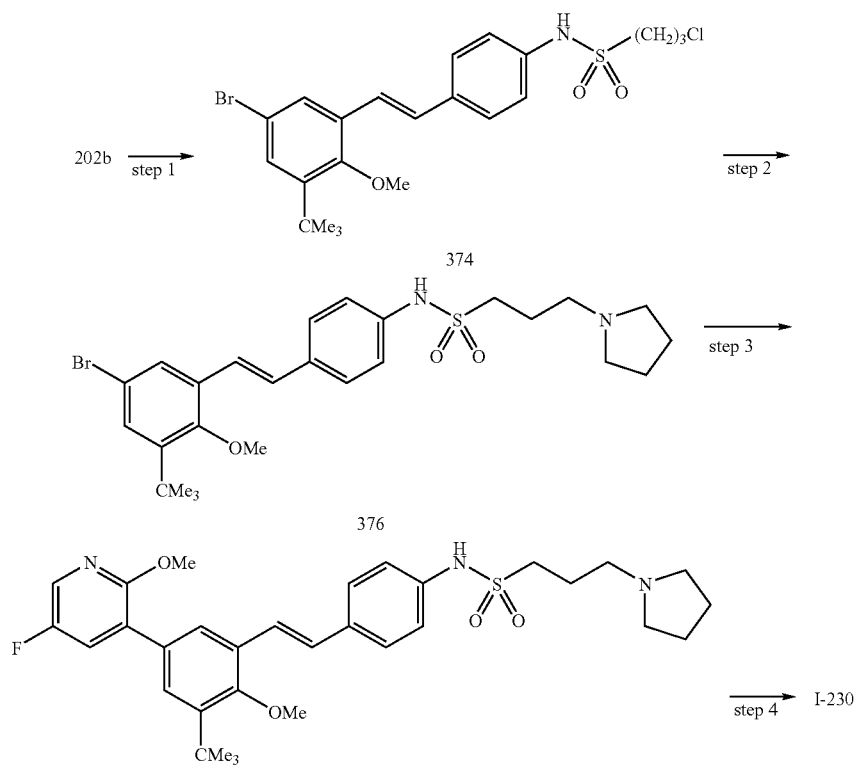

step 1—To a solution of 202b (1.14 g, 3.17 mmol) in pyridine (40 mL) cooled to 0° C. was added 3-chloropropane sulfonyl chloride (0.46 mL, 3.79 mmol). After 20 min the reaction mixture was warmed RT and stirred overnight. The reaction mixture was quenched with 1N HCl (120 mL) and thrice extracted with EtOAc (80 mL). The combined extracts were thrice washed with sat'd. aq. CuSO$_4$ (60 mL) and brine, step 4—To a solution of 378 (85.5 mg, 0.147 mmol) in HOAc (2 mL) in a 5 mL microwave vial was added dropwise 48% HBr (42 μL). The tube was sealed and reaction mixture was heated at 60° C. overnight. After cooling to RT, the reaction mixture was quenched by dropwise addition of acid mixture to ice cold sat'd. aq. NaHCO$_3$. The resulting mixture was thrice extracted with EtOAc and the combined extracts were washed with sat'd. aq. NaHCO$_3$, brine, dried (Na$_2$SO$_4$), filtered, and concentrated. The crude product was purified by SiO$_2$ chromatography eluting with a MeOH/DCM gradient (2 to 10% MeOH) to afford I-230 as a yellow solid: MS (ESI) (M+H)=568.

3-Morpholin-4-yl-propane-1-sulfonic acid (4-{(E)-2-[3-tert-butyl-5-(5-fluoro-2-oxo-1,2-dihydro-pyridin-3-yl)-2-methoxy-phenyl]-vinyl}-phenyl)-amide (I-231) was prepared analogously except in step 2, pyrrolidine was replace by morpholine. I-231 was recovered as a yellow solid: MS (ESI) (M+H)=584.

3-Pyrrolidin-1-yl-propane-1-sulfonic acid (4-{(E)-2-[3-tert-butyl-2-methoxy-5-(2-oxo-1,2-dihydro-pyridin-3-yl)-phenyl]-vinyl}-phenyl)-amide (I-234) was made analogously except in step 3, 107 was replaced with 37. I-234 was recovered as a light yellow solid: MS (ESI) (M+H)=550.

3-Pyrrolidin-1-yl-propane-1-sulfonic acid (4-{(E)-2-[3-tert-butyl-2-methoxy-5-(6-methyl-2-oxo-1,2-dihydro-pyridin-3-yl)-phenyl]-vinyl}-phenyl)-amide (1-235) was made analogously except in step 3, 107 was replaced with 2-methoxy-6-methyl-pyridin-3-yl boronic acid. I-234 was recovered as a light yellow solid: MS (ESI) (M+H)=564.

Example 83

2-Pyrrolidin-1-yl-ethanesulfonic acid (4-{(E)-2-[3-tert-butyl-5-(5-fluoro-2-oxo-1,2-dihydro-pyridin-3-yl)-2-methoxy-phenyl]-vinyl}-phenyl)-amide (I-232)

step 1—To a solution of 202b (552.4 mg, 1.54 mmol) in pyridine (14 mL) at 0° C. was added 2-chloroethane sulfonyl chloride (0.25 mL, 2.33 mmol). After 30 min the reaction mixture was warmed to RT and stirred overnight. The reaction mixture was quenched with 1N HCl and thrice extracted with EtOAc. The combined extracts were, thrice washed with sat'd. aq. CuSO$_4$ then brine, dried (Na$_2$SO$_4$), filtered, and concentrated. The vinyl sulfone 380 was recovered as light brown solid (570 mg, 83%) and used in the next step without further purification.

step 2—To a solution of 380 (570 mg, 1.27 mmol) in anhydrous THF (17 mL) was added pyrrolidine (0.17 mL, 2.05 mmol). The reaction mixture stirred at RT for 24 h and then poured into H$_2$O (35 mL) and thrice extracted with EtOAc. The combined extracts were washed with H$_2$O (100 mL) then brine (100 mL), dried (Na$_2$SO$_4$), filtered, and concentrated. The product 382 was recovered as a light brown solid (530 mg, 80%).

Palladium-catalyzed cross coupling with 107 (step 3) and cleavage of the methyl ether (step 4) was carried out in accord with steps 3 and 4 of example 82 to afford I-232 as a light yellow solid: MS (ESI) (M+H)=554.

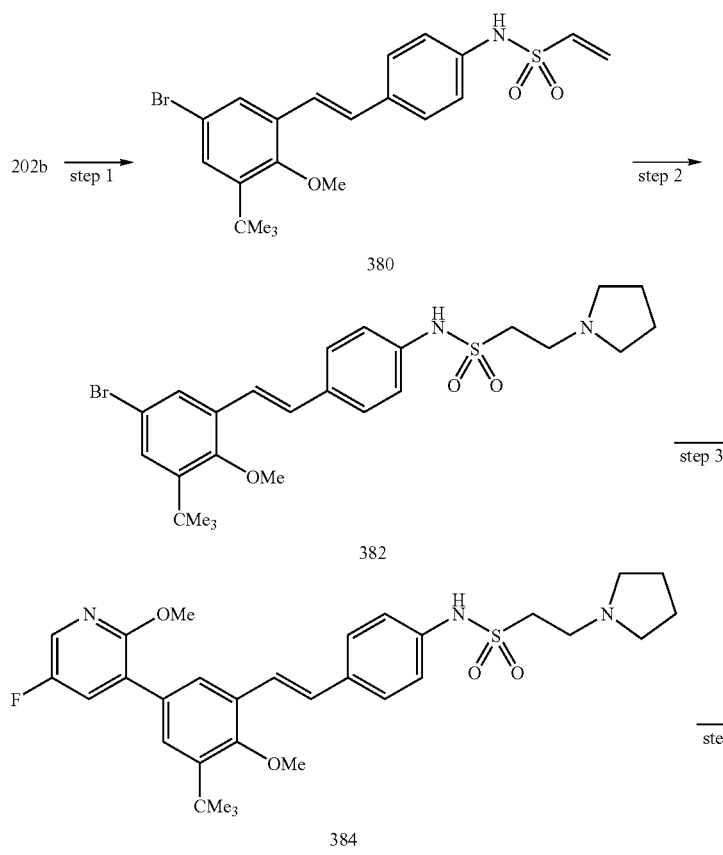

Example 84

N-(4-{(E)-2-[3-tert-Butyl-5-(5-fluoro-2-oxo-1,2-dihydro-pyridin-3-yl)-2-methoxy-phenyl]-vinyl}-3-fluoro-phenyl)-methanesulfonamide (I-236)

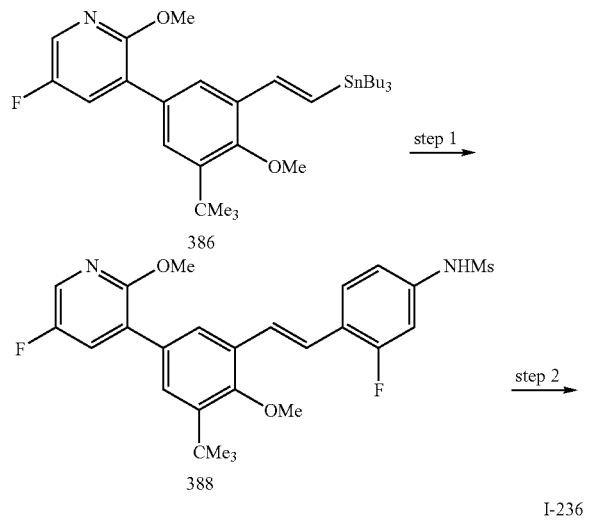

The palladium-catalyzed cross-coupling of D-2 and 107 was carried out in accord with the procedure in step 4 of Example 38 to afford 3-tert-butyl-5-(5-fluoro-2-methoxy-pyridin-3-yl)-2-methoxy-benzaldehyde (390). Conversion of 390 to 386 was carried out in accord with the procedures in steps 1 and 2 of Example 42.

step 1—A 25 mL three-neck flask was charged Pd$_2$(dba)$_3$ (18.1 mg, 0.020 mmol), tris-(2-furyl)phosphine (19.1 mg, 0.082 mmol) and anhydrous DMF (2.5 mL) and stirred at RT under Ar. To the resulting solution was added via cannula a solution of 386 (390.4 mg, 0.646 mmol) and N-(4-bromo-3-fluoro-phenyl)-methanesulfonamide (196 mg, 0.735 mmol) in DMF (4.5 mL) followed by LiCl (52.2 mg, 1.20 mmol). The reaction mixture was heated to 110° C. for 18 h. The reaction mixture was cooled and poured into H$_2$O (100 mL) and thrice extracted with EtOAc (60 mL). The combined extracts were washed with H$_2$O (125 mL) and brine, dried (Na$_2$SO$_4$), filtered and concentrated. The crude product was purified by SiO$_2$ chromatography eluting with a MeOH/DCM gradient (1 to 5% MeOH) to afford 132 mg (42%) of 388.

step 2—Cleavage of the methyl ether was carried out in accord with the procedure in step 3 of Example 1. The crude product was purified by SiO$_2$ chromatography eluting with a MeOH/DCM gradient (2 to 10% MeOH) to afford I-236: MS (WSI) (M+H)=489.

Example 85

N-[3,3-Dimethyl-7-(2-oxo-1,2-dihydro-pyridin-3-yl)-2,3-dihydro-benzofuran-5-yl]-4-methanesulfonylamino-benzamide (II-4)

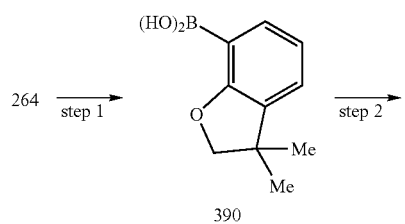

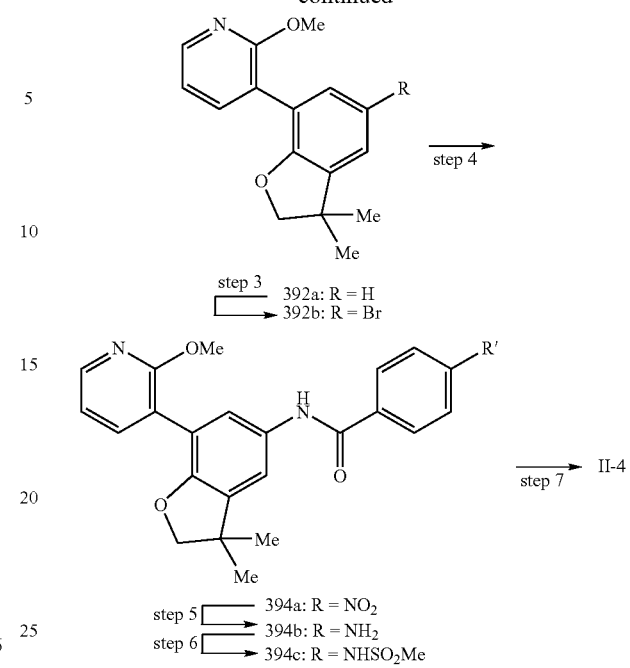

step 1—To a solution of tetramethylethylenediamine (908 mg, 7.81 mmol, redistilled) in dry THF (5 mL) under nitrogen was cooled in an ice bath was added n-BuLi (3.1 mL, 7.75 mmol, 2.5 M solution in hexane). The mixture was stirred for 5 min. and added a solution of 264 (775 mg, 5.22 mmol) in dry THF (3 mL). After stirring at 5° C. for 30 min the ice bath was removed and the reaction stirred at RT for 15 h. The solution was cooled in an ice bath and triisopropyl borate (2.4 mL, 1.96 gm, 10.4 mmol) was added and solution removed from the ice bath. The mixture was stirred at RT for 2 h then concentrated and 75 mL of 1M NaOH solution was added. The solution was thrice extracted with Et$_2$O (30 mL) and the aqueous basic layer was cooled in an ice bath and acidified with concentrated HCl. The resulting precipitate was twice extracted with Et$_2$O (50 mL). The combined extracts was washed with brine (25 mL), dried (MgSO$_4$), filtered and evaporated to afford 603 mg (60%) of 390 as a light brown solid.

step 2—A Schlenk flask was charged with a solution of 37 (260 mg, 1.38 mmol) and dioxane (6 mL) 390 (297 mg, 1.26 mmol), a solution of Na$_2$CO$_3$ (483 mg, 4.56 mmol) and H$_2$O (5 mL), and Pd(PPh$_3$)$_4$ (48 mg, 0.041 mmol). The flask was evacuated and backfilled with argon and sealed. The mixture was heated to 100° C. under argon for 14 h. The mixture was poured into EtOAc (40 m), washed with H$_2$O (30 mL), brine (30 mL), dried (MgSO$_4$), filtered and evaporated. The residue was purified by SiO$_2$ chromatography eluting with an EtOAc/hexane gradient (0 to 9% EtOAc) to afford 304 mg (86%) of 392a as a colorless oil: MS (M+H)=256.

step 3—To a solution of 392a (554 mg, 2.16 mmol) and DCM (10 mL) was added dropwise bromine (2.71 mL, 2.71 mmol, 1M solution in DCM) over 5 min. After 5 h the reaction was diluted with DCM (25 mL), washed sequentially with 10% sodium thiosulfate (20 mL), brine (20 mL), dried (MgSO$_4$), filtered and evaporated. The residue was purified by SiO$_2$ chromatography eluting with an EtOAc/hexane gradient (0 to 8% EtOAc) to afford 614 mg (84%) of 392b as a white solid: MS (M+H)=334.

step 4—A 10 mL screw cap tube was charged with 392b (400 mg, 1.19 mmol), 4-nitrobenzamide (248 mg, 1.49 mmol), CuI (23 mg, 0.12 mmol), K₂CO₃ (333 mg, 2.41 mmol), 1,2-trans diamino-cyclohexane (15 mg, 0.13 mmol) and dioxane (1 mL). The tube was flushed with argon, sealed, and heated to 125° C. for 18 h. The solution was cooled to RT and another aliquot of CuI (23 mg) and 1,2-trans diamino-cyclohexane (15 mg) was added and heated to 125° C. for 16 h. The reaction mixture was cooled to RT and H₂O (20 mL) was added and the solution was twice extracted with EtOAc (40 mL). The combined extracts were washed with brine, dried (MgSO₄), filtered and concentrated. The residue was purified by SiO₂ chromatography eluting with an EtOAc/DCM gradient (0 to 21% EtOAc) to afford 444 mg (88%) of 394a as a yellow solid: MS (M+H)=420.

step 5—A mixture of 394a (150 mg, 0.357 mmol), EtOAc (15 mL) and 15 mg of 10% Pd/C was stirred under an atmosphere of hydrogen gas for 4 h. The catalyst was filtered through a pad of CELITE and the filtrate evaporated to dryness to afford 137 mg of 394b as a white solid: MS (M+H)=390.

step 6—To a solution of 394b (133 mg, 0.341 mmol) and pyridine (2 mL) under nitrogen was cooled in an ice bath was added methanesulfonyl chloride (0.033 mL, 47 mg, 0.41 mmol). The solution was stirred 5° C. for 3 h., then quenched with H₂O (5 mL). The solution was stirred for 30 min. then ice (25 g) was added and acidified with concentrated HCl. The solution was saturated with solid NaCl and extracted with EtOAc (40 mL), washed with brine (20 mL), dried (MgSO₄), filtered and concentrated to afford 140 mg of 394c as a cream colored solid: MS (M+H)=468.

step 7—To a mixture of 394c (135 mg, 0.288 mmol) dissolved in MeCN (10 mL) and NaI (108 mg, 0.72 mmol) was added TMSCl (0.091 mL, 78 mg, 0.72 mmol) and the resulting solution maintained under nitrogen and heated to 70° C. for 45 min. The reaction mixture was cooled to RT and concentrated. The residue was suspended in a mixture of sat'd. aq. NaHCO₃ (15 mL) and 10% sodium bisulfite (5 mL). The resulting solid was filtered and the precipitate, washed with H₂O (4×5 mL) and air dried. The solid was dissolved in 50% MeOH/DCM, filtered, and evaporated. After drying the solid at 60° C. under high vacuum there was obtained 107 mg of II-4 as a light brown solid: MS (M+H)=454, mp>300° C.

Example 86

3-{3-tert-Butyl-5-[(E)-2-(2-fluoro-phenyl)-vinyl]-4-methoxy-phenyl}-1H-pyridin-2-one (I-237)

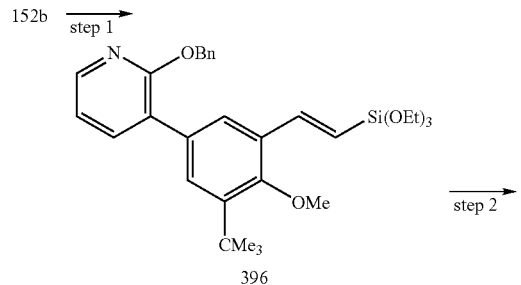

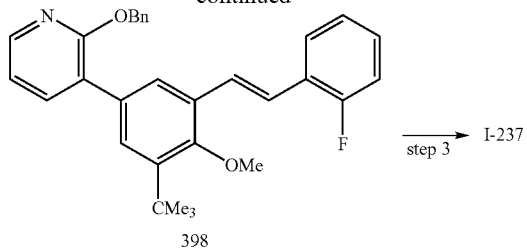

step 1—A solution of XPhos (0.035 g, 0.07 mmol) and PtCl₂ (0.010 g, 0.03 mmol) in THF (0.5 mL) was heated to 60° C. After 15 min a solution of 152b (0.278 g, 0.7 mmol) and (EtO)₃SiH (0.69 mL, 3.7 mmol) in THF (2.5 mL) was added. After 6.5 h the solution was cooled to RT and concentrated in vacuo to afford a crude oil. The crude product was purified by SiO₂ chromatography eluting with a EtOAc/hexane gradient (1% to 10% EtOAc) to afford 0.110 g (29%) of 396 as a clear oil.

step 2—TBAF (0.45 mL, 1.0 M THF) was added dropwise to a solution of 396 (0.110 g, 0.2 mmol) and o-fluoro-bromobenzene (0.068 g, 0.3 mmol) in THF (2.0 mL) at 0° C. After 5 min Pd₂(dba)₃-CHCl₃ (0.005 g, 0.025 mmol) is added and the dark solution was allowed to warm to RT. After 16 h the mixture was concentrated in vacuo. The crude oil was purified by SiO₂ chromatography eluting with an EtOAc/hexane gradient (1% to 5% EtOAc) to afford 0.55 g (59%) of 398 as a clear oil.

step 3—To a solution of 398 in HOAc (1.0 mL) in a screw-capped tube was added 48% HBr (0.019 mL). After 16 h the solution was concentrated in vacuo. The crude product was purified by SiO₂ chromatography eluting with a MeOH/DCM gradient (1% to 8% MeOH) to afford 0.036 g (95%) of I-237 as a white foam: MS (CI) m/z=378 (M+H).

2-{(E)-2-[3-tert-Butyl-2-methoxy-5-(2-oxo-1,2-dihydro-pyridin-3-yl)-phenyl]-vinyl}-benzonitrile (I-238) was prepared analogously except in step 2, o-fluoro-bromobenzene was replaced with o-bromobenzonitrile: MS (CI) m/z=385 (M+H).

3-{3-tert-Butyl-4-methoxy-5-[(E)-2-(2-trifluoromethyl-phenyl)-vinyl]-phenyl}-1H-pyridin-2-one (I-239)) was prepared analogously except in step 2, o-fluoro-bromobenzene was replaced with o-trifluoromethyl-bromobenzene: MS (CI) mz/=429 (M+H).

Example 86

3-[3-tert-Butyl-4-methoxy-5-((E)-2-pyridin-4-yl-vinyl)-phenyl]-1H-pyridin-2-one (I-240)

step 1—To a suspension of 4-chloromethyl-pyridine hydrochloride (2.72 g, 16.6 mmol) in MeCN (20 mL) was added PPh₃ (4.57 g, 17.4 mmol). The mixture was warmed to reflux. After 18 h the mixture was cooled taken up in 20 mL toluene and filtered. The collected solid was washed with toluene and dried in vacuum to afford triphenyl(4-pyridylmethyl)phosphonium chloride hydrochloride (6.61 g, 94%) as a white solid.

step 2—To a solution of triphenyl(4-pyridylmethyl)phosphonium chloride hydrochloride (0.496 g, 1.4 mmol) in THF (10 mL) cooled 0° C. was added n-butyllithium (1.7 mL, 1.6 M in hexanes). After 30 min a solution of D-2 (0.524 g, 1.4 mmol) in THF (3.0 mL) was added and the dark solution was allowed to warm to RT. After 1 h H₂O was added and the mixture was extracted with EtOAc. The combined extracts were washed sequentially with H₂O and brine, dried (Na₂SO₄), filtered and concentrated in vacuo. The crude product was purified by SiO₂ chromatography eluting with an EtOAc/hexane gradient (6% to 60% EtOAc) to afford 4-[(E)-2-(5-bromo-3-tert-butyl-2-methoxy-phenyl)-vinyl]-pyridine (0.017 g, 4%) as a clear oil and 4-[(Z)-2-(5-bromo-3-tert-butyl-2-methoxy-phenyl)-vinyl]-pyridine (0.240 g, 49%) as a clear oil.

step 3—Palladium-catalyzed cross-coupling of 4-[(E)-2-(5-bromo-3-tert-butyl-2-methoxy-phenyl)-vinyl]-pyridine (0.017 g, 0.05 mmol) and 112 (0.007 g, 0.05 mmol) was carried out in accord with the procedure described in step 4 of Example 14. The crude solid was purified by SiO₂ chromatography eluting with a MeOH/DCM gradient (1% to 7% MeOH) to afford 0.015 g (85%) of I-240 as a white solid: MS (CI) m/z=361 (M+H).

3-[3-tert-Butyl-4-methoxy-5-((E)-2-pyridin-2-yl-vinyl)-phenyl]-1H-pyridin-2-one (I-241) was prepared analogously except in step 1, 4-chloromethyl-pyridine hydrochloride was replaced with 2-chloromethyl-pyridine hydrochloride to afford I-241 as a white solid: MS (CI) m/z=361 (M+H).

Example 87

2-{(E)-2-[3-tert-Butyl-2-methoxy-5-(2-oxo-1,2-dihydro-pyridin-3-yl)-phenyl]-vinyl}-benzoic acid methyl ester (I-242)

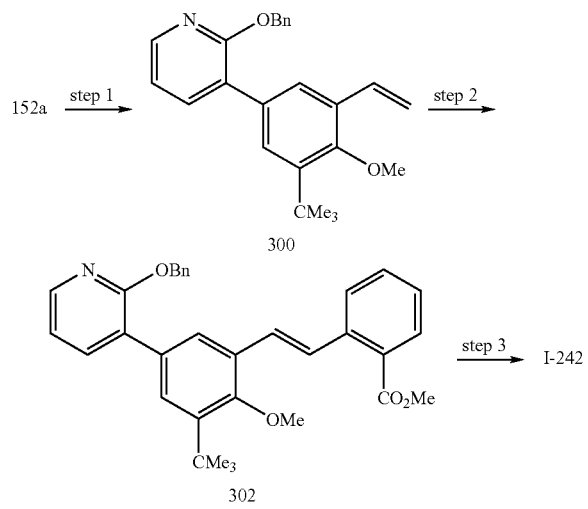

step 1—To a solution of methyltriphenylphosphonium bromide in THF (3.0 mL) cooled to ° C. was added lithium bis-(trimethylsilyl)amide (1.2 mL, 1.0 M THF). After 30 min this solution was transferred via cannula to a solution of 152a (0.79 g, 2.1 mmol) in THF (5.0 mL). After 16 h, H₂O was added and the mixture was extracted with EtOAc. The combined extracts were washed sequentially with H₂O and brine, dried (Na₂SO₄), filtered and concentrated in vacuo. The crude oil was purified by SiO₂ chromatography eluting with an EtOAc/hexane gradient (1% to 8% EtOAc) to afford 0.53 g (67%) of 300 as a clear oil.

step 2—To a solution of 300 (0.159 g, 0.4 mmol) in MeCN (1.5 mL) in a screw-capped tube was added Pd(OAc)₂ (0.014 g, 0.02 mmol), tri-o-tolylphospine (0.013 g, 0.04 mmol), and methyl 2-bromobenzoate (0.101 g, 0.5 mmol). The solution was warmed to 100° C. After 16 h the dark solution was cooled, taken up in EtOAc, filtered through CELITE and poured into H₂O. The mixture was extracted with EtOAc. The combined extracts were washed sequentially with H₂O, and brine, dried (Na₂SO₄), filtered and concentrated in vacuo. The crude oil was purified by SiO₂ chromatography eluting with an EtOAc/hexane gradient (2% to 20% EtOAc) to afford 0.126 g (62%) of 302 as a yellow foam.

step 3—To a solution of 302 (0.126 g, 0.3 mmol) in HOAc (1.0 mL) in a screw-capped tube was added 48% HBr (0.04 mL). After 16 h the solution was concentrated in vacuo, taken up in H₂O and the pH was adjusted to pH=8 with 2M NaOH. The mixture was extracted with EtOAc. The combined extracts were washed sequentially with H₂O and brine, dried (Na₂SO₄), filtered and concentrated. The crude oil was purified by SiO₂ chromatography eluting with a MeOH/DCM gradient (1% to 10% MeOH) to afford 0.074 g (59%) of I-242 as a white solid: MS (CI) m/z=418 (M+H).

3-{3-[(E)-2-(2-Acetyl-phenyl)-vinyl]-5-tert-butyl-4-methoxy-phenyl}-1H-pyridin-2-one was prepared analogously except in step 2, methyl 2-bromobenzoate was replaced with 2-bromo-acetophenone. The product was purified by SiO₂ chromatography eluting with a MeOH/DCM gradient (1% to 10% MeOH) to afford I-243 as a white solid: MS (CI) mz/=402 (M+H).

3-{3-tert-Butyl-5-[(E)-2-(2-methanesulfonyl-phenyl)-vinyl]-4-methoxy-phenyl}-1H-pyridin-2-one was prepared analogously except in step 2, methyl 2-bromobenzoate was replaced with 1-bromo-2-methanesulfonyl-benzene. The product was purified by SiO₂ chromatography eluting with a MeOH/DCM gradient (1% to 10% MeOH) to afford I-244 as white solid: MS (CI) mz/=438 (M+H).

4-{(L)-2-[3-tert-Butyl-2-methoxy-5-(2-oxo-1,2-dihydro-pyridin-3-yl)-phenyl]-vinyl}-nicotinonitrile was prepared analogously except in step 2, methyl 2-bromobenzoate was replaced with 4-bromo-nicotinonitrile. The product was purified by SiO₂ chromatography eluting with a MeOH/DCM gradient (1% to 10% MeOH) to afford I-245 as pale yellow solid: MS (C) mz/=386 (M+H).

2-{(E)-2-[3-tert-Butyl-2-methoxy-5-(2-oxo-1,2-dihydro-pyridin-3-yl)-phenyl]-vinyl}-benzoic acid was prepared from I-242 by hydrolysis with LiOH in aqueous methanol. Acidification of the solution resulted in precipitation of the product which was filtered and dried to afford I-246 as a white solid: MS (CD) mz/=404 (M+H).

Example 88

6-Amino-N-[3-tert-butyl-2-methoxy-5-(2-oxo-1,2-dihydro-pyridin-3-yl)-phenyl]-nicotinamide (I-247)

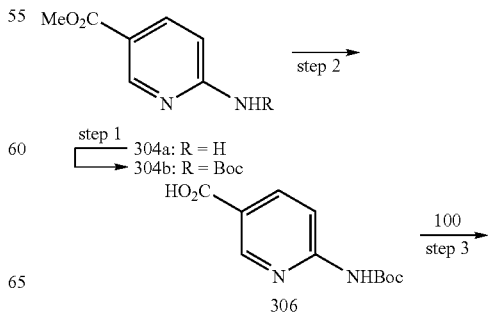

-continued

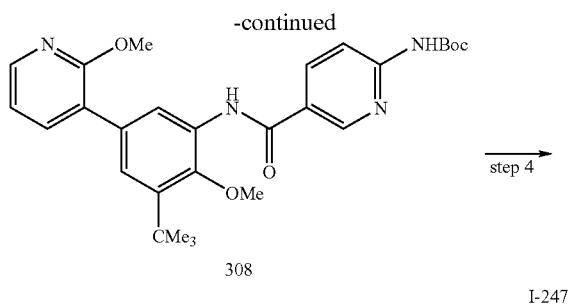

308

I-247 step 1—To a solution of 304a (4.72 g, 31.0 mmol) and DMAP (0.19 g, 1.6 mmol) in DCM (100 mL) was added in portions di-tert-butyl dicarbonate (7.45 g, 34.1 mmol). After 16 h the solution was concentrated in vacuo to afford a crude solid which was recrystallized from 50 mL hot EtOAc to afford 4.74 g (61%) of 304b as white needles.

step 2—To a solution of 304b (2.14 g, 14.0 mmol) in 70 mL MeOH/$H_2O$ (3:1) was added KOH (3.95 g, 70.3 mmol). The mixture was warmed to 50° C. After 2 h the solution was cooled, concentrated in vacuo and taken up in $H_2O$. 4M HCl was added drop-wise until the pH of the solution was approximately 6. The resulting precipitate was filtered to afford 306 (0.100 g, 3%) as a white solid. The mother liquor was extracted with EtOAc. The combined organics were sequentially washed with $H_2O$ and brine, dried ($Na_2SO_4$), filtered and concentrated to afford an additional 0.150 g (4%) 306 as white solid.

step 3—To a suspension of 306 (0.110 g, 0.5 mmol), 100, and HATU (0.193 g, 0.5 mmol) in DMF (2.5 mL) was added DIPEA (0.16 mL, 0.9 mmol). After 16 h $H_2O$ was added and the mixture was extracted with EtOAc. The combined organics were washed sequentially with $H_2O$ and brine, dried ($Na_2SO_4$), filtered and concentrated in vacuo. The crude product was purified by $SiO_2$ chromatography eluting with an EtOAc/hexane gradient (4% to 40% EtOAc) to afford 0.114 g (45%) of 308 as a solid.

step 4—To a solution of 308 (0.114 g, 0.2 mmol) in HOAc (1.0 mL) in a screw-capped tube was added HBr (0.12 mL, 48% $H_2O$). The solution was warmed to 70° C. After 3 h additional HBr (0.12 mL, 48% $H_2O$) was added. After an additional 2 hr the solution was cooled, concentrated in vacuo and treated with 10% $K_2CO_3$. The mixture was extracted with EtOAc. The combined extracts were washed sequentially with $H_2O$ and brine, dried ($Na_2SO_4$), filtered and concentrated in vacuo. The crude product was purified by $SiO_2$ eluting with a MeOH/DCM gradient (1 to 10% MeOH) to afford 0.031 g (39%) of I-247: MS (CI) mz/=393 (M+H).

Example 89

6-(2,2,2-Trifluoro-ethylamino)-pyridazine-3-carboxylic acid [3-tert-butyl-2-methoxy-5-(2-oxo-1,2-dihydro-pyridin-3-yl)-phenyl]-amide (I-248)

5-(2-Benzyloxy-pyridin-3-yl)-3-tert-butyl-2-methoxy-phenylamine was prepared by palladium-catalyzed cross-coupling of 5-bromo-1-tert-butyl-2-methoxy-3-nitrobenzene and 141 in accord with the procedure described in step 20f Example 22. Reduction of the nitro group to afford 5-(2-benzyloxy-pyridin-3-yl)-3-tert-butyl-2-methoxy-phenylamine (310) was carried out with Fe in accord with the procedure described in step 3 of Example 14 step 1—A solution of 6-hydroxy-pyridazine-carboxylic acid hydrate (0.286 g, 1.9 mmol, CASRN 37972-69-3) and $POCl_3$ (20 mL) was heated at reflux. After 2 h the solution was concentrated in vacuo, dissolved in THF (20 mL) and TEA (0.8 mL, 5.4 mmol) and cooled to 0° C. A solution of 310 (0.657 g, 1.9 mmol) in THF (5.0 mL) was added drop-wise and the solution was warmed to RT. After 18 h $H_2O$ was added and the mixture was extracted with EtOAc. The combined organics were washed sequentially with $H_2O$, washed with brine, dried ($Na_2SO_4$), filtered and concentrated in vacuo. The crude product was purified by $SiO_2$ chromatography eluting with an EtOAc/hexane gradient (4% to 40% EtOAc) to afford 0.598 g (63%) of 6-chloro-pyridazine-3-carboxylic acid [5-(2-benzyloxy-pyridin-3-yl)-3-tert-butyl-2-methoxy-phenyl]-amide 312 as a yellow solid.

step 2—A solution of 312 (0.059 g, 0.1 mmol) and 2,2,2-trifluoroethylamine (0.5 mL) in NMP (1.0 mL) in a screw-capped test tube was heated to 100° C. After 18 h the solution was cooled to RT poured into $H_2O$ and extracted with EtOAc. The combined organics were washed sequentially with $H_2O$ and brine, dried ($Na_2SO_4$), filtered and concentrated in vacuo. The crude product was purified by $SiO_2$ chromatography eluting with an EtOAc/hexane (6% to 60% EtOAc) to afford 0.029 g (37%) 6-(2,2,2-trifluoro-ethylamino)-pyridazine-3-carboxylic acid [5-(2-benzyloxy-pyridin-3-yl)-3-tert-butyl-2-methoxy-phenyl]-amide (314) as an oil.

step 3—To a solution of 314 (0.029 g, 0.1 mmol) in MeOH (5.0 mL) and EtOAc (4.0 mL) was added Pd(OH)$_2$ (0.005 g). The solution was stirred under 1 atm of $H_2$. After 18 h the mixture was filtered through a pad of CELITE and the filtrate concentrated in vacuo. The crude product was purified by $SiO_2$ chromatography eluting with a MeOH/DCM gradient (1% to 10% MeOH) to 0.018 g (74%) of I-248 as an oil: MS (CI) mz/=476 (M+H).

Example 90

N-[3-tert-Butyl-2-methoxy-5-(2-oxo-1,2-dihydro-pyridin-3-yl)-phenyl]-3-fluoro-4-(2,2,2-trifluoro-ethylamino)-benzamide (I-251)

step 1—To a solution of 310 (106 mg, 0.292 mmol) and TEA (0.06 mL, 0.439 mmol) in DCM (2 mL) cooled to 0° C. was added dropwise a solution of 3-fluoro-4-nitro-benzoyl chloride (89 mg, 0.439 mmol) in DCM (1 mL). The reaction mixture was warmed to RT and stirred for 1.5 h. The reaction mixture was diluted with DCM and washed with $H_2O$. The aqueous layer was back-extracted with DCM. The organic extracts were combined, dried (MgSO$_4$), filtered and concentrated. The crude residue was purified by $SiO_2$ chromatography eluting with an EtOAc/hexane gradient (0% to 25% EtOAc) to afford 154 mg (99%) of N-[5-(2-benzyloxy-pyridin-3-yl)-3-tert-butyl-2-methoxy-phenyl]-3-fluoro-4-nitro-benzamide (316) as a foamy, yellow solid.

step 2—To a suspension of 316 (595 mg, 1.12 mmol) in a 1:1 mixture of MeOH/$H_2O$ (4 mL each) at RT was added NH$_4$Cl (601 mg, 11.2 mmol) and iron powder (314 mg, 5.62 mmol). The reaction mixture was warmed to 105° C. and stirred overnight. The reaction was cooled to RT and filtered via Büchner funnel and the filtrate was rinsed with DCM. The filtrate was diluted with $H_2O$ and extracted with DCM. The extracts were washed with $H_2O$ and brine. The combined aqueous phases were back-extracted with DCM. The combined organic extracts were combined, dried (MgSO$_4$), filtered, and concentrated. The crude residue was purified by $SiO_2$ chromatography, eluting with an EtOAc/hexane gradient (0% to 40% EtOAc) to afford 405 mg (72%) of 4-amino- N-[5-(2-benzyloxy-pyridin-3-yl)-3-tert-butyl-2-methoxy-phenyl]-3-fluoro-benzamide (318) as a foamy, yellow solid.

step 3—To a solution of 318 (201 mg, 0.402 mmol) in TFA (4 mL) at RT was added trifluoroacetaldehyde hydrate (98 mg, 0.845 mmol) and H$_2$O (2 drops). The reaction mixture was stirred at RT for 5 min, and then sodium cyanoborohydride (33 mg, 0.523 mmol) was added. Gas evolution was briefly observed. The reaction mixture was stirred at RT for 4.5 h, then diluted with H$_2$O and EtOAc and carefully poured into sat'd NaHCO$_3$. The layers were separated, and the organic phase was subsequently twice washed sequentially with sat'd. NaHCO$_3$, H$_2$O and brine. The organic layer was dried (MgSO$_4$), filtered and concentrated. The crude residue was purified by SiO$_2$ chromatography, eluting with an EtOAc/hexane gradient (0% to 30% EtOAc) to afford 89 mg (38%) of N-[5-(2-benzyloxy-pyridin-3-yl)-3-tert-butyl-2-methoxy-phenyl]-3-fluoro-4-(2,2,2-trifluoro-ethylamino)-benzamide (320) as a foamy, light yellow solid.

step 4—To a solution of 320 (86 mg, 0.148 mmol) in a mixture of MeOH/EtOAc (2 mL and 1 mL, respectively) at RT was added 20% palladium (II) hydroxide on carbon (moist) (9 mg, 10 wt. %). The reaction mixture was stirred under 1 atm of H$_2$ for 1.5 h. The reaction mixture was filtered through a plug of CELITE and the pad washed with EtOAc. The filtrate was concentrated to afford 72 mg (99%) of I-251 as a light pink solid.

Example 91

N-[3-tert-Butyl-2-methoxy-5-(2-oxo-1,2-dihydro-pyridin-3-yl)-phenyl]-2-fluoro-4-hydroxy-benzamide (I-252)

step 1—A solution of 100 (100 mg, 0.349 mmol, 4-benzyloxy-3-fluoro-benzoic acid (86 mg, 0.349 mmol), HATU (146 mg, 0.384 mmol, DIPEA (0.122 mL, 0.698 mmol), and DMF (3 mL) is stirred at 50° under Ar overnight. The reaction was cooled, diluted with H$_2$O and extracted with EtOAc. The combined extracts were washed with H$_2$O, dried (MgSO$_4$), filtered and concentrated in vacuo. The crude product was purified by SiO$_2$ eluting with 20% EtOAc/hexane to afford 0.125 g (85%) of 4-benzyloxy-N-[3-tert-butyl-2-methoxy-5-(2-methoxy-pyridin-3-yl)-phenyl]-2-fluoro-benzamide (322) which could be recrystallized from EtOAc.

step 2—To a solution of 322 (88 mg, 0.171 mmol) and HOAc (3 mL) in a 2-5 mL microwave tube was added 48% HBr (0.037 mL, 0.684 mmol). The tube was sealed and heated to 60° for 4 h then to 40° overnight. The reaction was still incomplete so heating at was continued for 6 h at 70°. The reaction was cooled to RT, concentrated and stirred with dilute aq. K$_2$CO$_3$, then twice extracted with EtOAc, dried (MgSO4), filtered and concentrated. The crude product was purified on a SiO$_2$ TLC plate developed with 75% EtOAc/hexane to afford 25 mg (965%) of I-252 as a white solid: MS (M+H)=411.

Example 92

N-[3-tert-Butyl-2-methoxy-5-(2-oxo-1,2-dihydro-pyridin-3-yl)-phenyl]-4-(2,2,2-trifluoro-ethylamino)-benzamide (I-253)

step 1—To a mixture of methyl 4-(2,2,2-trifluoro-acetylamino)-benzoate (1 g, 4.05 mmol) in DCM (15 mL) in a 5-20 mL microwave vial is added tetrabutylammonium borohydride (3.12 g, 12.14 mmol). Bubbles formed and the solid dissolved. The vial was capped and heated in a 50° oil bath overnight, then cooled to RT and concentrated. Glacial HOAc was added dropwise to the colorless oil until gas evolution ceases. Toluene was added and the solvent concentrated in vacuo. The residue was made basic with dilute aqueous NaHCO$_3$ and extracted with EtOAc. The combined extracts were dried (MgSO$_4$), filtered and concentrated to afford 1.02 g of crude white solid was recrystallized from hexane to afford 0.349 g of methyl 4-(2,2,2-trifluoro-ethylamino)-benzoate (324).

step 2—A mixture of 324 (0.349 g, 1.497 mmol), KOH (0.420 g, 7.48 mmol), MeOH (3 mL), and H$_2$O (1 mL) was heated at reflux for 1 h. The solution was concentrated and H$_2$O (15 mL) was added and the pH adjusted to pH 2 with 6N HCl. A white solid precipitated and was filtered, washed with water, and air dried to afford 0.278 g (85%) of 4-(2,2,2-trifluoro-ethylamino)-benzoic acid (326) as a white solid.

step 3—A solution of 100 (100 mg, 0.276 mmol), 326 (66.5 mg, 0.303 mmol), HATU (126 mg, 0.331 mmol), DIPEA (0.096, 0.552 mmol), and DMF (3 mL) is stirred at 50° under argon for 1.5 days. The reaction was quenched with H$_2$O and the resulting solution extracted with EtOAc. The combined extracts were washed with H$_2$O, dried (MgSO$_4$), filtered and concentrated. The crude product was purified by SiO$_2$ chromatography eluting with 40% EtOAc/hexane to afford 60 mg of N-[5-(2-benzyloxy-pyridin-3-yl)-3-tert-butyl-2-methoxy-phenyl]-4-(2,2,2-trifluoro-ethylamino)-benzamide (328) as a colorless foam.

step 4—Cleavage of the benzyl ether to afford I-253 was carried out in accord with the procedure described in step 7 of Example 24. The white solid was recrystallized from EtOAc/hexane to afford 39 mg of I-253 as a white solid: MS [M+H] =474.

Example 93

N-[3-tert-Butyl-2-methoxy-5-(2-oxo-1,2-dihydro-pyridin-3-yl)-phenyl]-6-(2-methoxy-ethylamino)-nicotinamide (I-254)

A microwave vial is charged with 6-chloronicotinic acid (1 g, 6.35 mmol), 2-methoxyethylamine (1.214 mL, 13.96 mmol) and IPA (3.5 mL) sealed and irradiated in a microwave synthesizer at 180° for 40 min. The reaction was cooled, concentrated and purified by SiO$_2$ chromatography eluting with a MeOH/DCM gradient (5% to 10% MeOH containing 0.5% HOAc) to afford 0.24 g of 6-(2-methoxy-ethylamino)-nicotinic acid (330) as a white solid.

Condensation of 100 and 330 were carried out in accord with the procedure described in step 3 of Example 92 to afford N-[5-(2-benzyloxy-pyridin-3-yl)-3-tert-butyl-2-methoxy-phenyl]-6-(2-methoxy-ethylamino)-nicotinamide. Cleavage of the benzyl ether to afford I-254 was carried out in accord with the procedure described in step 7 of Example 24. The crude was purified on a preparative SiO$_2$ TLC plate and developed with 10% MeOH/DCM to afford I-254 as a white solid: MS [M+H]=451

Example 94

N-[3-tert-Butyl-2-methoxy-5-(2-oxo-1,2-dihydro-pyridin-3-yl)-phenyl]-6-cyclopropylamino-nicotinamide (I-255)

A microwave vial is charged with ethyl-6-chloronicotinate (1 g, 5.39 mmol) and cyclopropylamine (1 mL, 14.43 mmol), sealed and stirred at 80° overnight. After cooling to RT, the yellow solid was stirred with EtOAc and filtered. The filtrate was preadsorbed on SiO₂ and applied to the top of a SiO₂ column and eluted with an EtOAc/hexane gradient (0 to 30% EtOAc) to afford 0.71 g of ethyl 6-cyclopropylamino-nicotinoate (332) as an off white solid (17).

A mixture of 332 (0.71 g, 3.44 mmol, 1M NaOH (6.89 mL, 6.89 mmol) and EtOH (10 mL) was stirred and heated to 80° for 2 h. The solvent was evaporated and the residue dissolved in H₂O and the pH adjusted to ca. 2. The resulting precipitate was filtered, washed with water, air dried. to afford 168 mg of 6-cyclopropylamino-nicotinic acid (334) as a white powder.

Condensation of 100 and 334 was carried out in accord with the procedure described in step 3 of Example 92 to afford N-[5-(2-benzyloxy-pyridin-3-yl)-3-tert-butyl-2-methoxy-phenyl]-6-cyclopropylamino-nicotinamide. Cleavage of the benzyl ether was carried out in accord with the procedure described in step 7 of Example 24. The crude was recrystallized from EtOAc/hexane to afford I-255: MS [M+H]=433.

Example 95

N-[3-tert-Butyl-2-methoxy-5-(2-oxo-1,2-dihydro-pyridin-3-yl)-phenyl]4-cyclopropylamino-benzamide (I-256)

A mixture of ethyl 4-(cyclopropylamino)-benzoate (0.188 g, 0.916 mmol, CASRN 112033-48-4), 1 M NaOH (1.832 mL, 1.832 mmol) and EtOH (5 mL) was stirred and heated to 80° C. for 2 h. The EtOH was evaporated and the residue diluted with H₂O, adjusted to pH ca. 2 and the resulting precipitate filtered, washed with water and air dried to afford 94 mg of 4-(cyclopropylamino)-benzoic acid (336) as a white powder.

Condensation of 100 and 336 was carried out in accord with the procedure described in step 3 of Example 92 to afford N-[5-(2-benzyloxy-pyridin-3-yl)-3-tert-butyl-2-methoxy-phenyl]. Cleavage of the benzyl ether was carried out in accord with the procedure described in step 7 of Example 24. The crude product was recrystallized from EtOAc/hexane to I-256: MS [M+H]=432.

Example 96

N-[3-tert-Butyl-2-methoxy-5-(2-oxo-1,2-dihydro-pyridin-3-yl)-phenyl]-4-(2-methoxy-ethylamino)-benzamide (I-257)

To a solution of ethyl 4-(2,2,2-trifluoro-acetylamino)-benzoate (1.58 g, 6.05 mmol, CASRN 24568-14-7) in dry THF was added 2-methoxyethanol (1.192 mL, 15.12 mmol), diisopropyl azodicarboxylate (2.94 mL, 15.12 mmol) and P (3.97 g, 15.12 mmol) and the resulting solution stirred for 4 h. The reaction mixture was concentrated, dissolved in EtOAc, washed sequentially with water and brine, dried (MgSO4), filtered and concentrated. The crude product was purified by SiO₂ chromatography eluting with 50% EtOAc/hexane to afford 0.42 g of ethyl 4-(2-methoxy-ethylamino)-benzoate (338).

Hydrolysis of the ethyl ester was carried out as described in Example 95 to afford 4-(2-methoxy-ethylamino)-benzoic acid (340). Condensation of 100 and 340 was carried out in accord with the procedure described in step 3 of Example 92 to afford N-[5-(2-benzyloxy-pyridin-3-yl)-3-tert-butyl-2-methoxy-phenyl]. Cleavage of the benzyl ether was carried out in accord with the procedure described in step 7 of Example 24. The crude was recrystallized from EtOAc/hexane to I-257: MS [M+H]=450.

Example 97

N-(6-{(E)-2-[3-(1-Difluoromethyl-cyclopropyl)-2-methoxy-5-(2-oxo-1,2-dihydro-pyridin-3-yl)-phenyl]-vinyl}-pyridin-3-yl)-methanesulfonamide (I-258)

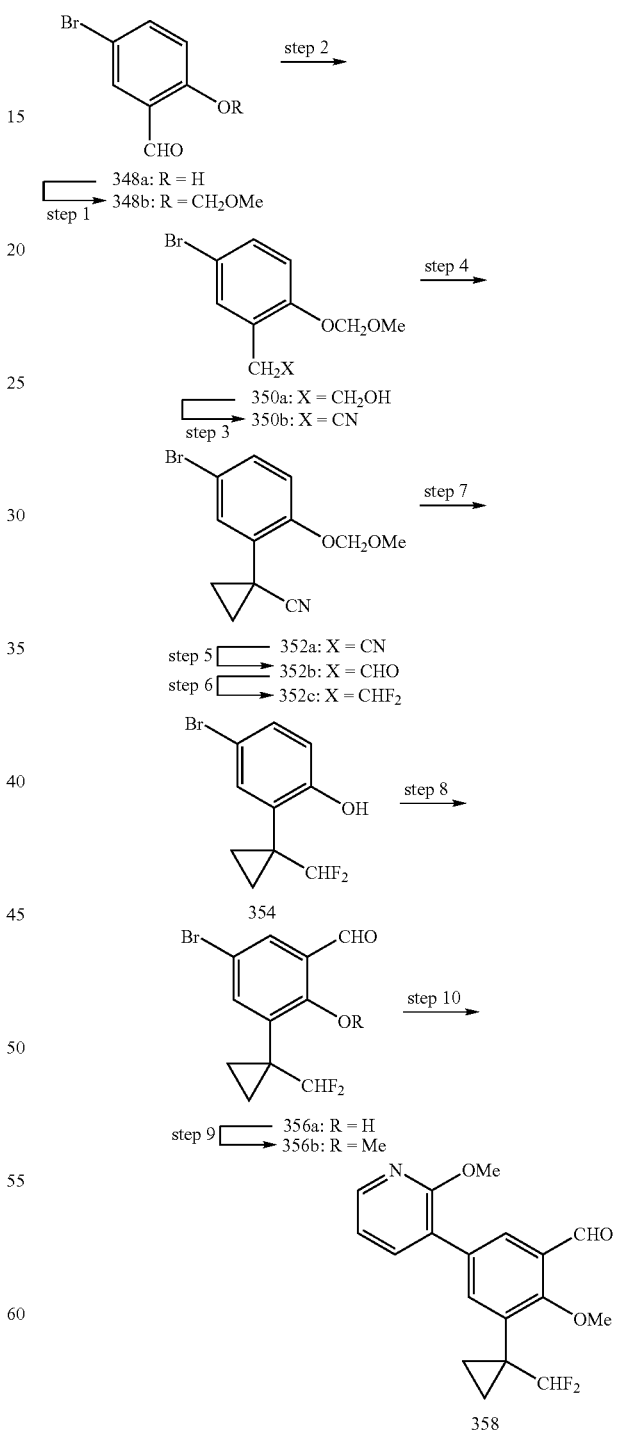

step 1—To a solution of 348a (10.0 g, 49.7 mmol) in DMF (100 mL) at RT was added K₂CO₃ (13.7 g, 99.4 mmol) followed by chloromethyl methyl ether (tech grade, 5.2 mL, 54.7 mmol). The reaction mixture was stirred at RT overnight then quenched with $H_2O$ and thrice extracted with EtOAc. The combined extracts were thrice washed with $H_2O$, dried ($MgSO_4$), filtered and concentrated to afford 11.6 g (96%) of 348b as a yellow oil.

step 2—To a solution of 348b (11.6 g, 47.3 mmol) in MeOH (100 mL) at 0° C. was slowly added $NaBH_4$ (1.87 g, 49.6 mmol). The reaction mixture was stirred at 0° C. for 1 h then quenched with $H_2O$ and brine. The resulting mixture was thrice extracted with EtOAc, dried ($MgSO_4$), filtered and concentrated to afford 11.3 g (97%) of alcohol 350a as a pale yellow oil.

step 3—To a solution of alcohol 350a (10.0 g, 40.5 mmol) in DCM (80 mL) at 0° C. were added TEA (7.3 mL, 52.6 mmol) and methanesulfonyl chloride (3.4 mL, 44.5 mmol). The reaction mixture was stirred for 1 h then quenched with $H_2O$ and extracted with DCM. The extracts were dried ($MgSO_4$), filtered and concentrated to a light yellow oil. To a solution of this oil in DMF (50 mL) was added LiBr (3.9 g, 44.5 mmol) and the reaction mixture was stirred at RT for 1 h. A solution of NaCN (3.0 g, 60.7 mmol) in $H_2O$ (5 mL) was slowly added, using an ice bath to control the exothermic reaction. After the addition was complete, the reaction mixture was stirred at RT for 1 h then quenched with $H_2O$ and thrice extracted with EtOAc (3×). The combined extracts were thrice washed with $H_2O$, dried ($MgSO_4$), filtered and concentrated to afford 10.5 g of nitrile 350b as a yellow oil.

step 4—To a solution of 350b (2.6 g, 10.1 mmol) in DMF (25 mL) at 0° C. was added NaH (60% in mineral oil, 0.89 g, 22.2 mmol). The reaction mixture was stirred at 0° C. for 0.5 h then 1,2-dibromoethane (0.96 mL, 11.1 mmol) was added dropwise. The reaction mixture was warmed to RT and stirred for 1 h then quenched with $H_2O$ and thrice extracted with EtOAc. The organic phase was thrice washed with $H_2O$ then dried ($MgSO_4$), filtered and concentrated. The residue was purified by $SiO_2$ chromatography eluting with 10% EtOAc/hexanes to afford 1.83 g (64%) of 352a as a yellow oil.

step 5—To a solution of 352a (1.83 g, 6.5 mmol) in DCM (40 mL) at −78° C. was a dropwise DIBAL (1.27 mL, 7.1 mmol). The reaction mixture was stirred at −78° C. for 2 h then quenched with MeOH (0.5 mL) and warmed to RT. A saturated solution of Rochelle's salt (40 mL) was added and the biphasic mixture was stirred vigorously for 30 min. The phases were separated and the aqueous phase was extracted with DCM. The combined extracts were dried ($MgSO_4$), filtered and concentrated. The crude residue was purified by $SiO_2$ chromatography eluting with 2% EtOAc/DCM to afford 1.49 g (81%) of 352b as a pale yellow oil.

step 6—To a solution of 352b (4.9 g, 17.2 mmol) in DCM (80 mL) was slowly added (diethylamino)sulfur triflouride (6.8 mL, 51.6 mmol). The reaction mixture was stirred at RT overnight then quenched by slowly pouring the reaction onto ice. The mixture was diluted with $H_2O$ and extracted with DCM. The combined extracts were dried ($MgSO_4$), filtered and concentrated. The crude residue was purified by $SiO_2$ chromatography eluting with 10% EtOAc/hexanes to afford 4.07 g (77%) of 352c as a colorless oil.

step 7—To a solution of 352c (4.05 g, 13.2 mmol) in DCM (60 mL) at 0° C. was added 4 Å powdered molecular sieves (4 g) followed by TMSBr (5.2 mL, 39.6 mmol). The reaction mixture was allowed to warm to RT and stirred overnight then filtered to remove the sieves which were rinsed with DCM. The filtrate was washed sequentially with sat'd. aq. $NaHCO_3$ and $H_2O$, dried ($MgSO_4$), filtered and concentrated. The crude residue was purified by $SiO_2$ chromatography eluting with an EtOAc/hexane gradient (10% to 20% EtOAc) to afford 2.85 g (82%) of 354 as a pale yellow oil.

step 8—To a solution of 354 (2.85 g, 10.8 mmol) in anhydrous MeCN (50 mL) was added TEA (5.6 mL, 40.5 mmol), $MgCl_2$ (1.54 g, 16.2 mmol), and paraformaldehyde (2.27 g, 75.6 mmol). The bright yellow reaction mixture was heated at reflux for 5 h then cooled to RT and quenched with 1.0 M aqueous HCl. The mixture was thrice extracted with EtOAc then the combined extracts were dried ($MgSO_4$), filtered and concentrated. The crude residue was purified by $SiO_2$ chromatography eluting an EtOAc/hexane gradient (10% to 20% EtOAc) to afford 1.04 g (33%) of 356a as an off-white solid.

step 9—To a solution of 356a (1.04 g, 3.6 mmol) in DMF (15 mL) was added $K_2CO_3$ (1.0 g, 7.2 mmol) followed by iodomethane (0.27 mL, 4.3 mmol). The reaction mixture was stirred at RT for 4 h then quenched with $H_2O$ and thrice extracted with EtOAc. The combined extracts were thrice washed with $H_2O$, dried ($MgSO_4$), filtered and concentrated to afford 1.06 g (97%) of 356b as a pale yellow solid which required no further purification.

step 10—A microwave vial was charged with 356b (340 mg, 1.11 mmol), 37 (203 mg, 1.33 mmol), $Na_2CO_3$ (235 mg, 2.22 mmol), $Pd(PPh_3)_4$ (50 mg, 0.05 mmol), MeOH (3 mL) and DCM (1 mL). The vial was sealed and irradiated in a microwave reactor at 120° C. for 20 min. The reaction was diluted with $H_2O$ and extracted with DCM. The combined extracts were dried ($MgSO_4$), filtered and concentrated. The crude residue was purified by $SiO_2$ chromatography eluting with an EtOAc/hexane gradient (10% to 20% EtOAc) to afford 250 mg (68%) of 358 as a yellow oil.

The conversion of 358 to I-258 was carried out by conversion of 358 to an acetylene with (1-diazo-2-oxo-propyl)-phosphonic acid diethyl ester, hydrostannylation with AIBN and $HSnBu_3$, coupling the vinyl stannane 5-amino-2-iodo-pyridine, conversion of the amine to the sulfonamide and cleavage of the methyl ether to afford the pyridone as described in steps 1-5 of Example 42

Example 98

(S)-2-Amino-3-methyl-butyric acid 3-{3-tert-butyl-5-[(E)-2-(4-methanesulfonylamino-phenyl)-vinyl]-4-methoxy-phenyl}-5-fluoro-2-oxo-2H-pyridin-1-ylmethyl ester (II-7)

step 1—A suspension of I-142 (193 mg, 0.410 mmol), 37% formaldehyde (9 mL, 121 mmol), and MeOH (9 mL) was stirred at 65° C. for 4 h. The MeOH was evaporated and $H_2O$ (50 mL) was added. The white solid was filtered, washed with water, and air dried to afford 150 mg of a white powder 340 consisting of 60% N-hydroxy methyl derivative and 40% unreacted SM and which was used directly without additional purification.

step 2—To a solution of 340 (1.1 g, 1.538 mmol) and TEA (0.043 mL, 0.308 mmol) in dry DMF (4 mL) was added Boc-L-Valine NCA (0.449 g, 1.846 mmol, CASRN 141468-55-5) in dry toluene (6 mL) and the resulting solution stirred for 1 h at RT. The reaction was diluted with $H_2O$ and extracted twice with EtOAc. The combined extracts were twice washed with water then with brine, dried (MgSO4), filtered and concentrated. The crude product was purified by $SiO_2$ chromatography eluting with 4% MeOH/DCM to afford 179 mg of (S)-2-tert-butoxycarbonylamino-3-methyl-butyric acid, 3-{3-tert-butyl-5-[(E)-2-(4-methanesulfonylamino-phenyl)-vinyl]4-methoxy-phenyl}-5-fluoro-2-oxo-2H-pyridin-1-yl-methyl ester (342) which could be further purified by recrystallization from EtOAc/hexane.

step 3—To a solution of 342 (0.886 g, 1.266 mmol and DCM (10 mL) at RT was added a HCl/dioxane solution (1.899 mL, 7.60 mmol, 4M solution) and the resulting solution stirred at RT for 3 h. The resulting solution was poured into DCM (150 mL) which produced a gummy oil. When the mixture was sonicated a white powder formed which was filtered, washed with DCM and air-dried. The solid was dried under high vacuum to remove all traces of solvent which afforded 698 g of II-7 as a white powder: MS (M+H)=600.

Example 99

Succinic acid mono-(3-{3-tert-butyl-5-[(E)-2-(4-methanesulfonylamino-phenyl)-vinyl]-4-methoxy-phenyl}-5-fluoro-2-oxo-2H-pyridin-1-ylmethyl) ester (II-6)

To a suspension of 340 (50 mg, 0.076 mmol) in DCM (5 mL) at RT was added succinic anhydride (11.40 mg, 0.114 mmol, DMAP (0.464 mg, 3.80 µmol, and DIPEA (0.021 mL, 0.121 mmol and the resulting solution stirred 2 h. The solvent was evaporated and $H_2O$ was added. The resulting solid was filtered, washed with $H_2O$ and air dried to afford 20 mg of II-6 which contained ca. 40% I-142

Example 100

Phosphoric acid mono-(3-{3-tert-butyl-5-[(E)-2-(4-methanesulfonylamino-phenyl)-vinyl]-4-methoxy-phenyl}-5-fluoro-2-oxo-2H-pyridin-1-ylmethyl) ester (II-8)

step 1—To a suspension of 340 (0.62 g, 0.743 mmol) in DCM (3 mL at RT was added freshly distilled $SOCl_2$ (0.271 mL, 3.72 mmol) and the resulting solution stirred for 1 h under inert atmosphere. The reaction was concentrated and diluted with DCM, washed with $NaHCO_3$, dried ($MgSO_4$), filtered and evaporated to afford N-(4-{(E)-2-[3-tert-butyl-5-(1-chloromethyl-5-fluoro-2-oxo-1,2-dihydro-pyridin-3-yl)-2-methoxy-phenyl]-vinyl}-phenyl)-methanesulfonamide (344) which was used with further purification.

step 2—To a mixture of freshly prepared phosphoric acid di-t-butyl ester (1.8 g, 1.734 mmol, CASRN 33494-81-4) and freshly prepared 344 (0.729 g, 3.47 mmol) in dry MeCN (100 mL) was added $Ag_2O$ (0.402 g, 1.734 mmol). A greenish-grey suspension results which was stirred overnight under argon in a foil-wrapped flask (18% chloride remain). The grey suspension was filtered through CELITE, washed with MeCN, and concentrated in vacuo. To this residue is added MeOH (20 mL), sonicated, filtered and the solid washed with MeOH. The filtrate was concentrated and the crude product purified by $SiO_2$ chromatography eluting with an EtOAc/hexane gradient (20 to 70% EtOAc) to afford 0.555 g of material which was rechromatographed under similar conditions to afford 0.47 g of phosphoric acid di-tert-butyl ester 3-{3-tert-butyl-5-[(E)-2-(4-methanesulfonylamino-phenyl)-vinyl]-4-methoxy-phenyl}-5-fluoro-2-oxo-2H-pyridin-1-ylmethyl ester (346) as a light yellow solid.

step 3—To a solution of 346 and DCM (10 mL) at RT under an Ar atmosphere was added TFA (0.523 mL, 6.78 mmol). The resulting solution was stirred for 3 h. The solution was concentrated in vacuo and the residue twice taken up in benzene and re-evaporated to afford 0.346 g of I-8: MS (M+H)= 581.

Example 101

3-tert-Butyl-N-(3-methanesulfonylamino-phenyl)-2-methoxy-5-(2-oxo-1,2-dihydro-pyridin-3-yl)-benzamide (I-259)

To a solution of 39 (0.040 g, 0.14 mmol) and DMF (3 mL) was added N-(3-aminophenyl) methanesulfonamide (0.052 g, 0.28 mmol), EDCI (0.038 g, 0.28 mmol), and HOBt (0.053 g, 0.28 mmol). The reaction was stirred overnight at RT. The reaction was then concentrated and partitioned between EtOAc and $H_2O$ (25 mL/25 mL). The aqueous layer was separated and twice washed EtOAc. The combined organic extracts were washed with brine (25 mL), dried ($Na_2SO_4$), filtered and concentrated. The crude product was purified on a preparatory $SiO_2$ TLC plate developed using 80% EtOAc/hexane to afford 0.024 g (37%) of I-259.

Example 102

3-tert-Butyl-N-(4-methanesulfonylamino-cyclohexyl)-2-methoxy-5-(2-oxo-1,2-dihydro-pyridin-3-yl)-benzamide (I-260)

N-(4-Amino-cyclohexyl)-methanesulfonamide, hydrochloride (360)

To trans 1,4-diaminocyclohexane (2.0 g, 17.5 mmol) in DCM at 0° C. (ice bath) was added methanesulfonyl chloride (1.63 mL, 21.0 mmol). The reaction was allowed to stir at RT for 1 h when a precipitate formed and was collected on a glass frit, rinsed with DCM, and dried to afford 2.56 g (64%) of 360.

To a solution of 39 (0.100 g, 0.35 mmol), and 360 (0.119 g, 0.52 mmol) dissolved in DMF (6 mL) was added EDCI (0.094 g, 0.70 mmol), HOBt (0.133 g, 0.70 mmol), and DIPEA (0.09 mL, 0.53 mmol). The reaction was run as described in Example 101, The crude product was purified by $SiO_2$ chromatography eluting with 2% MeOH/DCM and the resulting material further purified by HPLC on a C-8 column eluting with a MeCN/$H_2O$ gradient containing 0.1% $HCO_2H$ (20 to 98% MECN) to afford 0.010 g (6%) of I-260.

Example 103

N-(6-{(E)-2-[3-tert-Butyl-5-(5-chloro-2-oxo-1,2-dihydro-pyridin-3-yl)-2-methoxy-phenyl]-

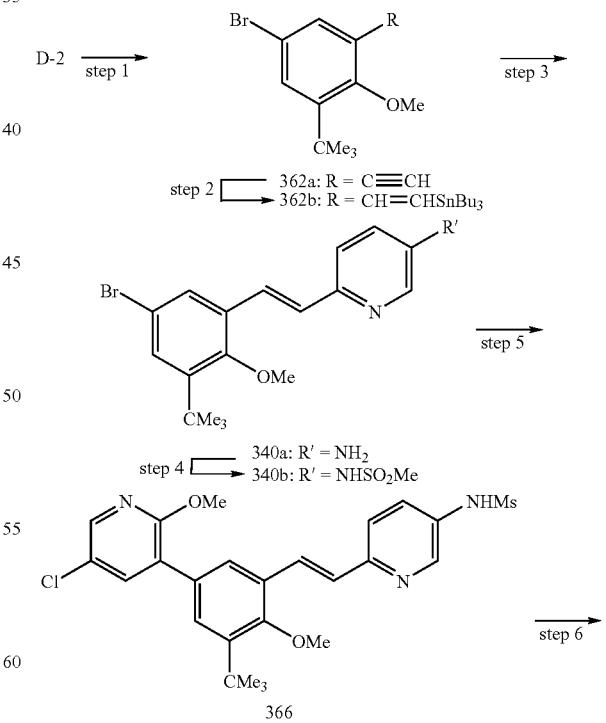

364a can be prepared from D-2 by treating the aldehyde with dimethyl 1-diazo-2-oxopropylphoshonate to form the acetylene (362a, see, e.g. step 3 of Example 9), hydrostannylation of the acetylene and palladium-catalyzed cross-coupling of the vinyl tin 362b and 5-amino 2-iodo-pyridine (e.g., steps 2 and 3 of Example 42).

step 1—: To a solution of 364a (0.50 g, 1.38 mmol) in pyridine (7 mL) at 0° C. was added methanesulfonyl chloride (0.19 g, 1.66 mmol). Stirring was continued at 0° C. for 2 h, followed by 2 h at RT. The reaction mixture was diluted with EtOAc, washed successively with aq. cupric sulfate and 2N HCl, dried ($Na_2SO_4$), filtered and concentrated. The crude residue was purified by $SiO_2$ chromatography eluting with EtOAc/hexane to afford 0.55 g (91%) of 364b as a white solid.

step 2—A mixture of 364b (0.10 g, 0.23 mmol), 5-chloro-2-methoxy-3-pyridineboronic acid (0.051 g, 0.27 mmol), $Pd(PPh_3)_4$ (0.026 g, 0.023 mmol) and $Na_2CO_3$ (0.072 g, 0.68 mmol) in DCM-MeOH (3:1, 4 mL) was irradiated in a microwave reactor at 115° C. for 45 min. The reaction mixture was filtered and the filtrate concentrated. The crude residue so obtained was purified by $SiO_2$ chromatography eluting with EtOAc/hexane to afford 0.072 g (63%) of 366 as a yellow solid.

step 3—A solution of 366 (0.072 g, 0.14 mmol) in HOAc (1 mL) was treated with 48% HBr (0.081 mL) and was heated in a sealed tube at 70° C. for 15 h. The reaction mixture was cooled to RT, diluted with EtOAc, and washed successively with water and sat'd. aq. $NaHCO_3$. The organic layer was dried ($Na_2SO_4$), filtered and concentrated. The crude residue was purified by trituration (DCM/hexane) to afford 0.052 g (73%) of I-261 as a white solid.

N-(6-{(E)-2-[3-tert-butyl-2-methoxy-5-(6-methyl-2-oxo-1,2-dihydro-pyridin-3-yl)-phenyl]-vinyl}-pyridin-3-yl)methanesulfonamide (I-262) was prepared analogously except in step 2, 5-chloro-2-methoxy-3-pyridineboronic acid was replaced with 2-methoxy-5-methyl-pyridin-3-yl boronic acid Example 104

N-(4-{(E)-2-[3-tert-butyl-2-methoxy-5-(6-methyl-2-oxo-1,2-dihydropyridin-3-yl)phenyl]vinyl}phenyl)methanesulfonamide (I-262)

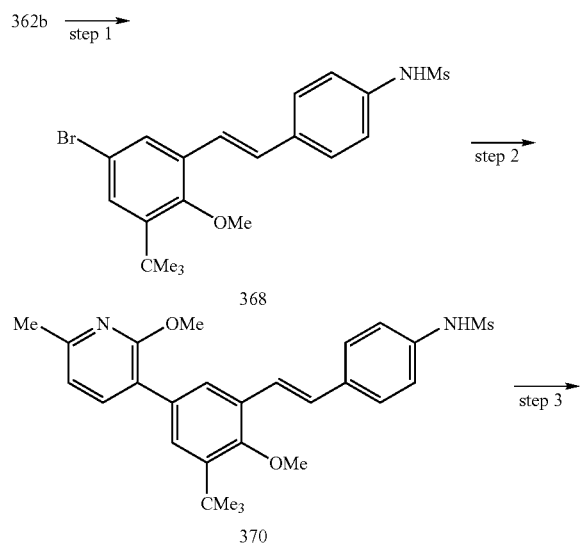

368 can be prepared from 362b by a palladium-catalyzed cross-coupling (step 1) of the vinyl tin 362b and N-(4-iodophenyl)methanesulfonamide (CASRN 102294-59-7) according to step 3 of Example 42).

step 2: A mixture of 368 (0.19 g, 0.42 mmol), 2-methoxy-6-methyl-3-pyridineboronic acid (0.085 g, 0.51 mmol), $Pd(PPh_3)_4$ (0.049 g, 0.042 mmol) and $Na_2CO_3$ (0.135 g, 1.3 mmol) in DCM-MeOH (3:1, 4 mL) was irradiated in a microwave reactor at 115° C. for 60 min. The reaction mixture was filtered and the filtrate concentrated. The crude residue was purified by $SiO_2$ chromatography eluting with EtOAc/hexane to afford 0.092 g (45%) of 370 as a colorless oil.

step 3: Demethylation of the ether was carried out in accord with the procedure described in step 3 of Example 103. The crude residue was purified by trituration with DCM followed by $H_2O$ to afford 0.024 g of I-262 as a white solid.

Example 105

N-(4-{(E)-2-[3-(1-chlorocyclopropyl)-5-(5-fluoro-2-oxo-1,2-dihydropyridin-3-yl)-2-methoxyphenyl]vinyl}-phenyl)methanesulfonamide (I-263)

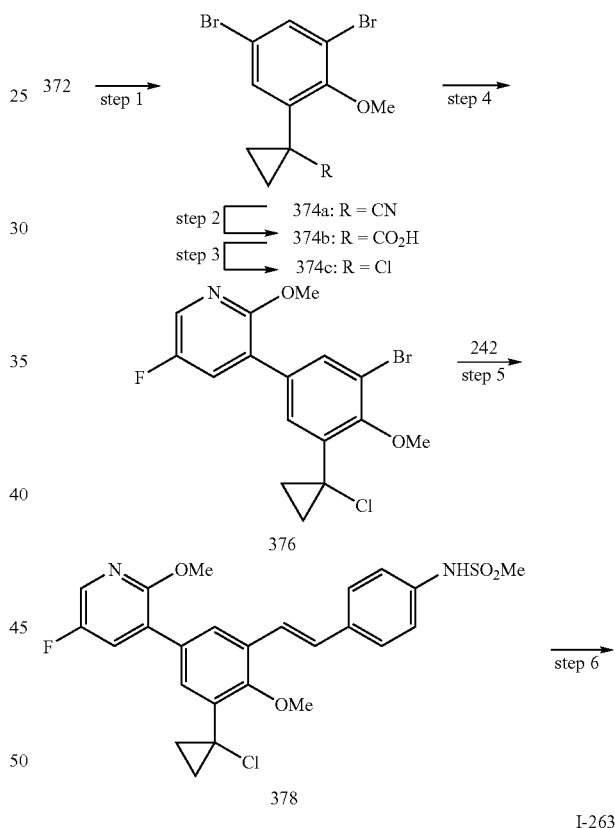

step 1—To a solution of 2,4-dibromo-6-cyanomethylanisole (372, 5.0 g, 16 mmol; CASRN 75098-07-6) in DMF (80 mL) was added sodium hydride (2.0 g, 49 mmol, 60% in mineral oil) and the resulting mixture was stirred at RT until bubbling subsided. To the reaction mixture was then slowly added 1,2-dibromoethane (3.5 g, 18 mmol) and stirring was continued for 1 h. $H_2O$ was added and the mixture extracted with $Et_2O$. The organic extract was washed consecutively with $H_2O$ and brine, dried ($Na_2SO_4$), filtered, and concentrated in vacuo. The crude product was purified by $SiO_2$ chromatography eluting with EtOAc/hexane to afford 4.6 g (85%) of 374a as a light yellow solid.

step 2—To a slurry of 374a (4.6 g, 14 mmol) in EtOH (50 mL) was added aq. solution of NaOH (25%, 22 mL, 140 mmol). The resulting mixture was stirred and heated at reflux for 16 h. The EtOH was removed under reduced pressure, and concentrated aqueous HCl was added at 0° C. to make the solution acidic. The precipitate was recovered by filtration and washed with hexane to afford 4.7 g (98%) of 374b.

step 3—To a slurry of 374b in benzene (150 mL) was added LiCl (1.4 g, 34 mmol), and nitrogen gas was bubbled through the resulting mixture for 10 min. Pb(OAc)$_4$ (15 g, 34 mmol) was added, and nitrogen gas was again bubbled through the resulting mixture for 10 min, followed by heating at reflux for 4 d under nitrogen. After cooling to RT, the mixture was filtered and the solids were washed with EtOAc. Saturated aq. NaHCO$_3$ was added, the mixture was filtered again, and the layers were separated. The organic layer was washed with brine, dried (Na$_2$SO$_4$), filtered, and then concentrated in vacuo. The crude material was purified by SiO$_2$ chromatography eluting with EtOAc/hexane to afford 2.0 g (17%) of 374c.

step 4—Palladium-catalyzed cross-coupling of 372c and 107 was carried out in accord with the procedure described in step 4 of example 38. The crude residue was purified by SiO$_2$ chromatography eluting with EtOAc/hexane to afford 376 as a colorless oil.

step 5—A mixture of 376 (0.15 g, 0.39 mmol), 242 (0.19 g, 0.59 mmol, see example 46), Pd(PPh$_3$)$_4$ (0.045 g, 0.039 mmol) and Na$_2$CO$_3$ (0.12 g, 1.2 mmol) in DCM-MeOH-toluene (1:2:1, 4 mL) was irradiated in microwave reactor at 120° C. for 60 min. The reaction mixture was filtered and the filtrate concentrated. The crude residue was purified by SiO$_2$ chromatography eluting with EtOAc/hexane to afford 0.13 g (64%) of 378 as a yellow oil.

step 6—Demethylation of the ether was carried out in accord with the procedure described in step 3 of Example 103. The crude residue was purified by SiO$_2$ chromatography eluting with DCM/MeOH/ NH$_4$OH), followed by recrystallization from DCM/hexane) to afford 0.057 g (45%) of I-263 as a white solid.

I-264 and I-265 were prepared analogously except in step 6, 107 was replaced by 5-chloro-2-methoxy-3-pyridineboronic acid and -2-methoxy-6-methyl-pyridin-3-yl boronic acid, respectively.

N-(4-{(E)-2-[3-(1-Chloro-cyclopropyl)-5-(5-fluoro-2-oxo-1,2-dihydro-pyridin-3-yl)-phenyl]-vinyl}-phenyl)-methanesulfonamide (I-273) and N-(4-{(E)-2-[3-(1-Chloro-cyclopropyl)-5-(2-oxo-1,2-dihydro-pyridin-3-yl)-phenyl]-vinyl}-phenyl)-methanesulfonamide (I-274) were prepared analogously starting from 1-(3,5-dibromo-phenyl)-cyclopropanecarbonitrile using 107 and 112 to introduce the pyridone ring.

Example 106

N-(4-{(E)-2-[3-(1-methoxycyclopropyl)-5-(2-oxo-1,2-dihydropyridin-3-yl)-2-methoxyphenyl]vinyl}-phenyl)methanesulfonamide (I-266)

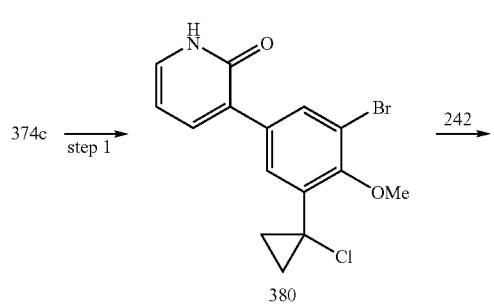

380

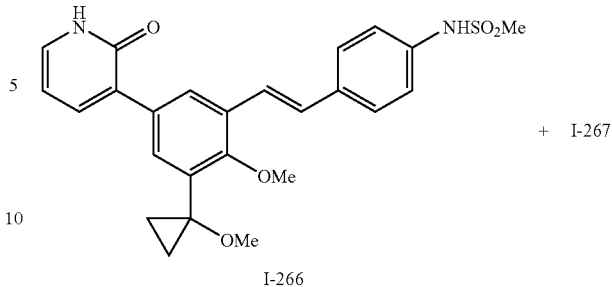

I-266 + I-267 step 1—A mixture of 374c (0.20 g, 0.59 mmol), 112 (0.082 g, 0.59 mmol), Pd(PPh$_3$)$_4$ (0.068 g, 0.059 mmol) and Na$_2$CO$_3$ (0.19 g, 1.8 mmol) in DCM-MeOH (3:1, 4 mL) was irradiated in a microwave reactor at 115° C. for 40 min. The reaction mixture was filtered and the filtrate concentrated. The crude residue was purified by SiO$_2$ chromatography eluting with EtOAc/hexane to afford 0.14 g (67%) of 380.

step 2—A mixture of 380 (0.14 g, 0.39 mmol), 242 (0.19 g, 0.59 mmol), Pd(PPh$_4$ (0.045 g, 0.039 mmol) and Na$_2$CO$_3$ (0.12 g, 1.2 mmol) in DCM-MeOH-toluene (1:2:1, 4 mL) was irradiated in a microwave reactor at 120° C. for 60 min. The reaction mixture was filtered and the filtrate concentrated. The crude product was purified by SiO$_2$ chromatography (DCM/MeOH/NH$_4$OH) followed by preparative HPLC to afford I-266 and I-267.

Example 107

N-(4-{(E)-2-[3-(1-Cyano-cyclopropyl)-2-methoxy-5-(2-oxo-1,2-dihydro-pyridin-3-yl)-phenyl]-vinyl}-phenyl)-methanesulfonamide (I-268)

The title compound was prepared by palladium-catalyzed cross coupling of 374a and 112 in accord with the procedure described is step 2 of Example 1 followed by cross-coupling of the product and 242 in accord with the procedure described in step 2 of Example 206.

Example 108

N-(4-{(E)-2-[3-(1-Difluoromethyl-cyclopropyl)-5-(5-fluoro-2-oxo-1,2-dihydro-pyridin-3-yl)-2-methoxy-phenyl]-vinyl}-phenyl)-methanesulfonamide (I-269)

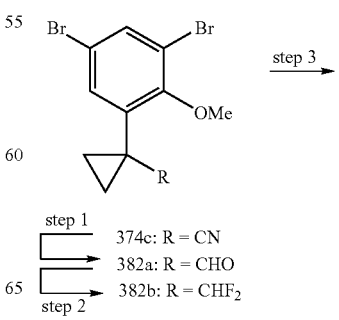

step 1 ⟶ 374c: R = CN
          382a: R = CHO
step 2 ⟶ 382b: R = CHF$_2$

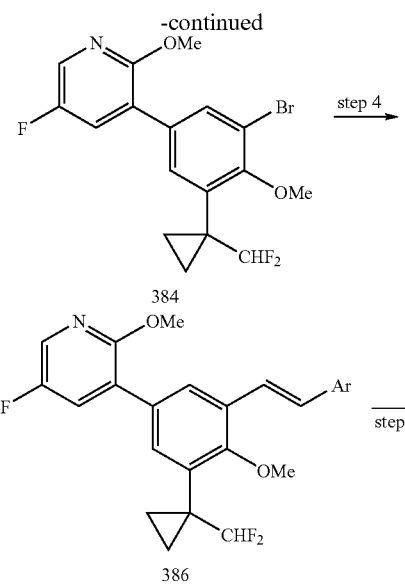

384

386

Ar = 4-methansulfonylamino-phenyl step 1—To a solution of 374c (2.0 g, 6.1 mmol) in DCM (60 mL) cooled to −78° C. was added DIBAL (9.1 mL, 9.1 mmol, 1.0 M solution in toluene). The resulting mixture was stirred at −78° C. for 2 h, then quenched with aq. potassium sodium tartrate. The resulting mixture was warmed to RT and stirred for 16 h. The organic layer was separated, washed with brine, dried (Na$_2$SO$_4$), filtered, and concentrated in vacuo. The crude product was purified by SiO$_2$ chromatography eluting with EtOAc/hexane to afford 1.94 g (95%) of 382a.

step 2—To a solution of 382a (0.97 g, 2.9 mmol) in DCM (14 mL) at RT was added diethylaminosulfur trifluoride (1.1 g, 8.7 mmol), and the resulting mixture was stirred for 16 h. DCM was added, and the mixture was washed sequentially with H$_2$O and brine, dried (Na$_2$SO$_4$), filtered, and concentrated in vacuo. The crude product was purified by SiO$_2$ chromatography eluting with EtOAc/hexane to afford 0.90 g (87%) of 382b.

step 3—Cross coupling of 382b and 107 was carried out as described in step 4 of Example 38. The crude product was purified by SiO$_2$ chromatography eluting with EtOAc/hexane to afford 0.19 g (67%) of 384.

step 4—Cross coupling of 384 and 242 was carried out in accord with the procedure described in step 3 of Example 46. The crude product was purified by SiO$_2$ chromatography eluting with EtOAc/hexane to afford I-386.

step 5—Cleavage of the methyl ether was carried out in accord with the procedure described in step 3 of Example 1. The product was purified by SiO$_2$ chromatography eluting with DCM/MeOH/NH$_4$OH to afford I-269 as a white solid.

I-270 was prepared analogously except in step 3, 107 was replaced with 37.

N-(4-{(E)-2-[3-(1-Difluoromethyl-cyclopropyl)-5-(2-oxo-1,2-dihydro-pyridin-3-yl)-phenyl]-vinyl}-phenyl)-methanesulfonamide I-275 was prepared analogously except 382a was replaced with 1-(3,5-dibromo-phenyl)-cyclopropanecarbaldehyde. The cross-coupling of 1,3-dibromo-5-(1-difluoromethyl-cyclopropyl)-benzene in step 3 was carried out with 112 respectively.

Example 109

N-(4-{(E)-2-[3-(1-Fluoro-cyclobutyl)-5-(2-oxo-1,2-dihydro-pyridin-3-yl)-phenyl]-vinyl}-phenyl)-methanesulfonamide (I-271)

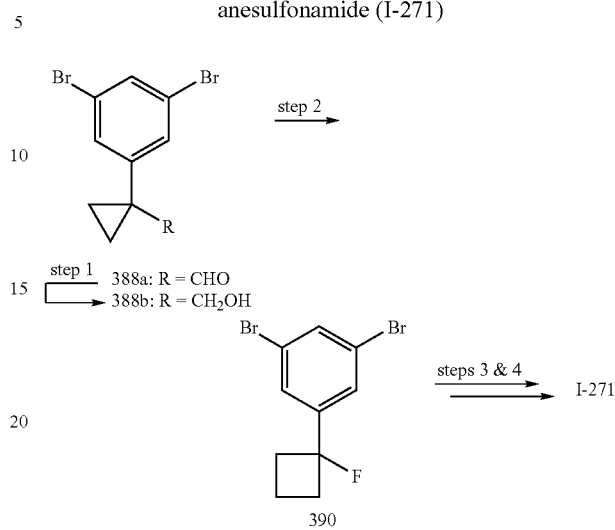

step 1—To a solution of 388a (1.7 g, 5.5 mmol, available by reduction of 374a) in MeOH (25 mL) cooled to 0° C. was added NaBH$_4$ (0.84 g, 22 mmol). The resulting mixture was stirred at 0° C. for 1 h, followed by the addition of sat'd. aq. NaHCO$_3$. MeOH was removed under reduced pressure, and the resulting mixture was partitioned between H$_2$O and EtOAc. The organic extract was washed with brine, dried (Na$_2$SO$_4$), filtered, and concentrated in vacuo. The crude product was purified by SiO$_2$ chromatography eluting with EtOAc/hexane to afford 0.61 g (36%) of 388b.

step 2—To a solution of 388b (0.61 g, 2.0 mmol) in DCM (10 mL) at −78° C. was added dropwise diethylaminosulfur trifluoride (0.49 g, 3.0 mmol), and the resulting mixture was stirred for 4 h. Water was added, and the mixture diluted with DCM. The organic layer was washed sequentially with water and brine, dried (Na$_2$SO$_4$), filtered, and concentrated in vacuo. The crude product was purified by SiO$_2$ chromatography eluting with hexane to afford 0.45 g (73%) of 390 as a colorless oil.

Palladium-catalyzed cross-coupling of 390 and 112 (step 3) was carried out in accord with the procedure described in step 2 of Example 1 to afford 3-[3-bromo-5-(1-fluorocyclobutyl)phenyl]-1H-pyridin-2-one (392) as an oil. Palladium-catalyzed cross-coupling of 392 and 242 (step 4) was carried out in accord with the procedure in step 3 of Example 46 to afford I-271 which was purified by SiO$_2$ chromatography eluting with DCM/MeOH/NH$_4$OH.

Example 110

N-(4-{(E)-2-[3-(2-Hydroxy-1,1-dimethyl-ethyl)-5-(2-oxo-1,2-dihydro-pyridin-3-yl)-phenyl]-vinyl}-phenyl)-methanesulfonamide (I-272)

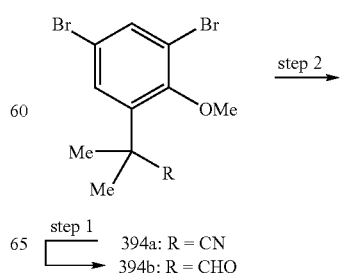

207

-continued

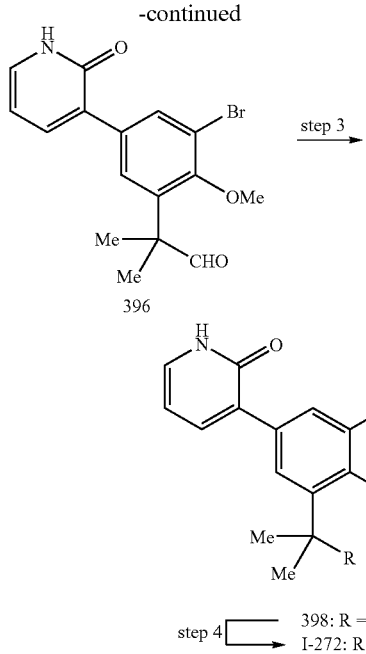

Ar = 4-methansulfonylamino-phenyl step 1—To a solution of 394a (1.4 g, 4.6 mmol; see WO2009/3999) in DCM (40 mL) cooled to −78° C. was added a solution of DIBAL (5.6 mL, 5.6 mmol, 1.0 M solution in toluene). The resulting mixture was stirred at −78° C. for 2 h, followed by the addition of 2 N aq. HCl. The resulting mixture was extracted with DCM and the organic layer was washed with brine, dried ($Na_2SO_4$), filtered, and concentrated in vacuo. The crude product was purified by $SiO_2$ chromatography eluting with EtOAc/hexane to afford 1.2 g (85%) of 394b as a colorless oil which solidified on standing.

step 2—Palladium-catalyzed cross-coupling of 394b and 112 was carried out in accord with the procedure described in step 2 of Example 1. The crude product was purified by $SiO_2$ chromatography eluting with DCM/MeOH/$NH_4OH$ to afford 396.

step 3: A mixture of 396 (0.53 g, 1.7 mmol), 242 (0.54 g, 1.7 mmol), Pd(PPh$_3$)$_4$ (0.19 g, 0.17 mmol) and $Na_2CO_3$ (0.53 g, 5.1 mmol) in DCM-MeOH (3:1, 10 mL) was irradiated in a microwave reactor at 115° C. for 40 min. The reaction mixture was filtered and the filtrate concentrated. The crude residue was subjected to $SiO_2$ chromatography eluting with EtOAc/hexane to afford impure N-(4-{(E)-2-[3-(1,1-dimethyl-2-oxoethyl)-2-methoxy-5-(2-oxo-1,2-dihydro-pyridin-3-yl)phenyl]vinyl}phenyl)methanesulfonamide, which was immediately dissolved in MeOH (5 mL) and treated with NaBH$_4$ (0.25 g, 6.6 mmol). The resulting mixture was stirred at RT for 1 h, then the MeOH was removed under reduced pressure, and the residue dissolved in DCM. The DCM solution was washed sequentially with sat'd. aq. $NH_4Cl$ and brine, dried ($Na_2SO_4$), filtered, and concentrated in vacuo. The crude product was purified by $SiO_2$ chromatography eluting with EtOAc/hexane/$NH_4OH$ to afford N-(4-{(E)-2-[3-(2-hydroxy-1,1-dimethylethyl)-5-(2-oxo-1,2-dihydropyridin-3-yl)phenyl]vinyl}phenyl)-methanesulfonamide (0.067 g).

208

Example 111

N-[3-tert-Butyl-2-methoxy-5-(2-oxo-1,2-dihydro-pyridin-3-yl)-phenyl]-4-methanesulfonylamino-2-(2-methoxy-ethoxy)-benzamide (I-276)

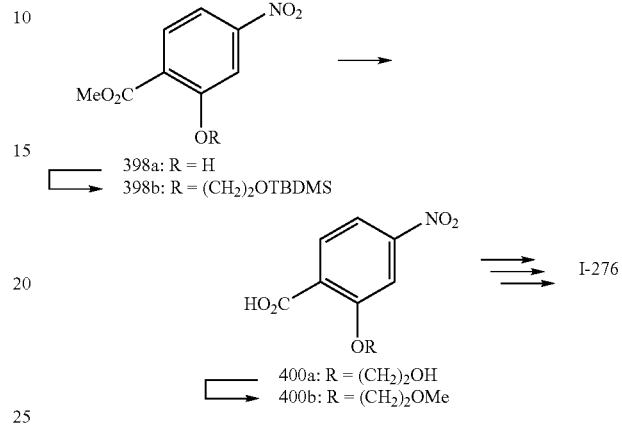

step 1—To a solution of 398a (0.65 g, 3.3 mmol) in DMF (15 mL) was added $K_2CO_3$ (0.68 g, 4.9 mmol), and the resulting mixture was stirred at RT for 30 min. A solution of (2-bromoethoxy)-tert-butyldimethylsilane (1.2 g, 4.9 mmol, CASRN 86864-60-0) in DMF (3 mL) was added to the thick red slurry and the resulting mixture was stirred at 100° C. for 15 h. The reaction mixture was cooled to RT, diluted with $H_2O$, and extracted with $Et_2O$. The organic extracts were washed brine, dried ($Na_2SO_4$), filtered and concentrated. The crude product was purified by $SiO_2$ chromatography eluting with EtOAc/hexane to afford 0.92 g (78%) of 398b as a yellow solid.

step 2—To a solution of 398b (0.50 g, 1.4 mmol) in THF/MeOH (5:1, 6 mL) was added 2.5 N aq. NaOH (1.1 mL), and the resulting mixture was stirred at RT for 1 h. The reaction mixture was made acidic by the addition of 2 N aq. HCl. Diatomaceous earth was added, and mixture was filtered over diatomaceous earth. The filtrate was dried ($Na_2SO_4$), filtered, and concentrated in vacuo to afford 400a.

step 3—To a solution of 400a (0.50 g, 2.2 mmol) in DMF (5 mL) at 0° C. was added sodium hydride (0.88 g, 22 mmol, 60% dispersion in mineral oil,) and the resulting mixture was stirred at 0° C. for 30 min. To the mixture was added iodomethane (1.6 g, 11 mmol), followed by DMF (5 mL), and the resulting mixture was stirred at RT for 60 h. To the mixture was added 2 N aq. HCl and the resulting solution extracted with $Et_2O$. The organic extracts were concentrated in vacuo, and the residue was dissolved in 2.5 N aq. NaOH. The aqueous layer was washed with $Et_2O$, then made acidic by the addition of 2 N aq. HCl. The precipitate was recovered by filtration and then dried in a vacuum oven to afford 0.38 g (72%) of 400b.

The acid was converted to the corresponding acid chloride and condensed with 100 as described in step 3 of Example 12. Reduction of the nitro substituent, condensation of the corresponding amine with mesyl chloride and cleavage of the methyl ether was carried out in accord with the procedures in steps 4 to 6 of Example 12 to afford I-276.

Example 112

N-(4-{2-[3-tert-Butyl-4-fluoro-2-methoxy-5-(2-oxo-1,2-dihydro-pyridin-3-yl)-phenyl]-ethyl}-phenyl)-methanesulfonamide (I-287)

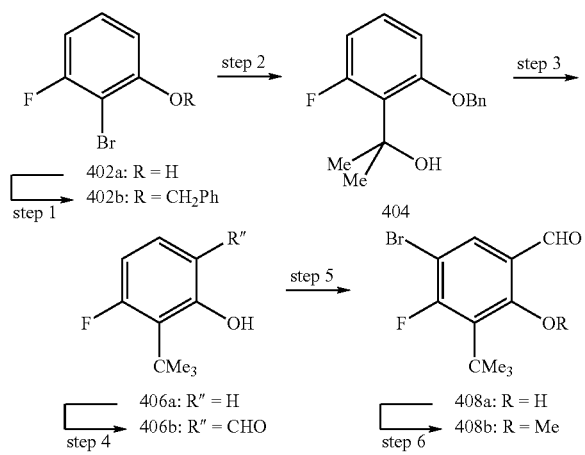

step, 1—To a solution of 402a (4.0 g, 21 mmol) in acetone (100 mL) was added benzyl bromide (5.0 g, 29 mmol) and K₂CO₃ (7.2 g, 52 mmol), and the resulting mixture was stirred at reflux for 15 h. The reaction mixture was cooled to RT and the acetone was removed in vacuo. The residue was partitioned between H₂O and EtOAc, and the organic layer washed sequentially with water and brine, dried (Na₂SO₄), filtered, and then concentrated in vacuo. The crude product was purified by SiO₂ chromatography eluting with EtOAc/hexane to afford 5.8 g (98%) of 402b as a light yellow oil.

step 2—To a solution of 402b (5.9 g, 20 mmol) in THF (24 mL) at −76° C. was added dropwise n-butyllithium (9.5 mL, 24 mmol, 2.5 M solution in hexane). The resulting mixture was stirred at −76° C. for 1 h, followed by dropwise addition of acetone (1.5 g, 26 mmol). Stirring was continued at −76° C. for 15 min then warmed to RT and stirred for an additional 1 h. The mixture was cooled to 0° C. and quenched with H₂O. The mixture was extracted with EtOAc, washed sequentially with H₂O and brine, dried (Na₂SO₄), filtered, and then concentrated in vacuo. The crude product was purified by SiO₂ chromatography eluting with EtOAc/hexane to afford 3.7 g (72%) of 404 as a light yellow oil.

step 3—To a solution of 404 (3.7 g, 14 mmol) in DCM(3 mL) at −76° C. was added dropwise TiCl₄ (5.4 g, 29 mmol). The resulting mixture was stirred at −76° C. for 1.5 h, followed by dropwise addition of Me₂Zn (57 mL, 57 mmol, 1.0 M solution in heptane). The resulting mixture was warmed to RT, stirred for an additional 3.5 h, then poured into an ice/water mixture and stirred for 30 min. The mixture was extracted with DCM, and the organic layer was dried (Na₂SO₄), filtered, and then concentrated in vacuo. The crude product was purified by SiO₂ chromatography eluting with EtOAc/hexane to afford 0.57 g (20%) of 406a as a yellow oil.

step 4—To a solution of 406a (0.40 g, 2.0 mmol) in MeCN (5 mL) was added paraformaldehyde (0.41 g, 14 mmol), MgCl₂ (0.29 g, 3.0 mmol) and TEA (0.77 g, 7.6 mmol). The resulting suspension was stirred and heated at reflux for 15 h. Upon cooling to RT, the mixture was partitioned between 1 M aq. HCl and DCM, and the organic layer was dried (Na₂SO₄), filtered, and concentrated in vacuo. The crude material was purified by SiO₂ chromatography eluting with EtOAc/hexane to afford 0.27 g (62%) of 406b as a yellow oil.

step 5—To a solution of 406b (0.27 g, 1.2 mmol) in DCM/MeOH (3:2, 13 mL) was added tetrabutylammonium tribromide (0.63 g, 1.3 mmol). The resulting orange solution was stirred at RT for 3.5 h, followed by removal of the solvents in vacuo. The mixture was partitioned between EtOAc and H₂O, and the organic layer was washed sequentially with water and brine, dried (Na₂SO₄), filtered, and then concentrated in vacuo. The crude product was purified by SiO₂ chromatography eluting with EtOAc/hexane to afford 0.12 g (35%) 408a as a brown solid.

step 6—To a solution of 408a (0.12 g, 0.43 mmol) in DMF (2 mL) was added K₂CO₃ (0.15 g, 1.1 mmol) and iodomethane (0.091 g, 0.64 mmol). The resulting light brown suspension was stirred at 60° C. for 2 h then cooled to RT. The mixture was partitioned between Et₂O and H₂O, and the organic layer was then washed sequentially with H₂O and brine, dried (Na₂SO₄), filtered, and concentrated in vacuo to 0.12 g (95%) of 408b.

The conversion of 408b to I-287 utilizing the Wadsworth-Emmons condensation of diethyl 4-nitrobenzylphosphate was carried out in accord with the procedure in step 2 of Example 32. Cross-coupling with 37 was carried out as described in step 2 of Example 1. Reduction of the nitro group, introduction of the sulfonamide and cleavage of the methyl ether were carried out as described in steps 2-4 of Example 6 to afford the title compound.

Example 113

N-(4-{(E)-2-[2-Methoxy-3-(1-methoxy-1-methyl-ethyl)-5-(2-oxo-1,2-dihydro-pyridin-3-yl)-phenyl]-vinyl}-phenyl)-methanesulfonamide (I-289)

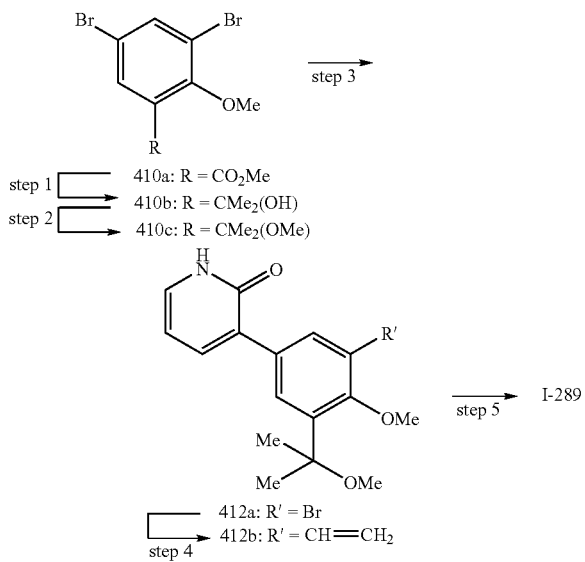

step 1—To a solution of 410a (1.5 g, 4.6 mmol, CASRN 15790-59-7) in THF (25 mL) cooled to 0° C. was added dropwise MeMgBr (4.8 mL, 14.4 mmol, 3.0 M in Et₂O). The resulting mixture was stirred for 1 h then quenched with sat'd. aq. NH₄Cl and extracted with EtOAc. The organic layer was then washed sequentially with H₂O and brine, dried (Na$_2$SO$_4$), filtered, and then concentrated in vacuo to afford 1.5 g (96%) of 410b as a yellow oil.

step 2—To a solution of 410b (1.2 g, 3.6 mmol) in THF (30 mL) cooled to 0° C. was added sodium hydride (0.18 g, 4.4 mmol, 60% dispersion in mineral oil). The resulting mixture was stirred at 0° C. for 40 min then iodomethane (0.62 g, 4.4 mmol) was added. The reaction was warmed to RT and stirred for 60 h. Additional sodium hydride (0.087 g, 2.2 mmol) and iodomethane (0.31 g, 2.2 mmol) were added and the mixture was then stirred at 60° C. for 16 h. The reaction mixture was cooled to RT, partitioned between EtOAc and H$_2$O. The organic extract was washed sequentially with H$_2$O and brine, dried (Na$_2$SO$_4$), filtered and concentrated in vacuo. The crude product was purified by SiO$_2$ chromatography eluting with EtOAc/hexane to afford 0.55 g (45%) of 410c as a light yellow oil.

step 3—A mixture of 410c (0.42 g, 1.2 mmol), 112 (0.16 g, 1.2 mmol), Pd(PPh$_3$)$_4$ (0.14 g, 0.12 mmol) and Na$_2$CO$_3$ (0.38 g, 3.6 mmol) in DCM-MeOH (3:1, 12 mL) was irradiated in a microwave reactor to 115° C. for 30 min. The reaction mixture was cooled, concentrated and then partitioned between DCM and H$_2$O. The organic extract was washed sequentially with H$_2$O and brine, dried (Na$_2$SO$_4$), filtered, and concentrated in vacuo. The crude product was purified by SiO$_2$ chromatography eluting with EtOAc/hexane to afford 0.31 g (74%) of 412a as a light yellow solid.

step 4: A mixture of 412a (0.11 g, 0.31 mmol), potassium vinyltrifluoroborate (0.16 g, 1.2 mmol), Pd(PPh$_3$)$_4$ (0.036 g, 0.031 mmol) and Na$_2$CO$_3$ (0.099 g, 0.93 mmol) in DCM-MeOH (3:1, 4 mL) was irradiated in a microwave reactor at 115° C. for 50 min. The reaction mixture was cooled, concentrated and then partitioned between EtOAc and H$_2$O. The organic extract was washed sequentially with H$_2$O and brine, dried (Na$_2$SO$_4$), filtered, and concentrated in vacuo. The crude product was purified by SiO$_2$ chromatography eluting with EtOAc/hexane to afford 0.063 g (61%) of 412b as a yellow oil.

step 5—A mixture of 412b (0.063 g, 0.21 mmol), 303 (0.069 g, 0.23 mmol), trans-dichlorobis(tri-ortho-tolylphosphine) palladium (II) (0.008 g, 0.010 mmol), TEA (0.043 g, 0.42 mmol) and tetrabutylammonium bromide (0.014 g, 0.043 mmol) was heated in a sealed tube at 120° C. for 15 h. The reaction mixture was cooled, partitioned between DCM and an aqueous acetate buffer (pH 4.6). The organic extract was then dried (Na$_2$SO$_4$), filtered, and concentrated in vacuo. The crude product was purified by SiO$_2$ chromatography eluting with MeOH/DCM to afford 0.010 g (10%) of I-289 as a brown powder.

Example 114

N-(4-{(E)-2-[3-(2-Hydroxy-1,1-dimethyl-ethyl)-2-methoxy-5-(2-oxo-1,2-dihydro-pyridin-3-yl)-phenyl]-vinyl}-phenyl)-methanesulfonamide (I-288)

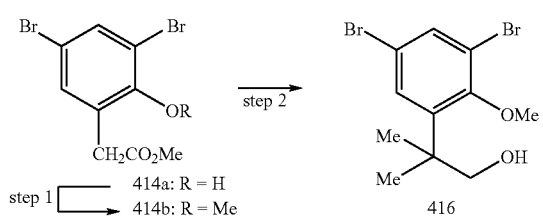

step 1—To a solution of 414a (0.65 g, 2.0 mmol, CASRN 21891-69-0) in DMF (7 mL) cooled to 0° C. was added sodium hydride (0.27 g, 6.8 mmol, 60% dispersion in mineral oil). The resulting mixture was stirred for 15 min then iodomethane (1.1 g, 8.0 mmol), was added and the reaction stirred for 2 h at to RT, and then for 1 h at 50° C. The reaction mixture was then partitioned between Et$_2$O and H$_2$O. The organic extract was washed sequentially with H$_2$O and brine, dried (Na$_2$SO$_4$), filtered, and concentrated in vacuo. The crude product was purified by SiO$_2$ chromatography eluting with EtOAc/hexane to afford 414b as a pale yellow oil.

step 2—To a solution of 414b (0.59 g, 1.6 mmol) in THF (8 mL) cooled to 0° C. was added dropwise LiALH$_4$ (1.7 mL, 1.7 mmol, 1 M solution in THF). The reaction mixture was stirred at 0° C. for 90 min, and then sat'd. aq. potassium sodium tartrate was added and the resulting mixture was stirred at RT for 2 h. The mixture was extracted with EtOAc and the organic extract washed sequentially with H$_2$O and brine, dried (Na$_2$SO$_4$), filtered, and concentrated in vacuo. The crude product was purified by SiO$_2$ chromatography eluting with EtOAc/hexane to afford 0.21 g (39%) of 416 as a colorless oil. Conversion of 416 to the title compound was carried out as described in steps 3 to 5 of Example 113

Example 115

N-(4-{(E)-2-[2-Methoxy-3-(3-methyl-oxetan-3-yl)-5-(2-oxo-1,2-dihydro-pyridin-3-yl)-phenyl]-vinyl}-phenyl)-methanesulfonamide (I-290)

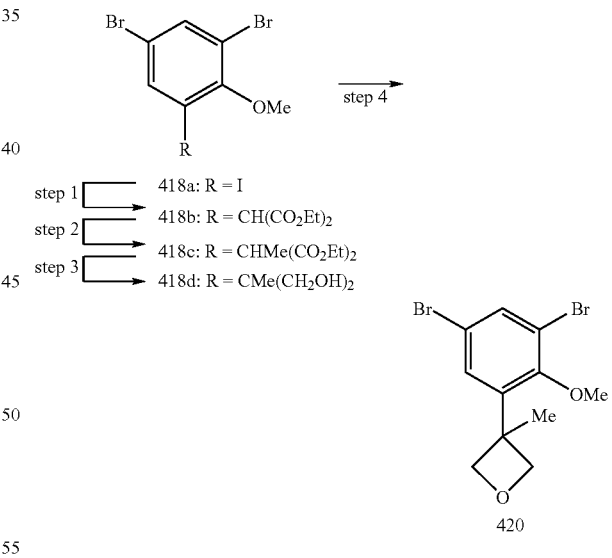

step 1—A mixture of 418a (5.4 g, 14 mmol; CASRN 861792-38-3), diethyl malonate (4.0 g, 25 mmol), CuI (0.13 g, 0.69 mmol), 2-phenylphenol (0.24 g, 1.4 mmol) and cesium carbonate (6.8 g, 21 mmol) in THF (14 mL) was stirred at 70° C. for 15 h. The resulting mixture was cooled to RT and partitioned between EtOAc and sat'd. aq. NH$_4$Cl. The organic extract was then washed sequentially with H$_2$O and brine, dried (Na$_2$SO$_4$), filtered, and concentrated in vacuo. The crude product was purified by SiO$_2$ chromatography eluting with EtOAc/hexane to afford 41 g (55%) of 418b as a pale yellow oil.

step 2—To a suspension of sodium hydride (0.86 g, 22 mmol, 60% dispersion in mineral oil) in THF (50 mL) cooled to 0° C. was added dropwise a solution of 418b (4.1 g, 7.7 mmol) in THF (10 mL). The resulting mixture was stirred at 0° C. for 20 min then iodomethane (3.6 g, 26 mmol) was added dropwise and the reaction warmed to RT and stirred for 48 h. The reaction mixture was partitioned between Et$_2$O and sat'd. aq. NH$_4$Cl. The organic extract was washed sequentially with H$_2$O and brine, dried (Na$_2$SO$_4$), filtered, and concentrated in vacuo. The crude product was purified by SiO$_2$ eluting with EtOAc/hexane to afford 2.9 g (84%) of 418c as a pale yellow oil.

step 3—To a solution of 418c (1.9 g, 4.4 mmol) in THF (9 mL) cooled to 0° C. was added dropwise LiAlH$_4$ (5.3 mL, 5.3 mmol, 1.0M solution in THF). The reaction mixture was stirred at 0° C. for 1 h, and then sat'd. aq. potassium sodium tartrate was added and the resulting mixture was stirred at RT for 2 h. The mixture was extracted with EtOAc, and the organic extract washed sequentially with H$_2$O and brine, dried (Na$_2$SO$_4$), filtered, and concentrated in vacuo. The crude product was purified by SiO$_2$ chromatography eluting with EtOAc/hexane to afford 0.68 g (44%) of 418d as a pale yellow oil.

step 4—A tube was charged with 418d (0.67 g, 1.9 mmol) and PPh$_3$ (1.0 g, 3.8 mmol), flushed with argon and sealed. A solution of diisopropyl azodicarboxylate (0.77 g, 3.8 mmol) and toluene (10 mL) was added via syringe and the resulting mixture was irradiated in a microwave reactor at 140° C. for 30 min. The reaction mixture was concentrated in vacuo and the crude product purified by SiO$_2$ chromatography eluting with EtOAc/hexane to afford 0.26 g (41%) 420 as a colorless oil.

Conversion of 420 to the I-290 was carried out as described in steps 3 to 5 of Example 113. I-291 was prepared analogously except in the step corresponding to step 3 of Example 113, 112 was replaced with 5-chloro-2-methoxy-pyridin-3-yl boronic acid.

Example 116

N-(4-{(E)-2-[4-Methoxy-3,3-dimethyl-7-(2-oxo-1,2-dihydro-pyridin-3-yl)-indan-5-yl]-vinyl}-phenyl)-methanesulfonamide (II-5)

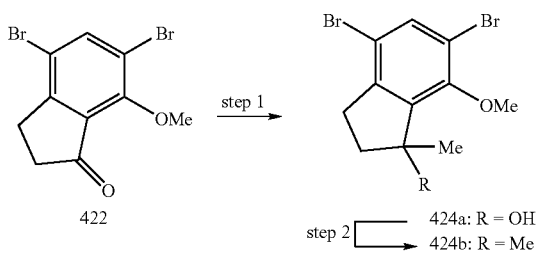

step 1—To a solution of 422 (1.5 g, 4.7 mmol; CASRN 125714-97-8) in THF (25 mL) cooed to 0° C. was added dropwise MeMgBr (3.2 mL, 9.6 mmol, 3M solution in Et$_2$O). The resulting mixture was stirred at 0° C. for 4 h and then at RT for 15 h. The reaction was quenched by adding sat'd. aq. NH$_4$Cl and extracted with EtOAc. The organic extract was then washed sequentially with H$_2$O and brine, dried (Na$_2$SO$_4$), filtered and concentrated in vacuo. The crude product was purified by SiO$_2$ chromatography eluting with EtOAc/hexane to afford 0.47 g (30%) of 424a as a yellow oil.

step 2—To a solution of 424a (0.45 g, 1.3 mmol) in DCM (5 mL) cooled to −76° C. was added dropwise titanium (IV) chloride (0.50 g, 2.7 mmol). The resulting mixture was stirred at −76° C. for 1.5 h then ZnMe$_2$ was added dropwise (5.3 mL, 5.3 mmol, 1.0 M solution in heptane). The resulting mixture was warmed to RT, stirred for an additional 3.5 h, then poured into an ice/H$_2$O mixture and stirred for 20 min. The mixture was extracted with DCM and the organic extract was washed with brine, dried (Na$_2$SO$_4$), filtered and concentrated in vacuo. The crude product was purified by SiO$_2$ chromatography eluting with hexane to afford 0.36 g (81%) of 424b as a colorless oil.

Conversion of 424b to the II-50 was carried out as described in steps 3 to 5 of Example 113.

Example 117

N-(4-{(E)-2-[5-(5-Chloro-2-oxo-1,2-dihydro-pyridin-3-yl)-3-cyclopropyl-2-methoxy-phenyl]-vinyl}-phenyl)-methanesulfonamide (I-292)

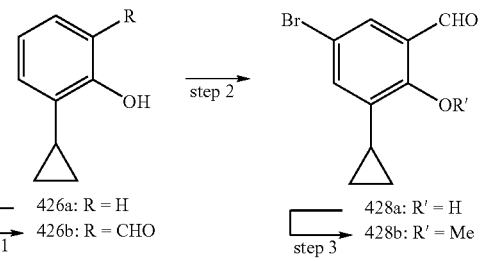

step 1—To a solution of 426a (0.44 g, 3.3 mmol) in MeCN (7 mL) was added paraformaldehyde (0.66 g, 22 mmol), MgCl$_2$ (0.47 g, 4.9 mmol) and TEA (1.2 g, 12 mmol). The resulting suspension was stirred and heated at reflux for 7 h. The reaction mixture was cooled to RT and partitioned between 1 M aq. HCl and DCM. The organic extract was dried (Na$_2$SO$_4$), filtered and concentrated in vacuo. The crude product was purified by SiO$_2$ chromatography eluting with EtOAc/hexane to afford 0.27 g (62%) of 426b as a light yellow oil.

step 2—To a solution of 426b (0.39 g, 2.4 mmol) in DCM/MeOH (3:2, 25 mL) was added tetrabutylammonium tribromide (1.2 g, 2.5 mmol). The resulting orange solution was stirred at RT for 1.5 h, followed by removal of the solvents under reduced pressure. The residue was partitioned between DCM and H$_2$O, and the organic layer was dried (Na$_2$SO$_4$), filtered and concentrated in vacuo. The crude product was purified by SiO$_2$ chromatography eluting with EtOAc/hexane to afford 0.58 g (95%) of 428a as a yellow solid.

step 3—To a solution of 428a (0.58 g, 2.3 mmol) in DMF (6 mL) was added K$_2$CO$_3$ (0.83 g, 6.0 mmol) and iodomethane (0.44 g, 3.1 mmol). The resulting light brown suspension was stirred at 60° C. for 2 h the cooled to RT. The mixture was partitioned between Et$_2$O and H$_2$O. The organic extract was washed sequentially with H$_2$O and brine, dried (Na$_2$SO$_4$), filtered, and then concentrated in vacuo to afford 0.60 g (98%) of 428b as a yellow oil.

The conversion of 428a to I-292 utilizing the Wadsworth-Emmons condensation of diethyl 4-nitrobenzylphosphate was carried out in accord with the procedure in step 2 of Example 32. Cross-coupling with 5-chloro-2-methoxy-pyridin-3-yl boronic acid was carried out as described in step 2 of Example 1. Reduction of the nitro group, introduction of the sulfonamide and cleavage of the methyl ether were carried out as described in steps 2-4 of Example 6 to afford the title compound.

Example 118

N-[3-tert-Butyl-5-(2-oxo-1,2-dihydro-pyridin-3-yl)-phenyl]-4-methanesulfonylamino-N-methyl-benzamide (I-293)

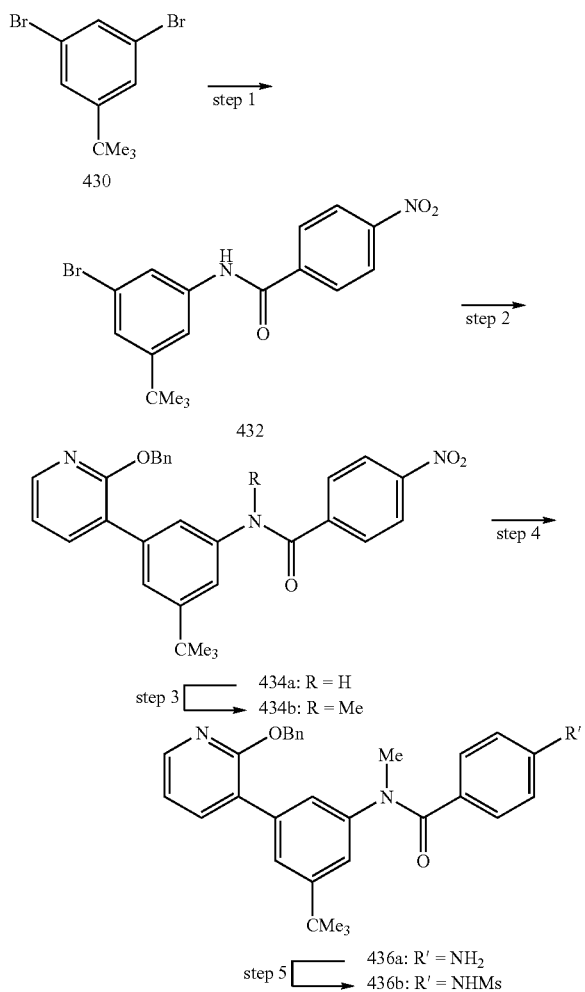

step 1—A tube was charged with of 430 (1.2 g, 4.1 mmol), 4-nitrobenzamide (0.72 g, 4.3 mmol), $K_2CO_3$ (1.15 g, 8.3 mmol), trans-1,2-diaminocyclohexane (0.052 g, 0.45 mmol) and CuI (0.078 g, 0.41 mmol) and dioxane (1 mL), flushed with argon, sealed, and then stirred and heated to 110° C. for 60 h. The reaction mixture cooled and partitioned between $H_2O$ and EtOAc. The organic layer was washed sequentially with $H_2O$ and brine, dried ($Na_2SO_4$), filtered and concentrated in vacuo. The crude product was purified by $SiO_2$ chromatography eluting with EtOAc/hexane to afford 0.40 g (265) of 432 as a yellow solid.

step 2—A mixture of 432 (0.20 g, 0.53 mmol), 141 (0.16 g, 0.69 mmol), $Pd(PPh_3)_4$ (0.061 g, 0.053 mmol) and $Na_2CO_3$ (0.17 g, 1.6 mmol) in DCM-MeOH (3:1, 8 mL) was irradiated in microwave reactor at 115° C. for 30 min. The reaction mixture was cooled, concentrated and partitioned between EtOAc and $H_2O$. The organic layer was washed sequentially with $H_2O$ and brine, dried ($Na_2SO_4$), filtered, and concentrated in vacuo to afford 0.21 g (83%) of 434a as a yellow solid.

step 3—To a solution of 434a (0.11 g, 0.22 mmol) in THF (2.5 mL) was added sodium hydride (0.013 g, 0.32 mmol, 60% dispersion in mineral oil). The resulting mixture was stirred for 15 min then iodomethane (0.062 g, 0.44 mmol) was added and stirring continued for 15 h. The reaction mixture was partitioned between EtOAc and $H_2O$. The organic layer was washed sequentially with $H_2O$ and brine, dried ($Na_2SO_4$), filtered, and concentrated in vacuo. The crude product was purified by $SiO_2$ chromatography eluting with EtOAc/hexane to afford 0.10 g (92%) of 434b as a yellow oil.

step 4—To a suspension of 434b (0.096 g, 0.19 mmol) in MeOH/$H_2O$ (1:1, 2 mL) was added $NH_4Cl$ (0.10 g, 1.9 mmol) and iron powder (0.052 g, 0.93 mmol), and the resulting mixture was stirred at reflux for 15 h. The mixture was filtered through a glass microfibre filter, and the solids rinsed with MeOH, EtOAc and DCM. The filtrate was concentrated and the residue partitioned between DCM and $H_2O$. The organic layer was washed with brine, dried ($Na_2SO_4$), filtered, and concentrated in vacuo. The crude product was purified by $SiO_2$ eluting with EtOAc/hexane to afford 0.085 g (94%) of 436a as a yellow oil.

step 5: To a solution of 436a (0.081 g, 0.17 mmol) in pyridine (1 mL) cooled to 0° C. was added methanesulfonyl chloride (0.024 g, 0.21 mmol). Stirring was continued at 0° C. for 15 min then at RT for 3 h. The reaction mixture was partitioned between aq. $CuSO_4$ and EtOAc. The organic layer was washed sequentially with $H_2O$ and brine, dried ($Na_2SO_4$), filtered and concentrated in vacuo. The crude product was purified by $SiO_2$ chromatography eluting with EtOAc/hexane to afford 0.84 g (89%) of 436b as a light yellow foam.

step 6—A flask containing a solution of 436b (0.081 g, 0.15 mmol) in EtOAc/MeOH (1:4, 5 mL) was evacuated and filled with argon three times, and then 10% Pd/C (0.008 g) was added. The resulting suspension was stirred at RT for 2 h under a $H_2$ atmosphere maintained with a balloon. The mixture was filtered through a glass microfibre filter, the solids rinsed with EtOAc and MeOH and the filtrate concentrated in vacuo to afford 0.64 g (95%) of I-293 as a light yellow powder.

Example 119

N-{3-[3-tert-Butyl-2-methoxy-5-(2-oxo-1,2-dihydro-pyridin-3-yl)-phenyl]-1-ethoxy-isoquinolin-7-yl}-methanesulfonamide (II-9)

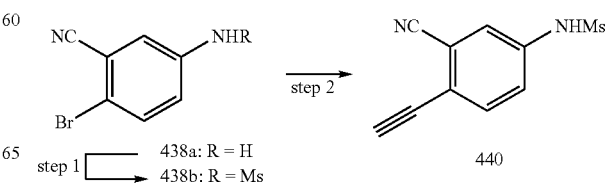

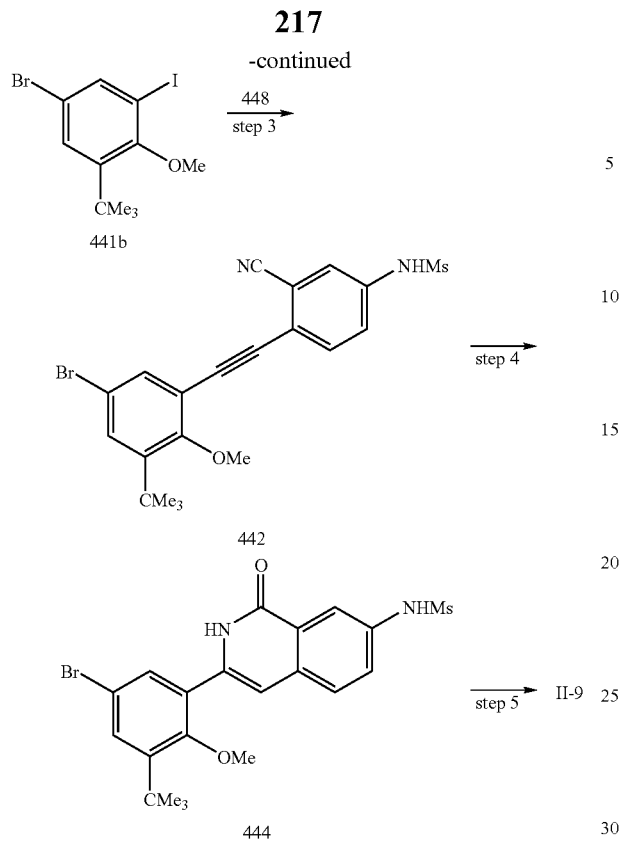

4-bromo-2-tert-butyl-6-iodo-phenol (441b)

To a ice-cold solution of 4-bromo-2-tert-butyl phenol (2.8 g, 86 wt %) dissolved in MeOH containing NaI (3.28 g) and NaOH (0.88 g) was added an aq. solution of NaOCl (4.5 wt %, 68.75 mL). The addition was continued until yellow color persisted (1.6 equivalents). To the resulting solution was added sat'd. aq. Na$_2$SO$_3$ (10 mL) and HOAc (2.5 mL) which resulted in the formation of a precipitate. The MeOH was evaporated and the residue suspended in H$_2$O (50 mL) and aged at 40° C. for 2 h. then slowly cooled to RT. The solid was filtered, washed with H$_2$O and dried in vacuo at 50° C. overnight to afford 6.74 g (87%) of 441a.

step 1—To a solution of 441a (4.40 g, 12.4 mmol), iodomethane (7.7 mL, 17.6 g, 124 mmol) in acetone (80 mL) was added K$_2$CO$_3$ (8.60 g, 62 mmol) and the resulting solution was stoppered and stirred overnight at RT. The reaction mixture was diluted with hexanes (100 mL) and the mixture was filtered over a plug of SiO$_2$. The filtrated was concentrated to afford 4.6 g (100%) of 442b.

step 1—To a mixture of 438a (3.20 g, 16.24 mmol) in DCM (75 mL) cooled to 0° C. was added pyridine (1.51 mL, 19.49 mmol) and followed by MsCl (2.62 mL, 32.49 mmol). The resulting mixture was allowed to warm to RT and stirred for 24 h. The reaction was cooled to 0° C. and quenched with 1N aq. HCl solution. The reaction was concentrated, diluted with H$_2$O and the resulting precipitate filtered and washed with H$_2$O, and dried in vacuo at 45° C. to afford 4.68 g of 438b.

step 2—Conversion of 438b to 440 was carried out in accord with the procedures in steps 4 and 5 of Example 58.

step 3—A solution 440 (440 mg, 2.0 mmol), 441b (880 mg, 2.4 mmol), CuI (19 mg, mmol), PdCl$_2$(PPh$_3$)$_2$ (140 mg, 0.20 mmol), TEA (10 mL) in DMF (20 mL) was stirred at 70° C. for 2 h. The mixture was cooled, quenched with aqueous 1N HCl and twice extracted with EtOAc. The organic extracts were washed sequentially with H$_2$O and brine, dried (MgSO$_4$), filtered and concentrated. The crude material was purified by SiO$_2$ chromatography eluting with an EtOAc/hexane gradient (10% to 70% EtOAc) to afford 468 mg (51%) of 442.

step 4—A solution of 442 (468 mg, 10 mmol) and hydrido (dimethylphosphinous acid-kP) Platinum (86 mg, 0.2 mmol, CASRN 173416-05-2)) in EtOH (40 mL) was heated at reflux for 2 h. The reaction mixture was cooled and concentrated. The crude material was purified by SiO$_2$ chromatography eluting with an EtOAc/hexane gradient (20% to 90% EtOAc) to afford 390 mg (81%) of 444.

step 5—A sealed tube containing the bromide 444 (70 mg, 0.15 mmol), 112 (30 mg, 0.22 mmol), Na$_2$CO$_3$ (46 mg, 0.44 mmol) and Pd(PPh$_3$)$_4$ (17 mg, 0.015 mmol) in MeOH (3 mL) and DCM (1 mL) was irradiated in a microwave reactor at 100° C. for 30 min. The mixture was concentrated and purified by SiO$_2$ chromatography eluting with 10% MeOH/DCM to afford 29.4 mg (40%) of II-9.

Example 120

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from E. coli strain BL21(DE) pLysS. The construct, containing the coding sequence of HCV NS5B Con1 (GenBank accession number AJ242654) was inserted into the plasmid construct pET17b, downstream of a T7 promoter expression cassette and transformed into E. coli. A single colony was grown overnight as a starter culture and later used inoculate 10 L of LB media supplemented with 100 µg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 µl enzymatic reaction contained 20 nM RNA template derived from the complementary sequence of the Internal Ribosome Entry Site (cIRES), 20 nM NS5B570n-Con1 enzyme, 0.5 µCi of tritiated UTP (Perkin Elmer catalog no. TRK-412; specific activity: 30 to 60 Ci/mmol; stock solution concentration from 7.5×10−5 M to 20.6×10−6 M), 1 µM each ATP, CTP, and GTP, 40 mM Tris-HCl pH 8.0, 40 mM NaCl, 4 mM DTT (dithiothreitol), 4 mM MgCl2, and 5 µl of compound serial diluted in DMSO. Reaction mixtures were assembled in 96-well filter plates (cat # MADVNOB, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 μl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode: Normal, Count Time: 1 min, Background Subtract: none, Cross talk reduction: Off).

Data was analyzed in Excel® (Microsoft®) and ActivityBase® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% (IC$_{50}$) was calculated by fitting $$Y = \% \text{ Min} + \frac{(\% \text{ Max} - \% \text{ Min})}{\left[1 + \frac{X}{(IC_{50})^S}\right]} \quad (i)$$

equation (i) to the data.where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

TABLE II contains physical constants and HCV NS5B RNA Polymerase Activity data for compounds in TABLE I.

TABLE II

| Cpd | IC$_{50}$[1] | mp | ms |
|---|---|---|---|
| I-1 | 3.965 | 157.6-159.2 | 228 |
| I-2 | 3.585 | 211.0-212.0 | 244 |
| I-3 | 0.525 | 224.0-225.0 | 242 |
| I-4 | 0.435 | 169.0-170.0 | 258 |
| I-5 | 4.685 | 201.0-202.0 | 272 |
| I-6 | 2.57 | 174.0-175.0 | 294 |
| I-7 | 3.26 | 212.0-213.0 | 256 |
| I-8 | 1.96 | 232.0-233.0 | 276 |
| I-9 | 3.1 | 257.2-257.7 | 336, 338 |
| I-10 | 1.6 | 167.0-168.0 | 274 |
| I-11 | 0.34 | 207.0-208.5 | 258 |
| I-12 | 0.892 | | 272 |
| I-13 | 0.36 | 243.4-246.2 | 322, 324 |
| I-14 | 0.332 | 224.2-226.2 | 272 |
| I-15 | 2.92 | 235.8-237.0 | 320 |
| I-16 | 0.532 | 211.4-213.5 | 278 |
| I-17 | 0.293 | 236.0-237.0 | 334 |
| I-18 | 0.957 | >300 | 316 |
| I-19 | 1.62 | 223.0-224.0 | 341 |
| I-20 | 0.378 | 178.0-179.0 | 366 |
| I-21 | 0.09 | 157.0-158.0 | 380 |
| I-22 | 0.33 | 180.2-181.8 | 330 |
| I-23 | 1.17 | 214.0-215.0 | 274 |
| I-24 | 1.53 | | 399 |
| I-25 | 0.031 | 226.0-228.0 | |
| I-26 | 0.866 | 206.3-207.1 | 288 |
| I-27 | 5.38* | | 268 |
| I-28 | 1.46 | | 254 |
| I-29 | 0.521 | 176.0-178.0 | 272 |
| I-30 | 0.728 | 213.0-214.0 | 286 |
| I-31 | 2.285 | | 399 |
| I-32 | 0.044 | 108.0-110.0 | 455 |
| I-33 | 0.011 | 208.7-211.9 | 455 |
| I-34 | 1.7 | | 405 |

TABLE II-continued

| Cpd | IC$_{50}$[1] | mp | ms |
|---|---|---|---|
| I-35 | 1.23 | | 419 |
| I-36 | 1.05 | | 406 |
| I-37 | 1.01 | | 391 |
| I-38 | 0.932 | | 392 |
| I-39 | 1.34 | | 395 |
| I-40 | 1.6 | | 434 |
| I-41 | 1.51 | | 420 |
| I-42 | 2.47 | | 426 |
| I-43 | 1.75 | | 372 |
| I-44 | 1.2 | | 426 |
| I-45 | 0.786 | 90.0-91.0 | 320 |
| I-46 | 0.534 | 180.0-181.0 | 318 |
| I-47 | 1.2 | | 426 |
| I-48 | 0.528 | 202.6-204.3 | 348 |
| I-49 | 0.071 | 209.0-210.0 | 380 |
| I-50 | 0.052 | 203.0-205.0 | 380 |
| I-51 | 0.01 | 96.4-135.6 | 441 |
| I-52 | 0.143 | 197.1-198.6 | 398 |
| I-53 | 1.93 | 244.0-246.0 | 260 |
| I-54 | 0.009 | 145.0-148.0 | 378 |
| I-55 | 0.059 | 185.0-187.0 | 378 |
| I-56 | 0.136 | 164.5-166.0 | 276 |
| I-57 | 0.061 | 123.3-125.5 | 382 |
| I-58 | 0.034 | 212.0-216.0 | 377 |
| I-59 | 0.009 | 145.0-150.0 | 377 |
| I-60 | 1.09 | | 365 |
| I-61 | 1.229 | 194.0-195.0 | 256 |
| I-62 | 4.13 | 154.0-155.0 | 274 |
| I-63 | 0.01 | 150.0-160.0 | 403 |
| I-64 | 0.008 | 239.0-241.0 | 469 |
| I-65 | 0.03 | 110.0-115.0 | 469 467[3] |
| I-66 | 0.065 | | 391 |
| I-67 | 0.01 | 125.0-130.0 | 473 |
| I-68 | 0.107 | 288.0-290.0 | 377 |
| I-69 | 0.013 | 278.0-280.0 | [484 |
| I-70 | 0.008 | 274.0-276.0 | 470 |
| I-71 | 0.006 | 226.0-228.0 | 457 |
| I-72 | 0.034 | 190.0-193.0 | 392 |
| I-73 | 0.054 | 286.0-288.0 | 458 |
| I-74 | 0.025 | 211.0-213.0 | 425 |
| I-75 | 0.071 | 230.0-232.0 | 484 |
| I-76 | 0.062 | 213.0-216.0 | 484 |
| I-77 | 1.83 | | 398 |
| I-78 | 1.13 | | 421 |
| I-79 | 1.167 | | 391 |
| I-80 | 0.097 | 180.0-182.0 | 482 |
| I-81 | 0.022 | 272.0-274.0 | 488 |
| I-82 | 0.006 | 254.0-256.0 | 468 |
| I-83 | 0.125 | 218.0-220.0 | 389 |
| I-84 | 0.032 | 140.0-145.0 | 378 |
| I-85 | 0.011 | 173.0-174.0 | 454 |
| I-86 | 0.278 | 237.0-239.0 | 404 |
| I-87 | 0.013 | 128.0-130.0 | 450 |
| I-88[4] | 0.129 | | 384 |
| I-89[4] | 0.496 | | 384 |
| I-90 | 1.86 | | 396.1 |
| I-91[4] | 1.48 | | 398.3 |
| I-92[4] | 1.69 | | 426.3 |
| I-93 | 1.9 | | 411.3 |
| I-94 | 0.01 | 191.0-193.0 | |
| I-95 | 0.017 | | 489 |
| I-96 | 0.027 | 133.0-135.0 | 533 |
| I-97 | 0.384 | | 407 |
| I-98 | 0.007 | 140.0-142.0 | 440 |
| I-99 | 0.59 | 209.0-211.0 | 375 |
| I-100 | 0.016 | 261.0-263.0 | 455 |
| I-101 | 0.753 | 136.0-138.0 | 383 |
| I-102 | 0.008 | 120.0-122.0 | 473 |
| I-103 | 0.008 | 111.0-113.0 | 473 |
| I-104 | 0.107 | | 484 |
| I-105 | 6.345 | | 286 |
| I-106 | 0.024 | 110.0-115.0 | 391 |
| I-107 | 2.49 | 252.0-253.0 | 368 |
| I-108 | 0.006 | 192.0-194.0 | 453 |
| I-109 | 0.007 | 240.0-242.0 | 469 |
| I-110 | 0.016 | 114.0-116.0 | 469 |
| I-111 | 0.023 | 290.0-291.0 | 476 |

TABLE II-continued

| Cpd | IC$_{50}$[1] | mp | ms |
|---|---|---|---|
| I-112 | 0.048 | 145.0-147.0 | 484 |
| I-113 | 0.133 | | 450 |
| I-114 | 0.015 | 143.0-145.0 | 451 |
| I-115 | 0.009 | 290.0-292.0 | 514 |
| I-116 | 0.011 | 263.0-265.0 | 504 |
| | | | 506 |
| I-117 | 0.040 | 118.0-120.0 | 462 |
| I-118 | 0.015 | 223.0-225.0 | 485 |
| I-119 | 0.040 | | 462 |
| I-120 | 0.003 | 283.0-285.0 | 410 |
| I-121 | 0.007 | 270.0-272.0 | 488 |
| I-122 | 0.003 | 170.0-172.0 | 468 |
| I-123 | 0.003 | 140.0-142.0 | 456 |
| I-124 | 0.003 | 131.0-133.0 | 456 |
| I-125 | 0.016 | 282.0-283.0 | 457 |
| I-126 | 0.003 | 282.0-284.0 | 453 |
| I-127 | 0.004 | 218.0-220.0 | 457 |
| I-128 | 0.005 | 142.0-144.0 | 379 |
| I-129 | 0.007 | 270.0-272.0 | 488 |
| I-130 | 0.003 | 170.0-172.0 | 468 |
| I-131 | 0.003 | 140.0-142.0 | 456 |
| I-132 | 0.003 | 131.0-133.0 | 456 |
| I-133 | 0.016 | 282.0-283.0 | 457 |
| I-134 | 0.003 | 282.0-284.0 | 453 |
| I-135 | 0.004 | 218.0-220.0 | 457 |
| I-136 | 0.005 | 142.0-144.0 | 379 |
| I-137 | 0.01 | 180.0-182.0 | 439 |
| I-138 | 0.01 | 288.0-290.0 | 478 |
| I-139 | 0.008 | 292.0-294.0 | 467 |
| I-140 | 0.322 | 258.0-260.0 | 453 |
| I-141 | 0.026 | 260.0-262.0 | 423 |
| I-142 | 0.006 | 268.0-270.0 | 471 |
| I-143 | 0.308 | | 453 |
| I-144 | 0.011 | 183.0-185.0 | 360 |
| I-145 | 0.053 | | 483 |
| I-146 | 0.003 | | 441 |
| I-147 | 0.002 | >300 | 448 |
| I-148 | 0.006 | 210.0-212.0 | 441 |
| I-149 | 0.026 | | 483 |
| I-150 | 0.003 | 266.0-268.0 | 478 |
| I-151 | 0.005 | 158.0-160.0 | 496 |
| I-152 | 0.016 | | 539 |
| I-153 | 0.008 | | 511 |
| I-154 | 0.01 | | 525 |
| I-155 | 0.003 | | 497 |
| I-156 | 0.006 | | 529 |
| I-157 | 0.004 | | 571 |
| I-158 | 0.019 | | 481 |
| I-159 | 0.008 | | 467 |
| I-160 | 0.004 | | 524 |
| I-161 | 0.014 | | 487 |
| | | | 489 |
| I-162 | | 148.0-150.0 | 437 |
| I-163 | | | 483 |
| I-164 | | | 497 |
| I-165 | | | 541 |
| I-166 | | 293.0-295.0 | 454 |
| I-167 | 0.021 | | 440 |
| I-168[5] | 0.003 | | 424 |
| I-169 | 0.029 | | 436 |
| I-170 | 0.006 | | 472 |
| I-171 | 0.004 | 283.0-285.0 | 376 |
| I-172 | 0.003 | | 454 |
| I-174 | 0.012 | | 394 |
| I-175 | 0.006 | | 472 |
| I-176 | 0.006 | 128.0-130.0 | 485 |
| I-177 | 0.008 | 198.0-200.0 | 480 |
| I-178 | 0.015 | 178.0-180.0 | 498 |
| I-179 | 0.008 | 206.0-208.0 | 499 |
| I-180 | 0.005 | 285.0-287.0 | 509 |
| I-181 | 0.008 | | 377 |
| I-182 | 0.009 | | 455 |
| I-183 | 0.007 | 250.0-252.0 | 395 |
| I-184 | 0.004 | 270.0-272.0 | 472 |
| I-185 | 0.854 | | 407 |
| I-186 | 0.004* | | 529 |
| I-187 | 0.003* | | 501 |
| I-188 | 0 | | 515 |
| I-189 | 0.001* | | 531 |
| I-190 | 0.001* | | 517 |
| I-191 | 0.027 | 158.0-160.0 | 484 |
| I-192 | 0.028 | | 512 |
| I-193 | 0.012 | 138.0-140.0 | 554 |
| I-194[4] | 0.047 | | 538 |
| I-195 | 0.018 | 133.0-135.0 | 574 |
| I-196 | 0.030 | 158.0-160.0 | 494 |
| I-197 | 0.084 | 240.0-242.0 | 498 |
| I-198 | 0.019 | | 499 |
| I-199 | 0.013 | 118.0-120.0 | 457 |
| I-200 | 0.005 | | 496 |
| I-201 | 0.001* | | 525 |
| I-202 | 0.001* | | 524 |
| I-203 | 0 | 260.0-262.0 | 497 |
| I-204 | 0.001* | | 511 |
| I-205 | 0.002* | 140.0-142.0 | 483 |
| I-206 | 0.002* | | 497 |
| I-207 | 0.004* | | 599 |
| I-208 | 0.001* | 140.0-145.0 | 511 |
| I-209 | 0.001* | 135.0-140.0 | 527 |
| I-210 | 0.001* | 140.0-145.0 | 513 |
| I-211 | 0.004* | >300 | 527 |
| I-212 | 0.009 | 153.0-155.0 | 451 |
| I-213 | 0.003* | 170.0-172.0 | 468 |
| I-214 | 0.005 | 148.0-150.0 | 442 |
| I-215 | 0.002* | | |
| I-216 | 0.006 | | 442 |
| I-217 | 0.005 | | 466 |
| I-218 | 0.069 | | 455 |
| I-219 | 0.008 | | 471 |
| I-220 | 0.004* | 125.0-130.0 | 587 |
| I-221 | 0.005* | 222.0-224.0 | 570 |
| I-222 | 0.011* | 230.0-235.0 | 528 |
| I-223 | 0.001* | 253.0-255.0 | 570 |
| I-224 | 0.001* | 233.0-235.0 | 497 |
| I-225 | 0.004* | 276.0-278.0 | 492 |
| I-226 | 0.006* | | 527 |
| I-226 | 0.003* | >300 | 467 |

TABLE II-continued

| Cpd | IC$_{50}$[1] | mp | ms |
|---|---|---|---|
| I-227 | 0.001* | 125.0-130.0 | 529 |
| I-228 | 0.005* | 266.0-268.0 | 485 |
| I-229 | 0.002* | 255.0-257.0 | 540 |
| I-230 | 0.006* | 150.0-155.0 | 568 |
| I-231 | 0.004* | 212.0-214.0 | 584 |
| I-232 | 0.001* | 191.0-195.0 | 554 |
| I-233 | 0.001* | 175.0-177.0 | 570 |
| I-234 | 0.004* | 240.0-243.0 | 550 |
| I-235 | 0.012* | 150.0-155.0 | 564 |
| I-236 | 0.001* | 280.1-285.6 | 489 |
| I-237 | 0.013* | 98.0-100.0 | 378 |
| I-238 | 0.002* |  | 385 |
| I-239 | 0.008* |  | 429 |
| I-240 | 0.005* |  | 361 |
| I-241 | 0.003* |  | 361 |
| I-242 | 0.002* | 105.0-110.0 | 418 |
| I-243 | 0 | 105.0-110.0 | 402 |
| I-244 | 0.001* | 155.0-160.0 | 438 |
| I-245 | 0.001* |  | 386 |
| I-246 | 0.001* | >300 | 404 |
| I-247 | 0.022 | 182.0-184.0 | 393 |
| I-248 | 0.019 | 188.0-190.0 | 476 |
| I-249[4] | 0.011* | >300 | 467 |
| I-250 | 0.023* | 238.0-240.0 | 497 |
| I-251 | 0.002* | 161.0-162.4 | 492 |
| I-252 | 0.038 | >300 | 411 |
| I-253 | 0.002 | 298.0-300.0 | 474 |
| I-254 | 0.141 | 140.0-142.0 | 451 |
| I-255 | 0.07 | 280.0-282.0 | 433 |
| I-256 | 0.019 | 264.0-266.0 | 432 |
| I-257 | 0.184 | 138.0-140.0 | 467 |
| I-258 | 0.001* | 292.0-294.0 | 488 |
| I-259 | 0.122 | 168.0-170.0 | 470 |
| I-260 | 0.035 | >300 | 476 |
| I-261 | 0.003* |  | 488 |
| I-262 | 0.001* |  | 467 |
| I-263 | 0.002* |  | 489 |
| I-264 | 0.005* |  | 505 |
| I-265 | 0.005* |  | 485 |
| I-266 | 0.003* |  | 467 |
| I-267 | 0.001* |  | 471 |
| I-268 | 0 |  | 462 |
| I-269 | 0.003* |  | 505 |
| I-270 | 0.001* |  | 487 |
| I-271 | 0.004* |  | 439 |
| I-272 | 0.006* |  | 439 |
| I-273 | 0.003* |  | 459 |
| I-274 | 0.002* |  | 441 |
| I-275 | 0.001* | 168.0-170.0 | 457 |
| I-276 | 0.02 |  | 544 |
| I-277 | 0.357 |  | 434 |
| I-278 | 0.014I | 292.0-294.0 | 406 |
| I-279 | 0.104 | 271.0-272.0 | 460 |
| I-280 | 0.010 | 273.0-275.0 | 410 |
| I-281 | 0.007 | 273.0-275.0 | 488 |
| I-282 | 0.013 | 292.0-294.0 | 484 |
| I-283 | 0.009 |  | 393 |
| I-284 | 6.27 | 124.0-126.0 | 479 |
| I-285 | 0.149 | 241.0-243.0 | 557 |
| I-286 | 0.019 | 291.0-292.0 | 484 |
| I-287 | 0.009 | 252.0-254.0 | 473 |
| I-288 | 0.005 0.002* | 266.0-268.0 | 469 |
| I-289 | 0.002* | 242.0-244.0 | 491[2] |
| I-290 | 0.003* | 279.0-281.0 | 501 |
| I-291 | 0.002* | 268.0-270.0 | 501 |
| I-292 | 0.029* |  | 471 |
| I-293 | 0.007 | 280-282 | 454 |
| II-1 | 0.005 | 284.0-286.0 | 437 |
| II-2 | 0.006 | 231.0-233.0 | 437 |
| II-3 |  | 264.0-266.0 | 455 |
| II-4 | 0.033 | >300 | 454 |
| II-5 | 0.001* | 283.0-286.6 | 465 |
| II-6 |  |  | 601 |
| II-7 |  | 188.0-190.0 |  |
| II-8 |  | 175.0-178.0 | 581 |
| II-9 | 0.003 |  | 522 |

[1] HCV NS5B RNA Polymerase Assay Example 120 (values with asterisk were measured with Internal Ribosome Entry Site (cIRES), 3 nM NS5B570n-Con1 RNA template
[2] (M + Na);
[3] (M − H)
[4] format salt
[5] HBr salt

Example 121

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., J. Virol. 2001 75(10):4614), immediately after the internal ribosome entry site (IRES) sequence, and fused with the neomycin phosphotransferase (NPTII) gene via a self-cleavage peptide 2A from foot and mouth disease virus (M.D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 µl of phosphate buffered saline (pH 7.0) (PBS) per well and lysed with 20 µl of 1×*R. luciferase* Assay lysis buffer prior to incubation at room temperature for 20 min. The plate was then inserted into the Centro LB 960 microplate luminometer (Berthold Technologies), and 100 µl of *R. luciferase* Assay buffer was injected into each well and the signal measured using a 2-second delay, 2-second measurement program. $IC_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks. Cells were then incubated for 2 h at 37° C., and the OD value was measured using the MRX Revelation microtiter plate reader (Lab System) at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration as described above.

TABLE III

| Compound Number | HCV Replicon Activity $IC_{50}$ (µM) | Compound Number | HCV Replicon Activity $IC_{50}$ (µM) |
|---|---|---|---|
| I-126 | 0.006 | I-187 | 0.0432 |
| I-267 | 0.0102 | I-203 | 0.01 |
| I-270 | 0.0344 | I-243 | 0.2082 |
| I-142 | 0.078 | 1-268 | 0.022 |
| I-129 | 0.101 | II-3 | 0.0546 |

Example 122

Pharmaceutical compositions of the subject Compounds for administration via several routes were prepared as described in this Example.

Composition for Oral Administration (A)

| Ingredient | % wt./wt. |
|---|---|
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

Composition for Oral Administration (B)

| Ingredient | % wt./wt. |
|---|---|
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

Composition for Oral Administration (C)

| Ingredient | % wt./wt. |
|---|---|
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
| --- | --- |
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:
1. A compound according to formula I

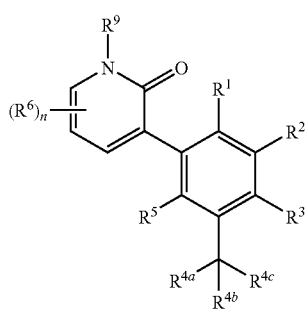

(I)

wherein:
$R^1$ is hydrogen, $C_{1-6}$ alkyl, $C_{1-6}$ haloalkyl, halogen, hydroxy, $C_{1-6}$ alkoxy, $C_{1-6}$ haloalkoxy, cyano, $NR^aR^b$, carboxy, $C_{1-3}$ alkoxycarbonyl, carboxamido, amino $C_{1-3}$alkyl, $C_{1-3}$ acylamino $C_{1-3}$alkyl, $C_{1-6}$ hydroxyalkyl, $R^2$ is selected from the group consisting of: (a) —[C($R^8$)$_2$]$_p$—$Ar^1$ (b) —[C($R^8$)$_2$]$_p$—$OAr^1$, (c) —(CH$_2$)$_n$C(=O)X, (d) —$NR^7$C(=O)$Ar^4$, (e) —$C_{1-6}$ alkyl, (f) —$C_{1-6}$ haloalkyl, (g) $C_{1-6}$ alkoxy, (h) $C_{1-6}$haloalkoxy, (i) $C_{1-6}$ hydroxyalkyl, (j) hydroxy, (k) halogen, (l) hydrogen, (m) phenylsulfonyl, (n) —O(CH$_2$)$_m$$Ar^1$, (o) —[C($R^8$)$_2$]$_1$, —$NR^eR^f$, (p) (E)- or (Z)-$R^{10}$C=$CR^{10}$$Ar^1$—, and (q) —C≡$CAr^1$ wherein $R^8$ is independently in each occurrence hydrogen, carboxyl, $C_{1-3}$ alkoxycarbonyl, carboxamido, $C_{1-3}$ hydroxyalkyl, $C_{1-3}$ alkyl, —(CH$_2$)$_r$$NR^gR^h$ or cyano, $R^{10}$ is independently in each occurrence hydrogen, $C_{1-6}$ alkyl, $C_{1-6}$ hydroxyalkyl, cyano, alkoxycarbonyl, carboxamido, carboxyl or $C_{1-3}$alkoxy-$C_{1-6}$alkyl, p is zero to four and r is 1 to 3;

$Ar^1$ is phenyl optionally independently substituted with one to three substitutents selected from the group consisting of (a) hydroxy, (b) $C_{1-6}$ alkoxy, (c) $C_{1-6}$ alkyl, (d) $C_{1-10}$ hydroxyalkyl wherein one or two carbon atoms optionally can be replaced by oxygen provided the replacement does not form a oxygen-oxygen bond, (e) $C_{1-3}$ alkoxy-$C_{1-6}$ alkyl, (f) halogen, (g) cyano, (h) $C_{1-6}$ alkoxycarbonyl, (i) $C_{1-6}$ alkylsulfonyl, (j) $X^1$(CH$_2$)$_{1-6}$CO$_2$H, (k) $C_{1-3}$ acylamino-$C_{1-6}$ alkyl, (l) (CH$_2$)$_n$$NR^aR^b$, (m) (CH$_2$)$_n$$CONR^aR^b$, (n) —O(CH$_2$)$_n$$CONR^aR^b$, (o) $X^2$(CH$_2$)$_{2-6}$$NR^gR^h$, (p) $X^1$-$C_{1-6}$ hydroxyalkyl, (q) $C_{1-6}$ haloalkyl, and (r) carboxyl;

$R^a$ and $R^b$ are (i) independently in each occurrence (a) hydrogen, (b) $C_{1-6}$ alkyl, (c) $C_{1-3}$ haloalkyl, (d) $C_{1-6}$ acyl, (e) $C_{1-6}$ alkylsulfonyl, (f) $C_{1-6}$ haloalkylsulfonyl, (g) $C_{3-7}$ cycloalkylsulfonyl, (h) $C_{3-7}$ cycloalkyl-$C_{1-3}$ alkyl-sulfonyl, (i) $C_{1-6}$ alkoxy-$C_{1-6}$ alkylsulfonyl, (j) (CH$_2$)$_{1-3}$$NR^gR^h$, (k) SO$_2$(CH$_2$)$_{1-6}$$NR^gR^h$ wherein $R^9$ and $R^{10}$ are as defined above, (l) sulfamoyl (m) $C_{1-3}$ alkylsulfamoyl, (n) $C_{1-3}$ dialkylsulfamoyl, (o) carbamoyl, (p) $C_{1-3}$ alkylcarbamoyl, (q) $C_{1-3}$ dialkylcarbamoyl, (r) benzoyl said benzoyl optionally independently substituted with one or two groups selected from the group consisting of amino, halogen, $C_{1-6}$ alkyl or $C_{1-3}$ alkylsulfonylamido, (r) $C_{1-6}$ carboxyalkylsulfonyl, (s) $C_{2-6}$ hydroxyalkylsulfonyl;

$R^e$ and $R^f$ when (i) taken independently are selected from (a) hydrogen, (b) $C_{1-3}$ alkyl, (c) $C_{4-7}$ cycloalkyl (d) $C_{3-7}$ cycloalkylcarbonyl or (e) phenyl said cycloalkyl and said phenyl are optionally independently substituted with one to three groups selected from $C_{1-3}$ alkylsulfonylamido, $C_{1-3}$ alkyl, $C_{1-3}$ alkoxy or halogen;

X is OH, $C_{1-6}$ alkoxy, $NR^eR^d$ or $Ar^3$;

$Ar^3$ is phenyl optionally substituted with one to three substitutents selected from the group consisting of: (a) halogen, (b) hydroxy, (c) $C_{1-3}$ hydroxyalkyl, (d) amino, (e) amino-$C_{1-3}$ alkyl, (f) $C_{1-3}$ alkylamino (g) $C_{1-3}$ alkylamino-$C_{1-3}$ alkyl, (h) $C_{1-3}$ dialkylamino, (i) $C_{1-3}$ dialkylamino-$C_{1-3}$ alkyl, (j) carboxamido, (k) $C_{1-6}$ alkylsulfonylamido, (l) $C_{1-6}$ alkylsulfonylamido-$C_{1-3}$ alkyl, (m) $NR^7$—$C_{1-3}$ alkyl-$C_{1-6}$ alkylsulfonamido, (n) $C_{1-6}$ alkyl, (o)$C_{1-6}$ alkoxycarbonyl and (p) carboxyl;

$R^e$ and $R^d$ are (i) independently in each occurrence: (a) hydrogen, (b) $Ar^2$, (c) $Ar^2$—$C_{1-6}$ alkyl, (d) $C_{3-6}$ cycloalkyl optionally substituted $C_{1-3}$ dialkylamino, $C_{1-6}$ alkylsulfonamido or $C_{1-3}$ hydroxyalkyl, (e) $C_{1-6}$ alkyl-$C_{3-7}$ cycloalkyl, (f) alkoxy-$C_{1-3}$ alkyl;

$Ar^2$ is phenyl optionally substituted with one to three substitutents independently selected from the group consisting of (a) $C_{1-3}$ alkyl (b) amino, (c) amino $C_{1-3}$ alkyl, (d) $C_{1-3}$ alkylamino, (e) $C_{1-3}$ alkylamino-$C_{1-3}$ alkyl, (f) $C_{1-3}$ dialkylamino, (g) —$OCH_2CO\ NR^gR^h$ (h) $C_{1-3}$ alkylsulfonylamido, (i) $C_{1-3}$ alkylsulfonamido-$C_{1-3}$ alkyl, (j) N—$C_{1-3}$ alkyl-$C_{1-6}$ alkylsulfonamido, (k) $C_{1-3}$ hydroxyalkyl, and (l) hydroxy;

$Ar^4$ is phenyl optionally substituted with one to three substituents independently selected in each occurrence from the group consisting of (a) amino, (b) $C_{1-3}$ alkylamino, (c) di-$C_{1-3}$ alkylamino, (d) $C_{1-3}$ haloalkylamino, (e) $C_{1-6}$ alkylsulfonylamido, (f) sulfamoyl, (g) $C_{1-3}$ alkylsulfamoyl, (h) $C_{1-3}$ dialkylsulfamoyl, (i) $C_{1-6}$ alkylsulfonylamido-$C_{1-3}$ alkyl, (j) $NR^7$—$C_{1-3}$ alkyl-$C_{1-6}$ alkylsulfonamido, (k) halogen, (l) $C_{1-3}$ alkyl, (m) $C_{1-3}$ alkoxy, (n) $C_{1-6}$ acylamino, (o) hydroxy, $(CH_2)_6CONR^aR^b$, (q) —$O(CH_2)_nCON$-$R^aR^b$, (r) —$O(CH_2)_nNR^iR^j$, (s) —$NR^i(CH_2)_nOR^j$, (t) $C_{1-3}$-haloalkyl, (u) $C_{1-3}$ alkoxy-$C_{1-6}$ alkoxy, (v) $C_{3-6}$ cycloalkylamine wherein $R^i$ and $R^j$ are independently hydrogen or $C_{1-3}$ alkyl;

$R^7$ is independently in each occurrence hydrogen or $C_{1-3}$ alkyl;

$R^3$ is hydrogen, $C_{1-6}$ alkyl, $C_{1-6}$ haloalkyl, $C_{1-6}$ alkoxy, $C_{1-6}$ haloalkoxy, $C_{1-3}$ alkoxy-$C_{1-6}$ alkoxy, halogen, O $(CH_2)_{2-6}X^3$ wherein $X^3$ is OH or $N(R^7)_2$ or $R^3$ and $R^{4a}$ together are $(CH_2)_2$ and with atoms to which they are attached form an indane;

$R^{4a}$, $R^{4b}$ and $R^{4c}$ (a) when taken independently are each selected independently from (i) $C_{1-3}$ alkyl, (ii) $C_{1-2}$ alkoxy, (iii) $C_{1-2}$ fluoroalkyl, (iv) $C_3$ hydroxyalkyl, (v) hydroxy (vi) $CO_2H$, (vii) $C_{1-6}$ alkoxycarbonyl, (viii) cyano or (ix) $N(R^7)_2$ or (b) when taken together, (i) $R^{4a}$ and $R^{4b}$ together are $C_{2-4}$ methylene and $R^{4c}$ is hydrogen, $C_{1-3}$ alkyl, $C_{1-2}$ alkoxy, halogen, cyano or $C_{1-2}$ fluoroalkyl or (c) either (i) $R^5$ and $R^{4a}$ or (ii) $R^3$ and $R^{4a}$ together are $(CH_2)_2$ and with atoms to which they are attached form an indane and $R^{4b}$ and $R^{4c}$ are $C_{1-3}$ alkyl or (d) $R^{4a}$, $R^{4b}$, $R^{4c}$ together with the carbon to which they are attached are cyclopropyl, trifluoromethyl or 2,2,2-trifluoroethyl;

$R^5$ is hydrogen, halogen, $C_{1-6}$ alkyl, hydroxy or $R^5$ and $R^{4a}$ together are $(CH_2)_2$ and together with atoms to which they are attached form an indane;

$R^6$ is (a) halogen, (b) $C_{1-6}$ alkyl wherein one or two non-adjacent carbon atoms optionally can be replaced by oxygen, (c) $C_{1-3}$ haloalkyl, (d) $C_{1-3}$ alkoxy, (e) $X^1$—$C_{2-6}$ hydroxyalkyl wherein one or two non-adjacent carbon atoms optionally can be replaced by oxygen, (f) cyano-$C_{1-3}$ alkyl, (g) $X^1(CH_2)_{1-6}CO_2H$ or (h) $X^1$—$(CH_2)_{2-6}NR^g R^h$;

$R^9$ is hydrogen, $CH_2OH$, $CH_2OR^{9a}$, $CH(Me)OH$, $CH(Me)OR^{9a}$ wherein $R^{9a}$ is (a) $CO(CH_2)_sCO_2H$ wherein s is one to four, (b) $C(O)CHR^{9b}NHR^{9c}$ wherein $R^{9b}$ is hydrogen, methyl, iso-propyl, iso-butyl, sec-butyl, phenyl or 4-hydroxy-phenyl and $R^{9c}$ is hydrogen or $C_{1-6}$ alkoxycarbonyl or $R^{9b}$ and $R^{9c}$ together are $(CH_2)_3$, (c) —$P(O)(OH)_2$ or (d) $COR^{11}$ wherein $R^{11}$ is $C_{1-6}$ alkyl or optionally substituted aryl;

$X^1$ is O, $NR^7$, or a bond;

$X^2$ is O or $NR^7$;

$R^g$ and $R^h$ are independently hydrogen or $C_{1-6}$ alkyl;

m is zero to three;

n is independently in each occurrence zero to two; or, pharmaceutically acceptable salts thereof.

2. A compound according to claim 1 wherein:
$R^2$ is —$[C(R^8)_2]_p$—$Ar^1$;
$Ar^1$ phenyl;
$R^3$ is hydrogen or $C_{1-6}$ alkoxy;
$R^9$ is hydrogen; and,
p is 2.

3. A compound according to claim 2 wherein $R^8$ is hydrogen.

4. A compound according to claim 3 wherein $R^1$ is hydrogen or hydroxy; $R^5$ are hydrogen, $R^3$ is hydrogen or methoxy, and $R^6$ is halogen, $C_{1-6}$ alkyl or $C_{1-6}$ alkoxy.

5. A compound according to claim 4 wherein $R^{4a}$, $R^{4b}$ and $R^{4c}$ are methyl.

6. A compound according to claim 5 wherein $Ar^1$ is phenyl substituted at least with $(CH_2)_nNR^aR^b$ wherein n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl.

7. A compound according to claim 6 wherein $Ar^1$ is optionally substituted 4-methanesulfonylamino-phenyl.

8. A compound according to claim 4 wherein (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) either (i) $R^5$ and $R^{4a}$ or (ii) $R^3$ and $R^{4a}$ together are $(CH_2)_2$ and with atoms to which they are attached form an indane and $R^{4b}$ and $R^{4c}$ are $C_{1-3}$ alkyl.

9. A compound according to claim 8 wherein $Ar^1$ is phenyl substituted at least with $(CH_2)_nNR^aR^b$ wherein n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl.

10. A compound according to claim 9 wherein $Ar^1$ is optionally substituted 4-methanesulfonylamino-phenyl.

11. A compound according to claim 1 wherein:
$R^2$ is (E) $R^{10}C=CR^{10}Ar^1$;
$Ar^1$ is phenyl;
$R^3$ is hydrogen or $C_{1-6}$ alkoxy;
$R^9$ is hydrogen; and,
p is 2.

12. A compound according to claim 11 wherein $R^{10}$ is hydrogen.

13. A compound according to claim 12 wherein $R^1$ and $R^5$ are hydrogen; $R^3$ is hydrogen or methoxy and $R^6$ is halogen, $C_{1-6}$ alkyl or $C_{1-6}$ alkoxy.

14. A compound according to claim 13 wherein $R^{4a}$, $R^{4b}$ and $R^{4c}$ are methyl.

15. A compound according to claim 14 wherein $Ar^1$ is phenyl substituted at least with $(CH_2)_nR^b$ wherein n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl.

16. A compound according to claim 15 wherein $Ar^1$ is optionally substituted 4-methanesulfonylamino-phenyl.

17. A compound according to claim 13 wherein (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) either (i) $R^5$ and $R^{4a}$ or (ii) $R^3$ and $R^{4a}$ together are $(CH_2)_2$ and with atoms to which they are attached form an indane and $R^{4b}$ and $R^{4c}$ are $C_{1-3}$ alkyl.

18. A compound according to claim 17 wherein $Ar^1$ is phenyl substituted at least with $(CH_2)_nNR^aR^b$ wherein n is zero or one, $R^a$ is hydrogen and $R^b$ is $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl.

19. A compound according to claim 18 wherein $Ar^1$ is optionally substituted 4-methanesulfonylamino-phenyl.

20. A compound according to claim 11 wherein $R^9$ is $CH_2OH$, $CH_2OR^{9a}$ wherein $R^{9a}$ is $(CH_2)_nCO_2H$ wherein s is one to four, $C(O)CHR^{9b}NHR^{9c}$ wherein $R^{9b}$ is hydrogen, methyl, iso-propyl, iso-butyl, sec-butyl, phenyl or 4-hydroxyphenyl and $R^{9c}$ is hydrogen or $C_{1-6}$ alkoxycarbonyl.

21. A compound according to claim 1 wherein $R^2$ is $NR^7C(=O)Ar^4$.

22. A compound according to claim 21 wherein $R^1$ and $R^5$ are hydrogen and $R^3$ is $C_{1-6}$ alkoxy.

23. A compound according to claim 22 wherein $Ar^4$ is phenyl substituted with one to three groups independently selected from $C_{1-3}$ alkyl, halogen, $(CH_2)_n NR^a R^b$ and $(CH_2)_n CO_2 NR^a R^b$, n is zero, one or two, $R^a$ is hydrogen or $C_{1-3}$ alkyl and $R^b$ is hydrogen, $C_{1-3}$ alkyl, $C_{1-3}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl.

24. A compound according to claim 23 wherein $R^{4a}$, $R^{4b}$ and $R^{4c}$ are methyl.

25. A compound according to claim 23 wherein (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or (c) either (i) $R^5$ and $R^{4a}$ or (ii) $R^3$ and $R^{4a}$ together are $(CH_2)_2$ and with atoms to which they are attached form an indane and $R^{4b}$ and $R^{4c}$ are $C_{1-3}$ alkyl.

26. A compound according to claim 1 wherein $R^2$ is $—(CH_2)_m C(=O)X$, m is zero and X is $NR^c R^d$.

27. A compound according to claim 26 wherein $R^1$ and $R^5$ are hydrogen, $R^3$ is $C_{1-6}$ alkoxy, $R^2$ is $—(CH_2)_m C(=O)X$, m is zero and X is $NR^c R^d$ $R^c$ is hydrogen and $R^d$ is $Ar^2$ said $Ar^2$ being phenyl optionally substituted with on to three groups independently selected from hydroxy, $C_{1-6}$ alkyl, $C_{1-6}$ hydroxyalkyl, halogen, $(CH_2)_n NR^a R^b$ and wherein n is one or two, $R^a$ is hydrogen or $C_{1-3}$ alkyl and $R^b$ is hydrogen, $C_{1-3}$ alkyl, $C_{1-3}$ acyl, $C_{1-3}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl.

28. A compound according to claim 27 wherein $R^{4a}$, $R^{4b}$ and $R^{4c}$ are methyl.

29. A compound according to claim 27 wherein (a) $R^{4a}$ and $R^{4b}$ are $C_{1-3}$ alkyl and $R^{4c}$ is selected from (i) $C_{1-2}$ alkoxy, (ii) $C_{1-2}$ fluoroalkyl, (iii) $C_{1-3}$ hydroxyalkyl or (iv) hydroxy or (b) $R^{4a}$ and $R^{4b}$ taken together are $C_{2-4}$ methylene and $R^{4c}$ is $C_{1-3}$ alkyl, $C_{1-2}$ alkoxy, halogen, cyano or $C_{1-2}$ fluoroalkyl or or (c) either (i) $R^5$ and $R^{4a}$ or (ii) $R^3$ and $R^{4a}$ together are $(CH_2)_2$ and with atoms to which they are attached form an indane and $R^{4b}$ and $R^{4c}$ are $C_{1-3}$ alkyl.

30. A compound according to claim 1 wherein $R^2$ is $—[C(R^5)_2]_p—NR^e R^f$.

31. A compound according to claim 30 wherein $R^8$ is hydrogen and p is one or two.

32. A compound according to claim 1 which compound is selected from the group consisting of:
- 3-(3-tert-butyl-phenyl)-1H-pyridin-2-one;
- 3-(5-tert-butyl-2-hydroxy-phenyl)-1H-pyridin-2-one;
- 3-(3-tert-butyl-5-methyl-phenyl)-1H-pyridin-2-one;
- 3-(3-tert-butyl-4-methoxy-phenyl)-1H-pyridin-2-one;
- 3-(3-tert-butyl-4-ethoxy-phenyl)-1H-pyridin-2-one;
- 3-(3-tert-butyl-4-difluoromethoxy-phenyl)-1H-pyridin-2-one;
- 3-(3-tert-butyl-5-methyl-phenyl)-5-methyl-1H-pyridin-2-one;
- 3-(3-tert-butyl-5-methyl-phenyl)-5-chloro-1H-pyridin-2-one;
- 3-[3-bromo-5-(1,1-dimethyl-propyl)-2-hydroxy-phenyl]-1H-pyridin-2-one;
- 3-(5-tert-butyl-2-hydroxy-3-hydroxymethyl-phenyl)-1H-pyridin-2-one;
- 3-(5-tert-butyl-2-hydroxy-3-methyl-phenyl)-1H-pyridin-2-one;
- 3-(3-tert-butyl-5-methyl-phenyl)-6-hydroxymethyl-1H-pyridin-2-one;
- 3-(3-bromo-5-tert-butyl-2-hydroxy-phenyl)-1H-pyridin-2-one;
- 3-(5-tert-butyl-3-ethyl-2-hydroxy-phenyl)-1H-pyridin-2-one;
- 3-(5-tert-butyl-2-hydroxy-biphenyl-3-yl)-1H-pyridin-2-one;
- 3-(5-tert-butyl-3-chloro-2-hydroxy-phenyl)-1H-pyridin-2-one;
- 3-(3-benzyl-5-tert-butyl-2-hydroxy-phenyl)-1H-pyridin-2-one;
- 3-[5-tert-butyl-2-hydroxy-3-(2-oxo-1,2-dihydro-pyridin-3-yl)-phenyl]-propionic acid;
- 3-tert-butyl-N-cyclopropyl-2-methoxy-5-(2-oxo-1,2-dihydro-pyridin-3-yl)-benzamide;
- 3-{5-tert-butyl-3-[2-(4-fluoro-phenyl)-ethyl]-2-hydroxy-phenyl}-1H-pyridin-2-one;
- 3-{3-tert-butyl-5-[2-(4-fluoro-phenyl)-ethyl]-4-methoxy-phenyl}-1H-pyridin-2-one;
- 3-[3-tert-butyl-2-methoxy-5-(2-oxo-1,2-dihydro-pyridin-3-yl)-phenyl]-propionic acid;
- 3-(3-tert-butyl-5-hydroxy-4-methoxy-phenyl)-1H-pyridin-2-one;
- 4-amino-N-[3-tert-butyl-2-methoxy-5-(2-oxo-1,2-dihydro-pyridin-3-yl)-phenyl]-2-chloro-benzamide;
- 3-(3-tert-butyl-4,5-dimethoxy-phenyl)-1H-pyridin-2-one;
- 3-[3-methyl-5-(1-methyl-cyclopentyl)-phenyl]-1H-pyridin-2-one;
- 3-[3-methyl-5-(1-methyl-cyclobutyl)-phenyl]-1H-pyridin-2-one;
- 3-(3-tert-butyl-4-methoxy-5-methyl-phenyl)-1H-pyridin-2-one;
- 3-(3-tert-butyl-5-ethyl-4-methoxy-phenyl)-1H-pyridin-2-one;
- 3-tert-butyl-N-cyclopropyl-2-methoxy-N-(2-methoxy-ethyl)-5-(2-oxo-1,2-dihydro-pyridin-3-yl)-benzamide;
- N-(3-{2-[3-tert-butyl-2-methoxy-5-(2-oxo-1,2-dihydro-pyridin-3-yl)-phenyl]-ethyl}-phenyl)-methanesulfonamide;
- N-(4-{2-[3-tert-butyl-2-methoxy-5-(2-oxo-1,2-dihydro-pyridin-3-yl)-phenyl]-ethyl}-phenyl)-methanesulfonamide;
- 3-tert-butyl-2-methoxy-5-(2-oxo-1,2-dihydro-pyridin-3-yl)-N-phenethyl-benzamide;
- 3-tert-butyl-2-methoxy-5-(2-oxo-1,2-dihydro-pyridin-3-yl)-N-(2-phenyl-propyl)-benzamide;
- N-benzyl-3-tert-butyl-2-methoxy-5-(2-oxo-1,2-dihydro-pyridin-3-yl)-benzamide;
- 3-tert-butyl-N-(4-dimethylamino-benzyl)-2-methoxy-5-(2-oxo-1,2-dihydro-pyridin-3-yl)-benzamide;
- 3-tert-butyl-N-(4-dimethylamino-phenyl)-2-methoxy-5-(2-oxo-1,2-dihydro-pyridin-3-yl)-benzamide;
- 3-tert-butyl-N-(2-dimethylamino-ethyl)-2-methoxy-5-(2-oxo-1,2-dihydro-pyridin-3-yl)-benzamide;
- 3-(3-tert-butyl-5-phenoxy-phenyl)-1H-pyridin-2-one;
- 3-(3-benzyl-5-tert-butyl-phenyl)-1H-pyridin-2-one;
- 3-(3-benzoyl-5-tert-butyl-4-methoxy-phenyl)-1H-pyridin-2-one;
- 3-(3-benzyl-5-tert-butyl-4-methoxy-phenyl)-1H-pyridin-2-one;
- 3-[3-tert-butyl-5-(3-fluoro-benzoyl)-4-methoxy-phenyl]-1H-pyridin-2-one;
- 3-[3-tert-butyl-5-(4-fluoro-benzoyl)-4-methoxy-phenyl]-1H-pyridin-2-one;

N-(4-{2-[5-tert-butyl-2-hydroxy-3-(2-oxo-1,2-dihydro-pyridin-3-yl)-phenyl]-ethyl}-phenyl)-methanesulfonamide;
3-[3-tert-butyl-5-(3,5-difluoro-benzoyl)-4-methoxy-phenyl]-1H-pyridin-2-one;
3-(3-tert-butyl-5-methyl-phenyl)-5-fluoro-1H-pyridin-2-one;
3-[3-tert-butyl-5-(3-hydroxy-benzoyl)-4-methoxy-phenyl]-1H-pyridin-2-one;
3-[3-tert-butyl-5-(4-hydroxy-benzoyl)-4-methoxy-phenyl]-1H-pyridin-2-one;
3-(3-tert-butyl-2-fluoro-4-methoxy-phenyl)-1H-pyridin-2-one;
N-[3-tert-butyl-2-methoxy-5-(2-oxo-1,2-dihydro-pyridin-3-yl)-phenyl]-benzamide;
3-[3-(3-amino-benzoyl)-5-tert-butyl-4-methoxy-phenyl]-1H-pyridin-2-one;
N-[3-tert-butyl-2-fluoro-5-(2-oxo-1,2-dihydro-pyridin-3-yl)-phenyl]-benzamide;
3-[4-methoxy-3-(1-methyl-cyclopropyl)-phenyl]-1H-pyridin-2-one;
3-[4-methoxy-3-(1-methoxy-1-methyl-ethyl)-phenyl]-1H-pyridin-2-one;
3-[3-tert-butyl-2-methoxy-5-(2-oxo-1,2-dihydro-pyridin-3-yl)-benzoyl]-benzamide;
N-(4-{2-[3-tert-butyl-2-methoxy-5-(6-methyl-2-oxo-1,2-dihydro-pyridin-3-yl)-phenyl]-ethyl}-phenyl)-methanesulfonamide;
N-{3-[3-tert-butyl-2-methoxy-5-(2-oxo-1,2-dihydro-pyridin-3-yl)-benzoyl]-benzyl}-methanesulfonamide;
3-[3-(4-aminomethyl-benzoyl)-5-tert-butyl-4-methoxy-phenyl]-1H-pyridin-2-one;
N-(4-{2-[3-tert-butyl-5-(5-fluoro-2-oxo-1,2-dihydro-pyridin-3-yl)-2-methoxy-phenyl]-ethyl}-phenyl)-methanesulfonamide;
3-tert-butyl-2-methoxy-5-(2-oxo-1,2-dihydro-pyridin-3-yl)-N-phenyl-benzamide;
3-tert-butyl-N-(4-methanesulfonylamino-2-methyl-phenyl)-2-methoxy-5-(2-oxo-1,2-dihydro-pyridin-3-yl)-benzamide;
N-[3-tert-butyl-2-methoxy-5-(2-oxo-1,2-dihydro-pyridin-3-yl)-phenyl]-4-methanesulfonylamino-benzamide;
N-{4-[3-tert-butyl-2-methoxy-5-(2-oxo-1,2-dihydro-pyridin-3-yl)-benzyloxy]-phenyl}-methanesulfonamide;
4-amino-N-[3-tert-butyl-2-methoxy-5-(2-oxo-1,2-dihydro-pyridin-3-yl)-phenyl]-benzamide;
N-[3-tert-butyl-2-fluoro-5-(2-oxo-1,2-dihydro-pyridin-3-yl)-phenyl]-4-methanesulfonylamino-benzamide;
N-(4-{2-[3-tert-butyl-5-(2-oxo-1,2-dihydro-pyridin-3-yl)-phenyl]-ethyl}-phenyl)-methanesulfonamide;
3-tert-butyl-N-[4-(methanesulfonyl-methyl-amino)-phenyl]-2-methoxy-5-(2-oxo-1,2-dihydro-pyridin-3-yl)-benzamide;
3-tert-butyl-N-[4-(methanesulfonylamino-methyl)-phenyl]-2-methoxy-5-(2-oxo-1,2-dihydro-pyridin-3-yl)-benzamide;
3-tert-butyl-N-(3-hydroxymethyl-2-methyl-phenyl)-2-methoxy-5-(2-oxo-1,2-dihydro-pyridin-3-yl)-benzamide;
3-tert-butyl-2-methoxy-5-(2-oxo-1,2-dihydro-pyridin-3-yl)-N-o-tolyl-benzamide;
N-[4-tert-butyl-2-[2-(4-methanesulfonylamino-phenyl)-ethyl]-6-(2-oxo-1,2-dihydro-pyridin-3-yl)-phenyl]-acetamide;
N-[3-tert-butyl-5-(5-fluoro-2-oxo-1,2-dihydro-pyridin-3-yl)-2-methoxy-phenyl]-4-methanesulfonylamino-benzamide;
4-methanesulfonylamino-N-[2-methoxy-3-(1-methyl-cyclopropyl)-5-(2-oxo-1,2-dihydro-pyridin-3-yl)-phenyl]-benzamide;
N-(4-{2-[3-tert-butyl-5-(2-oxo-1,2-dihydro-pyridin-3-yl)-phenyl]-ethyl}-phenyl)-acetamide;
1-(4-{2-[3-tert-butyl-5-(2-oxo-1,2-dihydro-pyridin-3-yl)-phenyl]-ethyl}-phenyl)-3,3-dimethyl-sulfamate;
1-(4-{2-[3-tert-butyl-5-(2-oxo-1,2-dihydro-pyridin-3-yl)-phenyl]-ethyl}-phenyl)-3-methyl-urea;
N-(4-{2-[5-tert-butyl-2-cyano-3-(2-oxo-1,2-dihydro-pyridin-3-yl)-phenyl]-ethyl}-phenyl)-methanesulfonamide;
3-tert-butyl-N-(4-dimethylamino-cyclohexyl)-2-methoxy-5-(2-oxo-1,2-dihydro-pyridin-3-yl)-benzamide;
3-tert-butyl-N-(2-hydroxymethyl-cyclohexyl)-2-methoxy-5-(2-oxo-1,2-dihydro-pyridin-3-yl)-benzamide;
N-(4-{2-[3-tert-butyl-5-(5-fluoro-2-oxo-1,2-dihydro-pyridin-3-yl)-phenyl]-ethyl}-phenyl)-methanesulfonamide;
N-(4-{2-[3-tert-butyl-5-(5-chloro-2-oxo-1,2-dihydro-pyridin-3-yl)-2-methoxy-phenyl]-ethyl}-phenyl)-methanesulfonamide;
N-(4-{2-[5-(5-bromo-2-oxo-1,2-dihydro-pyridin-3-yl)-3-tert-butyl-2-methoxy-phenyl]-ethyl}-phenyl)-methanesulfonamide;
3-tert-butyl-N-(3-hydroxymethyl-phenyl)-2-methoxy-5-(2-oxo-1,2-dihydro-pyridin-3-yl)-benzamide;
N-(4-{2-[2-amino-5-tert-butyl-3-(2-oxo-1,2-dihydro-pyridin-3-yl)-phenyl]ethyl}-phenyl)-methanesulfonamide;
3-[3-[2-(4-amino-phenyl)-ethyl]-4-methoxy-5-(1-methyl-cyclopropyl)-phenyl]-1H-pyridin-2-one;
N-{3-[3-tert-butyl-2-methoxy-5-(2-oxo-1,2-dihydro-pyridin-3-yl)-benzoyl]-phenyl}-methanesulfonamide;
3-tert-butyl-N-cyclohexyl-2-methoxy-5-(2-oxo-1,2-dihydro-pyridin-3-yl)-benzamide;
N-(4-{2-[3-tert-butyl-2-methoxy-5-(2-oxo-1,2-dihydro-pyridin-3-yl)-phenyl]-ethyl}-3-fluoro-phenyl)-methanesulfonamide;
N-(4-{2-[3-tert-butyl-2-methoxy-5-(2-oxo-1,2-dihydro-pyridin-3-yl)-phenyl]-ethyl}-2-fluoro-phenyl)-methanesulfonamide;
N-[3-tert-butyl-2-methoxy-5-(2-oxo-1,2-dihydro-pyridin-3-yl)-phenyl]-4-methanesulfonylamino-N-methyl-benzamide;
3-(5-tert-butyl-2-methoxy-phenyl)-6-ethyl-1H-pyridin-2-one;
3-[3-(3-aminomethyl-benzoyl)-5-tert-butyl-4-methoxy-phenyl]-1H-pyridin-2-one;
3-(3-benzenesulfonyl-5-tert-butyl-phenyl)-1H-pyridin-2-one;
N-(4-{2-[2-methoxy-3-(1-methyl-cyclopropyl)-5-(2-oxo-1,2-dihydro-pyridin-3-yl)-phenyl]ethyl}-phenyl)-methanesulfonamide;
N-(4-{2-[3-tert-butyl-2-methoxy-5-(2-oxo-1,2-dihydro-pyridin-3-yl)-phenyl]-ethyl}-3-methyl-phenyl)-methanesulfonamide;
N-(4-{2-[3-tert-butyl-2-methoxy-5-(2-oxo-1,2-dihydro-pyridin-3-yl)-phenyl]-ethyl}-2-methyl-phenyl)-methanesulfonamide;
4-methanesulfonylamino-cyclohexanecarboxylic acid [3-tert-butyl-2-methoxy-5-(2-oxo-1,2-dihydro-pyridin-3-yl)-phenyl]-amide;
3-tert-butyl-N-[3-(methanesulfonylamino-methyl)-phenyl]-2-methoxy-5-(2-oxo-1,2-dihydro-pyridin-3-yl)-benzamide;

3-tert-butyl-N-(4-carbamoylmethoxy-phenyl)-2-methoxy-5-(2-oxo-1,2-dihydro-pyridin-3-yl)-benzamide;
N-[3-tert-butyl-2-methoxy-5-(2-oxo-1,2-dihydro-pyridin-3-yl)-phenyl]-2-ethoxy-4-methanesulfonylamino-benzamide;
N-[3-tert-butyl-2-methoxy-5-(2-oxo-1,2-dihydro-pyridin-3-yl)-phenyl]-2-chloro-4-methanesulfonylamino-benzamide;
N-(4-{2-[5-tert-butyl-2-(2-hydroxy-ethoxy)-3-(2-oxo-1,2-dihydro-pyridin-3-yl)-phenyl]-ethyl}-phenyl)-methanesulfonamide;
N-{4-[3-tert-butyl-2-methoxy-5-(2-oxo-1,2-dihydro-pyridin-3-yl)-benzylamino]-cyclohexyl}-methanesulfonamide;
4-amino-N-[3-tert-butyl-2-methoxy-5-(2-oxo-1,2-dihydro-pyridin-3-yl)-phenyl]-3-fluoro-benzamide;
N-[3-tert-butyl-2-methoxy-5-(2-oxo-1,2-dihydro-pyridin-3-yl)-phenyl]-3-fluoro-4-methanesulfonylamino-benzamide;
4-tert-butyl-2-[2-(4-methanesulfonylamino-phenyl)-ethyl]-6-(2-oxo-1,2-dihydro-pyridin-3-yl)-benzamide;
N-(4-{(E)-2-[3-tert-butyl-2-methoxy-5-(2-oxo-1,2-dihydro-pyridin-3-yl)-phenyl]-vinyl}-phenyl)-methanesulfonamide;
N-[3-tert-butyl-2-methoxy-5-(2-oxo-1,2-dihydro-pyridin-3-yl)-phenyl]-4-methanesulfonylamino-3-methyl-benzamide;
N-[3-tert-butyl-2-methoxy-5-(2-oxo-1,2-dihydro-pyridin-3-yl)-phenyl]-4-methanesulfonylamino-3-methoxy-benzamide;
N-[3-tert-butyl-2-methoxy-5-(2-oxo-1,2-dihydro-pyridin-3-yl)-phenyl]-3-chloro-4-methanesulfonylamino-benzamide;
N-[3-tert-butyl-2-methoxy-5-(2-oxo-1,2-dihydro-pyridin-3-yl)-phenyl]-4-methanesulfonylamino-2-trifluoromethyl-benzamide;
4-tert-butyl-2-[2-(4-methanesulfonylamino-phenyl)-ethyl]-6-(2-oxo-1,2-dihydro-pyridin-3-yl)-benzoic acid methyl ester;
4-tert-butyl-2-[2-(4-methanesulfonylamino-phenyl)-ethyl]-6-(2-oxo-1,2-dihydro-pyridin-3-yl)-benzoic acid;
N-(4-{(E)-2-[5-tert-butyl-2-hydroxy-3-(2-oxo-1,2-dihydro-pyridin-3-yl)-phenyl]-vinyl}-phenyl)-methanesulfonamide;
N-(4-{(Z)-2-[3-tert-butyl-2-methoxy-5-(2-oxo-1,2-dihydro-pyridin-3-yl)-phenyl]-1-cyano-vinyl}-phenyl)-methanesulfonamide;
N-(4-{(E)-2-[3-tert-butyl-2-methoxy-5-(2-oxo-1,2-dihydro-pyridin-3-yl)-phenyl]-1-methyl-vinyl}-phenyl)-methanesulfonamide;
N-(4-{(E)-2-[5-tert-butyl-2-hydroxy-3-(6-methyl-2-oxo-1,2-dihydro-pyridin-3-yl)-phenyl]-vinyl}-phenyl)-methanesulfonamide;
N-(4-{(E)-2-[3-tert-butyl-5-(2-oxo-1,2-dihydro-pyridin-3-yl)-phenyl]-vinyl}-phenyl)-methanesulfonamide;
N-(4-{(E)-2-[3-tert-butyl-5-(5-fluoro-2-oxo-1,2-dihydro-pyridin-3-yl)-2-methoxy-phenyl]-vinyl}-phenyl)-methanesulfonamide;
N-(4-{(E)-2-[5-tert-butyl-2-hydroxy-3-(2-oxo-1,2-dihydro-pyridin-3-yl)-phenyl]-1-methyl-vinyl}-phenyl)-methanesulfonamide;
3-[3-tert-butyl-4-methoxy-5-((E)-styryl)-phenyl]-1H-pyridin-2-one;
N-(4-{(E)-2-[3-tert-butyl-2-methoxy-5-(2-oxo-1,2-dihydro-pyridin-3-yl)-phenyl]-1-hydroxymethyl-vinyl}-phenyl)-methanesulfonamide;
N-(4-{(E)-2-[3-tert-butyl-5-(2-oxo-1,2-dihydro-pyridin-3-yl)-phenyl]-vinyl}-2-fluoro-phenyl)-methanesulfonamide;
N-(4-{(E)-2-[3-tert-butyl-5-(2-oxo-1,2-dihydro-pyridin-3-yl)-phenyl]-vinyl}-3-cyano-phenyl)-methanesulfonamide;
N-(4-{(E)-2-[3-tert-butyl-5-(5-fluoro-2-oxo-1,2-dihydro-pyridin-3-yl)-phenyl]-vinyl}-phenyl)-methanesulfonamide;
N-(4-{(Z)-2-[3-tert-butyl-2-methoxy-5-(2-oxo-1,2-dihydro-pyridin-3-yl)-phenyl]-1-hydroxymethyl-vinyl}-phenyl)-methanesulfonamide;
N-(4-{(E)-2-[3-tert-butyl-2-methoxy-5-(2-oxo-1,2-dihydro-pyridin-3-yl)-phenyl]-vinyl}-3-cyano-phenyl)-methanesulfonamide;
2,2,2-Trifluoro-ethanesulfonic acid (4-{(E)-2-[3-tert-butyl-5-(5-fluoro-2-oxo-1,2-dihydro-pyridin-3-yl)-2-methoxy-phenyl]-vinyl}-phenyl)-amide;
N-(4-{(E)-2-[3-tert-butyl-5-(5-fluoro-2-oxo-1,2-dihydro-pyridin-3-yl)-2-methoxy-phenyl]-vinyl}-phenyl)-C-cyclopropyl-methanesulfonamide;
N-(4-{(E)-2-[3-tert-butyl-5-(5-fluoro-2-oxo-1,2-dihydro-pyridin-3-yl)-2-methoxy-phenyl]-vinyl}-phenyl)-C,C,C-trifluoro-methanesulfonamide;
Cyclopropanesulfonic acid (4-{(E)-2-[3-tert-butyl-5-(5-fluoro-2-oxo-1,2-dihydro-pyridin-3-yl)-2-methoxy-phenyl]-vinyl}-phenyl)-amide;
3-methoxy-propane-1-sulfonic acid (4-{(E)-2-[3-tert-butyl-5-(5-fluoro-2-oxo-1,2-dihydro-pyridin-3-yl)-2-methoxy-phenyl]-vinyl}-phenyl)-amide;
2-{(E)-2-[3-tert-butyl-2-methoxy-5-(2-oxo-1,2-dihydro-pyridin-3-yl)-phenyl]-vinyl}-5-methanesulfonylamino-benzoic acid methyl ester;
2-{(E)-2-[3-tert-butyl-5-(2-oxo-1,2-dihydro-pyridin-3-yl)-phenyl]-vinyl}-5-methanesulfonylamino-benzoic acid methyl ester;
2-{(E)-2-[3-tert-butyl-5-(2-oxo-1,2-dihydro-pyridin-3-yl)-phenyl]-vinyl}-5-methanesulfonylamino-benzoic acid;
N-(2-{(E)-2-[3-tert-butyl-2-methoxy-5-(2-oxo-1,2-dihydro-pyridin-3-yl)-phenyl]-vinyl}-5-methanesulfonylamino-benzyl)-acetamide;
N-(4-{(E)-2-[3-tert-butyl-5-(5-chloro-2-oxo-1,2-dihydro-pyridin-3-yl)-2-methoxy-phenyl]-vinyl}-phenyl)-methanesulfonamide;
N-(4-{(E)-2-[3-(1-hydroxymethyl-cyclopropyl)-5-(2-oxo-1,2-dihydro-pyridin-3-yl)-phenyl]-vinyl}-phenyl)-methanesulfonamide;
N-(4-{(E)-2-[3-tert-butyl-5-(6-hydroxymethyl-2-oxo-1,2-dihydro-pyridin-3-yl)-2-methoxy-phenyl]-vinyl}-phenyl)-methanesulfonamide;
N-(4-{(E)-2-[3-tert-butyl-2-methoxy-5-(6-methoxymethyl-2-oxo-1,2-dihydro-pyridin-3-yl)-phenyl]-vinyl}-phenyl)-methanesulfonamide;
N-[4-((E)-2-{3-tert-butyl-2-methoxy-5-[6-(2-methoxy-ethoxymethyl)-2-oxo-1,2-dihydro-pyridin-3-yl]-phenyl}-vinyl)-phenyl]-methanesulfonamide;
N-(4-{2-[3-tert-butyl-2-methoxy-5-(2-oxo-1,2-dihydro-pyridin-3-yl)-phenyl]-1-hydroxymethyl-ethyl}-phenyl)-methanesulfonamide;
N-(4-{2-[3-tert-butyl-2-methoxy-5-(2-oxo-1,2-dihydro-pyridin-3-yl)-phenyl]-1-cyano-ethyl}-phenyl)-methanesulfonamide;
3-[3-tert-butyl-2-methoxy-5-(2-oxo-1,2-dihydro-pyridin-3-yl)-phenyl]-2-(4-methanesulfonylamino-phenyl)-propionamide;

3-[3-tert-butyl-2-methoxy-5-(2-oxo-1,2-dihydro-pyridin-3-yl)-phenyl]-2-(4-methanesulfonylamino-phenyl)-propionic acid;

N-(4-{(E)-2-[2-methoxy-5-(2-oxo-1,2-dihydro-pyridin-3-yl)-3-(2,2,2-trifluoro-1-hydroxy-1-methyl-ethyl)-phenyl]-vinyl}-phenyl)-methanesulfonamide;

3-tert-butyl-N-(3-hydroxy-2-methyl-phenyl)-2-methoxy-5-(2-oxo-1,2-dihydro-pyridin-3-yl)-benzamide;

2-{(E)-2-[3-tert-butyl-5-(5-fluoro-2-oxo-1,2-dihydro-pyridin-3-yl)-2-methoxy-phenyl]-vinyl}-5-methanesulfonylamino-benzoic acid methyl ester;

N-(4-{(E)-2-[3-tert-butyl-5-(5-fluoro-2-oxo-1,2-dihydro-pyridin-3-yl)-2-methoxy-phenyl]-vinyl}-3-hydroxymethyl-phenyl)-methanesulfonamide;

2-{(E)-2-[3-tert-butyl-5-(5-fluoro-2-oxo-1,2-dihydro-pyridin-3-yl)-2-methoxy-phenyl]-vinyl}-5-methanesulfonylamino-benzoic acid;

2-{2-[3-tert-butyl-5-(5-fluoro-2-oxo-1,2-dihydro-pyridin-3-yl)-2-methoxy-phenyl]ethyl}-5-methanesulfonylamino-benzoic acid methyl ester;

2-{2-[3-tert-butyl-5-(5-fluoro-2-oxo-1,2-dihydro-pyridin-3-yl)-2-methoxy-phenyl]-ethyl}-5-methanesulfonylamino-benzoic acid;

N-(4-{1-aminomethyl-2-[3-tert-butyl-2-methoxy-5-(2-oxo-1,2-dihydro-pyridin-3-yl)-phenyl]ethyl}-phenyl)-methanesulfonamide;

N-(4-{2-[3-tert-butyl-2-methoxy-5-(2-oxo-1,2-dihydro-pyridin-3-yl)-phenyl]-1-dimethylaminomethyl-ethyl}-phenyl)-methanesulfonamide;

N-(4-{2-[3-tert-butyl-2-methoxy-5-(2-oxo-1,2-dihydro-pyridin-3-yl)-phenyl]-1-cyano-1-methyl-ethyl}-phenyl)-methanesulfonamide;

N-(4-{1-aminomethyl-2-[3-tert-butyl-2-methoxy-5-(2-oxo-1,2-dihydro-pyridin-3-yl)-phenyl]-1-methyl-ethyl}-phenyl)-methanesulfonamide;

N-(4-{2-[3-tert-butyl-2-methoxy-5-(2-oxo-1,2-dihydro-pyridin-3-yl)-phenyl]-1-hydroxymethyl-1-methyl-ethyl}-phenyl)-methanesulfonamide;

N-(4-{2-[2-hydroxy-5-(2-hydroxy-1,1-dimethyl-ethyl)-3-(2-oxo-1,2-dihydro-pyridin-3-yl)-phenyl]-ethyl}-phenyl)-methanesulfonamide;

N-(4-{(E)-2-[3-tert-butyl-5-(5-fluoro-2-oxo-1,2-dihydro-pyridin-3-yl)-2-methoxy-phenyl]-vinyl}-3-cyano-phenyl)-methanesulfonamide;

2-{(E)-2-[3-tert-butyl-2-methoxy-5-(6-methyl-2-oxo-1,2-dihydro-pyridin-3-yl)-phenyl]-vinyl}-5-methanesulfonylamino-benzoic acid methyl ester;

2-{(E)-2-[3-tert-butyl-2-methoxy-5-(2-oxo-1,2-dihydro-pyridin-3-yl)-phenyl]-vinyl}-5-methanesulfonylamino-N,N-dimethyl-benzamide;

2-{(E)-2-[3-tert-butyl-2-methoxy-5-(2-oxo-1,2-dihydro-pyridin-3-yl)-phenyl]-vinyl}-5-methanesulfonylamino-benzoic acid;

N-[4-{(E)-2-[3-tert-butyl-2-methoxy-5-(2-oxo-1,2-dihydro-pyridin-3-yl)-phenyl]-vinyl}-3-(1-hydroxy-1-methyl-ethyl)-phenyl]-methanesulfonamide;

N-(4-{(E)-2-[3-tert-butyl-2-methoxy-5-(2-oxo-1,2-dihydro-pyridin-3-yl)-phenyl]-vinyl}-3-hydroxymethyl-phenyl)-methanesulfonamide;

N-(4-{(E)-2-[3-tert-butyl-2-methoxy-5-(2-oxo-1,2-dihydro-pyridin-3-yl)-phenyl]-vinyl}-3-methoxymethyl-phenyl)-methanesulfonamide;

2-{(E)-2-[3-tert-butyl-5-(5-fluoro-2-oxo-1,2-dihydro-pyridin-3-yl)-2-methoxy-phenyl]-vinyl}-N-(2-dimethylamino-ethyl)-5-methanesulfonylamino-N-methyl-benzamide;

N-(4-{(E)-2-[3-tert-butyl-2-methoxy-5-(6-methyl-2-oxo-1,2-dihydro-pyridin-3-yl)-phenyl]-vinyl}-3-methoxymethyl-phenyl)-methanesulfonamide;

N-(4-{(E)-2-[3-tert-butyl-2-methoxy-5-(6-methoxy-2-oxo-1,2-dihydro-pyridin-3-yl)-phenyl]-vinyl}-3-methoxymethyl-phenyl)-methanesulfonamide;

N-(4-{(E)-2-[3-tert-butyl-2-methoxy-5-(6-methoxy-2-oxo-1,2-dihydro-pyridin-3-yl)-phenyl]-vinyl}-3-hydroxymethyl-phenyl)-methanesulfonamide;

2-{(E)-2-[3-tert-butyl-2-methoxy-5-(6-methoxy-2-oxo-1,2-dihydro-pyridin-3-yl)-phenyl]-vinyl}-5-methanesulfonylamino-benzoic acid;

N-(4-{2-[5-tert-butyl-2-hydroxy-3-(2-oxo-1,2-dihydro-pyridin-3-yl)-phenyl]-ethyl}-3-cyano-phenyl)-methanesulfonamide;

N-{4-[5-tert-butyl-2-hydroxy-3-(2-oxo-1,2-dihydro-pyridin-3-yl)-phenylethynyl]-3-fluoro-phenyl}-methanesulfonamide;

N-(4-{2-[3-tert-butyl-6-hydroxy-2-methoxy-5-(2-oxo-1,2-dihydro-pyridin-3-yl)-phenyl]-ethyl}-phenyl)-methanesulfonamide;

N-[4-{(E)-2-[3-tert-butyl-5-(5-fluoro-2-oxo-1,2-dihydro-pyridin-3-yl)-2-methoxy-phenyl]vinyl}-3-(3-hydroxy-3-methyl-butoxymethyl)-phenyl]-methanesulfonamide;

N-(4-{(E)-2-[3-tert-butyl-5-(5-fluoro-2-oxo-1,2-dihydro-pyridin-3-yl)-2-methoxy-phenyl]-vinyl}-3-dimethylaminomethyl-phenyl)-methanesulfonamide;

N-[4-((E)-2-{3-tert-butyl-5-[6-(1-hydroxy-ethyl)-2-oxo-1,2-dihydro-pyridin-3-yl]-2-methoxy-phenyl}-vinyl)-phenyl]-methanesulfonamide;

N-(4-{(E)-2-[3-tert-butyl-5-(6-cyanomethyl-2-oxo-1,2-dihydro-pyridin-3-yl)-2-methoxy-phenyl]-vinyl}-phenyl)-methanesulfonamide;

N-[4-((E)-2-{3-tert-butyl-5-[6-(2-hydroxy-ethoxymethyl)-2-oxo-1,2-dihydro-pyridin-3-yl]-2-methoxy-phenyl}-vinyl)-phenyl]-methanesulfonamide;

N-(4-{(E)-2-[3-tert-butyl-2-methoxy-5-(5-methyl-2-oxo-1,2-dihydro-pyridin-3-yl)-phenyl]-vinyl}-phenyl)-methanesulfonamide;

N-[4-{(E)-2-[3-tert-butyl-5-(5-fluoro-2-oxo-1,2-dihydro-pyridin-3-yl)-2-methoxy-phenyl]-vinyl}-3-(2-methoxy-ethyl)-phenyl]-methanesulfonamide;

ethanesulfonic acid (4-{(E)-2-[3-tert-butyl-5-(5-fluoro-2-oxo-1,2-dihydro-pyridin-3-yl)-2-methoxy-phenyl]-vinyl}-phenyl)-amide;

N-(4-{(E)-2-[3-tert-butyl-5-(5-fluoro-2-oxo-1,2-dihydro-pyridin-3-yl)-2-methoxy-phenyl]-vinyl}-3-fluoro-phenyl)-methanesulfonamide;

3-{3-tert-butyl-5-[(E)-2-(2-fluoro-phenyl)-vinyl]-4-methoxy-phenyl}-1H-pyridin-2-one;

2-{(E)-2-[3-tert-butyl-2-methoxy-5-(2-oxo-1,2-dihydro-pyridin-3-yl)-phenyl]-vinyl}-benzonitrile;

2-{(E)-2-[3-tert-butyl-2-methoxy-5-(2-oxo-1,2-dihydro-pyridin-3-yl)-phenyl]-vinyl}-benzoic acid methyl ester;

3-{3-[(E)-2-(2-Acetyl-phenyl)-vinyl]-5-tert-butyl-4-methoxy-phenyl}-1H-pyridin-2-one;

3-{3-tert-butyl-5-[(E)-2-(2-methanesulfonyl-phenyl)-vinyl]-4-methoxy-phenyl}-1H-pyridin-2-one;

2-{(E)-2-[3-tert-butyl-2-methoxy-5-(2-oxo-1,2-dihydro-pyridin-3-yl)-phenyl]-vinyl}-benzoic acid;

N-(4-{(E)-2-[3-tert-butyl-2-ethoxy-5-(2-oxo-1,2-dihydro-pyridin-3-yl)-phenyl]-vinyl}-phenyl)-methanesulfonamide;

N-(4-{(E)-2-[3-tert-butyl-2-(2-methoxy-ethoxy)-5-(2-oxo-1,2-dihydro-pyridin-3-yl)-phenyl]-vinyl}-phenyl)-methanesulfonamide;

N-[3-tert-butyl-2-methoxy-5-(2-oxo-1,2-dihydro-pyridin-3-yl)-phenyl]-3-fluoro-4-(2,2,2-trifluoro-ethylamino)-benzamide;
N-[3-tert-butyl-2-methoxy-5-(2-oxo-1,2-dihydro-pyridin-3-yl)-phenyl]-2-fluoro-4-hydroxy-benzamide;
N-[3-tert-butyl-2-methoxy-5-(2-oxo-1,2-dihydro-pyridin-3-yl)-phenyl]-4-(2,2,2-trifluoro-ethylamino)-benzamide;
N-[3-tert-butyl-2-methoxy-5-(2-oxo-1,2-dihydro-pyridin-3-yl)-phenyl]-4-cyclopropylamino-benzamide;
3-tert-butyl-N-(3-methanesulfonylamino-phenyl)-2-methoxy-5-(2-oxo-1,2-dihydro-pyridin-3-yl)-benzamide;
3-tert-butyl-N-(4-methanesulfonylamino-cyclohexyl)-2-methoxy-5-(2-oxo-1,2-dihydro-pyridin-3-yl)-benzamide;
N-(4-{(E)-2-[3-tert-butyl-2-methoxy-5-(6-methyl-2-oxo-1,2-dihydro-pyridin-3-yl)-phenyl]-vinyl}-phenyl)-methanesulfonamide;
N-(4-{(E)-2-[3-(1-chloro-cyclopropyl)-5-(5-fluoro-2-oxo-1,2-dihydro-pyridin-3-yl)-2-methoxy-phenyl]-vinyl}-phenyl)-methanesulfonamide;
N-(4-{(E)-2-[3-(1-chloro-cyclopropyl)-5-(5-chloro-2-oxo-1,2-dihydro-pyridin-3-yl)-2-methoxy-phenyl]-vinyl}-phenyl)-methanesulfonamide;
N-(4-{(E)-2-[3-(1-chloro-cyclopropyl)-2-methoxy-5-(6-methyl-2-oxo-1,2-dihydro-pyridin-3-yl)-phenyl]-vinyl}-phenyl)-methanesulfonamide;
N-(4-{(E)-2-[2-methoxy-3-(1-methoxy-cyclopropyl)-5-(2-oxo-1,2-dihydro-pyridin-3-yl)-phenyl]-vinyl}-phenyl)-methanesulfonamide;
N-(4-{(E)-2-[3-(1-chloro-cyclopropyl)-2-methoxy-5-(2-oxo-1,2-dihydro-pyridin-3-yl)-phenyl]-vinyl}-phenyl)-methanesulfonamide;
N-(4-{(E)-2-[3-(1-cyano-cyclopropyl)-2-methoxy-5-(2-oxo-1,2-dihydro-pyridin-3-yl)-phenyl]-vinyl}-phenyl)-methanesulfonamide;
N-(4-{(E)-2-[3-(1-difluoromethyl-cyclopropyl)-5-(5-fluoro-2-oxo-1,2-dihydro-pyridin-3-yl)-2-methoxy-phenyl]-vinyl}-phenyl)-methanesulfonamide;
N-(4-{(E)-2-[3-(1-difluoromethyl-cyclopropyl)-2-methoxy-5-(2-oxo-1,2-dihydro-pyridin-3-yl)-phenyl]-vinyl}-phenyl)-methanesulfonamide;
N-(4-{(E)-2-[3-(1-fluoro-cyclobutyl)-5-(2-oxo-1,2-dihydro-pyridin-3-yl)-phenyl]-vinyl}-phenyl)-methanesulfonamide;
N-(4-{(E)-2-[3-(2-hydroxy-1,1-dimethyl-ethyl)-5-(2-oxo-1,2-dihydro-pyridin-3-yl)-phenyl]-vinyl}-phenyl)-methanesulfonamide;
N-(4-{(E)-2-[3-(1-chloro-cyclopropyl)-5-(5-fluoro-2-oxo-1,2-dihydro-pyridin-3-yl)-phenyl]-vinyl}-phenyl)-methanesulfonamide;
N-(4-{(E)-2-[3-(1-chloro-cyclopropyl)-5-(2-oxo-1,2-dihydro-pyridin-3-yl)-phenyl]-vinyl}-phenyl)-methanesulfonamide;
N-(4-{(E)-2-[3-(1-difluoromethyl-cyclopropyl)-5-(2-oxo-1,2-dihydro-pyridin-3-yl)-phenyl]-vinyl}-phenyl)-methanesulfonamide;
N-[3-tert-butyl-2-methoxy-5-(2-oxo-1,2-dihydro-pyridin-3-yl)-phenyl]-4-methanesulfonylamino-2-(2-methoxy-ethoxy)-benzamide;
4-acetylamino-N-[3-tert-butyl-2-methoxy-5-(2-oxo-1,2-dihydro-pyridin-3-yl)-phenyl]-benzamide;
4-amino-N-[3-tert-butyl-2-methoxy-5-(2-oxo-1,2-dihydro-pyridin-3-yl)-phenyl]-3-methyl-benzamide;
4-amino-N-[3-tert-butyl-2-methoxy-5-(2-oxo-1,2-dihydro-pyridin-3-yl)-phenyl]-2-trifluoromethyl-benzamide;
4-amino-N-[3-tert-butyl-2-methoxy-5-(2-oxo-1,2-dihydro-pyridin-3-yl)-phenyl]-2-fluoro-benzamide;
N-[3-tert-butyl-2-methoxy-5-(2-oxo-1,2-dihydro-pyridin-3-yl)-phenyl]-2-fluoro-4-methanesulfonylamino-benzamide;
N-[3-tert-butyl-2-methoxy-5-(2-oxo-1,2-dihydro-pyridin-3-yl)-phenyl]-4-methanesulfonylamino-2-methyl-benzamide;
N-[3-tert-butyl-2-methoxy-5-(2-oxo-1,2-dihydro-pyridin-3-yl)-phenyl]-2-(2-dimethylamino-ethoxy)-4-methanesulfonylamino-benzamide;
N-[3-tert-butyl-2-methoxy-5-(6-methyl-2-oxo-1,2-dihydro-pyridin-3-yl)-phenyl]-4-methanesulfonylamino-benzamide;
N-(4-{2-[3-tert-butyl-4-fluoro-2-methoxy-5-(2-oxo-1,2-dihydro-pyridin-3-yl)-phenyl]-ethyl}-phenyl)-methanesulfonamide;
N-(4-{(E)-2-[3-(2-hydroxy-1,1-dimethyl-ethyl)-2-methoxy-5-(2-oxo-1,2-dihydro-pyridin-3-yl)-phenyl]-vinyl}-phenyl)-methanesulfonamide;
N-(4-{(E)-2-[2-methoxy-3-(1-methoxy-1-methyl-ethyl)-5-(2-oxo-1,2-dihydro-pyridin-3-yl)-phenyl]-vinyl}-phenyl)-methanesulfonamide;
N-(4-{(E)-2-[5-(5-chloro-2-oxo-1,2-dihydro-pyridin-3-yl)-3-cyclopropyl-2-methoxy-phenyl]-vinyl}-phenyl)-methanesulfonamide;
N-[3-tert-butyl-5-(2-oxo-1,2-dihydro-pyridin-3-yl)-phenyl]-4-methanesulfonylamino-N-methyl-benzamide;
N-(4-{(E)-2-[4-methoxy-3,3-dimethyl-7-(2-oxo-1,2-dihydro-pyridin-3-yl)-indan-5-yl]-vinyl}-phenyl)-methanesulfonamide;
succinic acid mono-(3-{3-tert-butyl-5-[(E)-2-(4-methanesulfonylamino-phenyl)-vinyl]-4-methoxy-phenyl}-5-fluoro-2-oxo-2H-pyridin-1-ylmethyl)ester;
(S)-2-amino-3-methyl-butyric acid 3-{3-tert-butyl-5-[(E)-2-(4-methanesulfonylamino-phenyl)-vinyl]-4-methoxy-phenyl}-5-fluoro-2-oxo-2H-pyridin-1-ylmethyl ester;
phosphoric acid mono-(3-{3-tert-butyl-5-[(E)-2-(4-methanesulfonylamino-phenyl)-vinyl]-4-methoxy-phenyl}-5-fluoro-2-oxo-2H-pyridin-1-ylmethyl)ester;
N-(4-{(E)-2-[2-methoxy-5-(2-oxo-1,2-dihydro-pyridin-3-yl)-3-trifluoromethyl-phenyl]-vinyl}-phenyl)-methanesulfonamide; and,
N-(4-{(E)-2-[2-Methoxy-5-(2-oxo-1,2-dihydro-pyridin-3-yl)-3-(2,2,2-trifluoro-ethyl)-phenyl]-vinyl}-phenyl)-methanesulfonamide; or,
a pharmaceutically acceptable salt thereof.

33. A pharmaceutical composition comprising a therapeutically effective quantity of a compound according to claim 1 admixed with at least one pharmaceutically acceptable carrier, diluent or excipient.

* * * * *